(12) United States Patent  
Hagiwara et al.

(10) Patent No.: US 8,101,774 B2  
(45) Date of Patent: Jan. 24, 2012

(54) ESTER DERIVATIVES AND MEDICINAL USE THEREOF

(75) Inventors: Atsushi Hagiwara, Osaka (JP); Taku Ikenogami, Osaka (JP); Kazunori Kurihara, Osaka (JP); Toshio Taniguchi, Osaka (JP); Mitsuru Takahashi, Osaka (JP); Akio Iida, Osaka (JP)

(73) Assignee: Japan Tobacco Inc., Tokyo (JP)

( * ) Notice: Subject to any disclaimer, the term of this patent is extended or adjusted under 35 U.S.C. 154(b) by 1321 days.

(21) Appl. No.: 11/250,636

(22) Filed: Oct. 17, 2005

(65) Prior Publication Data

US 2006/0089392 A1 Apr. 27, 2006

Related U.S. Application Data

(60) Provisional application No. 60/621,840, filed on Oct. 25, 2004, provisional application No. 60/658,820, filed on Mar. 4, 2005.

(30) Foreign Application Priority Data

Oct. 18, 2004 (JP) ................................ 2004-303513  
Feb. 25, 2005 (JP) ................................ 2005-050469

(51) Int. Cl.  
*C07D 213/56* (2006.01)  
*A61K 31/44* (2006.01)

(52) U.S. Cl. ....................... 546/316; 514/355

(58) Field of Classification Search .............. 546/328, 546/316  
See application file for complete search history.

(56) References Cited

U.S. PATENT DOCUMENTS

| | | | |
|---|---|---|---|
| 4,113,871 A | 9/1978 | Stach et al. | |
| 4,238,506 A | 12/1980 | Stach et al. | |
| 5,521,170 A | 5/1996 | Setoi et al. | |
| 5,683,682 A | 11/1997 | Betts | |
| 5,684,014 A | 11/1997 | Müller et al. | |
| 5,827,875 A | 10/1998 | Dickson, Jr. et al. | |
| 5,919,970 A | 7/1999 | Song et al. | |
| 5,962,440 A | 10/1999 | Sulsky | |
| 6,057,339 A | 5/2000 | Gregg | |
| 6,121,283 A | 9/2000 | Chang et al. | |
| 6,171,599 B1 | 1/2001 | Miyamoto et al. | |
| 6,211,242 B1* | 4/2001 | Setoi et al. | 514/616 |
| 6,235,730 B1 | 5/2001 | Sato et al. | |
| 6,288,234 B1 | 9/2001 | Griffin | |
| 6,369,075 B1 | 4/2002 | Ruggert et al. | |
| 6,509,038 B2 | 1/2003 | Baert et al. | |
| 6,617,325 B1 | 9/2003 | Lehmann-Lintz et al. | |
| 6,713,489 B2 | 3/2004 | Ruggeri et al. | |
| 6,818,644 B1 | 11/2004 | Lehmann-Lintz et al. | |
| 6,943,185 B2 | 9/2005 | Susilo et al. | |
| 7,081,255 B2 | 7/2006 | Baert et al. | |
| 7,625,948 B2 | 12/2009 | Hagiwara et al. | |
| 2002/0012706 A1 | 1/2002 | Vladyka, Jr. | |
| 2002/0028943 A1 | 3/2002 | Griffin | |
| 2002/0032238 A1 | 3/2002 | Priepke et al. | |
| 2003/0044528 A1 | 3/2003 | Tanno et al. | |
| 2003/0114442 A1 | 6/2003 | Heckel et al. | |
| 2004/0058903 A1 | 3/2004 | Takasugi et al. | |
| 2004/0058956 A1 | 3/2004 | Akiyama et al. | |
| 2005/0075367 A1 | 4/2005 | Hagiwara et al. | |
| 2006/0030623 A1 | 2/2006 | Furukawa et al. | |
| 2006/0153913 A1 | 7/2006 | Yamane et al. | |
| 2006/0205726 A1 | 9/2006 | Hagiwara et al. | |
| 2006/0263436 A1 | 11/2006 | Baert et al. | |

FOREIGN PATENT DOCUMENTS

| | | |
|---|---|---|
| CA | 2 079 938 | 4/1993 |
| CA | 2 291 471 | 12/1999 |
| CA | 2 324 800 | 10/2000 |
| CA | 2 376 881 | 1/2001 |
| DE | 2517229 A1 | 10/1976 |
| EP | 0023569 A1 | 2/1981 |
| EP | 1099701 | 5/2001 |
| EP | 1 350 792 A1 | 10/2003 |
| EP | 1 769 793 A1 | 4/2007 |
| JP | 47-25189 | 10/1972 |
| JP | 57-206612 | 2/1982 |
| JP | 3-1288 B | 1/1991 |
| JP | 3-28404 B | 4/1991 |
| JP | 05-097672 | 4/1993 |

(Continued)

OTHER PUBLICATIONS

Williams et. al. "Novel Microsomal Triglyceride Transfer Protein Inhibitors" Expert Opinion on Therapeutic Patents 2003, 13, 479-488.*  
George A. Patani "Bioisosterism: A Rational Approach in Drug Design" Chemical Reviews 1996, 96, 3147-3176.*  
Wermuth, Camille G. "Molecular Variation Based on Isosteric Replacements" in Chapter 13, The Practice of Medicinal Chemistry, Academic: 1996.*  
Nakamura, Toshio "Imidazole derivatives as new potent and selective 20-HETE synthase inhibitors." Bioorganic & Medicinal Chemistry Letters 2004, 14, 333-336.*

(Continued)

*Primary Examiner* — David K O Dell  
(74) *Attorney, Agent, or Firm* — Finnegan, Henderson, Farabow, Garrett & Dunner, LLP

(57) ABSTRACT

The present invention relates to an ester represented by the formula [1]:

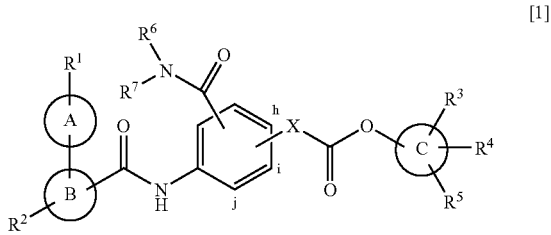

or its pharmaceutically acceptable salt, or use of the same.  
The compound represented by the formula [1] or its pharmaceutically acceptable salt is useful as an agent for the treatment or prophylaxis of hyperlipidemia or the like, since it disappears very rapidly in the living body and has an excellent MTP inhibitory activity.

7 Claims, No Drawings

FOREIGN PATENT DOCUMENTS

| | | |
|---|---|---|
| JP | 07-002800 | 1/1995 |
| JP | 08-179504 | 7/1996 |
| JP | 08-208476 | 8/1996 |
| JP | 9-59159 | 3/1997 |
| JP | 9-309834 | 12/1997 |
| JP | 11-035555 | 2/1999 |
| JP | 11-228569 | 8/1999 |
| JP | 11-509238 | 8/1999 |
| JP | 11-246404 | 9/1999 |
| JP | 2000-53570 A | 2/2000 |
| JP | 2000-169395 | 6/2000 |
| JP | 2000-281561 | 10/2000 |
| JP | 2001-172180 | 6/2001 |
| JP | 2002-220345 | 8/2002 |
| JP | 2003-505373 | 2/2003 |
| JP | 2003-73261 | 3/2003 |
| JP | 2003-509505 | 3/2003 |
| JP | 2003-531099 | 10/2003 |
| JP | 2003-321424 | 11/2003 |
| JP | 2004-10575 | 1/2004 |
| JP | 2004-510763 | 4/2004 |
| KR | 1999-0075252 A | 10/1999 |
| WO | WO 96/40640 | 12/1996 |
| WO | WO 97/26240 | 7/1997 |
| WO | WO 97/43257 | 11/1997 |
| WO | WO 98/23593 | 6/1998 |
| WO | WO 98/47875 | 10/1998 |
| WO | WO 99/63929 | 12/1999 |
| WO | WO 00/05201 | 2/2000 |
| WO | WO 00/32582 | 6/2000 |
| WO | WO 00/37422 | 6/2000 |
| WO | WO 00/56726 | 9/2000 |
| WO | WO 01/00183 | 1/2001 |
| WO | WO 01/00184 | 1/2001 |
| WO | WO 01/00189 | 1/2001 |
| WO | WO 01/05762 | 1/2001 |
| WO | WO 01/12601 | 2/2001 |
| WO | WO 01/21604 | 3/2001 |
| WO | WO 01/47898 | 7/2001 |
| WO | WO 01/47899 | 7/2001 |
| WO | WO 01/53260 | 7/2001 |
| WO | WO 01/77077 | 10/2001 |
| WO | WO 01/97810 | 12/2001 |
| WO | WO 02/04403 | 1/2002 |
| WO | WO 02/20501 | 3/2002 |
| WO | WO 02/28835 | 4/2002 |
| WO | WO 02/42271 | 5/2002 |
| WO | WO 02/42291 | 5/2002 |
| WO | WO 02/051385 | 7/2002 |
| WO | WO 02/081460 | 10/2002 |
| WO | WO 02/098839 | 12/2002 |
| WO | WO 03/072532 | 9/2003 |
| WO | WO 2005/021486 | 3/2005 |
| WO | WO 2006/008962 | 1/2006 |
| WO | WO 2006/046623 | 5/2006 |

OTHER PUBLICATIONS

Li, Bing et. al. "N-(Arylacetyl)-biphenylalanines as Potent VLA-4 Antagonists" Bioorganic & Medicinal Chemistry Letters 2002, 12, 2141-2144.*
Aggarwal et al., BMC Cardiovascular Disorders, 2005, 5:30, pp. 1-8.
Anastasiou, Theordore J., et al., "Syntheses of aminosalicylate-based polyanhydride prodrugs: esters, amides, and azos," Polymer Preprints (American Chemical Society, Division of Polymer Chemistry) 42(2), 121-122 (2001).
Chiou, W.L. et al., Pharmaceutical Application of Solid Dispersion Systems, J. Pharm. Sci. 60 (1971) 1281-1302.
Fischer et al., Journal of the Chemical Society (B), Rates of Base-catalyzed Hydrolysis of Substituted Aryl Benzoates (1971), pp. 1818-1819.
Hagiwara et al., CAPLUS AN 2003:696857 (Feb. 28, 2003), 2 pages only.
European Search Report of Application No. 04772363.0 dated Jan. 23, 2008.
PCT International Search Report of PCT/JP03/02398 dated Jun. 3, 2003.
PCT International Search Report (PCT/JP2004/012407) dated Feb. 15, 2005.
PCT International Search Report (PCT/JP2005/012448) dated Aug. 9, 2005.
PCT International Search Report (PCT/JP2005/019744) dated Dec. 13, 2005.
PCT International Search Report (PCT/JP2005/019041) dated Jan. 24, 2006.
http://www.mayoclinic.com/health/arteriosclerosis-atherosclerosis/DS00525/DSECTION=8.
http://www.mayoclinic.com/health/obesity/DS00314/DSECTION=7.
Rx for Success, Lipid Levels—The Risk of Arteriosclerosis, Prudential Financial, 2002, 2 pages.
http://www.nhlbi.nih.gov/health/dci/Diseases/Cad/CAD_WhatIs.html.
Japan Tobacco Inc. Clinical Development (Apr. 27, 2007).
http://cholesterol.about.com/od/treatments/a/mttpinhibitor.htm.
SciFinder Scholar, version 2007.1; Chemical Abstracts Service, Columbus, OH; RN 339202-67-4 (accessed Feb. 6, 2008).
SciFinder Scholar, version 2007.1; Chemical Abstracts Service, Columbus, OH; RN 339202-91-4 (accessed Feb. 6, 2008).
SciFinder Scholar, version 2007.1; Chemical Abstracts Service, Columbus, OH; RN 516466-52-7 (accessed Feb. 6, 2008).
SciFinder Scholar, version 2007.1; Chemical Abstracts Service, Columbus, OH; RN 901355-00-8 (accessed Feb. 6, 2008).
SciFinder Scholar, version 2007.1; Chemical Abstracts Service, Columbus, OH; RN 888922-25-6 (accessed Feb. 6, 2008).
SciFinder Scholar, version 2007.1; Chemical Abstracts Service, Columbus, OH; RN 900909-90-2 (accessed Feb. 6, 2008).
Ksander et al., Diaminoindanes as Microsomal Triglyceride Transfer Protein Inhibitors, J. Med. Chem., vol. 44 (26), pp. 4677-4687 (2001).
Robl et al., *Novel Series of Highly Potent Benzimidazole-Based Microsomal Triglyceride Transfer Protein Inhibitors*, J. Med. Chem., vol. 44 (6), pp. 851-856 (2001).
Shiomi. et al., MTP inhibitor decreases plasma cholesterol levels in LDL receptor-deficient WHHL rabbits by lowering the VLDL secretion, European Journal of Pharmacology, vol. 431, pp. 127-131 (2001).
Wetterau et al., Purification and Characterization of Microsomal Triglyceride and Cholesteryl Ester Transfer Protein from Bovine Liver Microsomes, Chem. Phys. Lipids, vol. 38, pp. 205-222 (1985).
U.S. Appl. No. 12/627,535, filed Nov. 30, 2009.
Chemical Abstract, XP002598214, Accession No. 2000:121819 (Feb. 22, 2000).
Supplementary European Search Report for EP Application No. EP 03 74 3078 (Sep. 13, 2010).
Okorokov, A.N., Diagnostics Of Diseases Of Internal Organs, vol. 2, Diagnostics of Rheumatic And Systemic Diseases Of Connective Tissues. Diagnostics Of Endocrine Diseases. Moscow, Medical Literature 2006, pp. 254-256.
Okorokov, A.N., Diagnostics Of Diseases Of Internal Organs, vol. 6, Diagnostics Of Diseases Of The Heart And Blood Vessels. Atherosclerosis And IHD (Ischemic Heart Disease). Moscow, Medical Literature 2006, pp. 82-85.
Office Action in Counterpart Russian Application No. 2007118503/04 received Jun. 22, 2010.

* cited by examiner

ESTER DERIVATIVES AND MEDICINAL USE THEREOF

This Application claims the benefit of priority of Japanese Patent Application Nos. 2004-303513, filed Oct. 18, 2004, and 2005-050469, filed Feb. 25, 2005; and U.S. Provisional Application Nos. 60/621,840, filed Oct. 25, 2004, and 60/658,820 filed Mar. 4, 2005.

TECHNICAL FIELD

The present invention relates to a novel ester derivative, and also relates to a pharmaceutical composition comprising a novel ester derivative which selectively inhibits microsomal triglyceride transfer protein (hereinafter also abbreviated as MTP) in the small intestine, or a pharmaceutically acceptable salt thereof. Further, the present invention relates to an agent for the treatment or prophylaxis of hyperlipidemia, arteriosclerosis, coronary artery diseases, obesity, diabetes or hypertension, comprising a novel ester or a pharmaceutically acceptable salt thereof as an active ingredient which selectively inhibits MTP in the small intestine. In addition, the present invention relates to an agent for the treatment or prophylaxis of hyperlipidemia, arteriosclerosis, coronary artery diseases, obesity, diabetes or hypertension, which has a novel function that has never been known before.

BACKGROUND ART

It has been said that hyperlipidemia, diabetes, hypertension or the like is one of the risk factors for arteriosclerosis. Hyperlipidemia is a condition where the concentration of lipid such as cholesterol is abnormally elevated in the blood. Types of hyperlipidemia, depending on the cause, include primary hyperlipidemia caused by genetic abnormality in enzyme, protein, lipoprotein and the like which participate in the metabolism of low-density lipoprotein (LDL), secondary hyperlipidemia due to various disease or drug administration, and acquired hyperlipidemia basically resulting from overnutrition.

Meanwhile, lipid taken in from food is absorbed in the small intestine by the action of bile acid, and secreted as chylomicron in the blood via lymphatic vessels. The triglyceride (TG) moiety of the secreted chylomicrons is hydrolyzed to free fatty acids by the action of lipoprotein lipase (LPL) existing in capillary vessels to become chylomicron remnants having a high content of cholesteryl ester (CE), which is then absorbed in the liver by the mediation of chylomicron remnant receptor in the liver. Further, in the liver, the absorbed chylomicron remnant and free fatty acids are converted to CE and TG, respectively, which are then associated with apolipoprotein B synthesized on rough surfaced endoplasmic reticulum to form very low density lipoprotein (VLDL). The VLDL is transferred to the Golgi apparatus, modified and secreted outside cells, and it becomes intermediate density lipoprotein (IDL) by the action of LPL. The IDL is converted to LDL by the action of hepatic triglyceride lipase (HTGL), and lipids are distributed to peripheral tissues.

It has long been indicated that, during the above-mentioned formation of chylomicron in the small intestine or VLDL in the liver, a protein having TG- or CE-transfer activity is existing in microsomal fractions of the small intestine or liver. Meanwhile, the protein, i.e. MTP (microsomal triglyceride transfer protein: hereinafter also abbreviated as MTP) was purified and separated from microsomal fractions of bovine liver by Wetterau et al. in 1985 (Wetterau J. R. et al: Chem. Phys. Lipids 38, 205-222 (1985)). MTP, however, began attracting a lot of attention in the field of clinical medicine only after it was reported in 1993 that the cause of abetalipoproteinemia lay in the deficit of MTP. In other word, the disease is characterized in that, while the genes related to apolipoprotein B are normal, apolipoprotein B is hardly detected in the serum, the level of serum cholesterol is 50 mg/dL or lower, the level of serum triglyceride is extremely low. By this finding, it has been shown that MTP is an integral protein involved in the association between apolipoprotein B and TG or CE, i.e. the formation of VLDL or chylomicron, and plays an essential role in secretion thereof. Accordingly, it was thought that MTP inhibitors can become to be an excellent anti-hyperlipidemic agent which can inhibit the production of lipoproteins such as chylomicron, VLDL, and the like. In addition, by inhibiting MTP in the small intestine and thus suppressing the production of chylomicron, it may be expected that excess absorption of triglycerides responsible for hyperliplidemia is inhibited, leading to creation of a new type of anti-hyperlipidemic agents.

Since lipid is by nature insoluble in water, lipid in the blood is combined with a hydrophilic protein known as apolipoprotein and exists as so-called lipoprotein. All the VLDL, IDL, LDL or chylomicron, etc. related to hyperlipidemia are a lipoprotein.

MTP exists in the microsome fractions of hepatocytes and intestinal epithelial cells, and catalyses the transfer of TG or CE in cells. In the liver and small intestine, along with the synthesis of apolipoprotein B (apolipoprotein B100 in the liver and apolipoprotein B48 in the small intestine), TG and CE are combined with respective apolipoprotein B by the transfer activity of MTP, and thus VLDL or chylomicron is formed. As a result, those lipoproteins are secreted outside the cells as VLDL in the liver or as chylomicron in the small intestine. It should be said that MTP is indispensable for the construction of those lipoproteins. Namely, if the activity of MTP is blocked, the transfer of lipid such as TG and CE, etc. to apolipoprotein is inhibited, whereby formation of a lipoprotein can be inhibited.

On the other hand, it has been elucidated that LDL in general is closely related to the progression of arteriosclerosis. That is, LDL permeating endothelium of blood vessels is deposited in intercellular matrix of vessel wall, where oxidative denaturation takes place and lipid peroxides or denaturated proteins induce a series of inflammation reactions. Consequently, macrophage emigration in blood vessels leading to lipid deposit or composition of layers of foamy cells, migration or proliferation of smooth muscle cells and increase in intercellular matrix, etc. take place, which leads to the development of arteriosclerosis plaque. On the basis of the above, it is supposed to be possible to prevent or treat arteriosclerosis, coronary artery diseases or hypertension by reducing the level of LDL.

As already mentioned, it is possible to inhibit the formation of lipoprotein such as chylomicron, VLDL, LDL, etc. by inhibiting the action of MTP. Accordingly, it has been expected that it should become possible to control TG, cholesterol and lipoproteins such as LDL, etc. in blood and to control lipid in cells by adjusting the activity of MTP, and therefore, a novel agent for the treatment or prophylaxis of hyperlipidemia, arteriosclerosis, coronary artery diseases, diabetes, obesity, or hypertension, and further, an agent for the treatment or prophylaxis of pancreatitis, hypercholesterolemia, hyperglyceridemia, etc. has been expected to be provided.

However, with the development of MTP inhibitors, some cases of fatty liver were reported and concern over hepatotoxicity has been raised (M. Shiomi and T. Ito, European Journal of Pharmacology 431, p. 127-131 (2001)). This is presumably because even if a compound exerts inhibitory activity against MTP in the small intestine, it is absorbed from the intestine and the like, and remains in the blood or liver, which results in also inhibiting MTP in the liver.

In the conventional manners, combined therapies of various combinations of different antihyperlipidemic drugs have been tried. However, when, for example, a statin-type drug and a resin-type drug are given together, undesirable side effects such as elevated GOT and GPT, constipation, blocking of absorption of vitamins A, D, E and K and the like are observed. On the other hand, when a statin-type drug and a fibrate drug are given together, side effects such as rhabdomyolysis or elevated CPK (creative phosphokinase) are observed. Thus, with regard to a combined therapy for hyperlipidemia, a medicament for a combined administration which can be administered in combination with a conventional antihyperlipidemic drug without causing any above-mentioned side effect has been desired.

Meanwhile, examples of the known compound having MTP inhibitory activity are described below.

The following compound is disclosed in WO97/26240.

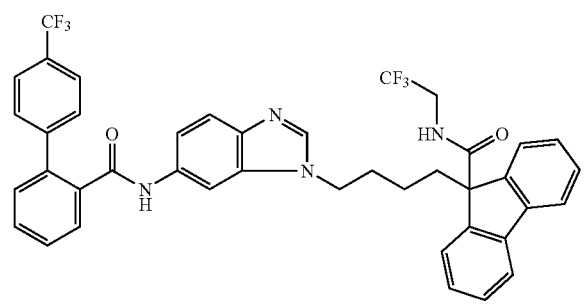

The following compound is disclosed in WO97/43257.

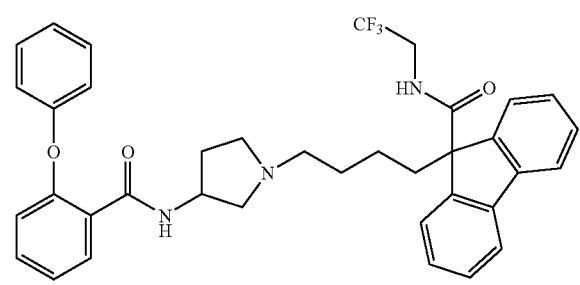

The following compound is disclosed in WO98/23593.

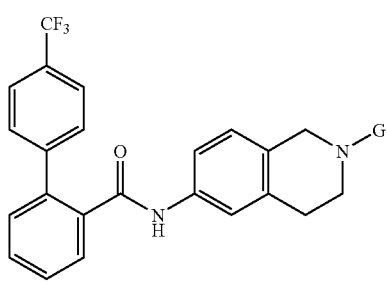

(In the formula, G is phenyl, heterocyclyl, —CH$_2$CN, diphenylmethyl, C$_2$-C$_{12}$ alkyl, C$_2$-C$_{12}$ perfluoroalkyl, C$_3$-C$_8$ cycloalkyl, C$_3$-C$_8$ cycloalkenyl, —(CH$_2$)$_n$—COOH, —(CH$_2$)$_n$—COO-alkyl, etc.)

The following compound is disclosed in WO99/63929.

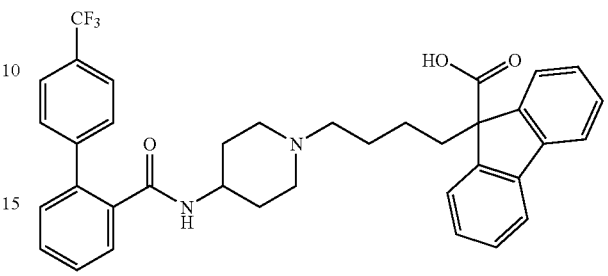

The following compound is disclosed in WO2000/5201.

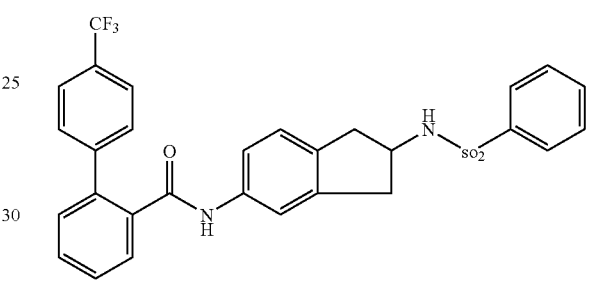

The following compound is disclosed in J. Med. Chem. (2001), 44(6) p. 851-856.

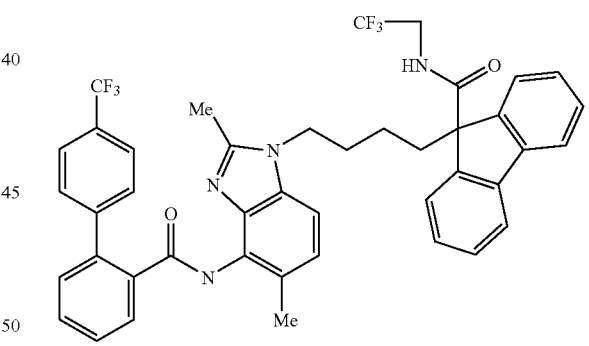

The following compound is disclosed in EP 1099701.

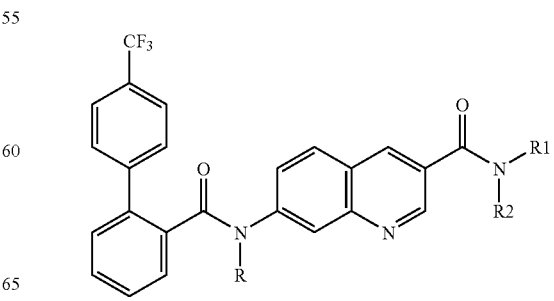

The following compound is disclosed in WO2001/77077.

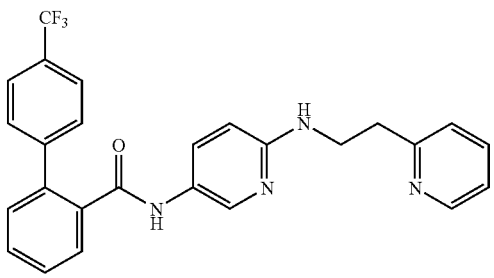

The following compound is disclosed in J. Med. Chem. (2001), 44 (6) p. 4677-4687.

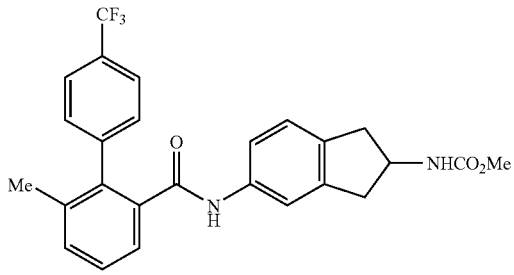

The following compound is disclosed in WO2002/4403.

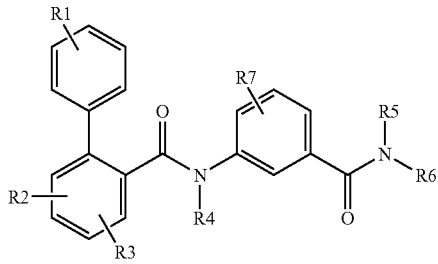

In the above literatures, however, there is no disclosure of a compound comprising ester as the essential structure, much less the disclosure or suggestion of the data indicating that the disclosed compound selectively inhibits MTP in the small intestine while rarely affects MTP in the liver.

Further, WO2002/28835 discloses the following compound represented by the formula:

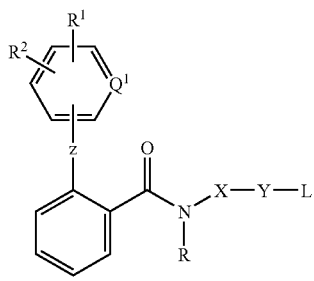

wherein
L is an unsaturated 3- to 10-membered heterocycle which may be substituted by a suitable substituent,
Y is $-(A^1)_m-(A^2)_n-(A^4)_k-$

[in the formula, $A^1$ is lower alkylene or lower alkenylene and these two groups may be substituted by a suitable substituent; $A^2$ is $-N(R^3)-$, $-CO-N(R^3)-$, $-NH-CO-NH-$, $-CO-O-$, $-O-$, $-O-(CH_2)_2-N(R^3)-$, $-S-$, $-SO-$, or $-SO_2-$ (in the formula, $R^3$ is hydrogen or a suitable substituent); $A^4$ is lower alkylene, lower alkenylene or lower alkynylene; and k, m and n are each independently 0 or 1].

However, the compound disclosed in this patent differs from the compound of the present invention in its structure with respect to the moiety of $-Y-L-$. Further, in this patent, there is no disclosure or suggestion of the data indicating that the disclosed compound selectively inhibits MTP in the small intestine while rarely affects MTP in the liver.

Furthermore, WO2003/72532 discloses the following compound having selective inhibition of MTP in the small intestine, represented by the formula:

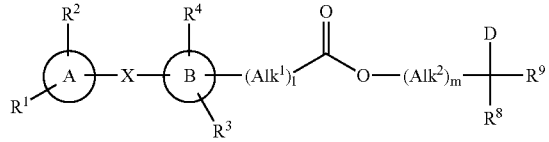

wherein $Alk^2$ is alkanediyl or alkenediyl;
m is 0 or an integer of 1 to 3;
D is $C_1$-$C_6$ alkyl, $C_2$-$C_6$ alkenyl, $C_2$-$C_7$ alkoxycarbonyl, $-N(R^{42})-CO(R^{43})$ (wherein $R^{42}$ is hydrogen or $C_1$-$C_6$ alkyl, and $R^{43}$ is $C_6$-$C_{14}$ aryl or $C_7$-$C_{16}$ aralkyl), or

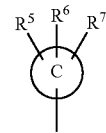

wherein $R^5$, $R^6$ and $R^7$ are each independently $C_1$-$C_6$ alkyl, $C_1$-$C_6$ alkoxy, $C_2$-$C_7$ alkoxycarbonyl, carboxyl, halogen, cyano, nitro, halo $C_1$-$C_6$ alkyl, $C_1$-$C_6$ acyl, hydroxy, amino, optionally substituted $C_6$-$C_{14}$ aryl or $-(CH_2)_r-CON(R^{16})(R^{17})$ (wherein $R^{16}$ and $R^{17}$ are each independently hydrogen, $C_1$-$C_6$ alkyl or halo $C_1$-$C_6$ alkyl, and r is 0 or an integer of 1 to 3); ring C is $C_6$-$C_{14}$ aryl, $C_7$-$C_{15}$ arylcarbonylamino, $C_8$-$C_{17}$ aralkylcarbonylamino, heterocyclic residue, $C_3$-$C_7$ cycloalkyl, or $C_7$-$C_{16}$ aralkyl, or ring C taken together with $R^7$ and $R^8$ may form a group of the formula:

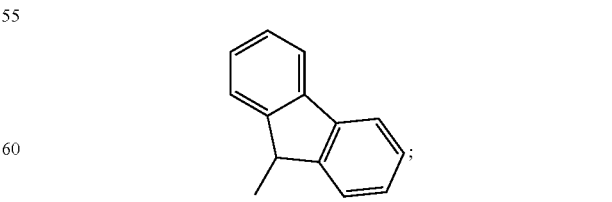

$R^8$ and $R^9$ are each independently hydrogen, $C_1$-$C_6$ alkyl, optionally substituted $C_6$-$C_{14}$ aryl, hydroxy-$C_1$-$C_6$ alkyl, $-CON(R^{18})(R^{19})$ (wherein $R^{18}$ and $R^{19}$ are each the same or different, and are hydrogen, $C_1$-$C_6$ alkyl, $C_3$-$C_7$ cycloalkyl, halo-$C_1$-$C_6$ alkyl, $C_2$-$C_{12}$ alkoxyalkyl or optionally substituted $C_6$-$C_{14}$ aryl), —COO($R^{20}$) or $(CH_2)_s$—OCOR($R^{20}$) (wherein $R^{20}$ is hydrogen, $C_1$-$C_6$ alkyl or $C_3$-$C_7$ cycloalkyl, and s is 0 or an integer of 1 to 3), —N($R^{21}$)($R^{22}$) (wherein $R^{21}$ and $R^{22}$ are each the same or different, and are hydrogen, $C_1$-$C_6$ alkyl, $C_1$-$C_6$ acyl or $C_1$-$C_6$ alkylsulfonyl, or $R^{21}$ and $R^{22}$ together with the nitrogen atom to which they are attached may form a group of the formula:

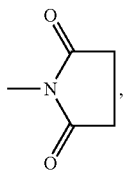

or $R^8$ and $R^9$ taken together may form $C_3$-$C_7$ cycloalkyl.

However, the compound disclosed in this patent literature differs from the compound of the present invention in its chemical structure with respect to the moiety of -(Alk$^2$)$_m$-CR$^8$R$^9$—.

In addition, WO2005/21486 discloses the following compound of the formula:

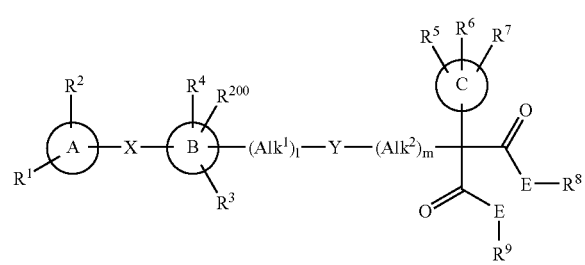

wherein $R^1$ and $R^2$ are each the same or different, and are hydrogen, $C_1$-$C_6$ alkyl, $C_3$-$C_7$ cycloalkyl, $C_1$-$C_6$ alkoxy, halo $C_1$-$C_6$ alkyl, halo $C_1$-$C_6$ alkyloxy, optionally substituted $C_6$-$C_{14}$ aryl, optionally substituted $C_7$-$C_{16}$ aralkyl, optionally substituted $C_6$-$C_{14}$ aryloxy, optionally substituted $C_7$-$C_{16}$ aralkyloxy, optionally substituted $C_7$-$C_{15}$ arylcarbonyl, optionally substituted heterocyclic ring, $C_2$-$C_7$ alkoxycarbonyl, halogen, $C_2$-$C_6$ alkenyl, $C_1$-$C_6$ acyl, cyano, —N($R^{40}$)($R^{41}$) (wherein $R^{40}$ and $R^{41}$ are each the same or different, and are hydrogen, $C_1$-$C_6$ alkyl or optionally substituted $C_6$-$C_{14}$ aryl) or —(CH$_2$)$_r$—O—CO—R$^{100}$ (wherein R$^{100}$ is $C_1$-$C_6$ alkyl, $C_1$-$C_6$ alkoxy or $C_2$-$C_{12}$ alkoxyalkyl, and r is 0 or an integer of 1 to 3);

ring A is $C_6$-$C_{14}$ aryl, heterocyclic ring,

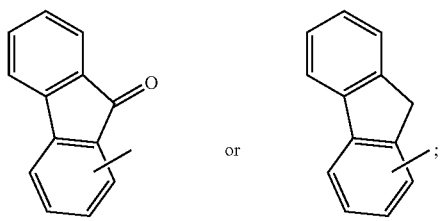

X is —COO—(CH$_2$)$_n$—, —CON)(R$^{10}$)—(CH$_2$)$_n$— or —N(R$^{10}$)—CO—(CH$_2$)$_n$— (wherein R$^{10}$ is hydrogen, $C_1$-$C_6$ alkyl or $C_3$-$C_8$ cycloalkyl, and n is 0 or an integer of 1 to 3);

$R^3$, $R^4$ and $R^{200}$ are each the same or different, and are hydrogen, hydroxy, halogen, optionally substituted $C_1$-$C_6$ alkyl, $C_1$-$C_6$ alkoxy, halo $C_1$-$C_6$ alkyl, $C_7$-$C_{16}$ aralkyloxy, $C_1$-$C_6$ acyl, $C_3$-$C_{10}$ alkoxycarbonylalkyl, optionally substituted heterocyclic ring, —CON($R^{11}$)($R^{12}$) [wherein $R^{11}$ and $R^{12}$ are each the same or different, and are hydrogen, optionally substituted $C_1$-$C_6$ alkyl, optionally substituted $C_6$-$C_{14}$ aryl, optionally substituted $C_7$-$C_{16}$ aralkyl or $C_1$-$C_6$ alkoxy, or $R^{11}$ and $R^{12}$ together with the nitrogen atom to which they are attached may form a group of the formula:

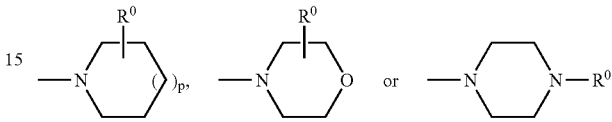

(wherein $R^0$ is hydrogen, hydroxy, $C_1$-$C_6$ alkyl or $C_1$-$C_6$ acyl, and p is 0 or an integer of 1 or 2)], —(CH$_2$)$_{q'}$—N($R^{13}$)($R^{14}$) [wherein $R^{13}$ and $R^{14}$ are each the same or different, and are hydrogen, $C_1$-$C_6$ alkyl, $C_2$-$C_7$ alkoxycarbonyl or $C_1$-$C_6$ acyl, or $R^{13}$ and $R^{14}$ together with the nitrogen atom to which they are attached may form a group of the formula:

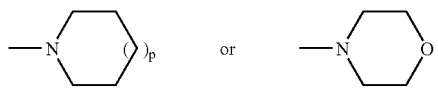

(wherein p has the same meaning as defined above), and q' is 0 or an integer of 1 to 3], —CO($R^{15}$) [wherein $R^{15}$ is hydroxy, $C_1$-$C_6$ alkyl, $C_1$-$C_6$ alkoxy, optionally substituted $C_6$-$C_{14}$ aryloxy or $C_7$-$C_{16}$ aralkyloxy], or —(CH$_2$)$_{r'}$—O—CO—R$^{100'}$ [wherein R$^{100'}$ is $C_1$-$C_6$ alkyl, $C_1$-$C_6$ alkoxy, $C_2$-$C_{12}$ alkoxyalkyl or —N($R^{40}$)($R^{41}$)($R^{40}$ and $R^{41}$ have the same meanings as defined above), and r' is 0 or an integer of 1 to 3];

ring B is

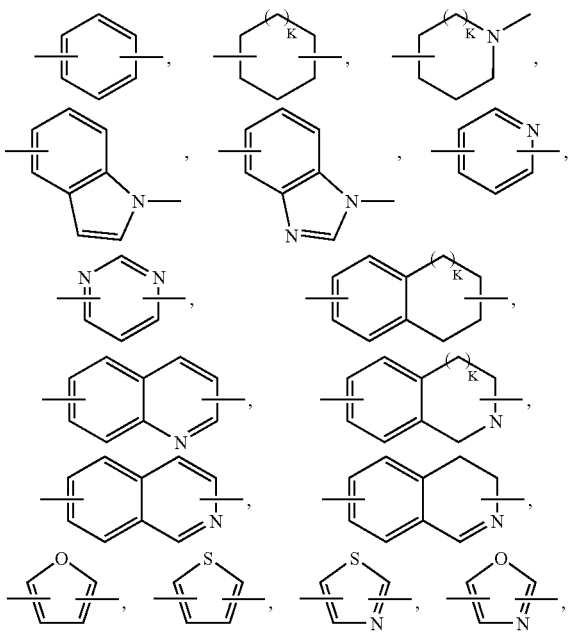

-continued

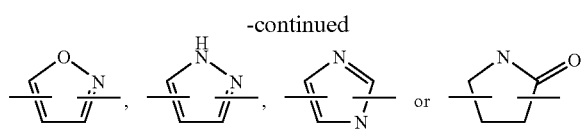

(wherein k is 0 or an integer of 1 or 2), or the nitrogen atom to which $R^{10}$ is attached, taken together with $R^3$, $R^{10}$ and ring B, may form a group of the formula:

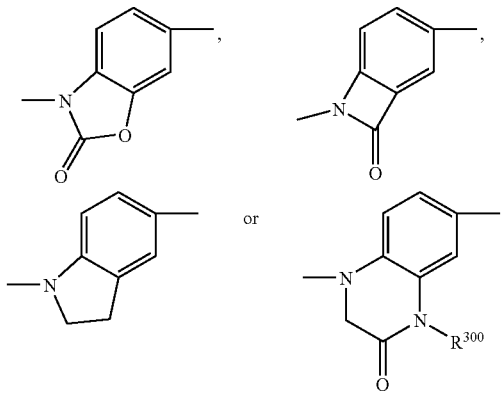

(wherein $R^{300}$ is optionally substituted $C_1$-$C_6$ alkyl);
Alk$^1$ is alkanediyl or alkenediyl;
Alk$^2$ is alkanediyl or alkenediyl;
l is 0 or an integer of 1 to 3;
m is 0 or an integer of 1 to 3;
ring C is

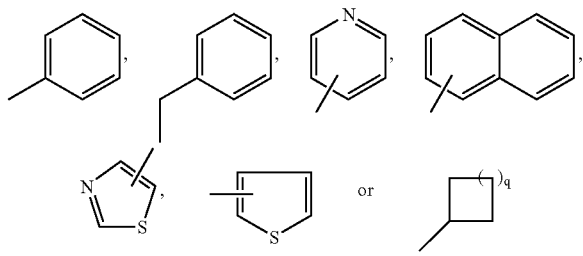

(q is 0 or an integer of 1 to 4);
$R^5$, $R^6$ and $R^7$ are each the same or different, and are hydrogen, $C_1$-$C_6$ alkyl, $C_1$-$C_6$ alkoxy, $C_2$-$C_7$ alkoxycarbonyl, carboxyl, halogen, cyano, nitro, halo $C_1$-$C_6$ alkyl, $C_1$-$C_6$ acyl, hydroxy, amino, optionally substituted $C_6$-$C_{14}$ aryl, —(CH$_2$)$_r$— —CON($R^{16}$)($R^{17}$) (wherein $R^{16}$ and $R^{17}$ are each the same or different, and are hydrogen, $C_1$-$C_6$ alkyl or halo $C_1$-$C_6$ alkyl, and r is 0 or an integer of 1 to 3) or —(CH$_2$)$_{r''}$—O—CO— $R^{100''}$ (wherein $R^{100''}$ is $C_1$-$C_6$ alkyl, $C_1$-$C_6$ alkoxy or $C_2$-$C_{12}$ alkoxyalkyl, and r'' is 0 or an integer of 1 to 3);
$R^8$ and $R^9$ are each the same or different, and are hydrogen, optionally substituted $C_1$-$C_6$ alkyl or optionally substituted $C_6$-$C_{14}$ aryl;
E is —O— or —N($R^{90}$)— (wherein $R^{90}$ is hydrogen or $C_1$-$C_6$ alkyl);
Y is —O—CO—O—, —O—CO—, —CO—O—, —CO—O—C($R^{110}$)($R^{111}$)—O—CO—, —CO—O—C($R^{110}$)($R^{111}$)—O—CO—O—, —O—CO—O—($R^{110}$)($R^{111}$)—O—CO—O—, —O—CO—O—C($R^{111}$)($R^{111}$)—O—CO—, —O—CO—C($R^{110}$)($R^{111}$)—O—, —O—CO—C($R^{110}$)($R^{111}$)—C($R^{110}$)($R^{111}$)—O—, or —O—C)($R^{110}$)($R^{111}$)—CO—O— (wherein $R^{110}$ and $R^{111}$ are each the same or different, and are hydrogen or $C_1$-$C_6$ alkyl; provided that when Y is —CO—O—, then $R^3$ is —(CH$_2$)$_{r'}$—O—CO—$R^{100'}$ ($R^{100'}$ and r' have the same meanings as defined above).

However, the compound disclosed in this patent literature differs from the compound of the present invention in its chemical structure.

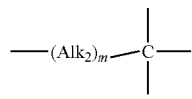

DISCLOSURE OF THE INVENTION

Although the development of new antihyperlipidemic drugs working due to its MTP inhibitory activity has been advanced nowadays, those drugs are not satisfactory in terms of their disappearing velocity in the blood or liver causing side effect such as a fatty liver, etc. Thus, the development of an antihyperlipidemic drug which can disappear very rapidly in the blood or liver has been strongly desired. A technical problem to be solved by the present invention is to provide excellent antihyperlipidemic drugs having high inhibitory activity which is seen in the case of conventional MTP inhibitors and being very rapidly metabolized in the blood or liver.

The inventors and those involved in the present invention have carried out intensive studies to provide a novel MTP inhibitor causing no above-mentioned side effect such as a fatty liver. As a result, they have found that an MTP inhibitor, which selectively inhibits MTP in the small intestine but substantially does not inhibit MTP in the liver, significantly lowers the level of unnecessary TG or cholesterol without causing a side effect such as a fatty liver, etc. Surprisingly, they have also found that the compound having ester structure represented by the below-mentioned formula [1] has lost MTP inhibitory activity very rapidly in the plasma or liver S9. Accordingly such ester compound of the present invention was found to be remarkably useful as an antihyperlipidemic drug which undergoes very rapid metabolism in the blood or liver.

Namely, the present invention relates to:
<1> an ester compound of the formula [1]:

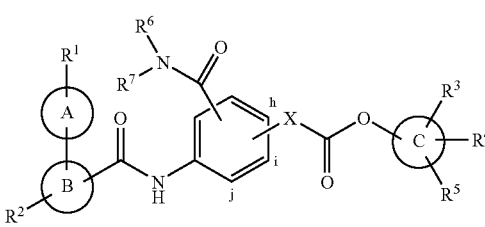

wherein
$R^1$ is 1) halogen, 2) $C_1$-$C_6$ alkyl, 3) $C_1$-$C_6$ alkoxy or 4) —CO—$C_1$-$C_6$ alkoxy (wherein $C_1$-$C_6$ alkyl or $C_1$-$C_6$ alkoxy in the above 2), 3) and 4) is optionally substituted by the same or different one or more substituents selected from Group A as defined below:
[Group A]
1) halogen,
2) hydroxy, 3) $C_1$-$C_6$ alkoxy, 4) —$NR^8R^9$ wherein $R^8$ and $R^9$ are each the same or different and are (a) hydrogen, (b) $C_1$-$C_6$ alkyl or (c) nitrogen-containing saturated heterocycle comprising a monocycle formed when $R^8$, $R^9$ and the adjacent nitrogen atom are taken together, 5) —$CONR^8R^9$ wherein $R^8$ and $R^9$ are each the same or different, and are hydrogen or $C_1$-$C_6$ alkyl, or a nitrogen-containing saturated heterocycle comprising a monocycle formed when $R^8$, $R^9$ and the adjacent nitrogen atom are taken together, 6) —$COR^{10}$ wherein $R^{10}$ is (a) hydrogen, (b) hydroxy, (c) $C_1$-$C_6$ alkyl or (d) $C_1$-$C_6$ alkoxy, 7) —$NR^{11}COR^{10}$ wherein $R^{10}$ is hydrogen, hydroxy, $C_1$-$C_6$ alkyl or $C_1$-$C_6$ alkoxy, and $R^{11}$ is (a) hydrogen or (b) $C_1$-$C_6$ alkyl, 8) —$NR^{11}CONR^8R^9$ wherein $R^8$ and $R^9$ are the same or different, and are hydrogen, $C_1$-$C_6$ alkyl, or a nitrogen-containing saturated heterocycle comprising a monocycle formed when $R^8$, $R^9$ and the adjacent nitrogen atom are taken together, and $R^{11}$ is hydrogen or $C_1$-$C_6$ alkyl, 9) —$NR^{11}SO_2R^{12}$ wherein $R^{11}$ is hydrogen or $C_1$-$C_6$ alkyl, and $R^{12}$ is $C_1$-$C_6$ alkyl, and 10) —$SO_2R^{12}$ wherein $R^{12}$ is $C_1$-$C_6$ alkyl, (wherein $C_1$-$C_6$ alkyl or $C_1$-$C_6$ alkoxy in the above 1) to 10) may be further substituted by the same or different one or more substituents selected from the Group A as defined above, and the nitrogen-containing saturated heterocycle comprising a monocycle in the above 4), 5) or 8) may be further substituted by the same or different one or more substituents selected from the Group A as defined above and $C_1$-$C_6$ alkyl, provided that when substitutable alkyl, alkoxy or nitrogen-containing saturated heterocycle comprising a monocycle is chosen as a substituent, these groups may be substituted as mentioned above, however, it is possible to select alkyl, alkoxy or nitrogen-containing heterocycle comprising a monocycle as such a substituent to be selected and this substituent may in turn be further substituted, and although such repeated substitution is not particularly limited, it is preferably within five times, more preferably twice, and especially preferably once));

$R^2$ is 1) hydrogen or 2) $C_1$-$C_6$ alkyl (wherein $C_1$-$C_6$ alkyl in the above 2) is optionally substituted by the same or different one or more substituents selected from the Group A as defined above);

$R^3$, $R^4$ and $R^5$ are each the same or different, and are 1) hydrogen or 2) a substituent selected from Group B as defined below:

[Group B]
1) halogen,
2) hydroxyl,
3) $C_1$-$C_6$ alkyl which is optionally substituted by the same or different one or more substituents selected from the Group A as defined above,
4) $C_1$-$C_6$ alkoxy which is optionally substituted by the same or different one or more substituents selected from the Group A as defined above,
5) cycloalkylalkoxy which is optionally substituted by one or more substituents selected from the Group A as defined above and $C_1$-$C_6$ alkyl substituted by the same or different one or more substituents selected from the Group A as defined above,
6) aralkyl which is optionally substituted by one or more substituents selected from the Group A as defined above and $C_1$-$C_6$ alkyl substituted by the same or different one or more substituents selected from the Group A as defined above,
7) aralkyloxy which is optionally substituted by the same or different one or more substituents selected from the Group A as defined above and $C_1$-$C_6$ alkyl optionally substituted by the same or different one or more substituents selected from the Group A as defined above,
8) —$COR^{13}$ wherein $R^{13}$ is
(a) hydroxy,
(b) $C_1$-$C_6$ alkyl which is optionally substituted by the same or different one or more substituents selected from the Group A as defined above,
(c) $C_1$-$C_6$ alkoxy which is optionally substituted by the same or different one or more substituents selected from the Group A as defined above; $C_1$-$C_6$ alkyl optionally substituted by the same or different one or more substituents selected from the Group A as defined above; aralkyloxy optionally substituted by the same or different one or more substituents selected from the Group A as defined above and $C_1$-$C_6$ alkyl optionally substituted by the same or different one or more substituents selected from the Group A as defined above; —CO-aralkyloxy optionally substituted by the same or different one or more substituents selected from the Group A as defined above and $C_1$-$C_6$ alkyl optionally substituted by the same or different one or more substituents selected from the Group A as defined above; and saturated or unsaturated heterocycle containing at least one heteroatom selected from the group consisting of nitrogen atom, oxygen atom and sulfur atom, optionally substituted by the same or different one or more substituents selected from the Group A as defined above and $C_1$-$C_6$ alkyl optionally substituted by the same or different one or more substituents selected from the Group A as defined above,
(d) cycloalkyl which is optionally substituted by the same or different one or more substituents selected from the Group A as defined above and $C_1$-$C_6$ alkyl optionally substituted by the same or different one or more substituents selected from the Group A as defined above,
(e) cycloalkylalkoxy which is optionally substituted by the same or different one or more substituents selected from the Group A as defined above and $C_1$-$C_6$ alkyl optionally substituted by the same or different one or more substituents selected from the Group A as defined above,
(f) aralkyl which is optionally substituted by the same or different one or more substituents selected from the Group A as defined above and $C_1$-$C_6$ alkyl optionally substituted by the same or different one or more substituents selected from the Group A as defined above,
(g) aralkyloxy which is optionally substituted by the same or different one or more substituents selected from the Group A as defined above and $C_1$-$C_6$ alkyl optionally substituted by the same or different one or more substituents selected from the Group A as defined above,
(h) $C_3$-$C_{14}$ carbocycle which is optionally substituted by the same or different one or more substituents selected from the Group A as defined above and $C_1$-$C_6$ alkyl optionally substituted by the same or different one or more substituents selected from the Group A as defined above, or
(i) —$OR^{19}$ wherein $R^{19}$ is a $C_3$-$C_{14}$ saturated or unsaturated carbocycle optionally substituted by the same or different one or more substituents selected from the Group A as defined above and $C_1$-$C_6$ alkyl optionally substituted by the same or different one or more substituents selected from the Group A as defined above, or a saturated or unsaturated heterocycle containing at least one heteroatom selected from nitrogen atom, oxygen atom and sulfur atom, optionally substituted by the same or different one or more substituents selected from the Group A as defined above and $C_1$-$C_6$ alkyl optionally substituted by the same or different one or more substituents selected from the Group A as defined above,
9) —NR$^{14}$R$^{15}$ wherein R$^{14}$ and R$^{15}$ are each the same or different, and are
(a) hydrogen,
(b) C$_1$-C$_6$ alkyl which is optionally substituted by the same or different one or more substituents selected from the Group A as defined above, or
(c) nitrogen-containing saturated heterocycle comprising a monocycle formed when R$^{14}$, R$^{15}$ and the adjacent nitrogen atom are taken together,
10) —CONR$^{14}$R$^{15}$ wherein R$^{14}$ and R$^{15}$ have the same meanings as defined above,
11)-NR$^{16}$COR$^{13}$ wherein R$^{13}$ has the same meaning as defined above, and R$^{16}$ is
(a) hydrogen, or
(b) C$_1$-C$_6$ alkyl optionally substituted by the same or different one or more substituents selected from the Group A as defined above,
12) —NR$^{16}$CONR$^{14}$R$^{15}$ wherein R$^{14}$, R$^{15}$ and R$^{16}$ have the same meanings as defined above,
13) —SR$^{17}$ wherein R$^{17}$ is
(a) C$_1$-C$_6$ alkyl which is optionally substituted by the same or different one or more substituents selected from the Group A as defined above, or
(b) cycloalkyl which is optionally substituted by the same or different one or more substituents selected from the Group A as defined above,
14) —SOR$^{17}$ wherein R$^{17}$ has the same meaning as defined above,
15) —SO$_2$R$^{17}$ wherein R$^{17}$ has the same meaning as defined above,
16) —SO$_2$NR$^{14}$R$^{15}$ wherein R$^{14}$ and R$^{15}$ have the same meanings as defined above,
17) C$_3$-C$_{14}$ saturated or unsaturated carbocycle which is optionally substituted by the same or different one or more substituents selected from the Group A as defined above and C$_1$-C$_6$ alkyl optionally substituted by the same or different one or more substituents selected from the Group A as defined above,
18) saturated or unsaturated heterocycle containing at least one heteroatom selected from nitrogen atom, oxygen atom and sulfur atom, which is optionally substituted by the same or different one or more substituents selected from the Group A as defined above and C$_1$-C$_6$ alkyl optionally substituted by the same or different one or more substituents selected from the Group A and —CO-aralkyloxy (said —CO-aralkyloxy is optionally substituted by the same or different one or more substituents selected from the Group A as defined above and C$_1$-C$_6$ alkyl optionally substituted by the same or different one or more substituents selected from the Group A),
19) aryloxy which is optionally substituted by the same or different one or more substituents selected from the Group A as defined above and C$_1$-C$_6$ alkyl optionally substituted by the same or different one or more substituents selected from the Group A as defined above, and
20) nitrile;
R$^6$ and R$^7$ are each the same or different, and are 1) hydrogen, 2) C$_1$-C$_6$ alkyl or 3) nitrogen-containing saturated heterocycle comprising a monocycle formed when R$^6$, R$^7$ and the adjacent nitrogen atom are taken together (wherein C$_1$-C$_6$ alkyl in the above 2) is optionally substituted by the same or different one or more substituents selected from the Group A; and the nitrogen-containing saturated heterocycle in the above 3) comprising a monocycle may be substituted by the same or different one or more substituents selected from the Group A as defined above and C$_1$-C$_6$ alkyl);

ring A, ring B and ring C are each the same or different and are 1) C$_3$-C$_{14}$ saturated or unsaturated carbocycle or 2) saturated or unsaturated heterocycle containing at least one heteroatom selected from nitrogen atom, oxygen atom and sulfur atom;
—X— is 1) —(CH$_2$)$_l$— (wherein l is an integer of 1 to 4), 2) —(CH$_2$)$_m$—NR$^{18}$—(CH$_2$)$_n$— wherein R$^{18}$ is C$_1$-C$_6$ alkyl, and m and n are each the same or different, and are an integer of 0 to 2, or 3)

wherein m and n have the same meanings as defined above, said C$_1$-C$_6$ alkyl group in the above 2) being optionally substituted by the same or different one or more substituents selected from the Group A as defined above,
or a pharmaceutically acceptable salt thereof,
<2> the ester compound according to the above <1>, wherein the substitution position of —X— on the benzene ring of the formula [1] is h-position, or a pharmaceutically acceptable salt thereof,
<3> the ester compound according to the above <1>, which is represented by the formula [2]:

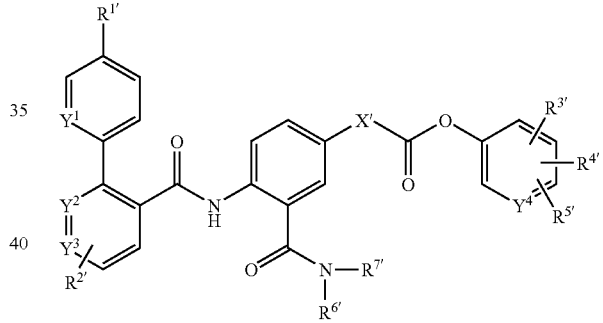

wherein
R$^{1'}$ is
1) C$_1$-C$_6$ alkyl which is optionally substituted by the same or different one or more halogens, or
2) —CO—C$_1$-C$_6$ alkoxy;
R$^{2'}$ is
1) hydrogen, or
2) C$_1$-C$_6$ alkyl,
R$^{3'}$, R$^{4'}$ and R$^{5'}$ are each the same or different, and are
1) hydrogen,
2) halogen,
3) C$_1$-C$_6$ alkyl which is optionally substituted by the same or different one or more halogens,
4) C$_1$-C$_6$ alkoxy,
5) —COR$^{13'}$ wherein R$^{13'}$ is
(a) hydroxy,
(b) C$_1$-C$_6$ alkyl,
(c) C$_1$-C$_6$ alkoxy which is optionally substituted by the same or different one or more substituents selected from (1) hydroxy, (2) C$_1$-C$_6$ alkoxy which is optionally substituted by phenyl, (3) —NR$^{11'}$CO—C$_1$-C$_6$ alkyl wherein R$^{11'}$ is hydrogen or C$_1$-C$_6$ alkyl, (4) —CONR$^{8'}$R$^{9'}$ wherein R$^{8'}$ and R$^{9'}$ are each the same or different, and are hydrogen or C$_1$-C$_6$ alkyl, or a nitrogen-containing saturated heterocycle comprising a monocycle formed when $R^{8'}$, $R^{9'}$ and the adjacent nitrogen atom are taken together, (5) —CO—$C_1$-$C_6$ alkoxy optionally substituted by phenyl, (6) phenyl optionally substituted by the same or different one or more substituents selected from halogen, $C_1$-$C_6$ alkoxy and —CO—$C_1$-$C_6$ alkoxy, and (7) heterocycle selected from pyridyl, tetrazolyl and thienyl, all of which may be substituted by the same or different one or more $C_1$-$C_6$ alkyl groups, or (d) —$OR^{19'}$ wherein $R^{19'}$ is a $C_3$-$C_{14}$ saturated or unsaturated carbocycle or piperidyl which is optionally substituted by —CO—$C_1$-$C_6$ alkyl, 6) heterocycle selected from oxadiazolyl and tetrazolyl, said heterocycle being optionally substituted by $C_1$-$C_6$ alkyl optionally substituted by the same or different one or more substituents selected from —$CONR^{8'}R^{9'}$ ($R^{8'}$ and $R^{9'}$ have the same meanings as defined above) and —CO-aralkyloxy, or 7) nitrile;

$R^{6'}$ and $R^{7'}$ are each the same or different, and are
1) hydrogen,
2) $C_1$-$C_6$ alkyl, or
3) nitrogen-containing heterocycle comprising a monocycle formed when $R^{6'}$, $R^{7'}$ and the adjacent nitrogen atom are taken together;

$Y^1$, $Y^2$, $Y^3$ and $Y^4$ are each the same or different, and are
1) carbon atom, or
2) nitrogen atom;

—X'— is
1) —$(CH_2)_l$— wherein l is an integer of 1 to 3,
2) —$CH_2$—$NR^{18'}$—$CH_2$— wherein $R^{18'}$ is $C_1$-$C_6$ alkyl, or
3)

or a pharmaceutically acceptable salt thereof,

<4> the ester compound according to the above <1>, which is represented by the formula:

[3]

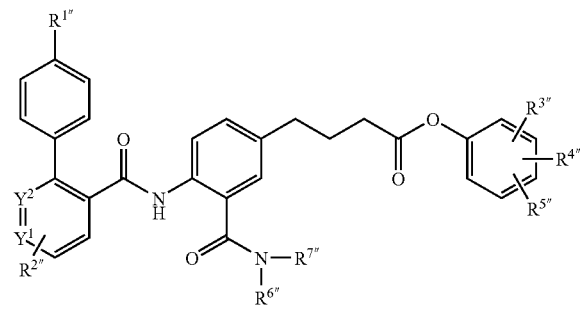

wherein
$R^{1''}$ is
1) $C_1$-$C_6$ alkyl which is optionally substituted by the same or different one or more halogens, or
2) —CO—$C_1$-$C_6$ alkoxy;

$R^{2''}$ is
1) hydrogen, or
2) $C_1$-$C_6$ alkyl;

$R^{3''}$, $R^{4''}$ and $R^{5''}$ are each the same or different, and are 1) hydrogen,
2) halogen,
3) $C_1$-$C_6$ alkyl which is optionally substituted by the same or different one or more halogens,
4) $C_1$-$C_6$ alkoxy, or
5) —$COR^{13''}$ wherein $R^{13''}$ is $C_1$-$C_6$ alkoxy optionally substituted by the same or different one or more substituents selected from (1) phenyl, (2) —CO—$NR^{8''}R^{9''}$ wherein $R^{8''}$ and $R^{9''}$ are each the same or different, and are hydrogen or $C_1$-$C_6$ alkyl, or (3) heterocycle selected from pyridyl, tetrazolyl and thienyl, said heterocycle being optionally substituted by the same or different one or more $C_1$-$C_6$ alkyl groups;

$R^{6''}$ and $R^{7''}$ are each the same or different, and are
1) hydrogen,
2) $C_1$-$C_6$ alkyl, or
3) nitrogen-containing saturated heterocycle comprising a monocycle formed when $R^{6''}$, $R^{7''}$ and the adjacent nitrogen atom are taken together; and $Y^2$ and $Y^3$ are each the same or different, and are
1) carbon atom, or
2) nitrogen atom, or a pharmaceutically acceptable salt thereof, <5> the ester compound according to the above <1>, which is selected from the group consisting of:

(1) {3-dimethylcarbamoyl-4-[(4'-trifluoromethylbiphenyl-2-carbonyl)amino]phenyl}acetic acid phenyl ester (hereinafter also referred to as Compound 1-3), (2) {3-dimethylcarbamoyl-4-[(4'-trifluoromethylbiphenyl-2-carbonyl)amino]phenyl}acetic acid 4-fluorophenyl ester hereinafter also referred to as Compound 1-4), (3) 3-{3-dimethylcarbamoyl-4-[(4'-trifluoromethylbiphenyl-2-carbonyl)amino]phenyl}propionic acid phenyl ester (hereinafter also referred to as Compound 1-1), (4) 4-(4-{(3-dimethylcarbamoyl-4-[(4'-trifluoromethylbiphenyl-2-carbonyl)amino]phenyl}butyryloxy)benzoic acid methyl ester (hereinafter also referred to as Compound 1-5), (5) 4-(4-{3-dimethylcarbamoyl-4-[(4'-trifluoromethylbiphenyl-2-carbonyl)amino]phenyl}butyryloxy)benzoic acid ethyl ester (hereinafter also referred to as Compound 1-6), (6) 4-(4-{3-dimethylcarbamoyl-4-[(4'-trifluoromethylbiphenyl-2-carbonyl)amino]phenyl}butyryloxy)benzoic acid isopropyl ester (hereinafter also referred to as Compound 1-7), (7) 4-(4-{3-dimethylcarbamoyl-4-[(4'-trifluoromethylbiphenyl-2-carbonyl)amino]phenyl}butyryloxy) benzoic acid propyl ester (hereinafter also referred to as Compound 1-8), (8) 4-(4-{3-dimethylcarbamoyl-4-[(5-methyl-4'-trifluoromethylbiphenyl-2-carbonyl)amino]phenyl}butyryloxy) benzoic acid methyl ester (hereinafter also referred to as Compound 1-9), (9) 4-(4-{3-dimethylcarbamoyl-4-[(4'-trifluoromethylbiphenyl-2-carbonyl)amino]phenyl}butyryloxy)-3-fluoro benzoic acid methyl ester (hereinafter also referred to as Compound 1-10),

(10) 3-chloro-4-(4-{3-dimethylcarbamoyl-4-[(4'-trifluoromethylbiphenyl-2-carbonyl)amino]phenyl}butyryloxy)benzoic acid methyl ester (hereinafter also referred to as Compound 1-11),

(11) 4-(4-{3-dimethylcarbamoyl-4-[(4'-trifluoromethylbiphenyl-2-carbonyl)amino]phenyl}butyryloxy)-3-methoxybenzoic acid methyl ester (hereinafter also referred to as Compound 1-12),

(12) 4-[4-(3-dimethylcarbamoyl-4-{[6-methyl-2-(4-trifluoromethylphenyl)pyridine-3-carbonyl]amino}phenyl)butyryloxy)benzoic acid methyl ester (hereinafter also referred to as Compound 1-13),

(13) 4-(4-{3-dimethylcarbamoyl-4-[(4'-trifluoromethylbiphenyl-2-carbonyl)amino]phenyl}butyryloxy)-2-methyl benzoic acid methyl ester (hereinafter also referred to as Compound 1-14),
(14) 4-(4-{3-(pyrrolidine-1-carbonyl)-4-[(4'-trifluoromethylbiphenyl-2-carbonyl)amino]phenyl}butyryloxy)benzoic acid methyl ester (hereinafter also referred to as Compound 1-15),
(15) 3-fluoro-4-(4-{3-(pyrrolidine-1-carbonyl)-4-[(4'-trifluoromethylbiphenyl-2-carbonyl)amino] phenyl}butyryloxy)benzoic acid ethyl ester (hereinafter also referred to as Compound 1-16),
(16) 1-{3-dimethylcarbamoyl-4-[(4'-trifluoromethylbiphenyl-2-carbonyl)amino]phenyl}piperidine-4-carboxylic acid 4-methoxycarbonylphenyl ester (hereinafter also referred to as Compound 3-1),
(17) 1-{3-dimethylcarbamoyl-4-[(4'-trifluoromethylbiphenyl-2-carbonyl)amino]phenyl}piperidine-4-carboxylic acid 2-fluoro-4-methoxycarbonylphenyl ester (hereinafter also referred to as Compound 3-2),
(18) 4-(4-{3-dimethylcarbamoyl-4-[(4'-trifluoromethylbiphenyl-2-carbonyl)amino]phenyl}butyryloxy)-2-methoxybenzoic acid methyl ester (hereinafter also referred to as Compound 1-17),
(19) 4-[2-({3-dimethylcarbamoyl-4-[(4'-trifluoromethylbiphenyl-2-carbonyl)amino]benzyl}methylamino)acetoxy]benzoic acid methyl ester (hereinafter also referred to as Compound 2-1),
(20) 2-chloro-4-(4-{3-dimethylcarbamoyl-4-[(4'-trifluoromethylbiphenyl-2-carbonyl)amino]phenyl}butyryloxy)benzoic acid methyl ester (hereinafter also referred to as Compound 1-18),
(21) 4-(4-{3-dimethylcarbamoyl-4-[2-(5-trifluoromethylpyridin-2-yl)benzoylamino]phenyl}butyryloxy)benzoic acid methyl ester (hereinafter also referred to as Compound 1-19),
(22) 4-(4-{3-dimethylcarbamoyl-4-[(4'-trifluoromethylbiphenyl-2-carbonyl)amino]phenyl}butyryloxy)-3-trifluoromethylbenzoic acid methyl ester (hereinafter also referred to as Compound 1-20),
(23) 4-[4-{3-dimethylcarbamoyl-4-[(4'-trifluoromethylbiphenyl-2-carbonyl)amino]phenyl}butyryloxy)-2-trifluoromethylbenzoic acid methyl ester (hereinafter also referred to as Compound 1-21),
(24) 4-{3-dimethylcarbamoyl-4-[(4'-trifluoromethylbiphenyl-2-carbonyl)amino]phenyl}butyric acid 4-(3-methyl-[1,2,4]oxadiazol-5-yl)phenyl ester (hereinafter also referred to as Compound 1-2),
(25) 4-{3-dimethylcarbamoyl-4-[(4'-trifluoromethylbiphenyl-2-carbonyl)amino]phenyl}butyric acid 4-acetylphenyl ester (hereinafter also referred to as Compound 1-22),
(26) 4-{3-dimethylcarbamoyl-4-[(4'-trifluoromethylbiphenyl-2-carbonyl)amino]phenyl}butyric acid 4-cyanophenyl ester (hereinafter also referred to as Compound 1-23),
(27) 4-(4-{3-dimethylcarbamoyl-4-[(4'-trifluoromethylbiphenyl-2-carbonyl)amino]phenyl}butyryloxy)benzoic acid benzyl ester (hereinafter also referred to as Compound 1-24),
(28) 4-(4-{3-dimethylcarbamoyl-4-[(4'-trifluoromethylbiphenyl-2-carbonyl)amino]phenyl}butyryloxy) benzoic acid (hereinafter also referred to as Compound 1-25),
(29) 4-(4-{3-(morpholine-4-carbonyl)-4-[(4'-trifluoromethylbiphenyl-2-carbonyl)amino]phenyl}butyryloxy)benzoic acid methyl ester (hereinafter also referred to as Compound 1-26),
(30) 4-(3-{3-dimethylcarbamoyl-4-[(4'-trifluoromethylbiphenyl-2-carbonyl)amino]phenyl}propionyloxy)benzoic acid methyl ester (hereinafter also referred to as Compound 1-27),
(31) 4-[4-(3-dimethylcarbamoyl-4-{[3-(4-trifluoromethylphenyl)pyridine-4-carbonyl]amino}phenyl)butyryloxy]benzoic acid methyl ester (hereinafter also referred to as Compound 1-30),
(32) 4-[4-(3-dimethylcarbamoyl-4-{[3-(4-trifluoromethylphenyl)pyridine-4-carbonyl]amino}phenyl)butyryloxy]benzoic acid isopropyl ester (hereinafter also referred to as Compound 1-29),
(33) 4-[4-(3-dimethylcarbamoyl-4-{[2-(4-trifluoromethylphenyl)pyridine-3-carbonyl]amino}phenyl)butyryloxy]benzoic acid methyl ester (hereinafter also referred to as Compound 1-28),
(34) 4-[4-(3-dimethylcarbamoyl-4-{[2-(4-trifluoromethylphenyl)pyridine-3-carbonyl]amino}phenyl)butyryloxy]benzoic acid isopropyl ester (hereinafter also referred to as Compound 1-31),
(35) 5-[4-(3-dimethylcarbamoyl-4-{[6-methyl-2-(4-trifluoromethylphenyl)pyridine-3-carbonyl]amino}phenyl)butyryloxy]pyridine-2-carboxylic acid methyl ester (hereinafter also referred to as Compound 1-32),
(36) 4-(4-{3-dimethylcarbamoyl-4-[(4'-trifluoromethylbiphenyl-2-carbonyl)amino]phenyl}butyryloxy)isophthalic acid dimethyl ester (hereinafter also referred to as Compound 1-33),
(37) 3-chloro-4-(4-{3-dimethylcarbamoyl-4-[(4'-trifluoromethylbiphenyl-2-carbonyl)amino]phenyl}butyryloxy)-5-methylbenzoic acid methyl ester (hereinafter also referred to as Compound 1-34),
(38) 3-chloro-4-[4-(3-dimethylcarbamoyl-4-{[6-methyl-2-(4-trifluoromethylphenyl)pyridine-3-carbonyl]amino}phenyl)butyryloxy]-5-methylbenzoic acid methyl ester (hereinafter also referred to as Compound 1-35),
(39) 3-chloro-4-[4-(3-dimethylcarbamoyl-4-{[6-methyl-2-(4-trifluoromethylphenyl)pyridine-3-carbonyl]amino}phenyl)butyryloxy]-5-methoxybenzoic acid methyl ester (hereinafter also referred to as Compound 1-36),
(40) 3-chloro-4-[4-(3-dimethylcarbamoyl-4-{[6-methyl-2-(4-trifluoromethylphenyl)pyridine-3-carbonyl]amino}phenyl)butyryloxy]-5-methoxybenzoic acid isopropyl ester (hereinafter also referred to as Compound 1-37),
(41) 4-[4-(3-dimethylcarbamoyl-4-{[6-methyl-2-(4-trifluoromethylphenyl)pyridine-3-carbonyl]amino}phenyl)butyryloxy]-3-fluoro-5-methoxybenzoic acid isopropyl ester (hereinafter also referred to as Compound 1-38),
(42) 4-[4-(3-dimethylcarbamoyl-4-{[6-methyl-2-(4-trifluoromethylphenyl)pyridine-3-carbonyl]amino}phenyl)butyryloxy]-3,5-dimethoxybenzoic acid methyl ester (hereinafter also referred to as Compound 1-39),
(43) 3-chloro-4-[4-(3-dimethylcarbamoyl-4-{[6-methyl-2-(4-trifluoromethylphenyl)pyridine-3-carbonyl]amino}phenyl)butyryloxy]-5-ethoxybenzoic acid methyl ester (hereinafter also referred to as Compound 1-40),
(44) 4-[4-(3-dimethylcarbamoyl-4-{[6-methyl-2-(4-trifluoromethylphenyl)pyridine-3-carbonyl]amino}phenyl)butyryloxy]-3-fluoro-5-methylbenzoic acid methyl ester (hereinafter also referred to as Compound 1-41),
(45) 4-[4-(3-dimethylcarbamoyl-4-{[6-methyl-2-(4-trifluoromethylphenyl)pyridine-3-carbonyl]amino}phenyl)butyryloxy]-3-ethyl-5-fluorobenzoic acid methyl ester (hereinafter also referred to as Compound 1-42),

(46) 4-[4-(3-dimethylcarbamoyl-4-{[6-methyl-2-(4-trifluoromethylphenyl)pyridine-3-carbonyl]amino}phenyl)butyryloxy]-3,5-dimethoxybenzoic acid ethyl ester (hereinafter also referred to as Compound 1-43),

(47) 4-[4-(3-dimethylcarbamoyl-4-{[6-methyl-2-(4-trifluoromethylphenyl)pyridine-3-carbonyl]amino}phenyl) butyryloxy]-3,5-dimethoxybenzoic acid isopropyl ester (hereinafter also referred to as Compound 1-44),

(48) 4-[4-(3-dimethylcarbamoyl-4-{[6-methyl-2-(4-trifluoromethylphenyl)pyridine-3-carbonyl]amino}phenyl)butyryloxy]-3-methyl-5-trifluoromethylbenzoic acid methyl ester (hereinafter also referred to as Compound 1-45),

(49) 4-[4-(3-dimethylcarbamoyl-4-{[2-(4-methoxycarbonylphenyl)-6-methylpyridine-3-carbonyl]amino}phenyl) butyryloxy]-5-methylisophthalic acid dimethyl ester (hereinafter also referred to as Compound 4-2),

(50) 4-[4-(3-dimethylcarbamoyl-4-{[6-methyl-2-(4-trifluoromethylphenyl)pyridine-3-carbonyl]amino}phenyl)butyryloxy]-3-methoxy-5-methylbenzoic acid methyl ester (hereinafter also referred to as Compound 1-46),

(51) 4-[4-(3-dimethylcarbamoyl-4-{[6-methyl-2-(4-trifluoromethylphenyl)pyridine-3-carbonyl]amino}phenyl)butyryloxy]-3-methoxy-5-trifluoromethylbenzoic acid methyl ester (hereinafter also referred to as Compound 1-47),

(52) 3-chloro-4-[4-(3-dimethylcarbamoyl-4-{[6-methyl-2-(4-trifluoromethylphenyl)pyridine-3-carbonyl]amino}phenyl)butyryloxy]-5-methoxybenzoic acid ethyl ester (hereinafter also referred to as Compound 1-48),

(53) 4-[4-(3-dimethylcarbamoyl-4-{[6-methyl-2-(4-trifluoromethylphenyl)pyridine-3-carbonyl]amino}phenyl)butyryloxy]-3-ethoxy-5-methoxybenzoic acid methyl ester (hereinafter also referred to as Compound 1-49),

(54) 3-bromo-4-[4-(3-dimethylcarbamoyl-4-{[6-methyl-2-(4-trifluoromethylphenyl)pyridine-3-carbonyl]amino}phenyl)butyryloxy]-5-methoxybenzoic acid methyl ester (hereinafter also referred to as Compound 1-50),

(55) 4-[4-(3-dimethylcarbamoyl-4-{[6-methyl-2-(4-trifluoromethylphenyl)pyridine-3-carbonyl]amino}phenyl)butyryloxy]-5-ethylisophthalic acid dimethyl ester (hereinafter also referred to as Compound 1-51)

(56) 4-[4-(3-dimethylcarbamoyl-4-{[6-methyl-2-(4-trifluoromethylphenyl)pyridine-3-carbonyl]amino}phenyl)butyryloxy]-5-methylisophthalic acid 1-ethyl ester 3-methyl ester (hereinafter also referred to as Compound 1-52),

(57) 4-[4-(3-dimethylcarbamoyl-4-{[6-methyl-2-(4-trifluoromethylphenyl)pyridine-3-carbonyl]amino}phenyl)butyryloxy]-5-methoxyisophthalic acid dimethyl ester (hereinafter also referred to as Compound 1-53),

(58) 4-[4-(3-dimethylcarbamoyl-4-{[6-methyl-2-(4-trifluoromethylphenyl)pyridine-3-carbonyl]amino}phenyl)butyryloxy]-5-methoxyisophthalic acid 1-ethyl ester 3-methyl ester (hereinafter also referred to as Compound 1-54),

(59) 2'-{2-dimethylcarbamoyl-4-[3-(4-methoxycarbonylphenoxycarbonyl)propyl]phenyl-carbamoyl}biphenyl-4-carboxylic acid methyl ester (hereinafter also referred to as Compound 4-3),

(60) 3-chloro-4-[4-(3-dimethylcarbamoyl-4-{[2-(4-methoxycarbonylphenyl)-6-methylpyridine-3-carbonyl] amino}phenyl)butyryloxy]-5-methylbenzoic acid methyl ester (hereinafter also referred to as Compound 4-1),

(61) 3-chloro-4-[4-(3-dimethylcarbamoyl-4-{[2-(4-methoxycarbonylphenyl)-6-methylpyridine-3-carbonyl] amino}phenyl)butyryloxy]-5-methoxybenzoic acid methyl ester (hereinafter also referred to as Compound 4-4),

(62) 3-chloro-4-[4-(3-dimethylcarbamoyl-4-{[6-methyl-2-(4-trifluoromethylphenyl)pyridine-3-carbonyl] amino}phenyl)butyryloxy]-5-methylbenzoic acid methyl ester sulfonate (hereinafter also referred to as Compound 1-55),

(63) 3-chloro-4-[4-(3-dimethylcarbamoyl-4-{[6-methyl-2-(4-trifluoromethylphenyl)pyridine-3-carbonyl] amino}phenyl)butyryloxy]-5-methoxybenzoic acid methyl ester sulfonate (hereinafter also referred to as Compound 1-56),

(64) 4-[4-(3-dimethylcarbamoyl-4-{[6-methyl-2-(4-trifluoromethylphenyl)pyridine-3-carbonyl]amino}phenyl)butyryloxy]-3,5-dimethoxybenzoic acid methyl ester sulfonate (hereinafter also referred to as Compound 1-57),

(65) 3-chloro-4-[4-(3-dimethylcarbamoyl-4-{[6-methyl-2-(4-trifluoromethylphenyl)pyridine-3-carbonyl] amino}phenyl)butyryloxy]-5-methylbenzoic acid methyl ester benzenesulfonate (hereinafter also referred to as Compound 1-58),

(66) 3-chloro-4-[4-(3-dimethylcarbamoyl-4-{[6-methyl-2-(4-trifluoremethylphenyl)pyridine-3-carbonyl] amino}phenyl)butyryloxy]-5-methylbenzoic acid methyl ester methanesulfonate (hereinafter also referred to as Compound 1-59),

(67) 3-chloro-4-[4-(3-dimethylcarbamoyl-4-{[6-methyl-2-(4-trifluoromethylphenyl)pyridine-3-carbonyl] amino}phenyl)butyryloxy]-5-methylbenzoic acid methyl ester toluene-4-sulfonate (hereinafter also referred to as Compound 1-60),

(68) 3-chloro-4-[4-(3-dimethylcarbamoyl-4-{[6-methyl-2-(4-trifluoromethylphenyl)pyridine-3-carbonyl] amino}phenyl)butyryloxy]-5-methylbenzoic acid methyl ester naphthalene-1,5-disulfonate (hereinafter also referred to as Compound 1-61),

(69) 3-chloro-4-[4-(3-dimethylcarbamoyl-4-{[6-methyl-2-(4-trifluoromethylphenyl)pyridine-3-carbonyl] amino}phenyl)butyryloxy]-5-methylbenzoic acid methyl ester hydrochloride (hereinafter also referred to as Compound 1-62),

(70) 4-[4-(3-dimethylcarbamoyl-4-{[6-methyl-2-(4-trifluoromethylphenyl)pyridine-3-carbonyl]amino}phenyl)butyryloxy]benzoic acid isopropyl ester sulfate (hereinafter also referred to as Compound 1-63),

(71) 4-[4-(3-dimethylcarbamoyl-4-{(4'-trifluoromethylbiphenyl-2-carbonyl)amino}phenyl)butyryloxy]-3,5-dimethylbenzoic acid methyl ester (hereinafter also referred to as Compound 1-64),

(72) 4-[4-(3-dimethylcarbamoyl-4-{[6-methyl-2-(4-trifluoromethylphenyl)pyridine-3-carbonyl]amino}phenyl)butyryloxy]-3,5-dimethylbenzoic acid methyl ester (hereinafter also referred to as Compound 1-65),

(73) 4-[4-(3-dimethylcarbamoyl-4-{(4'-trifluoromethylbiphenyl-2-carbonyl)amino}phenyl)butyryloxy]-3-methylbenzoic acid methyl ester (hereinafter also referred to as Compound 1-66),

(74) 4-[4-(3-dimethylcarbamoyl-4-{(4'-trifluoromethylbiphenyl-2-carbonyl) amino}phenyl) butyryloxy]-3-ethylbenzoic acid methyl ester (hereinafter also referred to as Compound 1-67),

(75) 4-[4-(3-dimethylcarbamoyl-4-{(4'-trifluoromethylbiphenyl-2-carbonyl)amino}phenyl)butyryloxy]-3-isopropylbenzoic acid methyl ester (hereinafter also referred to as Compound 1-68),

(76) 4-[4-(3-dimethylcarbamoyl-4-{[6-methyl-2-(4-trifluoromethylphenyl)pyridine-3-carbonyl]amino}phenyl)butyryloxy]-3-methylbenzoic acid methyl ester (hereinafter also referred to as Compound 1-69),

(77) 4-[4-(3-dimethylcarbamoyl-4-{[6-methyl-2-(4-trifluoromethylphenyl)pyridine-3-carbonyl]amino}phenyl)butyryloxy]isophthalic acid dimethyl ester (hereinafter also referred to as Compound 1-70),

(78) 4-[4-(3-dimethylcarbamoyl-4-{[6-methyl-2-(4-trifluoromethylphenyl)pyridine-3-carbonyl]amino}phenyl)butyryloxy]benzoic acid ethyl ester (hereinafter also referred to as Compound 1-71),

(79) 4-[4-(3-dimethylcarbamoyl-4-{[6-methyl-2-(4-trifluoromethylphenyl)pyridine-3-carbonyl]amino}phenyl)butyryloxy]isophthalic acid 1-isopropyl ester 3-methyl ester (hereinafter also referred to as Compound 1-72),

(80) 3-chloro-4-[4-(3-dimethylcarbamoyl-4-{[6-methyl-2-(4-trifluoromethylphenyl)pyridine-3-carbonyl]amino}phenyl)butyryloxy]-5-ethylbenzoic acid methyl ester (hereinafter also referred to as Compound 1-73),

(81) 3-chloro-4-[4-(3-dimethylcarbamoyl-4-{[6-methyl-2-(4-trifluoromethylphenyl)pyridine-3-carbonyl]amino}phenyl)butyryloxy]-5-isopropylbenzoic acid methyl ester (hereinafter also referred to as Compound 1-74),

(82) 3-chloro-4-[4-(3-dimethylcarbamoyl-4-{[6-methyl-2-(4-trifluoromethylphenyl)pyridine-3-carbonyl]amino}phenyl)butyryloxy]-5-methoxybenzoic acid propyl ester (hereinafter also referred to as Compound 1-75),

(83) 4-[4-(3-dimethylcarbamoyl-4-{(4'-trifluoromethylbiphenyl-2-carbonyl)amino}phenyl)butyryloxy]benzoic acid 2-isopropoxyethyl ester (hereinafter also referred to as Compound 1-76),

(84) 4-[4-(3-dimethylcarbamoyl-4-{(4'-trifluoromethylbiphenyl-2-carbonyl)amino}phenyl)butyryloxy]benzoic acid 2-acetylaminoethyl ester (hereinafter also referred to as Compound 1-77),

(85) 4-[(4-(3-dimethylcarbamoyl-4-{(4'-trifluoromethylbiphenyl-2-carbonyl)amino}phenyl)butyryloxy]benzoic acid benzyloxycarbonylmethyl ester (hereinafter also referred to as Compound 1-78),

(86) 4-[4-(3-dimethylcarbamoyl-4-{(4'-trifluoromethylbiphenyl-2-carbonyl)amino}phenyl)butyryloxy]benzoic acid 4-chlorobenzyl ester (hereinafter also referred to as Compound 1-79),

(87) 4-[4-(3-dimethylcarbamoyl-4-{[6-methyl-2-(4-trifluoromethylphenyl)pyridine-3-carbonyl]amino}phenyl)butyryloxy]benzoic acid benzyl ester (hereinafter also referred to as Compound 1-80),

(88) 4-[4-(3-dimethylcarbamoyl-4-{[6-methyl-2-(4-trifluoromethylphenyl)pyridine-3-carbonyl]amino}phenyl)butyryloxy]benzoic acid isopropyl ester (hereinafter also referred to as Compound 1-81),

(89) 4-[4-(3-dimethylcarbamoyl-4-{(4'-trifluoromethylbiphenyl-2-carbonyl)amino}phenyl)butyryloxy]benzoic acid pyridin-2-ylmethyl ester (hereinafter also referred to as Compound 1-82),

(90) 4-[4-(3-dimethylcarbamoyl-4-{(4'-trifluoromethylbiphenyl-2-carbonyl)amino}phenyl)butyryloxy]benzoic acid pyridin-3-ylmethyl ester (hereinafter also referred to as Compound 1-83),

(91) 4-[4-(3-dimethylcarbamoyl-4-{(4'-trifluoromethylbiphenyl-2-carbonyl)amino}phenyl)butyryloxy]benzoic acid pyridin-4-ylmethyl ester (hereinafter also referred to as Compound 1-84),

(92) 4-[4-(3-dimethylcarbamoyl-4-{(4'-trifluoromethylbiphenyl-2-carbonyl)amino}phenyl)butyryloxy]benzoic acid dimethylcarbamoylmethyl ester (hereinafter also referred to as Compound 1-85),

(93) 4-[4-(3-dimethylcarbamoyl-4-{(4'-trifluoromethylbiphenyl-2-carbonyl)amino}phenyl)butyryloxy]benzoic acid methoxycarbonylmethyl ester (hereinafter also referred to as Compound 1-86),

(94) 4-[4-(3-dimethylcarbamoyl-4-{(4'-trifluoromethylbiphenyl-2-carbonyl) amino}phenyl) butyryloxy]benzoic acid 3-chlorobenzyl ester (hereinafter also referred to as Compound 1-87),

(95) 4-(3-dimethylcarbamoyl-4-{(4'-trifluoromethylbiphenyl-2-carbonyl)amino}phenyl)butyric acid 4-propionylphenyl ester (hereinafter also referred to as Compound 1-88),

(96) 4-[4-(3-dimethylcarbamoyl-4-{(4'-trifluoromethylbiphenyl-2-carbonyl)amino}phenyl)butyryloxy]benzoic acid 2-benzyloxyethyl ester (hereinafter also referred to as Compound 1-89),

(97) 4-[4-(3-dimethylcarbamoyl-4-{(4'-trifluoromethylbiphenyl-2-carbonyl)amino}phenyl)butyryloxy]benzoic acid 3-benzyloxypropyl ester (hereinafter also referred to as Compound 1-90),

(98) 4-[4-(3-dimethylcarbamoyl-4-{(4'-trifluoromethylbiphenyl-2-carbonyl)amino}phenyl)butyryloxy]benzoic acid 2-(2-oxopyrrolidin-1-yl)ethyl ester (hereinafter also referred to as Compound 1-91),

(99) 4-[4-(3-dimethylcarbamoyl-4-{(4'-trifluoromethylbiphenyl-2-carbonyl)amino}phenyl)butyryloxy]benzoic acid 3-hydroxypropyl ester (hereinafter also referred to as Compound 1-92), (100) 4-(3-dimethylcarbamoyl-4-{(4'-trifluoromethylbiphenyl-2-carbonyl)amino}phenyl)butyric acid 4-butyrylphenyl ester (hereinafter also referred to as Compound 1-93), (101) 4-[4-(3-dimethylcarbamoyl-4-{[6-methyl-2-(4-trifluoromethylphenyl)pyridine-3-carbonyl]amino}phenyl)butyryloxy]benzoic acid pyridin-3-ylmethyl ester (hereinafter also referred to as Compound 1-94), (102) 4-(3-dimethylcarbamoyl-4-{(4'-trifluoromethylbiphenyl-2-carbonyl)amino}phenyl)butyric acid 4-(2-methyl-2H-tetrazol-5-yl)phenyl ester (hereinafter also referred to as Compound 1-95), (103) 4-[4-(3-dimethylcarbamoyl-4-{(4'-trifluoromethylbiphenyl-2-carbonyl)amino}phenyl)butyryloxy]benzoic acid 4-methoxybenzyl ester (hereinafter also referred to as Compound 1-96), (104) 4-[4-(3-dimethylcarbamoyl-4-{(4'-trifluoromethylbiphenyl-2-carbonyl)amino}phenyl)butyryloxy]benzoic acid 3-methoxybenzyl ester (hereinafter also referred to as Compound 1-97), (105) 4-[4-(3-dimethylcarbamoyl-4-{(4'-trifluoromethylbiphenyl-2-carbonyl)amino}phenyl)butyryloxy]benzoic acid thiophen-2-ylmethyl ester (hereinafter also referred to as Compound 1-98), (106) 4-[4-(3-dimethylcarbamoyl-4-{(4'-trifluoromethylbiphenyl-2-carbonyl)amino}phenyl)butyryloxy]benzoic acid thiophen-3-ylmethyl ester (hereinafter also referred to as Compound 1-99), (107) 4-[4-(3-dimethylcarbamoyl-4-{[6-methyl-2-(4-trifluoromethylphenyl)pyridine-3-carbonyl]amino}phenyl)butyryloxy]benzoic acid 6-methylpyridin-2-ylmethyl ester (hereinafter also referred to as Compound 1-100), (108) 4-[4-(3-dimethylcarbamoyl-4-{(4'-trifluoromethylbiphenyl-2-carbonyl)amino}phenyl)butyryloxy]benzoic acid 6-methylpyridin-2-ylmethyl ester (hereinafter also referred to as Compound 1-101), (109) 4-[(4-(3-dimethylcarbamoyl-4-{(4'-trifluoromethylbiphenyl-2-carbonyl)amino}phenyl)butyryloxy]benzoic acid isopropoxycarbonylmethyl ester (hereinafter also referred to as Compound 1-102), (110) 4-[4-(3-dimethylcarbamoyl-4-{(4'-trifluoromethylbiphenyl-2-carbonyl)amino}phenyl)butyryloxy]benzoic acid 4-(t-butoxycarbonyl)benzyl ester (hereinafter also referred to as Compound 1-103), (111) 4-(3-dimethylcarbamoyl-4-{(4'-trifluoromethylbiphenyl-2-carbonyl)amino}phenyl)butyric acid 4-(2-benzyloxycarbonylmethyl-2H-tetrazol-5-yl)phenyl ester (hereinafter also referred to as Compound 1-104), (112) 4-(3-dimethylcarbamoyl-4-{(4'-trifluoromethylbiphenyl-2-carbonyl)amino}phenyl)butyric acid 4-(2-dimethylcarbamoylmethyl-2H-tetrazol-5-yl)phenyl ester (hereinafter also referred to as Compound 1-105), (113) 4-[4-(3-dimethylcarbamoyl-4-{(4'-trifluoromethylbiphenyl-2-carbonyl)amino}phenyl)butyryloxy]benzoic acid 1-phenylethyl ester (hereinafter also referred to as Compound 1-106), (114) 4-[4-(3-dimethylcarbamoyl-4-{(4'-trifluoromethylbiphenyl-2-carbonyl)amino}phenyl)butyryloxy]benzoic acid indan-1-yl ester (hereinafter also referred to as Compound 1-107), (115) 4-[4-(3-dimethylcarbamoyl-4-{(4'-trifluoromethylbiphenyl-2-carbonyl)amino}phenyl)butyryloxy]benzoic acid 1,2,3,4-tetrahydronaphthalen-1-yl ester (hereinafter also referred to as Compound 1-108), (116) 4-[4-(3-dimethylcarbamoyl-4-{(4'-trifluoromethylbiphenyl-2-carbonyl)amino}phenyl)butyryloxy]benzoic acid 1-acetylpiperidin-4-yl ester (hereinafter also referred to as Compound 1-109), (117) 4-[4-(3-dimethylcarbamoyl-4-{[6-methyl-2-(4-trifluoromethylphenyl)pyridine-3-carbonyl]amino}phenyl)butyryloxy]-5-methylisophthalic acid dimethyl ester (hereinafter also referred to as Compound 1-110), (118) 4-[4-(3-dimethylcarbamoyl-4-{[6-methyl-2-(4-trifluoromethylphenyl)pyridine-3-carbonyl]amino}phenyl)butyryloxy]-5-methylisophthalic acid 1-isopropyl ester 3-methyl ester (hereinafter also referred to as Compound 1-111), (119) 3-chloro-4-[4-(3-dimethylcarbamoyl-4-{[6-methyl-2-(4-trifluoromethylphenyl)pyridine-3-carbonyl]amino}phenyl)butyryloxy]-5-methylbenzoic acid ethyl ester (hereinafter also referred to as Compound 1-112), (120) 3-chloro-4-[4-(3-dimethylcarbamoyl-4-{[6-methyl-2-(4-trifluoromethylphenyl)pyridine-3-carbonyl]amino}phenyl)butyryloxy]-5-methoxybenzoic acid dimethylcarbamoylmethyl ester (hereinafter also referred to as Compound 1-113), (121) 3-chloro-4-[4-(3-dimethylcarbamoyl-4-{[6-methyl-2-(4-trifluoromethylphenyl)pyridine-3-carbonyl]amino}phenyl)butyryloxy]-5-methoxybenzoic acid 2-acetylaminoethyl ester (hereinafter also referred to as Compound 1-114), (122) 4-(3-dimethylcarbamoyl-4-{(4'-trifluoromethylbiphenyl-2-carbonyl)amino}phenyl)butyric acid 4-(2-isopropyl-2H-tetrazol-5-yl)phenyl ester (hereinafter also referred to as Compound 1-115), (123) 4-[4-(3-dimethylcarbamoyl-4-{[6-methyl-2-(4-trifluoromethylphenyl)pyridine-3-carbonyl]amino}phenyl)butyryloxy]-5-ethylisophthalic acid 1-ethyl ester 3-methyl ester (hereinafter also referred to as Compound 1-116), (124) 4-[4-(3-dimethylcarbamoyl-4-{[6-methyl-2-(4-trifluoromethylphenyl)pyridine-3-carbonyl]amino}phenyl)butyryloxy]-5-methoxyisophthalic acid 3-methylester 1-propyl ester (hereinafter also referred to as Compound 1-117), (125) 4-[4-(3-dimethylcarbamoyl-4-{[6-methyl-2-(4-trifluoromethylphenyl)pyridine-3-carbonyl]amino}phenyl)butyryloxy]-3-methoxy-5-(1-methoxyvinyl)benzoic acid ethyl ester (hereinafter also referred to as Compound 1-118), (126) 4-[4-(3-dimethylcarbamoyl-4-{[6-methyl-2-(4-trifluoromethylphenyl)pyridine-3-carbonyl]amino}phenyl)butyryloxy]-3-methoxy-5-methylbenzoic acid ethyl ester (hereinafter also referred to as Compound 1-119), (127) 4-[4-(3-dimethylcarbamoyl-4-{[6-methyl-2-(4-trifluoromethylphenyl)pyridine-3-carbonyl]amino}phenyl)butyryloxy]-3-ethyl-5-methoxybenzoic acid methyl ester (hereinafter also referred to as Compound 1-120), (128) 4-[4-(3-dimethylcarbamoyl-4-{[6-methyl-2-(4-trifluoromethylphenyl)pyridine-3-carbonyl]amino}phenyl)butyryloxy]-3-methoxy-5-methylbenzoic acid isopropyl ester (hereinafter also referred to as Compound 1-121), (129) 4-[4-(3-dimethylcarbamoyl-4-{[6-methyl-2-(4-trifluoromethylphenyl)pyridine-3-carbonyl]amino}phenyl)butyryloxy]-3-ethyl-5-methoxybenzoic acid ethyl ester (hereinafter also referred to as Compound 1-122), and (130) 4-[4-(3-dimethylcarbamoyl-4-{[6-methyl-2-(4-trifluoromethylphenyl)pyridine-3-carbonyl]amino}phenyl)butyryloxy]-5-isopropylisophthalic acid dimethyl ester (hereinafter also referred to as Compound 1-123), or a pharmaceutically acceptable salt thereof, <6> a pharmaceutical composition comprising the ester compound according to any one of the above <1> to <5>, or a pharmaceutically acceptable salt thereof, <7> a pharmaceutical composition which is an agent for the treatment or prophylaxis of a disease selected from hyperlipidemia, arteriosclerosis, coronary artery diseases, obesity, diabetes and hypertension, comprising the ester according to any one of the above <1> to <5>, or a pharmaceutically acceptable salt thereof, <8> an inhibitor of the microsomal triglyceride transfer protein, comprising the ester compound according to any one of the above <1> to <5>, or a pharmaceutically acceptable salt thereof, <9> an agent of lowering at least one of blood lipid parameters selected from triglyceride, total cholesterol, chylomicron, VLDL, LDL, and apolipoprotein B, comprising the ester compound according to any one of the above <1> to <5>, or a pharmaceutically acceptable salt thereof, <10> a method for the treatment or prophylaxis of a disease selected from hyperlipidemia, arteriosclerosis, coronary artery diseases, obesity, diabetes and hypertension, which comprises administering a pharmaceutically effective amount of the ester compound according to any one of the above <1> to <5>, or a pharmaceutically acceptable salt thereof, to a mammal, <11> a method of inhibiting the microsomal triglyceride transfer protein, which comprises administering a pharmaceutically effective amount of the ester compound according to any one of the above <1> to <5>, or a pharmaceutically acceptable salt thereof, to a mammal, <12> a method of lowering at least one of blood lipid parameters selected from triglyceride, total cholesterol, chylomicron, VLDL, LDL, and apolipoprotein B, which comprises administering a pharmaceutically effective amount of the ester compound according to any one of the above <1> to <5>, or a pharmaceutically acceptable salt thereof, to a mammal, <13> a commercial package comprising the pharmaceutical composition according to the above <6> or <7> and written matter associated therewith, the written matter stating that the pharmaceutical composition can or should be used for the treatment or prevention of a disease selected from hyperlipidemia, arteriosclerosis, coronary artery diseases, obesity, diabetes and hypertension, <14> use of the ester compound according to anyone of the above <1> to <5> or a pharmaceutically acceptable salt thereof, for the production of a drug for the treatment or prophylaxis of hyperlipidemia, arteriosclerosis, coronary artery diseases, obesity, diabetes and hypertension, <15> use of the ester compound according to any one of the above <1> to <5> or a pharmaceutically acceptable salt thereof, for the production of a drug which inhibits the microsomal triglyceride transfer protein, <16> use of the ester compound according to any one of the above <1> to <5> or a pharmaceutically acceptable salt thereof, for the production of a drug which lowers at least one of blood lipid parameters selected from triglyceride, total cholesterol, chylomicron, VLDL, LDL, and apolipoprotein B, <17> the pharmaceutical composition according to the above <6> or <7> for the combination use with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension, <18> the inhibitor of the microsomal triglyceride transfer protein according to the above <8> for the combination use with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension, <19> the agent of lowering at least one of blood lipid parameters selected from the group consisting of triglyceride, total cholesterol, chylomicron, VLDL, LDL, and apolipoprotein B according to the above <9> for the combination use with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension, <20> the method for the treatment or prophylaxis of a disease selected from hyperlipidemia, arteriosclerosis, coronary artery diseases, obesity, diabetes and hypertension according to the above <10>, which further comprises the combination use with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension, <21> the method of inhibiting the microsomal triglyceride transfer protein according to the above <11>, which further comprises the combination use with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension, <22> the method of lowering at least one of blood lipid parameters selected from triglyceride, total cholesterol, chylomicron, VLDL, LDL, and apolipoprotein B, according to the above <12>, which further comprises the combination use with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension, <23> a commercial package comprising the pharmaceutical composition according to the above <6> or <7> for the combination use with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension, and written matter associated therewith, the written matter stating that the pharmaceutical composition can or should be used for the treatment or prevention of a disease selected from hyperlipidemia, arteriosclerosis, coronary artery diseases, obesity, diabetes and hypertension, <24> use of the ester compound according to any one of the above <1> to <5> or a pharmaceutically acceptable salt thereof for the production of a drug for the treatment or prophylaxis of a disease selected from the group consisting of hyperlipidemia, arteriosclerosis, coronary artery diseases, obesity, diabetes and hypertension in combination with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension, <25> use of the ester compound according to any one of the above <1> to <5> or a pharmaceutically acceptable salt thereof for the production of a drug of inhibiting the microsomal triglyceride transfer protein in combination with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension, and <26> use of the ester compound according to any one of the above <1> to <5> or a pharmaceutically acceptable salt thereof for the production of a drug of lowering at least one of blood lipid parameters selected from triglyceride, total cholesterol, chylomicron, VLDL, LDL, and apolipoprotein B in combination with a drug selected from the group consisting of (1) an agent for the treatment and/or prophylaxis of hyperlipidemia, (2) an agent for the treatment and/or prophylaxis of obesity, (3) an agent for the treatment and/or prophylaxis of diabetes and (4) an agent for the treatment and/or prophylaxis of hypertension.

EFFECT OF THE INVENTION

The present invention can provide a drug having excellent MTP inhibitory activity, effective for hyperlipidemia, arteriosclerosis, coronary artery diseases, obesity, diabetes or hypertension. Further, since the drug has excellent MTP inhibitory activity which is rapidly lost in the plasma or liver, there can be provided a drug selectively inhibiting MTP in the small intestine, i.e. a useful MTP inhibitor causing no side effect on the liver, in accordance with the present invention.

BEST MODE FOR CARRYING OUT THE INVENTION

Definition of each substituent used in the description of the present invention is given below.

"$C_1$-$C_6$ alkyl" refers to a linear or branched alkyl of 1 to 6 carbon atoms, including, for example, methyl, ethyl, propyl, isopropyl, butyl, isobutyl, sec-butyl, tert-butyl, pentyl, isopentyl, neopentyl, tert-pentyl, 2-methylbutyl 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl 1-ethylbutyl, and 2-ethylbutyl, and the like, among which $C_1$-$C_4$ alkyl is preferable. As the $C_1$-$C_6$ alkyl, methyl, ethyl or isopropyl is especially preferred.

"$C_1$-$C_4$ alkyl" refers to a linear or branched alkyl of 1 to 4 carbon atoms, including, for example, methyl, ethyl, propyl, isopropyl, butyl, isobutyl, sec-butyl, tent-butyl, and the like, among which methyl, ethyl or isopropyl is preferable.

A preferable example of $C_1$-$C_6$ alkyl for $R^1$ and $R^2$ is methyl, a preferable example of $C_1$-$C_6$ alkyl for $R^3$, $R^4$ and $R^5$ is methyl, ethyl or isopropyl, and a preferable example of $C_1$-$C_6$ alkyl for $R^6$ and $R^7$ is methyl.

"Halogen" means fluorine, chlorine, bromine or iodine, and preferred is fluorine, chlorine or bromine.

A preferable example of halogen for $R^3$, $R^4$ and $R^5$ is fluorine, chlorine or bromine.

"$C_1$-$C_6$ alkoxy" refers to an alkoxy group wherein the alkyl moiety is the "$C_1$-$C_6$ alkyl" as defined above, and includes specifically methoxy, ethoxy, propoxy, isopropyloxy, butoxy, isobutyloxy, tert-butyloxy, pentyloxy, 2-methylbutyloxy, 1-ethylpropyloxy, hexyloxy, isohexyloxy, 4-methylpentyloxy, 3-methylpentyloxy, 2-methylpentyloxy, 1-methylpentyloxy, 3,3-dimethylbutyloxy, 2,2-dimethylbutyloxy, 1,1-dimethylbutyloxy, 1,2-dimethylbutyloxy, 1,3-dimethylbutyloxy, 2,3-dimethylbutyloxy, 1-ethylbutyloxy, 2-ethylbutyloxy, and the like. A preferable example of $C_1$-$C_6$ alkoxy is $C_1$-$C_4$ alkoxy.

"$C_1$-$C_4$ alkoxy" refers to an alkoxy group wherein the alkyl moiety is the "$C_1$-$C_4$ alkyl" as defined above, and includes specifically methoxy, ethoxy, propoxy, isopropyloxy, butoxy, isobutyloxy, tert-butyloxy, and the like. $C_1$-$C_4$ alkoxy is preferably methoxy, ethoxy, propoxy or isopropyloxy.

A preferable example of $C_1$-$C_6$ alkoxy for $R^3$, $R^4$ and $R^5$ is $C_1$-$C_4$ alkoxy, and especially preferred is methoxy or ethoxy.

A preferable example of $C_1$-$C_6$ alkoxy for $R^{13}$ is $C_1$-$C_4$ alkoxy, and especially preferred is methoxy, ethoxy, propoxy or isopropyloxy.

"Carbocycle" or "$C_3$-$C_{14}$ saturated or unsaturated carbocycle" refers to a saturated or unsaturated cyclic hydrocarbon group of 3 to 14 carbon atoms, and includes specifically aryl, cycloalkyl, cycloalkenyl, and a fused carbocycle thereof.

Here, "aryl" refers to an aromatic hydrocarbon group of 6 to 14 carbon atoms, and specifically includes phenyl, naphthyl, biphenyl, anthoryl, azurenyl, phenanthoryl, indenyl, pentalenyl, and the like. A preferable example of the aryl is an aromatic hydrocarbon group of 6 to 10 carbon atoms, and especially preferred is phenyl.

Here, "cycloalkyl" refers to a saturated cycloalkyl group of 3 to 8 carbon atoms, and specifically includes cyclopropyl, cyclobutyl, cyclopentyl, cyclohexyl, cycloheptyl, cyclooctyl and the like. A preferable example of cycloalkyl is a cycloalkyl of 3 to 6 carbon atoms, and specifically includes cyclopropyl, cyclobutyl, cyclopentyl, cyclohexyl and the like. Especially preferred is cyclopropyl or cyclohexyl.

Also, "cycloalkenyl" refers to a cycloalkenyl group of 3 to 8 carbon atoms and contains at least one double bond, preferably 1 or 2 double bonds. Specifically, there are exemplified cyclopropenyl, cyclobutenyl, cyclopentenyl, cyclohexenyl, cyclohexadienyl (2,4-cyclohexadien-1-yl, 2,5-cyclohexadien-1-yl, etc.), cycloheptenyl, cyclooctenyl, or the like.

As a fused carbocycle formed by fusion of these "aryl", "cycloalkyl" or "cycloalkenyl" groups, there are exemplified indanyl, fluorenyl, 1,4-dihydronaphthyl, 1,2,3,4-tetrahydro-1-naphthyl, 1,2,3,4-tetrahydro-2-naphthyl, 5,6,7,8-tetrahydro-2-naphthyl, perhydronaphthyl, or the like.

A preferable example of "carbocycle" or "$C_3$-$C_{14}$ saturated or unsaturated carbocycle" for ring A, ring B and ring C includes aryl, and more preferably phenyl.

"Aralkyl" is an arylalkyl group wherein the aryl moiety is the aryl as defined above, and the alkyl moiety is "$C_1$-$C_6$ alkyl" as defined above. Specific examples of such aralkyl include benzyl, phenethyl, 3-phenylpropyl, 4-phenylbutyl, 6-phenylhexyl and the like. A preferable example of the aralkyl is an arylalkyl group wherein the alkyl moiety is "$C_1$-$C_4$ alkyl" as defined above.

"Aralkyloxy" refers to an arylalkoxy group wherein the aryl moiety is the aryl as defined above and the alkoxy moiety is "$C_1$-$C_6$ alkoxy" as defined above. Specific examples of such aralkyloxy include benzyloxy, phenethyloxy, 1-phenylethoxy, 3-phenylpropyloxy, 4-phenylbutyloxy, 6-phenylhexyloxy, and the like. A preferable example of the aralkyloxy is an arylalkoxy group wherein the alkoxy moiety is "$C_1$-$C_4$ alkoxy" as defined above, and benzyloxy is especially preferable.

"Cycloalkylalkoxy" refers to a cycloalkylalkoxy group wherein the cycloalkyl moiety is "cycloalkyl" as defined above and the alkoxy moiety is "$C_1$-$C_6$ alkoxy" as defined above, and specifically includes cyclopropylmethoxy, cyclobutylmethoxy, cyclopentylmethoxy, cyclohexylmethoxy, and the like. A preferable example of the cycloalkylalkoxy is a cycloalkylalkoxy group wherein the alkoxy moiety is "$C_1$-$C_4$" alkoxy as defined above.

"Aryloxy" refers to an aryloxy group wherein the aryl moiety is "aryl" as defined above, and specifically includes phenoxy, naphthyloxy, biphenyloxy, and the like.

"Heterocycle" or "saturated or unsaturated heterocycle containing at least one heteroatom selected from nitrogen atom, oxygen atom and sulfur atom" refers to a 5- or 6-membered saturated or unsaturated (including partial saturation and full saturation) monocyclic heterocycle containing at least one heteroatom, preferably 1 to 4 heteroatoms selected from nitrogen atom, oxygen atom and sulfur atom in addition to the carbon atom, a fused heterocycle from a plural of heterocycles, and a fused ring between these heterocycles and a carbocycle selected from benzene, cyclopentane and cyclohexane.

"Saturated 5- or 6-membered monocyclic heterocycle" includes pyrrolidinyl, 2-oxopyrrolidinyl, tetrahydrofuryl, tetrahydrothienyl, imidazolidinyl, pyrazolidinyl, 1,3-dioxolanyl, 1,3-oxathiolanyl, oxazolidinyl, thiazolidinyl, isothiazolidinyl, piperidyl (for example, 2-piperidyl, 4-piperidyl, etc.), piperidino, piperazinyl, tetrahydropyranyl, tetrahydrothiopyranyl, dioxanyl (for example, 1,4-dioxanyl), morpholinyl, morpholino, thiomorpholinyl, thiomorpholino, 2-oxopyrrolidinyl, 2-oxopiperidinyl, 4-oxopiperidinyl, 2,6-dioxopiperidinyl, and the like.

"Unsaturated 5- or 6-membered monocyclic heterocycle" includes pyrrolyl, furyl, thienyl, imidazolyl, 1,2-dihydro-2-oxoimidazolyl, pyrazolyl, diazolyl, oxazolyl, isooxazolyl, thiazolyl, isothiazolyl, 1,2,4-triazolyl, 1,2,3-triazolyl, tetrazolyl, oxadiazolyl (for example, 1,3,4-oxadiazolyl, 1,2,4-oxadiazolyl, 1,3,4-thiadiazolyl, 1,2,4-thiadiazolyl, furazanyl, etc.), pyridyl, pyrimidinyl, 3,4-dihydro-4-oxopyrimidinyl, pyridazinyl, pyrazinyl, 1,3,5-triazinyl, thiazinyl, oxadiazinyl, imidazolinyl (for example, 2-imidazolinyl, 3-imidazolinyl, etc.), pyrazolinyl (for example, 1-pyrazolinyl, 2-pyrazolinyl, 3-pyrazolinyl, etc.), oxazolinyl (for example, 2-oxazolinyl, 3-oxazolinyl, 4-oxazolinyl, etc.), isoxazolinyl (for example, 2-isoxazolinyl, 3-isoxazolinyl, 4-isoxazolinyl, etc.), thiazolinyl (for example, 2-thiazolinyl, 3-thiazolinyl, 4-thiazolinyl, etc.), isothiazolinyl (for example, 2-isothiazolinyl, 3-isothiazolinyl, 4-isothiazolinyl, etc.), pyranyl, (for example, 2H-pyranyl, 4H-pyranyl, etc.), 2-oxopyranyl, 2-oxo-2,5-dihydrofuranyl, 1,1-dioxo-1H-isothiazolyl, and the like.

"Fused heterocycle" includes indolyl (for example, 1,3-dihydro-1,3-dioxoisoindolyl, benzofuranyl (for example, 4-benzofuranyl, 7-benzofuranyl, etc.), indazolyl, isobenzofuranyl, benzothiophenyl (for example, 4-benzothiophenyl, 7-benzothiophenyl, etc.), benzooxazolyl (for example, 4-benzooxazolyl, 7-benzooxazolyl, etc.), benzimidazolyl (for example, 4-benzimidazolyl, 7-benzimidazolyl, etc.), benzothiazolyl (for example, 4-benzothiazolyl, 7-benzothiazolyl, etc.), indolidinyl, quinolyl, dihydroquinolyl, isoquinolyl, 1,2-dihydro-2-oxoquionolyl, quinazolinyl, quinoxalinyl, cinnolinyl, phthalazinyl, quinolidinyl, puryl, pteridinyl, indolinyl, isoindolinyl, 5,6,7,8-tetrahydroquinolyl, 1,2,3,4-tetrahydroquinolyl, 2-oxo-1,2,3,4-tetrahydroquinolyl, benzo[1,3]dioxolyl, 3,4-methylenedioxypyridyl, 4,5-ethylenedioxypyrimidinyl, 2H-chromenyl, chromanyl, isochromanyl, benzofurazanyl, and the like.

"Heterocycle" or "saturated or unsaturated heterocycle containing at least one heteroatom selected from nitrogen atom, oxygen atom and sulfur atom" is preferably a 5- or 6-membered saturated or unsaturated (including partial saturation and full saturation) monocyclic heterocycle containing at least one heteroatom, preferably 1 to 4 heteroatoms, selected from nitrogen atom, oxygen atom and sulfur atom in addition to the carbon atom, and includes especially preferably pyridyl, tetrazolyl, oxadiazolyl (for example, 1,3,4-oxadiazolyl, 1,2,4-oxadiazolyl, 1,3,4-thiadiazolyl, 1,2,4-thiadiazolyl, furazanyl, etc.), thienyl, piperidyl (for example, 2-piperidyl, 4-piperidyl, etc.), piperidino, 2-oxopyrrolidinyl, and the like.

A preferable example of "heterocycle" or "saturated or unsaturated heterocycle containing at least one heteroatom selected from nitrogen atom, oxygen atom and sulfur atom" for ring A, ring B and ring C is an unsaturated 5- or 6-membered monocyclic heterocycle, and pyridyl is more preferable.

"Nitrogen-containing saturated heterocycle comprising a monocycle formed when $R^5$, $R^7$ and the adjacent nitrogen atom are taken together", "nitrogen-containing saturated heterocycle comprising a monocycle formed when $R^8$, $R^9$ and the adjacent nitrogen atom are taken together" or "nitrogen-containing saturated heterocycle comprising a monocycle formed when $R^{14}$, $R^{15}$ and the adjacent nitrogen atom are taken together" means a heterocycle comprising a 5- or 6-membered monocycle containing at least one nitrogen atom. Specific examples of such heterocycles are pyrrolidinyl, piperidyl (for example, 2-piperidyl, 4-piperidyl, etc.), piperidino, morpholinyl, morpholino, thiomorpholino, piperadinyl, piperazine, pyrrolidino, or the like.

"Optionally substituted by the same or different one or more substituents" means the case where the substitution is performed by the minimum number of one substituent to the possible maximum number of the substituents. For example, methyl may be substituted by 1 to 3 substituents, and ethyl may be substituted by 1 to 5 substituents. When the substitution is performed by two or more substituents, they are the same or different from each other, and there is no particular limitation on the substitution position and thus it is arbitrary.

The term "optionally substituted by the same or different one or more substituents" means preferably "optionally substituted by the same or different 1 to 5 substituents", and especially preferably "optionally substituted by the same or different 1 to 3 substituents".

Detailed explanation of each substituent is given below.
$R^1$ is preferably
1) $C_1$-$C_6$ alkyl optionally substituted by the same or different one or more halogens (said optionally substituted $C_1$-$C_6$ alkyl is preferably $C_1$-$C_4$ alkyl optionally substituted by the same or different one or more halogens, and more preferably $C_1$-$C_4$ alkyl optionally substituted by the same or different 1 to 3 halogens, furthermore preferably methyl optionally substituted by the same or different 1 to 3 halogens, and still furthermore preferably methyl optionally substituted by three halogen atoms. Specifically, examples of such alkyl are trifluoromethyl, trichloromethyl, tribromomethyl, or the like, and more preferably trifluoromethyl) or 2) —CO—$C_1$-$C_6$ alkoxy (more preferable example of said —CO—$C_1$-$C_6$ alkoxy is —CO—$C_1$-$C_4$ alkyl. Specific examples include —CO-methoxy, —CO-ethoxy, —CO-propoxy, —CO-isopropyloxy, —CO-butoxy, —CO-isobutyloxy, —CO-tert-butyloxy, or the like, and furthermore preferably —CO-methoxy).

$R^2$ is preferably
1) hydrogen, or
2) $C_1$-$C_6$ alkyl (more preferable example of said $C_1$-$C_6$ alkyl is $C_1$-$C_4$ alkyl, including methyl, ethyl, propyl, isopropyl, butyl, isobutyl, sec-butyl, tert-butyl and the like, and furthermore preferably methyl)

$R^3$, $R^4$ and $R^5$ are each preferably the same or different, and are
1) hydrogen,
2) halogen (including preferably fluorine, chlorine and bromine),
3) $C_1$-$C_6$ alkyl optionally substituted by the same or different one or more halogens (said optionally substituted $C_1$-$C_6$ alkyl is more preferably $C_1$-$C_4$ alkyl optionally substituted by the same or different one or more halogens, further preferably $C_1$-$C_4$ alkyl optionally substituted by the same or different 1 to 3 halogens, furthermore preferably methyl optionally substituted by the same or different 1 to 3 halogens, and still furthermore preferably methyl optionally substituted by the same or different 3 halogens. Specific examples are trifluoromethyl, trichloromethyl, tribromomethyl, or the like, and more preferably trifluoromethyl),
4) $C_1$-$C_6$ alkoxy (more preferable examples of said $C_1$-$C_6$ alkoxy are $C_1$-$C_4$ alkoxy. Preferable examples of such alkoxy are methoxy, ethoxy, propoxy, isopropyloxy, butoxy, isobutyloxy, tert-butyloxy, or the like, and more preferable examples are methoxy or ethoxy),
5) —COR$^{13}$ wherein R$^{13}$ is
 (a) hydroxy,
 (b) $C_1$-$C_6$ alkyl (said $C_1$-$C_6$ alkyl is more preferably $C_1$-$C_4$ alkyl including specifically methyl, ethyl, propyl, isopropyl, butyl, isobutyl, sec-butyl, tert-butyl, and the like, and furthermore preferably methyl, ethyl, and propyl),
 (c) $C_1$-$C_6$ alkoxy which is optionally substituted by the same or different one or more substituents selected from
 (1) hydroxy,
 (2) $C_1$-$C_6$ alkoxy which is optionally substituted by aryl (said optionally substituted $C_1$-$C_6$ alkoxy is more preferably $C_1$-$C_4$ alkoxy optionally substituted by aryl, and includes specifically methoxy, ethoxy, propoxy, isopropyloxy, butoxy, isobutyloxy, tert-butyloxy, and the like, all being optionally substituted by phenyl, and furthermore preferably benzyloxy, phenethyloxy and 1-phenylethoxy),
 (3) —NR$^{11}$CO—$C_1$-$C_6$ alkyl wherein R$^{11}$ is hydrogen or $C_1$-$C_6$ alkyl (said $C_1$-$C_G$ alkyl is preferably $C_1$-$C_4$ alkyl, and includes specifically methyl, ethyl, propyl, isopropyl, butyl, isobutyl, sec-butyl, tert-butyl, and the like, and more preferably methyl),
 (4) —CONR$^8$R$^9$ wherein R$^8$ and R$^9$ are each the same or different, and are hydrogen, $C_1$-$C_6$ alkyl (said $C_1$-$C_6$ alkyl is more preferably $C_1$-$C_4$ alkyl including specifically methyl, ethyl, propyl, isopropyl, butyl, isobutyl, sec-butyl, tert-butyl, and the like, and furthermore preferably methyl), or a nitrogen-containing saturated heterocycle comprising a monocycle formed when R$^8$, R$^9$ and the adjacent nitrogen atom are taken together (said nitrogen-containing heterocycle includes specifically pyrrolidinyl, piperidyl (for example, 2-piperidyl, 4-piperidyl, etc.), piperidino, morpholinyl, morpholino, thiomorpholino, piperazinyl, piperazino, pyrrolidino, and the like), (5) —CO—$C_1$-$C_6$ alkoxy wherein said $C_1$-$C_6$ alkoxy is optionally substituted by phenyl, and examples of said —CO—$C_1$-$C_6$ alkoxy are preferably —CO—$C_1$-$C_4$ alkoxy including specifically —CO-methoxy, —CO-ethoxy, —CO-propoxy, —CO-isopropyloxy, —CO-butoxy, —CO-isobutyloxy, —CO-tert-butyloxy, and the like, and more preferably —CO-methoxy and —CO-isopropyloxy, (6) aryl optionally substituted by the same or different one or more substituents selected from halogen (said halogen is preferably fluorine, chlorine or bromine, and more preferably chlorine), $C_1$-$C_6$ alkoxy (said $C_1$-$C_6$ alkoxy is preferably $C_1$-$C_4$ alkoxy including specifically methoxy, ethoxy, propoxy, isopropyloxy, butoxy, isobutyloxy, tert-butyloxy, and the like, and more preferably methoxy) and —CO—$C_1$-$C_6$ alkoxy (said —CO—$C_1$-$C_6$ alkoxy is preferably —CO—$C_1$-$C_4$ alkoxy including specifically —CO-methoxy, —CO-ethoxy, —CO-propoxy, —CO-isopropyloxy, —CO-butoxy, —CO-isobutyloxy, —CO-tert-butyloxy, and the like, and more preferably —CO-isopropyloxy), said optionally substituted aryl being preferably phenyl optionally substituted by the same or different one or more substituents selected from chlorine, methoxy and —CO-isopropyloxy, and more preferably phenyl optionally substituted by the same or different 1 to 3 substituents selected from chlorine, methoxy and —CO-isopropyloxy, and (7) heterocycle selected from pyridyl, tetrazolyl and thienyl [said heterocycle is optionally substituted by the same or different one or more $C_1$-$C_6$ alkyl groups (said $C_1$-$C_6$ alkyl is preferably $C_1$-$C_4$ alkyl including specifically methyl, ethyl, propyl, isopropyl, butyl, isobutyl, sec-butyl, tort-butyl, and the like, and more preferably methyl)], said optionally substituted $C_1$-$C_6$ alkoxy being preferably $C_1$-$C_4$ alkoxy optionally substituted by the same or different one or more substituents selected from the above (1) to (7), and includes specifically methoxy, ethoxy, propoxy, isopropyloxy, butoxy, isobutyloxy, tert-butyloxy, and the like, and more preferably methoxy, ethoxy, propoxy and isopropyloxy, all of which is optionally substituted by the same or different one or more substituents selected from the above (1) to (7), or (d) —$OR^{19}$ wherein $R^{19}$ is a saturated or unsaturated carbocycle of 3 to 14 carbon atoms (said carbocycle includes specifically aryl, cycloalkyl, cycloalkenyl, fused carbocycle formed when these rings are fused, or the like, and more preferably a fused carbocycle formed when aryl and cycloalkyl are fused, and examples of such carbocycles are indenyl, indanyl, pentalenyl, fluorenyl, 1,4-dihydronaphthyl, 1,2,3,4-tetrahydro-1-naphthyl, 1,2,3,4-tetrahydro-2-naphthyl, 5,6,7,8-tetrahydro-2-naphthyl, or the like, more preferably a fused carbocycle formed when phenyl and cycloalkyl are fused, and furthermore preferably indanyl, 1,2,3,4-tetrahydro-1-naphthyl, 1,2,3,4-tetrahydro-2-naphthyl) or piperidyl optionally substituted by —CO—$C_1$-$C_6$ alkyl (said —CO—$C_1$-$C_6$ alkyl is preferably —CO—$C_1$-$C_4$ alkyl including specifically —CO-methyl, —CO-ethyl, —CO-propyl, —CO-isopropyl, —CO-butyl, —CO-isobutyl, —CO-sec-butyl, —CO-tert-butyl, and the like, and more preferably —CO-methyl), 6) heterocycle selected from oxadiazolyl and tetrazolyl {said heterocycle is optionally substituted by $C_1$-$C_6$ alkyl [said $C_1$-$C_6$ alkyl is preferably $C_1$-$C_4$ alkyl including specifically methyl, ethyl, propyl, isopropyl, butyl, isobutyl, sec-butyl, tert-butyl, and the like, and more preferably methyl and isopropyl] optionally substituted by the same or different one or more substituents selected from

—$CONR^8R^9$ wherein $R^8$ and $R^9$ are each the same or different, and are (a) hydrogen, (b) $C_1$-$C_6$ alkyl (said $C_1$-$C_6$ alkyl is preferably $C_1$-$C_4$ alkyl including specifically methyl, ethyl, propyl, isopropyl, butyl, isobutyl, sec-butyl, tert-butyl and the like, and more preferably methyl), or (c) nitrogen-containing saturated heterocycle comprising a monocycle formed when $R^8$, $R^9$ and the adjacent nitrogen atom are taken together (said nitrogen-containing saturated heterocycle includes specifically pyrrolidinyl, piperidyl (for example, 2-piperidyl, 4-piperidyl, and the like), piperidino, morpholinyl, morpholino, thiomorpholino, piperazinyl, piperazino, pyrrolidino, and the like), and —CO-aralkyloxy (said —CO-aralkyloxy includes specifically —CO-benzyloxy, —CO-phenethyloxy, —CO-1-phenylethoxy, —CO-3-phenylpropyloxy, —CO-4-phenylbutyloxy, —CO-6-phenylhexyloxy, and the like, and more preferably —CO-phenethyloxy)), or 7) nitrile;

$R^6$ and $R^7$ are each the same or different, and are 1) hydrogen,

2) $C_1$-$C_E$, alkyl (said $C_1$-$C_6$ alkyl is preferably $C_1$-$C_4$ alkyl including specifically methyl, ethyl, propyl, isopropyl, butyl, isobutyl, sec-butyl, tert-butyl, and the like, and more preferably methyl) or 3) nitrogen-containing saturated heterocycle comprising a monocycle formed when $R^6$, $R^7$ and the adjacent nitrogen atom are taken together (said nitrogen-containing saturated heterocycle includes specifically pyrrolidinyl, piperidyl (for example, 2-piperidyl, 4-piperidyl, etc.), piperidino, morpholinyl, morpholino, thiomorpholino, piperazinyl, piperazino, pyrrolidino, and the like, and preferably pyrrolidinyl and morpholino);

$Y^1$, $Y^2$ and $Y^3$ are each preferably the same or different, and are 1) carbon atom, or 2) nitrogen atom;

—X— is preferably

1) —$(CH_2)_l$— wherein l is preferably an integer of 1 to 3,

2) —$CH_2$—$NR^{18}$—$CH_2$— wherein $R^{18}$ is $C_1$-$C_6$ alkyl (said $C_1$-$C_6$ alkyl is preferably $C_1$-$C_4$ alkyl including specifically methyl, ethyl, propyl, isopropyl, butyl, isobutyl, sec-butyl, tert-butyl, and the like, and more preferably methyl), or

3)

Examples of the substituent represented by the formula:

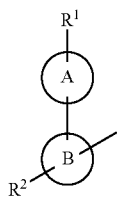

(wherein R¹, R², ring A and ring B have the same meanings as defined for the above formula [1]) in the formula [1] are

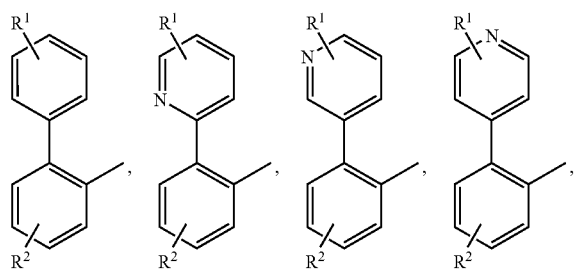

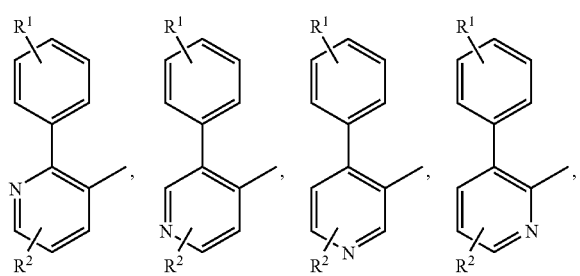

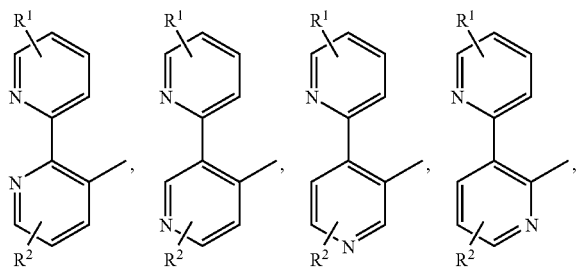

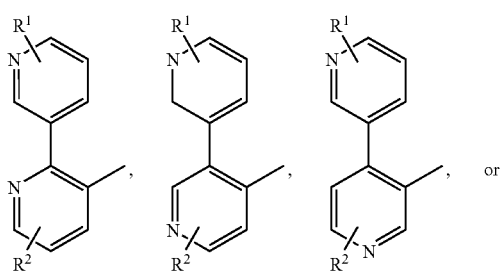 or

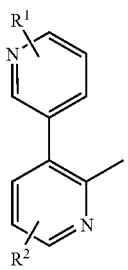

(wherein $R^1$ and $R^2$ have the same meanings as defined for the above formula [1]), preferably the following substituent represented
by the formula:

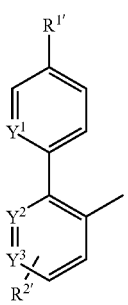

(wherein $R^{1'}$, $R^{2'}$, $Y^1$, $Y^2$ and $Y^3$ have the same meanings as defined for the above formula [2]) in the formula [2].

Specific examples of the following substituent represented by the formula:

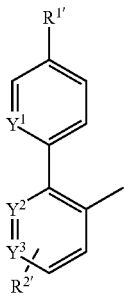

(wherein $R^{1'}$, $R^{2'}$, $Y^1$, $Y^2$ and $Y^3$ have the same meanings as defined for the above formula [2]) in the formula [2] are

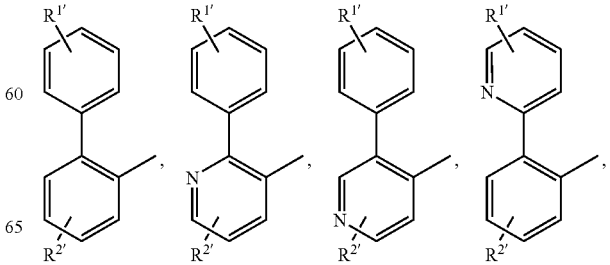

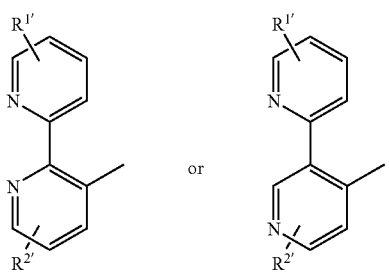

(wherein R$^{1'}$ and R$^{2'}$ have the same meanings as defined for the above formula [2]). More specifically, there are exemplified

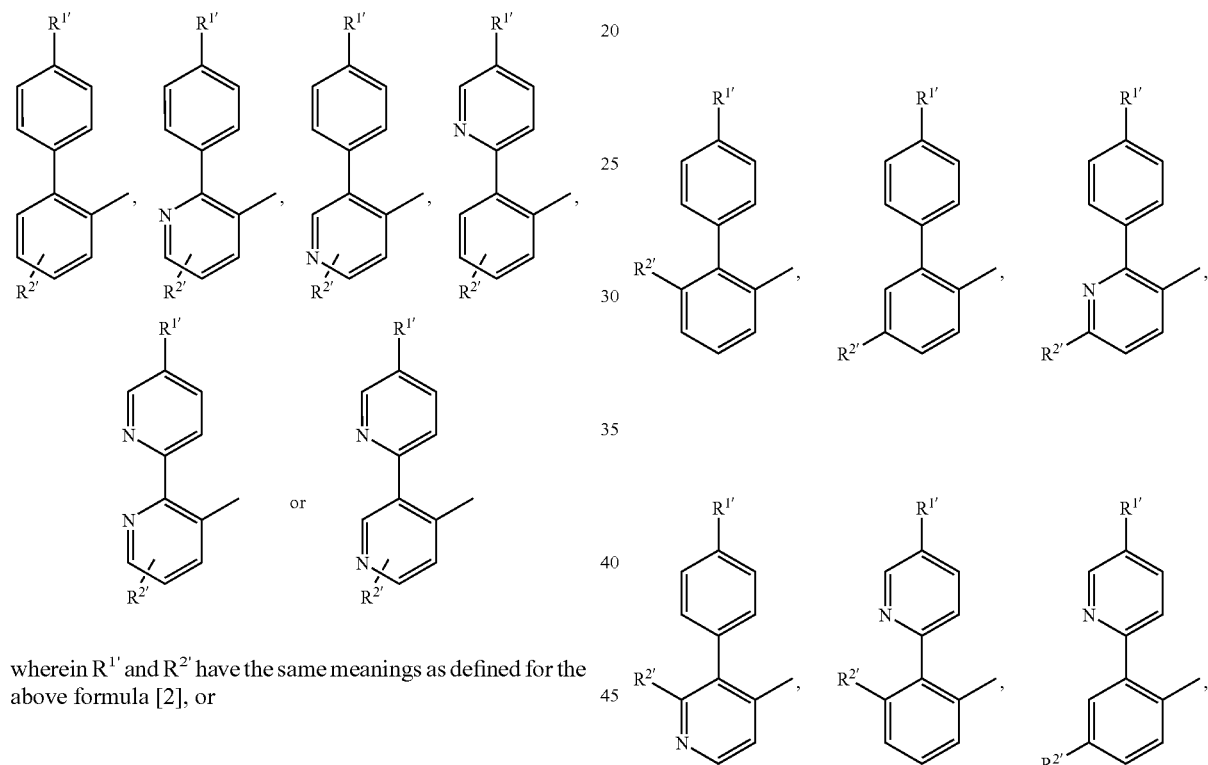

wherein R$^{1'}$ and R$^{2'}$ have the same meanings as defined for the above formula [2], or

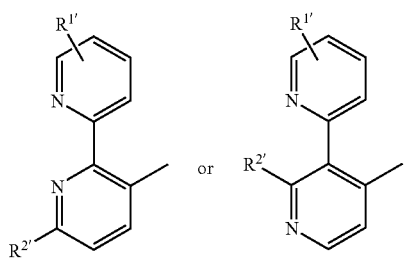

wherein R$^{1'}$ and R$^{2'}$ have the same meanings as defined for the above formula [2]. Especially preferable examples are the following substituents represented by the formulae:

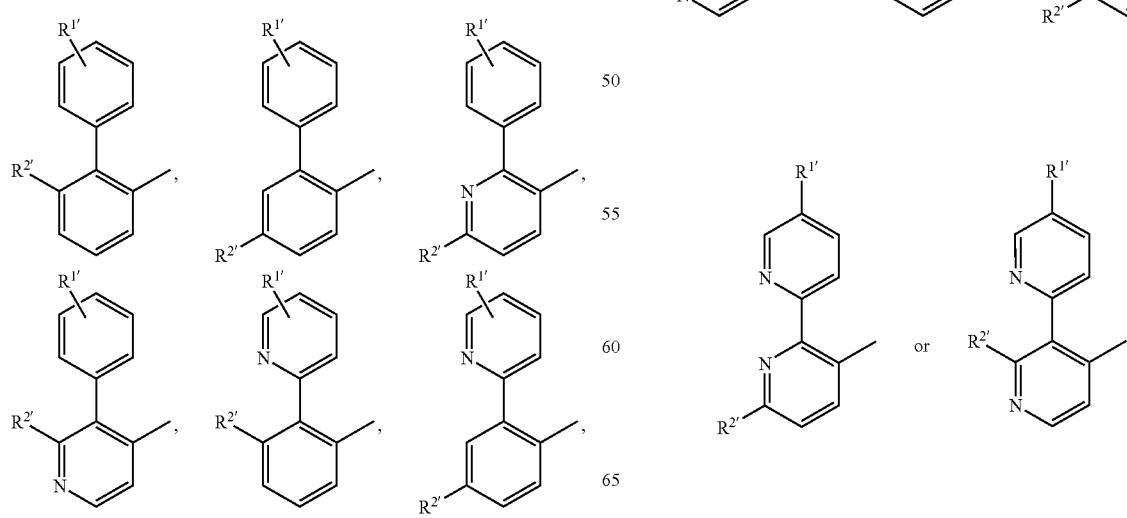

wherein R$^{1'}$ and R$^{2'}$ have the same meanings as defined above.

Most preferable example is the following substituent represented by the formula:

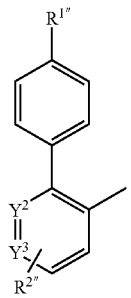

(wherein $R^{1''}$, $R^{2''}$, $Y^2$ and $Y^3$ have the same meanings as defined for the above formula [3]) in the formula [3]. Specific examples of the following substituent represented by the formula:

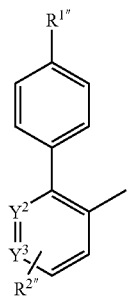

(wherein $R^{1''}$, $R^{2''}$, $Y^2$ and $Y^3$ have the same meanings as defined for the above formula [3]) in the formula [3] are

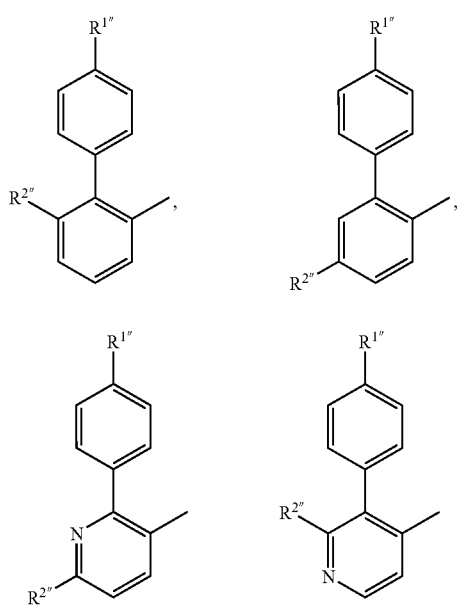

wherein $R^{1''}$ and $R^{2''}$ have the same meanings as defined for the above formula [3].

Ring C in the formula [1] is preferably the following substituent represented by the formula:

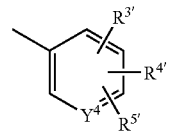

wherein $R^{3'}$, $R^{4'}$ and $R^{5'}$ have the same meanings as defined for the above formula [2], and specifically

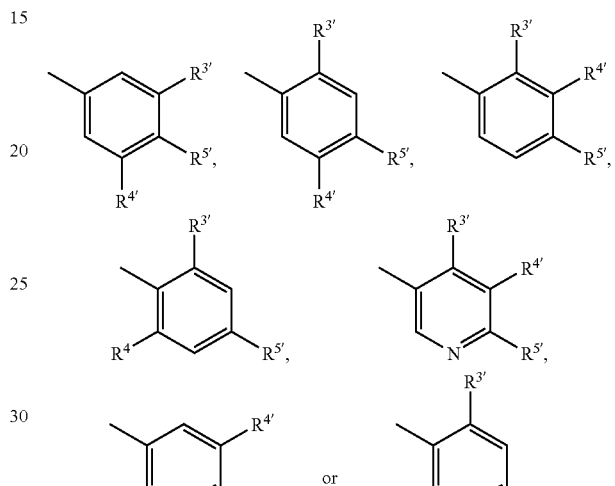

wherein $R^{3'}$, $R^{4'}$ and $R^{5'}$ have the same meanings as defined for the above formula [3], and more preferably the following substituent represented by the formula:

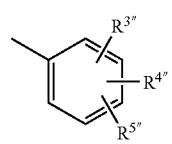

wherein $R^{3''}$, $R^{4''}$ and $R^{5''}$ have the same meanings as defined for the above formula [3], specifically

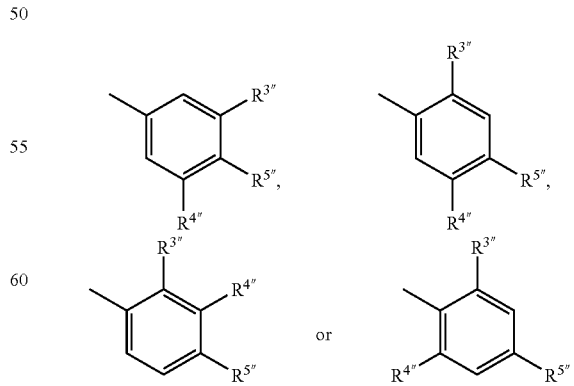

wherein $R^{3''}$, $R^{4''}$ and $R^{5''}$ have the same meanings as defined for the above formula [3].

R³ and R⁴ are each preferably the same or different, and are
1) hydrogen,
2) halogen (said halogen is preferably fluorine, chlorine or bromine),
3) $C_1$-$C_6$ alkyl optionally substituted by the same or different one or more halogens (said optionally substituted $C_1$-$C_6$ alkyl is more preferably $C_1$-$C_4$ alkyl optionally substituted by the same or different one or more halogens, further preferably $C_1$-$C_4$ alkyl optionally substituted by the same or different 1 to 3 halogens, furthermore preferably methyl optionally substituted by the same or different 1 to 3 halogens, and still furthermore preferably methyl optionally substituted by the same or different 3 halogens. Specific examples are trifluoromethyl, trichloromethyl, tribromomethyl, or the like, and more preferably trifluoromethyl),
4) $C_1$-$C_6$ alkoxy (said $C_1$-$C_6$ alkoxy is preferably $C_1$-$C_4$ alkoxy including specifically methoxy, ethoxy, propoxy, isopropyloxy, butoxy, isobutyloxy, tert-butyloxy and the like, and more preferably methoxy and ethoxy), or
5) —COR¹³ wherein R¹³ is $C_1$-$C_6$ alkoxy (preferably $C_1$-$C_4$ alkoxy) and specifically includes methoxy, ethoxy, propoxy, isopropyloxy, butoxy, isobutyloxy, tert-butyloxy, and the like, and more preferably methoxy;

R⁵ is preferably
1) hydrogen,
2) halogen (said halogen includes preferably fluorine, chlorine and bromine),
3) —COR¹³ wherein R¹³ is
  (a) hydroxy,
  (b) $C_1$-$C_6$ alkyl (said $C_1$-$C_6$ alkyl is more preferably $C_1$-$C_4$ alkyl including specifically methyl, ethyl, propyl, isopropyl, butyl, isobutyl, sec-butyl, tert-butyl, and the like, and furthermore preferably methyl, ethyl, and propyl),
  (c) $C_1$-$C_6$ alkoxy wherein said $C_1$-$C_6$ alkoxy is optionally substituted by the same or different one or more substituents selected from
    (1) hydroxy,
    (2) $C_1$-$C_6$ alkoxy optionally substituted by aryl (said optionally substituted $C_1$-$C_6$ alkoxy is more preferably $C_1$-$C_4$ alkoxy optionally substituted by aryl, and includes specifically methoxy, ethoxy, propoxy, isopropyloxy, butoxy, isobutyloxy, tert-butyloxy, and the like, all being optionally substituted by phenyl, and furthermore preferably benzyloxy, phenethyloxy and 1-phenylethoxy),
    (3) —NR¹¹CO—$C_1$-$C_6$ alkyl wherein R¹¹ is hydrogen or $C_1$-$C_6$ alkyl (said $C_1$-$C_6$ alkyl is preferably $C_1$-$C_4$ alkyl, and includes specifically methyl, ethyl, propyl, isopropyl, butyl, isobutyl, sec-butyl, tert-butyl, and the like, and more preferably methyl),
    (4) —CONR⁸R⁹ wherein R⁸ and R⁹ are each the same or different, and are hydrogen, $C_1$-$C_6$ alkyl (said $C_1$-$C_6$ alkyl is more preferably $C_1$-$C_4$ alkyl including specifically methyl, ethyl, propyl, isopropyl, butyl, isobutyl, sec-butyl, tert-butyl, and the like, and furthermore preferably methyl), or a nitrogen-containing saturated heterocycle comprising a monocycle formed when R⁸, R⁹ and the adjacent nitrogen atom are taken together (said nitrogen-containing saturated heterocycle includes specifically pyrrolidinyl, piperidyl (for example, 2-piperidyl, 4-piperidyl, etc.), piperidino, morpholinyl, morpholino, thiomorpholino, piperazinyl, piperazino, pyrrolidino, and the like),
    (5) —CO—$C_1$-$C_6$ alkoxy (said $C_1$-$C_6$ alkoxy is optionally substituted by phenyl, and examples of said —CO—$C_1$-$C_6$ alkoxy is preferably —CO—$C_1$-$C_4$ alkoxy including specifically —CO-methoxy, —CO-ethoxy, —CO-propoxy, —CO-isopropyloxy, —CO-butoxy, —CO-isobutyloxy, —CO-tert-butyloxy, and the like, and more preferably —CO-methoxy and —CO-isopropyloxy),
    (6) phenyl optionally substituted by the same or different one or more substituents selected from halogen (said halogen is preferably fluorine, chlorine or bromine, and more preferably chlorine), $C_1$-$C_6$ alkoxy (said $C_1$-$C_6$ alkoxy is preferably $C_1$-$C_4$ alkoxy including specifically methoxy, ethoxy, propoxy, isopropyloxy, butoxy, isobutyloxy, tert-butyloxy, and the like, and more preferably methoxy) and —CO—$C_1$-$C_6$ alkoxy (said —CO—$C_1$-$C_6$ alkoxy is preferably —CO—$C_1$-$C_4$ alkoxy including specifically —CO-methoxy, —CO-ethoxy, —CO-propoxy, —CO-isopropyloxy, —CO-butoxy, —CO-isobutyloxy, —CO-tert-butyloxy, and the like, and more preferably —CO-isopropyloxy), said optionally substituted phenyl being preferably phenyl optionally substituted by the same or different one or more substituents selected from chlorine, methoxy and —CO-isopropyloxy, and more preferably phenyl optionally substituted by the same or different 1 to 3 substituents selected from chlorine, methoxy and —CO-isopropyloxy, and
    (7) heterocycle selected from pyridyl, tetrazolyl and thienyl [said heterocycle is optionally substituted by the same or different one or more $C_1$-$C_6$ alkyl groups (said $C_1$-$C_6$ alkyl is preferably $C_1$-$C_4$ alkyl including specifically methyl, ethyl, propyl, isopropyl, butyl, isobutyl, sec-butyl, tert-butyl, and the like, and more preferably methyl)],
    said optionally substituted $C_1$-$C_6$ alkoxy being preferably $C_1$-$C_4$ alkoxy optionally substituted by the same or different one or more substituents selected from the above (1) to (7), and including specifically methoxy, ethoxy, propoxy, isopropyloxy, butoxy, isobutyloxy, tert-butyloxy, and the like optionally substituted by the same or different one or more substituents selected from the above (1) to (7), and more preferably methoxy, ethoxy, propoxy and isopropyloxy, optionally substituted by the same or different one or more substituents selected from the above (1) to (7), or
  (d) —OR¹⁹ wherein R¹⁹ is a saturated or unsaturated carbocycle of 3 to 14 carbon atoms (said carbocycle includes specifically aryl, cycloalkyl, cycloalkenyl, and fused carbocycle formed when these rings are fused, and the like, and more preferably a fused carbocycle formed when aryl and cycloalkyl are fused, and examples of such carbocycles are indenyl, indanyl, pentalenyl, fluorenyl, 1,4-dihydronaphthyl, 1,2,3,4-tetrahydro-1-naphthyl, 1,2,3,4-tetrahydro-2-naphthyl, 5,6,7,8-tetrahydro-2-naphthyl, or the like, more preferably a fused carbocycle formed when phenyl and cycloalkyl are fused including indanyl, 1,2,3,4-tetrahydro-1-naphthyl, 1,2,3,4-tetrahydro-2-naphthyl), or piperidyl, optionally substituted by —CO—$C_1$-$C_6$ alkyl (said —CO—$C_1$-$C_6$ alkyl is preferably —CO—$C_1$-$C_4$ alkyl including specifically —CO-methyl, —CO-ethyl, —CO-propyl, —CO-isopropyl, —CO-butyl, —CO-isobutyl, —CO-sec-butyl, —CO-tert-butyl, and the like, and more preferably —CO-methyl),
4) heterocycle selected from oxadiazolyl and tetrazolyl said heterocycle is optionally substituted by $C_1$-$C_6$ alkyl [said $C_1$-$C_6$ alkyl is preferably $C_1$-$C_4$ alkyl including specifically methyl, ethyl, propyl, isopropyl, butyl, isobutyl, sec-butyl, tert-butyl, and the like, and more preferably methyl and isopropyl] optionally substituted by the same or different one or more substituents selected from
—CONR$^8$R$^9$
wherein R$^8$ and R$^9$ are each the same or different, and are
  (a) hydrogen,
  (b) C$_1$-C$_6$ alkyl (said C$_1$-C$_6$ alkyl is preferably C$_1$-C$_4$ alkyl including specifically methyl, ethyl, propyl, isopropyl, butyl, isobutyl, sec-butyl, tert-butyl and the like, and more preferably methyl), or
  (c) nitrogen-containing saturated heterocycle comprising a monocycle formed when R$^8$, R$^9$ and the adjacent nitrogen atom are taken together (said nitrogen-containing saturated heterocycle includes specifically pyrrolidinyl, piperidyl (for example, 2-piperidyl, 4-piperidyl, and the like), piperidino, morpholinyl, morpholino, thiomorpholino, piperazinyl, piperazino, pyrrolidino, and the like), and
—CO-aralkyloxy
(said —CO-aralkyloxy includes specifically —CO-benzyloxy, —CO-phenethyloxy, —CO-1-phenylethoxy, —CO-3-phenylpropyloxy, —CO-4-phenylbutyloxy, —CO-6-phenylhexyloxy, and the like, and more preferably —CO-phenethyloxy)}, or
5) nitrile.

A preferable substitution position of —X— on the benzene ring of the formula [1] is h-position.

A preferable ester compound represented by the formula [1] is one represented by the formula [2], and more preferable one is represented by the formula [3]. The alkyl group represented by R$^{1'}$, R$^{2'}$, R$^{3'}$, R$^{4'}$, R$^{5'}$, R$^{13'}$ and R$^{18'}$ in the formula [2] and the alkyl group represented by R$^{1''}$, R$^{2''}$, R$^{3''}$, R$^{4''}$ and R$^{5''}$ in the formula [3] have the same meanings as hereinbefore defined for the alkyl group represented by R', R$^2$, R$^3$, R$^4$, R$^5$, R$^{13}$ and R$^{18}$; the alkoxy group represented by R$^{3'}$, R$^{4'}$, R$^{5'}$ and R$^{13'}$ in the formula [2] and the alkoxy group represented by R$^{3''}$, R$^{4''}$, R$^{5''}$ and R$^{13''}$ in the formula [3] have the same meanings as hereinbefore defined for the alkoxy group represented by R$^3$, R$^4$, R$^5$ and R$^{13}$; the halogen represented by R$^{3'}$, R$^{4'}$ and R$^{5'}$ in the formula [2] and the halogen represented by R$^{3''}$, R$^{4''}$ and R$^{5''}$ in the formula [3] have the same meanings as hereinbefore defined for the halogen represented by R$^3$, R$^4$, R$^5$ and R$^{13}$; R$^{6'}$ and R$^{7'}$ in the formula [2] and R$^{6''}$ and R$^{7''}$ in the formula [3] have the same meanings as hereinbefore defined for R$^6$ and R$^7$; the —CO—C$_1$-C$_6$ alkoxy group represented by R$^{1'}$ as the substituent in the formula [2] and the —CO—C$_1$-C$_6$ alkoxy group represented by R$^{1''}$ as the substituent in the formula [3] have the same meanings as hereinbefore defined for the —CO—C$_1$-C$_6$ alkoxy group represented by R$^1$; R$^{8'}$ and R$^{9'}$ in the formula [2] has the same meaning as hereinbefore defined for R$^8$ and R$^9$; the alkyl group represented by R$^{8''}$ and R$^{9''}$ in the formula [3] has the same meaning as hereinbefore defined for the alkyl group represented by R$^8$ and R$^9$; the alkyl group represented by R$^{11'}$ as the substituent for the alkoxy group represented by R$^{13'}$ in the formula [2] has the same meaning as hereinbefore defined for the alkyl group represented by R$^{11}$ as the substituent for the alkoxy group represented by R$^{13}$; and the carbocycle represented by R$^{19'}$ of —OR$^{19'}$ represented by R$^{13'}$ in the formula [2] has the same meaning as hereinbefore defined for the carbocycle represented by R$^{19}$.

"Pharmaceutically acceptable salt" may include any salt so far as a non-toxic salt of a compound represented by the formula [1] can be formed. The pharmaceutically acceptable salt of the compound represented by the formula [1] can be prepared by adding a desired acid or base to the compound represented by the formula [1] dissolved in a solvent, and collecting the precipitated solid by filtration or concentration under reduced pressure. Examples of the solvents used in the reaction are ethers (e.g. diethyl ether, tetrahydrofuran, diisopropyl ether, 1,4-dioxan (hereinafter abbreviated as dioxane), 1,2-dimethoxyethane, diethylene glycol dimethyl ether (also referred to as diglyme), etc.); alcohols (e.g. methanol, ethanol, isopropanol, n-propanol, tert-butanol, etc.); hydrocarbons (e.g. benzene, toluene, hexane, xylene, etc.); halogenated hydrocarbons (e.g. methylene chloride, chloroform, carbon tetrachloride, 1,2-dichloroethane, etc.); polar solvents (e.g. acetone, methyl ethyl ketone, N,N-dimethylformamide, dimethyl sulfoxide, etc.); or water, and they may be used alone or in combination of two or more these solvents. Examples of the acid to be used are inorganic acids (e.g. hydrochloric acid, sulfuric acid, phosphoric acid, hydrobromic acid, etc.) or organic acids (e.g. oxalic acid, malonic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, toxic acid, naphthalene-1,5-disulfonic acid, etc.). Examples of the base to be used are inorganic bases (e.g. sodium hydroxide, potassium hydroxide, calcium hydroxide, magnesium hydroxide, ammonium hydroxide, etc.), organic bases (e.g. methylamine, diethylamine, triethylamine, triethanolamine, ethylene diamine, tris(hydroxymethyl)methylamine, guanidine, colline, cinchonine, etc.) or amino acids (e.g. lysine, arginine, alanine, etc.).

The present invention encompasses hydrated compounds, hydrates, and solvates of each compound or a pharmaceutically acceptable salt thereof.

In addition, there exist various isomers in the compounds represented by the formula [1]. For example, E- and Z-geometric isomers can exist. Also, in the case where an asymmetric carbon atom is present, enantiomers and diastereomers can exist as a stereoisomer due to the presence of the asymmetric carbon atom, and tautomeric isomers also can exist. Accordingly, all these isomers and mixtures thereof are included within the present invention. In addition to the compounds represented by the formula [1], the present invention can include their prodrugs and metabolites as an equivalent compound.

Here, "prodrug" refers to a derivative of the compound of the present invention, which has a group capable of being chemically or metabolically converted and shows pharmaceutical activity after it is hydrolyzed or solvolyzed or converted under physiological conditions. The prodrug can be used for the improvement of oral absorption or for the application to a targeting site. Since it is fully established in the medical field that what is a group to be degradable or how such a group is introduced into a compound, the technology known per se like these may be used in the present invention. Modification site for such prodrug formation is, for example, a site of a highly reactive functional group such as hydroxy, carboxyl, amino, thiol, and the like.

For example, there may be listed a derivative in which a substituent such as —CO—C$_1$-C$_6$ alkyl, —CO$_2$—C$_1$-C$_6$ alkyl, —CONH—C$_1$-C$_6$ alkyl, —CO—C$_2$-C$_6$ alkenyl, —CO$_2$—O$_2$—C$_6$ alkenyl, —CONH—C$_2$-C$_6$ alkenyl, —CO-aryl, —CO$_2$-aryl, —CONH-aryl, —CO-heterocycle, —CO$_2$-heterocycle, —CONH-heterocycle, etc. (wherein any of said C$_1$-C$_6$ alkyl, C$_2$-C$_6$ alkenyl, aryl and heterocycle may be substituted with halogen, C$_1$-C$_6$ alkyl, hydroxy, C$_1$-C$_6$ alkoxy, carboxyl, amino, amino acid residue, —PO$_3$H$_2$, —SO$_3$H, —CO-polyethyleneglycol residue, —CO$_2$-polyethyleneglycol residue, —CO-polyethyleneglycol monoalkyl ether residue or —CO$_2$-polyethyleneglycol monoalkyl ether residue) is attached to the hydroxy group of the compound.

Also, there may be exemplified a derivative in which a substituent such as —CO—C$_1$-C$_6$ alkyl, —CO$_2$—C$_1$-C$_6$ alkyl, —CO—$C_2$-$C_6$ alkenyl, —$CO_2$—$C_2$-$C_6$ alkenyl, —$CO_2$-aryl, —CO-aryl, —CO-heterocycle, —$CO_2$-heterocycle, etc. (wherein any of said $C_1$-$C_6$ alkyl, $C_2$-$C_6$ alkenyl, aryl and heterocycle may be substituted with halogen, $C_1$-$C_6$ alkyl, hydroxy, $C_1$-$C_6$ alkoxy, carboxyl, amino, amino acid residue, —$PO_3H_2$, —CO-polyethyleneglycol residue, —$CO_2$-polyethyleneglycol residue, —CO-polyethyleneglycol monoalkyl ether residue, —$CO_2$-polyethyleneglycol monoalkyl ether residue or —$PO_3H_2$, etc.) is attached to the amino group of the compound.

Furthermore, there may be exemplified a derivative in which a substituent such as $C_1$-$C_6$ alkoxy, aryloxy, etc. (wherein said $C_1$-$C_6$ alkoxy or aryloxy may be substituted with halogen, $C_1$-$C_6$ alkyl, hydroxy, $C_1$-$C_6$ alkoxy, carboxyl, amino, amino acid residue, —$PO_3H_2$, —$SO_3H$, polyethyleneglycol residue or polyethyleneglycol monoalkyl ether residue, etc.) is attached to the carboxyl group of the compound.

"$C_2$-$C_6$ alkenyl" refers to a linear or branched alkenyl group of 2 to 6 carbon atoms, and its example includes vinyl, n-propenyl, isopropenyl, n-butenyl, isobutenyl, sec-butenyl, tert-butenyl, n-pentenyl, isopentenyl, neopentenyl, 1-methylpropenyl, n-hexenyl, isohexenyl, 1,1-dimethylbutenyl, 2,2-dimethylbutenyl, 3,3-dimethylbutenyl, 3,3-dimethylpropenyl, 2-ethylbutenyl, etc.

The compounds of the present invention may include hydrous substances, hydrates or solvates, depending on the case, and may further include their metabolites. Furthermore, the compounds of the present invention include racemates and optically active compounds. The optically active compounds are preferably those wherein one of enantiomers is in enantiomer excess of about 90% or higher, more preferably in enantiomer excess of about 99% or higher.

"Pharmaceutical composition" includes a so-called "composition" comprising a pharmaceutically active ingredient and a pharmaceutically acceptable carrier, and further includes a combination drug with other drugs. It goes without saying that the pharmaceutical composition of the present invention may be combined with any other drugs within a range such that the combination is permitted in the clinical field. Therefore, it may also be said that the pharmaceutical composition of the present invention is a pharmaceutical composition for the combined use with other drugs.

Also, the compounds of the present invention can be administered to human beings as well as animals such as mouse, rat, hamster, rabbit, cat, dog, cow, horse, sheep, monkey and the like. Accordingly, the pharmaceutical composition of the present invention is useful as a drug for not only naturally human beings but also animals.

"MTP in the small intestine" means a microsomal triglyceride transfer protein (MTP) existing in intestinal epithelial cells.

"MTP in the liver" means MTP existing in hepatocytes.

The expression "selectively inhibit MTP in the small intestine" means that the level of inhibition is at least about 5 times higher, preferably about 10 times higher, than MTP inhibition in other parts of body such as liver and heart, especially liver. For example, it means that when a compound inhibiting MTP in the small intestine is administered to the living body, the compound is metabolized to the amount at which it does not substantially inhibit the MTP in the liver. To be more specific, on the basis of liver S9 metabolic stability test or metabolic stability test in the plasma, it means that in the test using human or mammal (e.g. hamster, etc.) liver S9 or plasma, the remaining rate of unaltered form 10 or 60 minutes after the incubation is, for example, less than about 50%, preferably less than about 30%, more preferably less than about 10%, and still more preferably less than about 5%. In addition, on the basis of metabolic stability test using S9 in the human or mammal (e.g. hamster, etc.) small intestine, it means that the remaining rate of unaltered form is about 5 times or more higher, preferably about 10 times or more higher than that in the case of treatment with liver S9. The unaltered form means a compound which does not undergo metabolism in the living body and of which chemical structure is not changed in the living body. The compound of the present invention has a characteristic property of selective inhibition to the MTP in the small intestine.

The expression "it is metabolized to the amount at which the remaining MTP inhibitor in the liver does not substantially inhibit the MTP in the liver" means that almost all of the orally administered MTP inhibitors are metabolized to an inactive metabolite before arriving at the liver or at the moment of arriving at the liver and show substantially no MTP inhibitory activity in the liver, i.e. the MTP inhibitors are converted to those that do not substantially inhibit TG release from the liver. More specifically, it means the condition where TG-releasing activity of the liver is kept at the level of about 80% or more, preferably about 90% or more, more preferably 100% of the normal level. In terms of metabolism, it means that the ratio of inactive metabolite to unaltered form in portal vein blood is approximately 8 or more to 1 one hour after the oral administration to hamsters, i.e. about 80% or more of the agent (compound) is metabolized before arriving at the liver, or on the basis of liver S9 metabolic stability test, it means that 10 minutes after the test using human or mammal (e.g. hamster, etc.) S9 the remaining rate of unaltered form is about 20% or less, preferably about 10% or less, more preferably about 8% or less. The compound of the present invention has a characteristic property of being metabolized to the amount at which it does not substantially inhibit the liver MTP.

The expression "MTP inhibitor does not substantially inhibit MTP in the liver" has essentially the same meaning with the above "it is metabolized to the amount at which the remaining MTP inhibitor in the liver does not substantially inhibit the MTP in the liver", and means the condition where TG-releasing activity of the liver is kept at the level of about 80% or more, preferably about 90% or more, more preferably 100% of the normal level. The compound of the present invention has a characteristic property of no substantial inhibition of the liver MTP.

The compound of the present invention or its pharmaceutically acceptable salt may be contained as an active ingredient in a pharmaceutical composition (preferably a pharmaceutical composition for the treatment or prophylaxis of hyperlipidemia, arteriosclerosis, coronary artery diseases, obesity, diabetes or hypertension), microsomal triglyceride transfer protein inhibitors, or agents of lowering at least one of blood lipid parameters selected from triglyceride, total cholesterol, chylomicron, VLDL, LDL, and apolipoprotein B, together with a pharmaceutically acceptable carrier.

As "pharmaceutically acceptable carrier", various organic or inorganic carrier materials which are conventionally used as formulation material are used, and it is formulated as excipient, lubricant, binder, disintegrating agent, solvent, solubilizer, suspending agent, isotonizing agent, buffer, soothing agent, etc. If desired, pharmaceutical additives such as preservative, antioxidant, coloring agent, sweetening agent, etc. may be also used. Preferable examples of said excipient include lactose, sucrose, D-mannitol, starch, crystalline cellulose, light anhydrous silicic acid, etc. Preferable examples of said lubricant include magnesium stearate, calcium stearate, talc, colloidal silica, etc. Preferable examples of said binder include crystalline cellulose, sucrose, D-mannitol, dextrin, hydroxypropyl cellulose, hydroxypropyl methylcellulose, polyvinylpyrrolidone, etc. Preferable examples of said disintegrating agent include starch, carboxymethylcellulose, carboxymethylcellulose calcium, crosscarmellose sodium, sodium carboxymethylstarch, etc. Preferable examples of said solvent include water for injection, alcohol, propylene glycol, macrogol, sesame-seed oil, corn oil, propylene glycol fatty acid ester, etc. Preferable examples of said solubilizer include polyethyleneglycol, propyleneglycol, D-mannitol, benzyl benzoate, ethanol, trisaminomethane, cholesterol, triethanolamine, sodium carbonate, sodium citrate, etc. Preferable examples of said suspending agent include surfactants (e.g. stearyl triethanolamine, sodium lauryl sulfate, lauryl aminopropionic acid, lecithin, benzalkonium chloride, benzethonium chloride, glycerin monostearate, etc), polyvinyl alcohol, polyvinylpyrrolidone, carboxymethylcellulose sodium, methylcellulose, hydroxymethyl cellulose, etc. Preferable examples of said isotonizing agent include sodium chloride, glycerin, D-mannitol, etc. Preferable examples of said buffer include phosphate, acetate, carbonate, citrate, etc. Preferable examples of said soothing agent include benzyl alcohol, etc. Preferable examples of said preservative include paraoxybenzoic acid esters, chlorobutanol, benzyl alcohol, phenethyl alcohol, dehydroacetic acid, sorbic acid, etc. Preferable examples of said antioxidant include sulfites, ascorbic acid, etc. Preferable examples of said sweetening agent include aspartame, saccharin sodium, stevia, etc. Preferable examples of said coloring agent include food colors such as food yellow No. 5, food red No. 2 and food blue No. 2, lake colors for food, iron oxide, etc.

When the compound of the present invention or its pharmaceutically acceptable salt is used as an active ingredient for pharmaceutical compositions (preferably pharmaceutical compositions for the treatment or prophylaxis of hyperlipidemia, arteriosclerosis, coronary artery disease, obesity, diabetes, or hypertension), microsomal triglyceride transfer protein inhibitors, or agents of lowering at least one of blood lipid parameters selected from triglyceride, total cholesterol, chylomicron, VLDL, LDL, and apolipoprotein B, it can be administered systemically or topically and orally or parenterally. Although the dose depends on the age, body weight, symptom, therapeutic efficacy, or the like, the daily dose for an adult is usually in the range of 0.1 mg to 1 g per one dose and can be administered once to several times a day. Also, the compound of the present invention can be administered to human beings as well as animals other than human beings, especially mammals, for the treatment or prevention of said diseases.

In the formulation of the compounds of the present invention or its pharmaceutically acceptable salt into solid compositions and liquid compositions for oral administration or injections, etc., for parenteral administration, there may be added appropriate additives such as diluents, dispersants, adsorbents, solubilizers, etc. In addition, the composition of the present invention may take the known form such as tablets, pills, powders, granules, suppositories, injections, eye drops, solutions, capsules, troches, aerosols, elixirs, suspensions, emulsions, syrups, etc.

When the pharmaceutical composition of the present invention (preferably pharmaceutical compositions for the treatment or prophylaxis of hyperlipidemia, arteriosclerosis, coronary artery disease, obesity, diabetes, or hypertension), microsomal triglyceride transfer protein inhibitors, or agents of lowering at least one of blood lipid parameters selected from triglyceride, total cholesterol, chylomicron, VLDL, LDL, and apolipoprotein B are formulated into solid preparations such as tablets, pills, powders, granules, etc., examples of such an additive include lactose, mannitol, glucose, hydroxypropyl cellulose, microcrystalline cellulose, starch, polyvinylpyrrolidone, magnesium aluminometasilicate or powdery silicic anhydride. In the case where the compounds of the present invention are formulated into tablets or pills, they may be coated with a gastroenteric or enteric coating film containing a substance such as white sugar, gelatin, hydroxypropyl cellulose or hydroxymethyl cellulose phthalate. Furthermore, the tablets or pills may be multi-layered tablets comprising two or more layers.

As the pharmaceutical compositions of the present invention (preferably pharmaceutical compositions for the treatment or prophylaxis of hyperlipidemia, arteriosclerosis, coronary artery disease, obesity, diabetes, or hypertension), microsomal triglyceride transfer protein inhibitors, or lowering agents of at least one of blood lipid parameters selected from triglyceride, total cholesterol, chylomicron, VLDL, LDL, IDL and apolipoprotein B, there are also exemplified capsules in which are filled with liquid, semi-solid or solid contents prepared by dissolving the compounds of the present invention or its pharmaceutically acceptable salt in a solvent and adding an additive thereto. Examples of said solvents are purified water, ethanol, vegetable oil, etc., among which ethanol or a mixture of purified water and ethanol is preferably used. Any additives commonly used in the preparation of capsules can be used without any particular limitation. Such additives include, for example, propylene glycol fatty acid esters; low molecular weight polyethylene glycols such as polyethylene glycol 200 to 600, etc., glycerine fatty acid esters thereof, and medium chain fatty acid triglycerides thereof; alcohols/polyols such as stearyl alcohol, cetanol, polyethylene glycol, etc., or esters thereof; lipids such as sesame oil, soy bean oil, peanut oil, corn oil, hydrogenated oil, paraffin oil, bleached wax; fatty acids such as triethyl citrate, triacetin, stearic acid, palmitic acid, myristic acid, etc., and derivatives thereof. These additives are suitable for preparing liquid or semi-solid contents. In the capsules of the present invention, propylene glycol fatty acid esters are preferable as such an additive. Examples of the propylene glycol fatty acid esters are propylene glycol monocaprylate (Capmul PG-8 (Brand name)), Sefol 218 (Brandname)), Capryo 190 (Brand name), propylene glycol monolaurate (Lauroglycol FCC (Brand name), propylene glycol monooleate (Myverol P-O6 (Brand name)), propylene glycol myristate, propylene glycol monostearate, propylene glycol lisinolate (Propymuls (Brand name)), propylene glycol dicaprylate/dicaprate (Captex (Trademark) 200 (Brand name)) propylene glycol dilaurate, propylene glycol distearate and propylene glycol dioctanoate (Captex (Trademark) 800 (Brand name)). Although there is no particular limitation to the materials constituting the capsules of the present invention, they include, for example, polysaccharides derived from natural products such as agar, alginic acid salt, starch, xanthan, dextran, etc; proteins such as gelatin, casein, etc.; chemically processed products such as hydroxystarch, pullulan, hydroxypropyl cellulose, hydroxypropyl methylcellulose, polyvinyl alcohol or derivatives thereof, polyacryl derivatives, polyvinylpyrrolidone or derivatives thereof, polyethylene glycol, etc.

In the case where the pharmaceutical compositions of the present invention (preferably pharmaceutical compositions for the treatment or prophylaxis of hyperlipidemia, arteriosclerosis, coronary artery disease, obesity, diabetes, or hypertension), microsomal triglyceride transfer protein inhibitors, or agents of lowering at least one of blood lipid parameters selected from triglyceride, total cholesterol, chylomicron, VLDL, LDL, and apolipoprotein B are liquid formulations for oral administration such as pharmaceutically acceptable emulsions, solubilizers, suspensions, syrups or elixirs, etc., diluents to be used include, for example, purified water, ethanol, vegetable oils, emulsifiers, etc. In addition to such diluents, auxiliary agents such as wetting agents, suspending agents, sweeteners, condiments, flavors or antiseptics may be added to said liquid formulations.

In the case where the pharmaceutical compositions of the present invention (preferably pharmaceutical compositions for the treatment or prophylaxis of hyperlipidemia, arteriosclerosis, coronary artery disease, obesity, diabetes, or hypertension), microsomal triglyceride transfer protein inhibitors, or lowering agents of at least one of blood lipid parameters selected from triglyceride, total cholesterol, chylomicron, VLDL, LDL, and apolipoprotein B are parenteral formulations such as injections, there are employed sterilized aqueous or non-aqueous solutions, solubilizers, suspending agents, emulsifiers, etc. Examples of the aqueous solutions, solubilizers and suspending agents include distilled water for injections, physiological saline, cyclodextrin, and derivatives thereof; organic amines such as triethanolamine, diethanolamine, monoethanolamine, triethylamine, etc.; and inorganic alkaline solutions. When aqueous solutions are employed, for example, propylene glycol, polyethylene glycol or vegetable oils such as olive oil, or alcohols such as ethanol may be further added. Further, surfactants (for mixed micelle formation) such as polyoxyethylene hydrogenated castor oils, sucrose fatty acid esters, or lecithin or hydrogenated lecithin (for liposome formation), etc. can be used as a solubilizer. Furthermore, with regard to the parenteral formulations of the present invention, they may be formulated into emulsions comprising non-aqueous solubilizers such as vegetable oils, together with lecithin, polyoxyethylene hydrogenated castor oil or polyoxyethylene-polyoxypropylene glycol, etc.

Further, the present invention provides a pharmaceutical composition for the treatment or prophylaxis of hyperlipidemia, arteriosclerosis, coronary artery diseases, obesity, diabetes or hypertension, microsomal triglyceride transfer protein inhibitors, or agents of lowering at least one of blood lipid parameters selected from triglyceride, total cholesterol, chylomicron, VLDL, LDL, IDL and apolipoprotein. B. That is, the present invention is characterized by selective inhibition of MTP (microsomal triglyceride transfer protein) in the small intestine. Above all, a pharmaceutical composition or an agent which does not substantially inhibit MTP in the liver, while inhibits only MTP in the small intestine is desirable. Specifically, it is preferable that MTP inhibition of the agent in the liver is approximately ⅓ or less, preferably ¹⁄₁₀₀ or less when compared to that in the small intestine as estimated in terms of $ED_{50}$ or $ED_{20}$ As one preferred embodiment of the therapeutic or prophylactic agents of the present invention for said diseases, they inhibit MTP in the small intestine, and they are then metabolized in the small intestine, blood, and liver to the amount at which the residual agent arriving at the liver does not substantially inhibit MTP in the liver. It is particularly preferable that, when 300 mg/kg of the compound of the present invention is administered orally, the rate of liver TG release inhibition exerted by the residual compound reaching the liver is about 20% or less, preferably less than about 10%, more preferably about 0%. Specifically, it is desirable that the agent has about 40% or less, preferably about 20% or less inhibition rate of liver TG release when assayed by the method of Test Examples which will be hereinafter mentioned.

"Combination use" means a use of a plural of active ingredients as a drug, including specifically a use of combination drugs, a use of kits, and a separate administration via the same or different administration route.

The pharmaceutical compositions of the present invention (preferably pharmaceutical compositions for the treatment or prophylaxis of hyperlipidemia, arteriosclerosis, coronary artery disease, obesity, diabetes, or hypertension), microsomal triglyceride transfer protein inhibitors, or agents of lowering at least one of blood lipid parameters selected from triglyceride, total cholesterol, chylomicron, VLDL, LDL, IDL and apolipoprotein B can be used in combination with other pharmaceutical compositions or agents. As other agents, there may be exemplified drugs for the treatment or prophylaxis of hyperlipidemia, arteriosclerosis, coronary artery disease, obesity, diabetes, or hypertension, and they can be used alone or in combination with two or more kinds of said drugs. For example, one to three other drugs or agents can be combined for use.

Examples of the "agents for the treatment and/or prophylaxis of hyperlipidemia" include a statin-type drug, more specifically, lovastatin, simvastatin, pravastatin, fluvastatin, atorvastatin or cerivastatin.

Examples of the "agents for the treatment and/or prophylaxis of obesity" include mazindol or olristat.

Examples of the "agents for the treatment and/or prophylaxis of diabetes" include insulin preparations, sulfonylurea drugs, insulin secretion-promotor drugs, sulfonamide drugs, biguanide drugs, α-glucosidase inhibitors, insulin resistance-improving drugs, etc., more specifically insulin, glibenclamid, tolbutamide, glyclopyramide, acetohexamide, glimepiride, tolazamide, gliclazide, nateglinide, glibuzol, metformin hydrochloride, buformin hydrochloride, voglibose, acarbose, pioglitazone hydrochloride, etc.

Examples of the "agents for the treatment and/or prophylaxis of hypertension" include loop diuretics, angiotensin converting enzyme inhibitors, angiotensin II receptor antagonists, calcium antagonists, β-blockers, α,β-blockers and α-blockers, and more specifically, furosemide delayed release, captopril, captopril delayed release, enalapril maleate, alacepril, delapril hydrochloride, silazapril, lisinopril, benazepril hydrochloride, imidapril hydrochloride, temocapril hydrochloride, quinapril hydrochloride, trandolapril, perindopril erbumine, losartan potassium, candesartan cilexetil, nicardipine hydrochloride, nicardipine hydrochloride delayed release, nilvadipine, nifedipine, nifedipine delayed release, benidipine hydrochloride, diltiazem hydrochloride, diltiazem hydrochloride delayed release, nisoldipine, nitrendipine, manidipine hydrochloride, barnidipine hydrochloride, efonidipine hydrochloride, amlodipine besylate, felodipine, cilnidipine, aranidipine, propranolol hydrochloride, propranolol hydrochloride delayed release, pindolol, pindolol delayed release, indenolol hydrochloride, carteolol hydrochloride, carteolol hydrochloride delayed release, bunitrolol hydrochloride, bunitrolol hydrochloride delayed release, atenolol, asebutolol hydrochloride, metoprolol tartrate, metoprolol tartrate delayed release, nipradilol, penbutolol sulfate, tilisolol hydrochloride, carvedilol, bisoprolol fumarate, betaxolol hydrochloride, celiprolol hydrochloride, bopindolol malonate, bevantolol hydrochloride, labetalol hydrochloride, arotinolol hydrochloride, amosulalol hydrochloride, prazosin hydrochloride, terazosin hydrochloride, doxazosin mesylate, bunazocin hydrochloride, bunazocin hydrochloride delayed release, urapidil, and phentolamine mesylate, etc.

There is no particular limitation on the timing for the administration of pharmaceutical compositions (preferably pharmaceutical compositions for the treatment or prophylaxis of hyperlipidemia, arteriosclerosis, coronary artery disease, obesity, diabetes, or hypertension), microsomal triglyceride transfer protein inhibitors, agents of lowering at least one of blood lipid parameters selected from triglyceride, total cholesterol, chylomicron, VLDL, LDL, and apolipoprotein B, or combination drugs according to the present invention, and they may be administered simultaneously or intermittently.

The amount of such drugs for combination use can be determined based on their clinical doses, and can be chosen appropriately depending on the subjects, age, body weight, symptom, medication time, dosage form, administration route, combination, etc. There is no particular limitation on the dosage form of the drugs for combination use, and it may be sufficient that the pharmaceutical compositions or agents and other drugs for combination use according to the present invention are combined at the time of administration.

General Production

Next, a process for preparing a compound represented by the formula [1] will be illustrated below as an example, but it goes without saying that the process of the present invention is not limited thereto. In the production of the compound of the present invention, the order of the reaction may be appropriately varied. The reaction may start first from reasonable step or substitution site. For example, a compound represented by the formula (C) may be introduced prior to the introduction of a compound represented by the formula (B), and vice versa.

In addition, optional change of substituents (conversion or further modification of substituents) in each step may be inserted. In the case where a functional group is present, it may be protected and deprotected. Further, in order to accelerate the reaction, any reagents other than the reagent hereinbefore mentioned may be appropriately used. The starting material which is not described as to its preparation is a commercially available product or a compound which can be easily prepared by combination of the known synthetic methods.

Further, the reaction in each step may be carried out in the usual manner, and separation and purification may be conducted by the appropriate selection or combination of conventional methods such as crystallization, recrystallization, column chromatography, preparative HPLC, etc. Depending on the cases, separation and purification is not done, and subsequent step may be carried out.

A pharmaceutically acceptable salt of a compound represented by the formula [1] can be obtained by adding a desired acid or base to a solution of a compound represented by the formula [1] which is dissolved in a solvent, and collecting the resulting solid or concentrating it under reduced pressure. Examples of the solvent used in the reaction are ethers such as diethyl ether, tetrahydrofuran, diisopropyl ether, dioxane, 1,2-dimethoxyethane, diglyme, etc.; alcohols such as methanol, ethanol, isopropanol, n-propanol, tert-butanol, etc.; hydrocarbons such as benzene, toluene, hexane, xylene, etc.; halogenated hydrocarbons such as methylene chloride, chloroform, carbon tetrachloride, 1,2-dichloroethane, etc.; polar solvents such as acetone, methyl ethyl ketone, N,N-dimethylformamide, dimethyl sulfoxide, etc.; esters such as ethyl acetate, methyl acetate, butyl acetate, etc.; or water, and they may be used alone or in combination of two or more solvents thereof. Examples of the acid to be used are inorganic acids such as hydrochloric acid, sulfuric acid, phosphoric acid, hydrobromic acid, etc., or organic acids such as oxalic acid, malonic acid, citric acid, fumaric acid, lactic acid, malic acid, succinic acid, tartaric acid, acetic acid, trifluoroacetic acid, gluconic acid, ascorbic acid, methanesulfonic acid, benzenesulfonic acid, toric acid, naphthalene-1,5-disulfonic acid, etc. Examples of the base to be used are inorganic bases such as sodium hydroxide, potassium hydroxide, calcium hydroxide, magnesium hydroxide, ammonium hydroxide, etc.; organic bases such as methylamine, ethylamine, triethylamine, triethanolamine, ethylene diamine, tris(hydroxymethyl)methylamine, guanidine, colline, cinchonine, etc.; or amino acids such as lysine, arginine, alanine, etc.

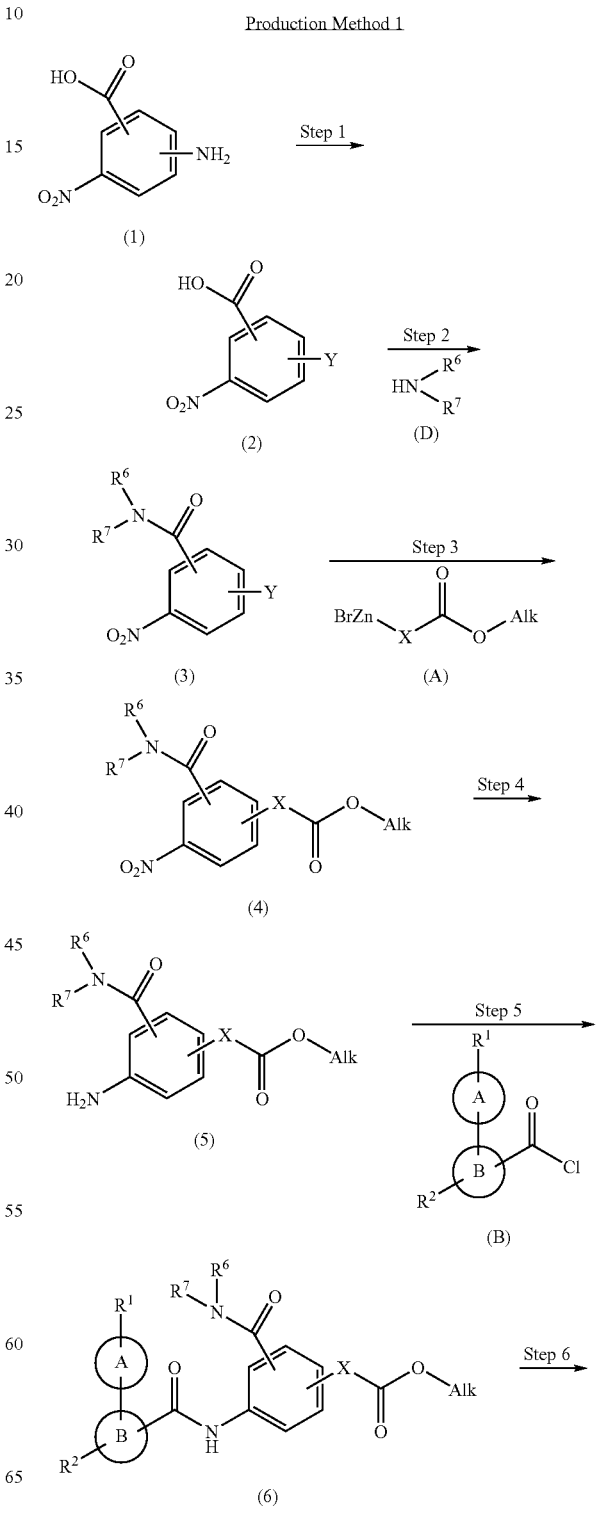

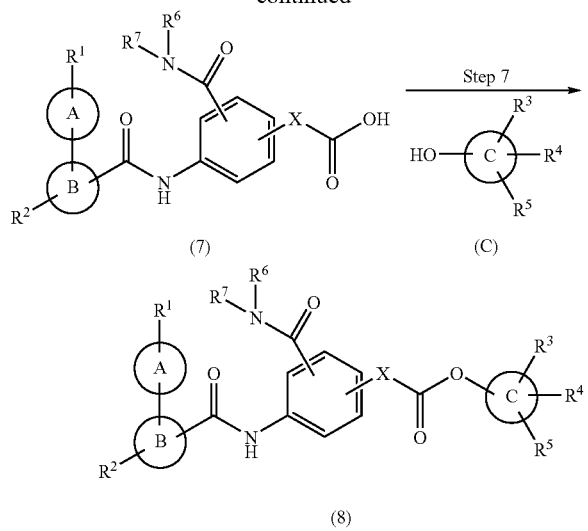

wherein $R^1$ to $R^7$, and X have each the same meanings as defined for the formula [1], Y is halogen such as chlorine, iodine and bromine, and Alk is $C_1$-$C_6$ alkyl.

Step 1: Sandmeyer Reaction

A compound represented by the formula (2) can be prepared by treating an aniline compound represented by the formula (1) with sodium nitrite in an aqueous acidic solution or an aqueous acidic suspension to convert into a diazonium salt and reacting the diazonium salt with a potassium halide or a sodium halide, preferably potassium iodide or sodium iodide (Sandmeyer Reaction).

The aqueous acidic solution used in the reaction includes, for example, hydrochloric acid, sulfuric acid, acetic acid, phosphoric acid and the like, and they can be used alone or in combination of two or more solvents thereof. A preferable aqueous acidic solution is a mixed aqueous solution of sulfuric acid and phosphoric acid.

The reaction temperature is about −20° C. to 120° C., preferably about 0° C. to room temperature.

The reaction time is about 10 minutes to 8 hours, preferably about 30 minutes to 4 hours.

Step 2: Amidation Reaction

A compound represented by the formula (3) can be prepared by reacting a carboxylic acid represented by the formula (2) with oxalyl chloride or thionyl chloride in a solvent to give an acid chloride, and condensing the acid chloride with an amine represented by the formula (D) in a solvent in the presence of a base. This reaction is a general amidation reaction using an acid chloride and an amine.

Examples of the solvent used for obtaining the acid chloride are ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; or esters such as ethyl acetate, methyl acetate, butyl acetate, etc. and they may be used alone or in combination of two or more solvents thereof. A preferable solvent used in this reaction includes methylene chloride, chloroform, and toluene, all of which contain a catalytic amount of N,N-dimethylformamide.

The reaction temperature is about −20° C. to 120° C., preferably about 0° C. to room temperature.

The reaction time is about 10 minutes to 8 hours, preferably about 30 minutes to 4 hours.

Examples of the solvent used in the amidation reaction between the acid chloride and the amine are ethers such as diethyl ether, tetrahydrofuran, diisopropyl ether, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; or esters such as ethyl acetate, methyl acetate, butyl acetate, etc., and they may be used alone or in combination of two or more solvents thereof. A preferable solvent used in this reaction includes methylene chloride, chloroform, toluene, ethyl acetate and tetrahydrofuran.

Examples of the base used in the reaction are organic bases such as triethylamine, pyridine, dimethylaminopyridine, and N-methylmorpholine; alkali metal hydroxides such as lithium hydroxide, sodium hydroxide, and potassium hydroxide; alkali metal carbonates such as sodium carbonate, potassium carbonate, sodium hydrogen carbonate and potassium hydrogen carbonate, among which triethylamine, sodium hydroxide or sodium hydrogen carbonate is preferable.

The reaction temperature is about 0° C. to 80° C., preferably about 0° C. to room temperature.

The reaction time is about 10 minutes to 48 hours, preferably about 30 minutes to 24 hours.

Alternatively, a compound represented by the formula (3) can be prepared by condensing a compound represented by the formula (2) with a compound represented by the formula (D) in the presence of, for example, a water-soluble carbodiimide such as 1-ethyl-3-(3'-dimethylaminopropyl)carbodiimide (hereinafter also referred to as WSC) hydrochloride, dicyclohexylcarbodiimide (DCC), diphenylphosphoryl azide (DPPA) carbonyldiimidazole (CDI), and bromo-tris-pyrrolidinophosphonium hexafluorophosphate (Pybrop), or if necessary, by condensation reaction using a combination of an acid additive (e.g. 1-hydroxy-1H-benzotriazole (HOST), etc.) and a base. Further, a compound represented by the formula (3) can also be prepared by converting a compound represented by the formula (2) into a mixed anhydride, followed by the reaction with a compound represented by the formula (D) in the presence of a base.

Step 3; Negishi Reaction

A compound represented by the formula (4) can be prepared by cross-coupling reaction between a compound represented by the formula (3) and a compound represented by the formula (A) (Reformatsky reagent) in a solvent in the presence of a catalyst comprising a palladium and a phosphorus ligand.

Examples of the solvent used in the reaction are ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; or polar solvents such as acetone, N,N-dimethylformamide, N,N-dimethylacetamide, dimethyl sulfoxide, etc., and they may be used alone or in combination of two or more solvents thereof. A preferable solvent used in this reaction includes ethers such as diethyl ether, tetrahydrofuran, dioxane, 1,2-dimethoxyethane, and diglyme; and polar solvents such as N,N-dimethylformamide and N,N-dimethylacetamide.

Examples of the catalyst used in the reaction are bis(triphenylphosphine)palladium(II) dichloride, tetrakis(triphenylphosphine)palladium(0) and the like, and bis(triphenylphosphine)palladium(II) dichloride is preferable.

The reaction temperature is about −20° C. to 120° C., preferably about 0° C. to room temperature.

The reaction time is about 10 minutes to 8 hours, preferably about 30 minutes to 4 hours.

Step 4: Reduction of Nitro Group

This reaction is a general reduction reaction for the nitro group attached directly to an aromatic ring. A compound represented by the formula (5) can be prepared by hydrogenation of a nitro compound represented by the formula (4) in a solvent in the presence of a catalyst.

Examples of the solvent used in the reaction are ethers such as diethyl ether, tetrahydrofuran, dioxane, 1,2-dimethoxyethane, diglyme, etc.; alcohols such as methanol, ethanol, isopropyl alcohol, tert-butanol, etc.; or esters such as ethyl acetate, methyl acetate, butyl acetate, etc.; and they may be used alone or in combination of two or more solvents thereof. A preferable example of the solvent used in this reaction is an alcohol solvent such as methanol, ethanol, isopropyl alcohol, and tert-butanol, or a mixed solvent of said alcohol solvent and tetrahydrofuran and/or water.

The catalyst used in the reaction includes palladium-carbon, palladium hydroxide, Raney-nickel, and platinum oxide, among which palladium-carbon is preferred.

The reaction temperature is about 0° C. to 120° C., preferably about room temperature to 50° C.

The reaction time is about 30 minutes to 8 days, preferably about 1 hour to 96 hours.

Alternatively, a compound represented by the formula (5) can also be prepared by reacting a nitro compound represented by the formula (4) with a metal reagent such as iron, zinc, tin and tin chloride in the presence or absence of an acid at room temperature or under heating.

Step 5: Reaction of Acid Chloride with Amine

This step is a general reaction between an acid chloride and an amine, and a compound represented by the formula (6) can be prepared by condensing an acid chloride represented by the formula (B) with an amine represented by the formula (5) in a solvent in the presence of a base.

Examples of the solvent used in the reaction are ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; or esters such as ethyl acetate, methyl acetate, butyl acetate, etc., and they may be used alone or in combination of two or more solvents thereof. A preferable example of the solvent used in this reaction is methylene chloride, chloroform, toluene, ethyl acetate or tetrahydrofuran.

Examples of the base used in the reaction are organic bases such as triethylamine, pyridine, dimethylaminopyridine, N-methylmorpholine, etc.; alkali metal hydroxides such as lithium hydroxide, sodium hydroxide, potassium hydroxide, etc.; alkali metal carbonates such as sodium carbonate, potassium carbonate, sodium hydrogen carbonate, potassium hydrogen carbonate, etc., among which triethylamine, sodium hydroxide or sodium hydrogen carbonate is preferable.

The reaction temperature is about 0° C. to 80° C., preferably about 0° C. to room temperature.

The reaction time is about 10 minutes to 48 hours, preferably about 30 minutes to 24 hours.

Step 6: Hydrolysis Reaction

A compound represented by the formula (7) can be prepared by ester hydrolysis of a compound represented by the formula (6) in a solvent in the presence of a base.

Examples of the solvent used in the reaction are ethers such as diethyl ether, tetrahydrofuran, dioxane, 1,2-dimethoxyethane, diglyme, etc.; alcohols such as methanol, ethanol, isopropyl alcohol, tert-butanol, etc.; or water, and they may be used alone or in combination of two or more solvents thereof. A preferable example of the solvent used in this reaction is a mixed solvent of tetrahydrofuran and ethanol or methanol.

Examples of the base used in the reaction are alkali metal hydroxides such as lithium hydroxide, sodium hydroxide, potassium hydroxide, etc.; or alkali metal carbonates such as sodium carbonate, potassium carbonate, etc., among which sodium hydroxide is preferable.

The reaction temperature is about 0° C. to 120° C., preferably about room temperature to 80° C.

The reaction time is about 1 hour to 24 hours, preferably about 2.5 hours to 12 hours.

Step 7: Condensation Between Carboxylic Acid and Phenol

This step is a general condensation reaction between a carboxylic acid and a phenol. One of the objective compounds represented by the formula (8), i.e. a compound represented by the formula [1] of the present invention can be prepared by condensing a carboxylic acid represented by the formula (7) with a phenol represented by the formula (C) in a solvent in the presence of a base and a condensing agent.

Examples of the solvent used in the reaction are ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; or polar solvents such as acetone, N,N-dimethylformamide, dimethyl sulfoxide, etc., and they may be used alone or in combination of two or more solvents thereof. A preferable example of the solvent used in this reaction is tetrahydrofuran, acetone, methylene chloride, or N,N-dimethylformamide.

Examples of the base used in the reaction are an organic base such as triethylamine, pyridine, dimethylaminopyridine, N-methylmorpholine, etc., among which dimethylaminopyridine is preferable.

Examples of the condensing agent used in the reaction are WSC hydrochloride, dicyclohexylcarbodiimide (DCC) diphenylphosphoryl azide (DPPA), carbonyldiimidazole (CDI), or bromo-tris-pyrrolidinophosphonium hexafluorophosphate (Pybrop), or if necessary, a combination of an acid additive (e.g. 1-hydroxy-1H-benzotriazole (HOST), etc.) and said condensing agent, among which 1-ethyl-3-(3'-dimethylaminopropyl)carbodiimide hydrochloride is preferable.

The reaction temperature is about 0° C. to 80° C., preferably about 0° C. to room temperature.

The reaction time is about 1 hour to 48 hours, preferably about 3 hours to 24 hours.

As an alternative method, a carboxylic acid represented by the formula (7) may be converted into a mixed anhydride, which may be then reacted with a phenol represented by the formula (C) in the presence of a base.

In addition, other compounds represented by the formula (8) may be obtained by conversion or modification of a substituent in a compound represented by the formula (8). For example, a carboxylic acid represented by the formula (8) may be obtained by hydrogenation of a compound represented by the formula (8) wherein any one of substituents of $R^3$ to $R^5$ has a benzyl ester bond, in a solvent in the presence of a catalyst.

The solvent and the base used in this reaction are those as mentioned above in the preceding paragraph of step 4.

Examples of the compounds prepared according to Production Method 1 include Compound 1-1 to Compound 1-123.

Production Method 2

A compound represented by the formula [1] wherein X is $-(CH_2)_m-NR^{18}-(CH_2)_n-$ (m, $R^{18}$ and n have each the same meanings as the definitions for the formula [1]) will be illustrated below:

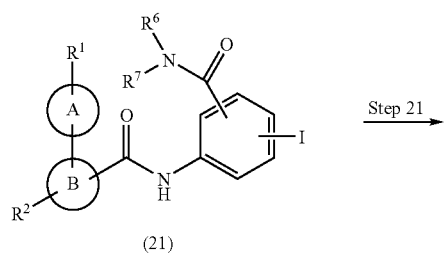

(21)

Step 21 →

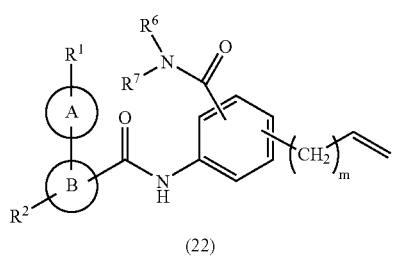

(22)

Step 22 →

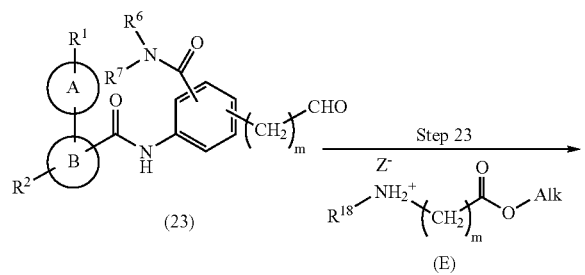

(23)

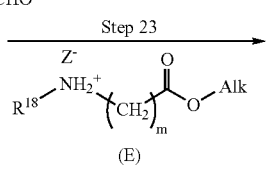

(E)

Step 23 →

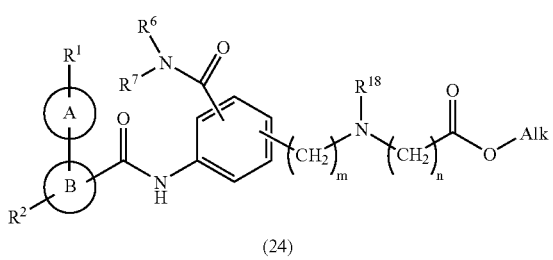

(24)

Step 24 ↙

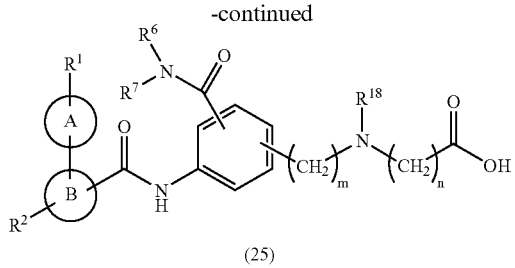

(25)

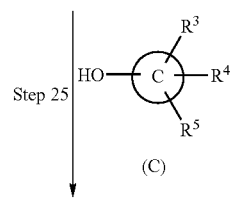

(C)

Step 25 ↓

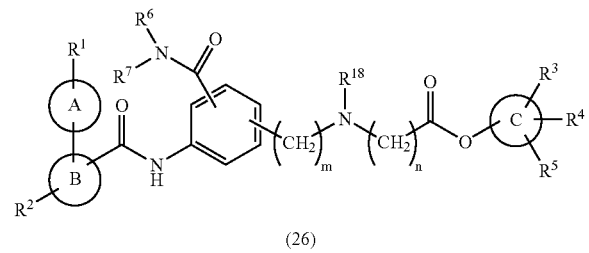

(26)

wherein $R^1$ to $R^7$, $R^{18}$, ring A, ring B, ring C, m and n have each the same meanings as defined for the formula [1], $Z^-$ is a halogen ion such as chlorine ion, iodine ion and bromine ion, and Alk is a $C_1$-$C_6$ alkyl.

Step 21: Coupling Reaction

A compound represented by the formula (22) can be prepared by subjecting a compound represented by the formula (21) to Stille cross-coupling reaction with a trialkyl-1-alkenyltin (e.g. tributylvinyltin, etc.) or to Suzuki vinyl-coupling reaction with a 1-alkenylboronic acid (e.g. vinylboronic acid pinacol ester, vinylboronic acid dibutyl ester, etc.) in a solvent in the presence of a palladium complex and in the presence or absence of a base and an additive.

Examples of the solvent used in the reaction are ethers such as diethyl ether, tetrahydrofuran, dioxane, 1,2-dimethoxyethane, diglyme, etc.; hydrocarbons such as benzene, toluene, hexane, xylene, etc.; esters such as ethyl acetate, methyl acetate, butyl acetate, etc.; halogenated hydrocarbons such as methylene chloride, chloroform, carbon tetrachloride, 1,2-dichloroethane, etc.; alcohols such as methanol, ethanol, isopropyl alcohol, tert-butanol, etc.; polar solvents such as acetone, N,N-dimethylformamide, dimethyl sulfoxide, etc.; or water, and they may be used alone or in combination of two or more solvents thereof. A preferable example of the solvent used in this reaction is a hydrocarbon solvent such as benzene, toluene, hexane, xylene, etc.

Examples of the palladium complex used in the reaction are dichlorobis(triphenylphosphine)palladium(II), tetrakis(triphenylphosphine)palladium(0), (1,1'-bis(diphenylphosphino)ferrocene)dichloropalladium(II), etc., among which tetrakis(triphenylphosphine)palladium(0) is preferable. In the case where palladium-carbon, palladium(II) acetate, tris(dibenzylideneacetone)dipalladium(0), or palladium(0)bis(dibenzylideneacetone) is used, an additive such as triphenylphosphine, tri-o-tolylphosphine, tri-n-butylphosphine, tri(2-furyl)phosphine, diphenylphosphinoferrocene, etc. is used.

Examples of the base used in the reaction are sodium carbonate, potassium carbonate, sodium hydrogen carbonate, potassium hydrogen carbonate, potassium phosphate, triethylamine or the like. Suzuki vinyl coupling reaction with 1-alkenylboronic acids is carried out using any one of these bases.

The reaction temperature is about −20° C. to 200° C., preferably about 0° C. to 150° C.

The reaction time is about 10 minutes to 24 hours, preferably about 1 hour to 12 hours.

Step 22: Carbonyl Formation Reaction

A compound represented by the formula (23) can be prepared by converting directly a compound represented by the formula (22) into an aldehyde or a ketone from olefins in a solvent via a 1,2-diol without isolation.

Examples of the solvent used in the reaction are ethers such as diethyl ether, tetrahydrofuran, dioxane, 1,2-dimethoxyethane, diglyme, etc.; polar solvents such as acetone, etc.; or water, and they may be used alone or in combination of two or more solvents thereof. A preferable example of the solvent used in this reaction is a mixed solvent of acetone and water.

Examples of a reagent for directly converting an olefine into an aldehyde or a ketone via a 1,2-diol are ozone-dimethyl sulfide, sodium metaperiodate-osmium tetroxide, etc., among which sodium metaperiodate-osmium tetroxide is preferable. The above reaction may be performed by stepwise reaction or two-step reaction.

The reaction temperature is about −20° C. to 80° C., preferably about 0° C. to room temperature.

The reaction time is about 10 minutes to 24 hours, preferably about 1 hour to 6 hours.

Step 23: Reductive Amination Reaction

A compound represented by the formula (24) can be prepared by reductive amination of a compound represented by the formula (23) and a compound represented by the formula (E) in a solvent in the presence or absence of an acid.

Examples of the solvent used in the reaction are ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; or esters such as ethyl acetate, methyl acetate, butyl acetate, etc.; and they may be used alone or in combination of two or more solvents thereof. A preferable example of the solvent used in this reaction is a halogenated hydrocarbon solvent such as methylene chloride, dichloromethane, chloroform, carbon tetrachloride, 1,2-dichloroethane, etc.

Examples of the reducing agent used in the reaction are sodium borohydride, sodium cyanoborohydride, sodium triacetoxyborohydride, hydrogen/palladium-carbon, etc., among which sodium triacetoxyborohydride is preferable.

Examples of the acid used in the reaction are acetic acid, hydrochloric acid, p-toluenesulfonic acid, methanesulfonic acid, etc., among which hydrochloric acid or acetic acid is preferable.

The reaction temperature is about −20° C. to 80° C., preferably about 0° C. to room temperature.

The reaction time is about 10 minutes to 24 hours, preferably about 30 minutes to 6 hours.

Step 24: Hydrolysis Reaction

A compound represented by the formula (25) can be prepared by ester hydrolysis of a compound represented by the formula (24) in a solvent in the presence of a base. In the case where the ester (24) is a benzyl ester, the benzyl group may also be removed by hydrogenolysis.

Examples of the solvent used in the reaction are ethers such as diethyl ether, tetrahydrofuran, dioxane, 1,2-dimethoxyethane, diglyme, etc.; alcohols such as methanol, ethanol, isopropyl alcohol, tert-butanol, etc.; or water; and they may be used alone or in combination of two or more solvents thereof. A preferable example of the solvent used in this reaction is a mixed solvent of tetrahydrofuran and ethanol or methanol.

Examples of the base used in the reaction are an alkali metal hydroxide such as lithium hydroxide, sodium hydroxide, potassium hydroxide, etc., among which sodium hydroxide is preferable.

The reaction temperature is about 0° C. to 120° C., preferably about room temperature to 80° C.

The reaction time is about 1 hour to 24 hours, preferably about 2 hours to 12 hours.

Step 25: Condensation Reaction Between Carboxylic Acid and Phenol

This step is a general condensation reaction between a carboxylic acid and a phenol. One of the objective compounds represented by the formula (26) can be prepared by condensing a carboxylic acid represented by the formula (25) with a phenol represented by the formula (C) in a solvent in the presence of a base and a condensing agent.

Examples of the solvent used in the reaction are ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; polar solvents such as acetone, N,N-dimethylformamide, dimethyl sulfoxide, etc.; and they may be used alone or in combination of two or more solvents thereof. A preferable example of the solvent used in this reaction is tetrahydrofuran, acetone, methylene chloride or N,N-dimethylformamide.

Examples of the base used in the reaction are organic amines such as triethylamine, pyridine, dimethylaminopyridine, N-methylmorpholine, etc., among which dimethylaminopyridine is preferable.

Examples of the condensing agent used in the reaction are WSC hydrochloride, dicyclohexylcarbodiimide (DCC), diphenylphosphoryl azide (DPPA), carbonyldiimidazole (CDI), or bromo-tris-pyrrolidinophosphonium hexafluorophosphate (Pybrop), or if necessary, a combination of an acid additive (e.g. 1-hydroxy-1H-benzotriazole (HOBT), etc.) and said condensing agent, among which 1-ethyl-3-(3'-dimethylaminopropyl)carbodiimide hydrochloride is preferable.

The reaction temperature is about 0° C. to 80° C., preferably about 0° C. to room temperature.

The reaction time is about 1 hour to 48 hours, preferably about 3 hours to 24 hours.

As an alternative method, a carboxylic acid compound represented by the formula (25) may be converted into a mixed anhydride, followed by the reaction with a phenol represented by the formula (C) in the presence of a base.

In addition, other compounds represented by the formula (26) may be obtained by conversion or modification of a substituent in a compound represented by the formula (26). For example, a compound represented by the formula (26) may be obtained by hydrogenation of a compound represented by the formula (26) wherein any one of substituents of $R^3$ to $R^5$ has a benzyl ester bond, in a solvent in the presence of a catalyst. The solvent and the base used in this reaction are those as mentioned above in the preceding paragraph of step 4 of Production Method 1.

A compound prepared according to Production Method 2 includes, for example, compound 2-1.

Production Method 3

A compound represented by the formula [1] wherein X is

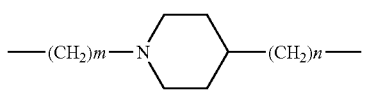

(wherein m is 0, and n has the same meaning as defined for a compound of the formula [1]) will be illustrated below:

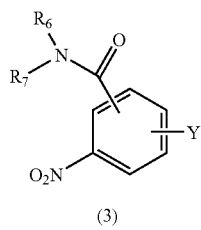

(3)

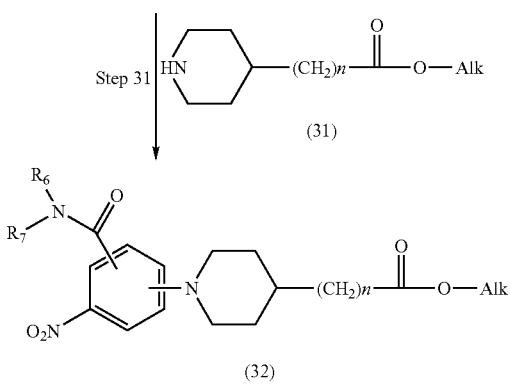

wherein $R^6$, $R^7$ and n have each the same meanings as defined for the formula [1], Y is a halogen such as fluorine, chlorine, iodine and bromine, and Alk is an $C_1$-$C_6$ alkyl.

Step 31: Aromatic Nucleophilic Substitution

A compound represented by the formula (32) can be prepared by reacting a compound represented by the formula (3) obtained in step 2 of Production Method 1, with a compound represented by the formula (31) in a solvent in the presence of a base.

Examples of the solvent used in the reaction are ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; alcohols such as methanol, ethanol, isopropyl alcohol, tert-butanol, etc.; polar solvents such as acetone, N,N-dimethylformamide, dimethyl sulfoxide, etc.; or water, and they may be used alone or in combination of two or more solvents thereof.

A preferable example of the solvent used in this reaction is acetone, N,N-dimethylformamide, dimethyl sulfoxide or the like.

Examples of the base used in the reaction are potassium carbonate, sodium carbonate, sodium hydrogen carbonate, sodium hydride, triethylamine, pyridine, potassium tert-butoxide, sodium acetate, potassium fluoride, butyl lithium, phenyl lithium or the like, among which potassium carbonate is preferable.

When necessary, a combination of a copper catalyst (e.g. copper iodide, etc.) or a palladium catalyst (e.g. palladium acetate, etc.) with a phosphorus ligand (e.g. 2,2-bis(diphenylphosphino)-1,1-binaphthyl, etc.) may be employed.

The reaction temperature is about 40° C. to 200° C., preferably about 80° C. to 150° C.

The reaction time is about 60 minutes to 24 hours, preferably about 4 hours to 8 hours.

Following a similar reaction to the methods as described in step 4 to step 7 of Production Method 1, there can be obtained a compound represented by the formula (8), i.e. a compound represented by the formula [1] of the present invention.

Examples of the compound prepared according to Production Method 3 include Compound 3-1 and Compound 3-2.

Production Method 4

A compound represented by the formula [1] wherein $R^1$ is —CO—$C_1$-$C_6$ alkoxy will be illustrated below:

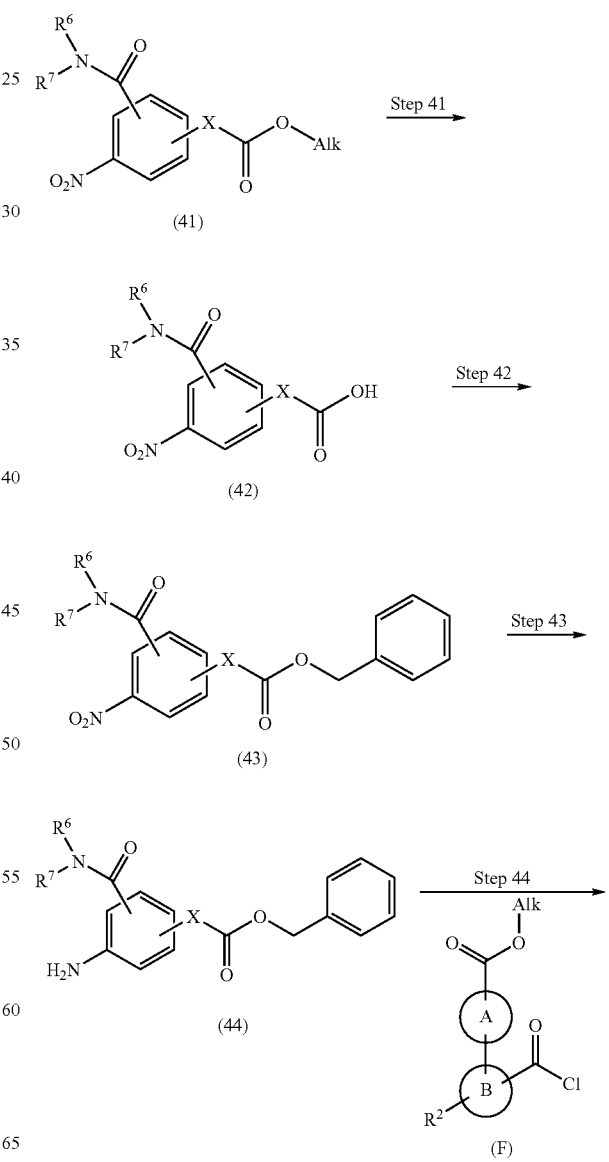

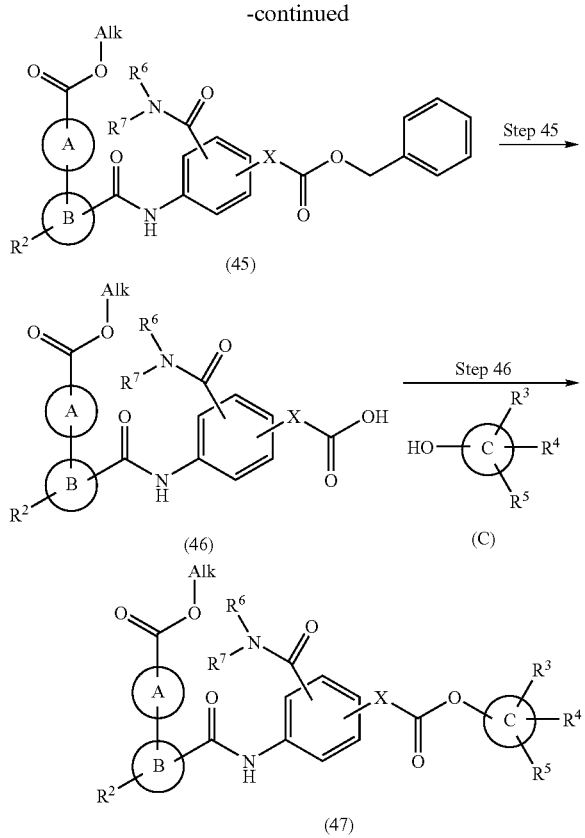

wherein $R^2$ to $R^7$, and X have each the same meanings as defined for the formula [1], and Alk is a $C_1$-$C_6$ alkyl group.

Step 41: Hydrolysis Reaction

A compound represented by the formula (42) can be prepared by hydrolysis of the ester of a compound represented by the formula (41) similarly obtained according to the methods as described in step 1 to step 3 of Production Method 1, in a solvent in the presence of a base.

Examples of the solvent used in the reaction are ethers such as diethyl ether, tetrahydrofuran, dioxane, 1,2-dimethoxyethane, diglyme, etc.; alcohols such as methanol, ethanol, isopropyl alcohol, tert-butanol, etc.; or water, and they may be used alone or in combination of two or more solvents thereof. A preferable example of the solvent used in this reaction is a mixed solvent of tetrahydrofuran and ethanol or methanol.

Examples of the base used in the reaction are alkali metal hydroxides such as lithium hydroxide, sodium hydroxide, potassium hydroxide, etc.; or alkali metal carbonates such as sodium carbonate, potassium carbonate, etc., among which sodium hydroxide is preferable.

The reaction temperature is about 0° C. to 120° C., preferably about room temperature to 80° C.

The reaction time is about 1 hour to 24 hours, preferably about 1 hour to 6 hours.

Step 42: Esterification Reaction

A compound represented by the formula (43) can be prepared by treating a carboxylic acid represented by the formula (42) with an alkyl halide (e.g. benzyl bromide, etc.) according to the general esterification reaction, in a solvent in the presence of a base. In this step, a protecting group which is removable under the condition other than alkaline conditions, such as benzyl ester, p-methoxybenzyl ester, etc. is chosen.

Examples of the solvent used in the reaction are ethers such as diethyl ether, tetrahydrofuran, dioxane, 1,2-dimethoxyethane, diglyme, etc.; or polar solvents such as acetone, N,N-dimethylformamide, dimethyl sulfoxide, etc., and they may be used alone or in combination of two or more solvents thereof. A preferable example of the solvent used in this reaction is N,N-dimethylformamide.

Examples of the base used in the reaction are an organic base such as triethylamine, pyridine, dimethylaminopyridine, N-methylmorpholine, etc.; an alkali metal hydroxide such as lithium hydroxide, sodium hydroxide, potassium hydroxide, etc.; or an alkali metal carbonate such as sodium carbonate, potassium carbonate, sodium hydrogen carbonate, potassium hydrogen carbonate, etc., among which potassium carbonate or sodium hydrogen carbonate is preferable.

The reaction temperature is about 0° C. to 120° C., preferably about room temperature to 80° C.

The reaction time is about 1 hour to 24 hours, preferably about 1 hour to 6 hours.

In this step, it is possible to select tert-butyl ester which is removable with an acid, and an allyl ester which is removable by hydrogenation using a palladium catalyst.

Step 43: Reduction Reaction of Nitro Group

This reaction is a general reduction reaction for the nitro group attached directly to an aromatic ring. An amine compound represented by the formula (44) can be prepared by treating a nitro compound represented by the formula (43) with a metal reagent in a solvent in the presence or absence of an acid at room temperature or under heating.

Examples of the solvent used in the reaction are ethers such as diethyl ether, tetrahydrofuran, dioxane, 1,2-dimethoxyethane, diglyme, etc.; alcohols such as methanol, ethanol, isopropyl alcohol, tert-butanol, etc.; esters such as ethyl acetate, methyl acetate, butyl acetate, etc.; or water, and they may be used alone or in combination of two or more solvents thereof. A preferable example of the solvent used in this reaction is a mixed solvent of ethanol, tetrahydrofuran and water.

Example of the metal reagent used in the reaction is iron, zinc, tin or tin chloride, among which iron is preferable.

The reaction temperature is about 0° C. to 120° C., preferably about room temperature to 100° C.

The reaction time is about 30 minutes to 8 days, preferably about 1 hour to 5 hours.

In the case where the ester group in the nitro compound is an ester group which is not removable by hydrogenation, such as tert-butyl ester and allyl ester, said ester compound is subjected to hydrogenation with palladium-carbon, palladium hydroxide, Raney-nickel or platinum oxide, thereby to also give a corresponding compound represented by the formula (44).

Step 44: Amidation Reaction of Acid Chloride with Amine

This step is a general condensation reaction between an acid chloride and an amine. A compound represented by the formula (45) can be prepared by condensing an acid chloride represented by the formula (F) with an amine represented by the formula (44) in a solvent in the presence of a base.

Examples of the solvent used in the reaction are ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; or water, and they may be used alone or in combination of two or more solvents thereof. A preferable example of the solvent used in this reaction is chloroform, toluene, ethyl acetate or tetrahydrofuran.

Examples of the base used in the reaction are an organic base such as triethylamine, pyridine, dimethylaminopyridine, N-methylmorpholine, etc.; an alkali metal hydroxide such as lithium hydroxide, sodium hydroxide, potassium hydroxide, etc.; or an alkali metal carbonate such as sodium carbonate, potassium carbonate, sodium hydrogen carbonate, potassium hydrogen carbonate, etc., among which triethylamine or sodium hydrogen carbonate is preferable.

The reaction temperature is about 0° C. to 80° C., preferably about 0° C. to room temperature.

The reaction time is about 10 minutes to 48 hours, preferably about 30 minutes to 24 hours.

Step 45: Deprotection of Ester Group

This step is a deprotection of an ester group. In the case where benzyl ester, etc., which is removable by hydrogenation is employed, a carboxylic acid represented by the formula (46) can be prepared by hydrogenation of an ester represented by the formula (45) in a solvent in the presence of a catalyst.

Examples of the solvent used in the reaction are ethers such as diethyl ether, tetrahydrofuran, dioxane, 1,2-dimethoxyethane, diglyme, etc.; alcohols such as methanol, ethanol, isopropyl alcohol, tert-butanol, etc.; or esters such as ethyl acetate, methyl acetate, butyl acetate, etc., and they may be used alone or in combination of two or more solvents thereof. A preferable example of the solvent used in this reaction is an alcohol solvent such as methanol, ethanol, isopropyl alcohol, tert-butanol, or a mixed solvent of said alcohol and tetrahydrofuran.

Examples of the catalyst used in the reaction are palladium-carbon, palladium hydroxide, Raney-nickel, platinum oxide, etc., among which palladium-carbon is preferable.

The reaction temperature is about 0° C. to 120° C., preferably about room temperature to 50° C.

The reaction time is about 30 minutes to 8 hours, preferably about 1 hour to 4 hours.

In addition, tert-butyl ester may be deprotected with an acid, and allyl ester may be deprotected using a catalyst such as dichlorobis(triphenylphosphine)palladium(II) or tetrakis(triphenylphosphine)palladium(0).

Step 46: Condensation Between Carboxylic Acid and Phenol

This step is a general condensation reaction between a carboxylic acid and a phenol. One of the objective compounds represented by the formula (47), i.e. a compound represented by the formula [1] of the present invention can be prepared by condensing a carboxylic acid represented by the formula (46) with a phenol represented by the formula (C) in a solvent in the presence of a base and a condensing agent.

Examples of the solvent used in the reaction are ethers such as diethyl ether, tetrahydrofuran, dioxane, 1,2-dimethoxyethane, diglyme, etc.; hydrocarbons such as benzene, toluene, hexane, xylene, etc.; halogenated hydrocarbons such as methylene chloride, chloroform, carbon tetrachloride, 1,2-dichloroethane, etc.; esters such as ethyl acetate, methyl acetate, butyl acetate, etc.; or polar solvents such as acetone, N,N-dimethylformamide, dimethyl sulfoxide, etc., and they may be used alone or in combination of two or more solvents thereof. A preferable example of the solvent used in this reaction is tetrahydrofuran, acetone, chloroform or N,N-dimethylformamide.

Examples of the base used in the reaction are an organic amine such as triethylamine, pyridine, dimethylaminopyridine, N-methylmorpholine, etc., among which dimethylaminopyridine is preferable.

Examples of the condensing agent used in the reaction are 1-ethyl-3-(3'-dimethylaminopropyl)carbodiimide hydrochloride (WSC.HCl), dicyclohexylcarbodiimide (DCC), diphenylphosphoryl azide (DPPA), carbonyldiimidazole (CD), or bromo-tris-pyrrolidinophosphonium hexafluorophosphate (Pybrop), or if necessary, a combination of an acid additive (e.g. 1-hydroxy-1H-benzotriazole (HOBT), etc.) and said condensing agent, among which 1-ethyl-3-(3'-dimethylaminopropyl) carbodiimide hydrochloride (WSC.HCl) is preferable.

The reaction temperature is about 0° C. to 80° C., preferably about 0° C. to room temperature.

The reaction time is about 1 hour to 48 hours, preferably about 3 hours to 24 hours.

As an alternative method, a carboxylic acid compound represented by the formula (7) may be converted into a mixed anhydride, followed by the reaction with a phenol represented by the formula (C) in the presence of a base.

Examples of the compounds prepared according to Production Method 4 include Compound 4-1 to Compound 4-4.

The starting materials used in the present invention, for example, the compound represented by the formula (B), the compound represented by the formula (C), and Compound 21 in Production Method 1 to Production Method 4 can be easily prepared by the known method, the method known per se, or the following method mentioned below.

EXAMPLES

The present invention is illustrated in detail by the following Working Examples, Reference Examples, Test Examples, and Formulation Examples, but it goes without saying that the present invention is not limited thereto.

Reference Example 1

Production of
6-methyl-2-(4-trifluoromethylphenyl)nicotinic acid

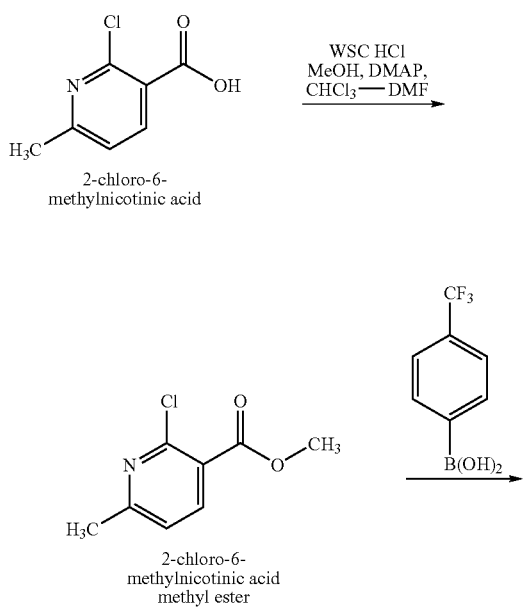

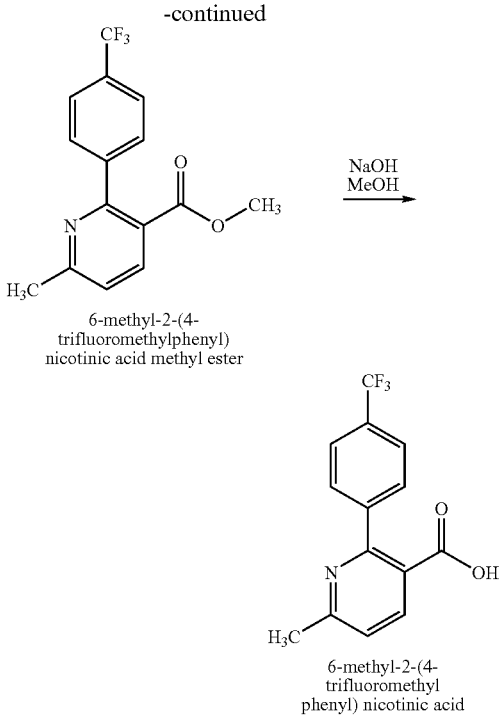

6-methyl-2-(4-trifluoromethylphenyl)
nicotinic acid methyl ester 6-methyl-2-(4-trifluoromethyl
phenyl) nicotinic acid In the above reaction scheme, Me is methyl, WSC is 1-ethyl-3-(3'-dimethylaminopropyl)carbodiimide, DMAP is dimethylaminopyridine, and DMF is dimethylformamide. Hereinafter, each symbol has the same meaning as defined above.

a) 2-Chloro-6-methylnicotinic acid methyl ester

2-Chloro-6-methylnicotinic acid (25.0 g) was suspended in a mixed solvent of dimethylformamide (100 mL) and chloroform (100 mL), and to this suspension were added dimethylaminopyridine (21.3 g) and methanol (4.67 g). Finally, 1-ethyl-3-(3'-dimethylaminopropyl)carbodiimide (WSC) hydrochloride (33.5 g) was added to the mixture, followed by stirring at room temperature for 6 hours. After the reaction mixture was concentrated, ethyl acetate (300 mL) was added thereto. The mixture was washed successively with water, 10% ammonium chloride, water, and saturated brine, dried over sodium sulfate, and concentrated. The residue was purified by column chromatography on silica gel (hexane:ethyl acetate=1:4, v/v) to give the title compound (24.6 g) as a colorless oil.

b) 6-Methyl-2-(4-trifluoromethylphenyl)nicotinic acid methyl ester

2-Chloro-6-methylnicotinic acid methyl ester (18.6 g) and 4-trifluoromethylphenylboronic acid (22.0 g) were dissolved in a mixed solvent of ethanol (100 mL) and toluene (100 mL), and to this solution were added 2M sodium carbonate (100 mL) and tetrakis(triphenylphosphine)palladium(0) (2.90 g). The mixture was stirred at 120° C. for 3 hours under heating. Ethyl acetate (200 mL) was added to the reaction solution. The aqueous layer was separated off. The organic layer was washed successively with 0.1N sodium hydroxide, water, and saturated brine, dried over sodium sulfate, and concentrated. The residue was purified by column chromatography on silica gel with (hexane:ethyl acetate=1:4, v/v) to give the title compound (25.8 g) as a colorless oil.

c) 6-Methyl-2-(4-trifluoromethylphenyl)nicotinic acid

6-Methyl-2-(4-trifluoromethyl-phenyl)nicotinic acid methyl ester (7.26 g) was dissolved in methanol (30 mL). 4M sodium hydroxide (7.2 mL) was added thereto at 0° C. under cooling. The mixture was stirred at 45° C. for 3 hours. Water (30 mL) was added to the mixture at 0° C. under cooling, followed by acidification (pH=3) with 1M hydrochloric acid (about 30 mL) to give the precipitate. The precipitate was filtered and dried to give the title compound as a colorless solid (6.5 g). $^1$H-NMR ($\delta$, 300 MHz, CDCl$_3$): 2.66 (3H, s), 7.61 (2H, d, J=8.3 Hz), 7.67 (2H, d, J=8.3 Hz), 7.27 (1H, d, J=7.9 Hz), 8.18 (1H, d, J=7.9 Hz)

Reference Example 2

Production of 3-ethyl-5-fluoro-4-hydroxybenzoic acid methyl ester

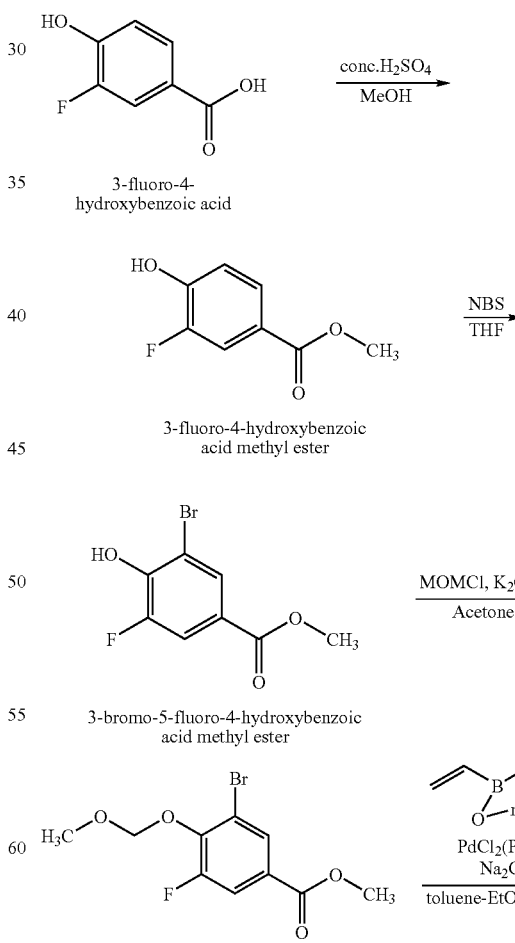

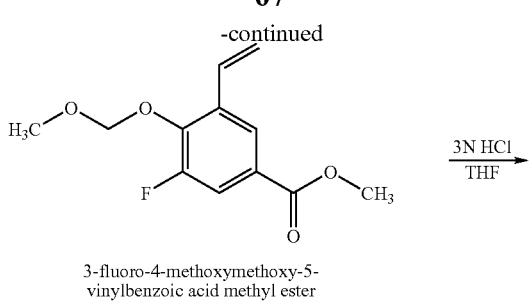

3-fluoro-4-methoxymethoxy-5-vinylbenzoic acid methyl ester

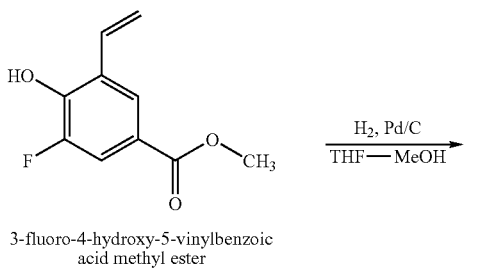

3-fluoro-4-hydroxy-5-vinylbenzoic acid methyl ester

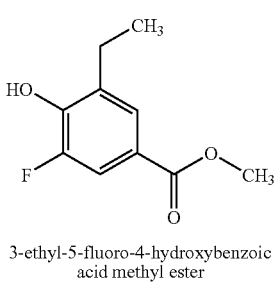

3-ethyl-5-fluoro-4-hydroxybenzoic acid methyl ester

In the above reaction scheme, Me is methyl; conc. $H_2SO_4$ is concentrated sulfuric acid; NBS is N-bromosuccinimide; THF is tetrahydrofuran; MOMCl is chloromethyl methyl ether; nBu is n-butyl; $PdCl_2(PPh_3)_2$ is dichlorobis (triphenylphosphine) palladium (II); Pd/C is palladium-carbon, and Et is ethyl. Hereinafter, each symbol has the same meaning as defined above.

a) 3-Fluoro-4-hydroxybenzoic acid methyl ester

To a solution of 3-fluoro-4-hydroxybenzoic acid (3.0 g) in methanol (30 mL) was added conc. sulfuric acid (3 mL), and the mixture was heated for 5 hours under reflux. The reaction solution was allowed to stand for cooling down to room temperature, and then concentrated in vacuo. The residue was diluted with ethyl acetate, washed successively with water, saturated aqueous sodium bicarbonate, water, and saturated brine, dried over anhydrous sodium sulfate, and concentrated to give the title compound (2.99 g).

b) 3-Bromo-5-fluoro-4-hydroxybenzoic acid methyl ester

To a solution of 3-fluoro-4-hydroxybenzoic acid methyl ester (1.0 g) in THF (10 mL) was added N-bromosuccinimide (1.26 g) under ice-cooling, and the mixture was stirred at room temperature for 2 hours The reaction solution was diluted with ethyl acetate, washed successively with saturated aqueous sodium bicarbonate and saturated brine, dried over anhydrous sodium sulfate, and concentrated. The residue was purified by column chromatography on silica gel (hexane:ethyl acetate=3:1, v/v) to give the title compound (1.16 g). (In the above, THF is tetrahydrofuran)

c) 3-Bromo-5-fluoro-4-methoxymethoxybenzoic acid methyl ester

To a solution of 3-bromo-5-fluoro-4-hydroxybenzoic acid methyl ester (637 mg) in acetone (7 mL) were added potassium carbonate (708 mg) and chloromethyl methyl ether (412 mg), and the mixture was stirred at room temperature overnight. The reaction mixture was diluted with ethyl acetate, washed with water and saturated brine, dried over anhydrous sodium sulfate, and concentrated in vacuo. The residue was purified by column chromatography on silica gel (hexane:ethyl acetate=9:1, v/v) to give the title compound (608 mg).

d) 3-Fluoro-4-methoxymethoxy-5-vinylbenzoic acid methyl ester

To a solution of 3-bromo-5-fluoro-4-methoxymethoxybenzoic acid methyl ester (300 mg) and vinylboronic acid dibutyl ester (226 mg) in toluene (4 mL)-ethanol (2 mL) were added dichlorobis(triphenylphosphine)palladium (II) (36 mg) and an aqueous solution (1 mL) of sodium carbonate (217 mg). The mixture was stirred at 100° C. for 8 hours, and then allowed to stand for cooling down to room temperature. The resulting insoluble materials were filtered through a Celite pad, and the filtrate was concentrated in vacuo. The residue was diluted with ethyl acetate, washed with water and saturated brine, and dried over anhydrous sodium sulfate. After concentration in vacuo, the residue was purified by column chromatography on silica gel (hexane:ethyl acetate=30:1, v/v) to give the title compound (190 mg).

e) 3-Fluoro-4-hydroxy-5-vinylbenzoic acid methyl ester

A solution of 3-fluoro-4-methoxymethoxy-5-vinylbenzoic acid methyl ester (185 mg) in THF (2 mL)-3N hydrochloric acid (1 mL) was stirred at 60° C. for 3 hours under heating. The mixture was allowed to stand for cooling down to room temperature, diluted with ethyl acetate, washed successively with water, saturated aqueous sodium bicarbonate and saturated brine, dried over anhydrous sodium sulfate, and concentrated in vacuo. The residue was purified by column chromatography on silica gel (hexane:ethyl acetate=9:1, v/v) to give the title compound (121 mg). (In the above, THF is tetrahydrofuran).

f) 3-Ethyl-5-fluoro-4-hydroxybenzoic acid methyl ester

A suspension of 3-fluoro-4-hydroxy-5-vinylbenzoic acid methyl ester (121 mg) and 10% palladium carbon (20 mg) in THF (1 mL)-methanol (1 mL) was hydrogenated at room temperature over night at medium pressure (3 kgf/cm$^2$). The catalyst was filtered off through a Celite pad, and the filtrate was concentrated to give the title compound (121 mg).

$^1$H-NMR (δ, 300 MHz, DMSO-D$_6$): 1.14 (3H, t, J=7.5 Hz), 2.63 (2H, q, J=7.5 Hz), 3.80 (3H, s), 7.52 (1H, dd, J=1.9, 10.9 Hz), 7.56 (1H, s).

Reference Example 3

Production of 3-fluoro-4-hydroxy-5-methylbenzoic acid methyl ester

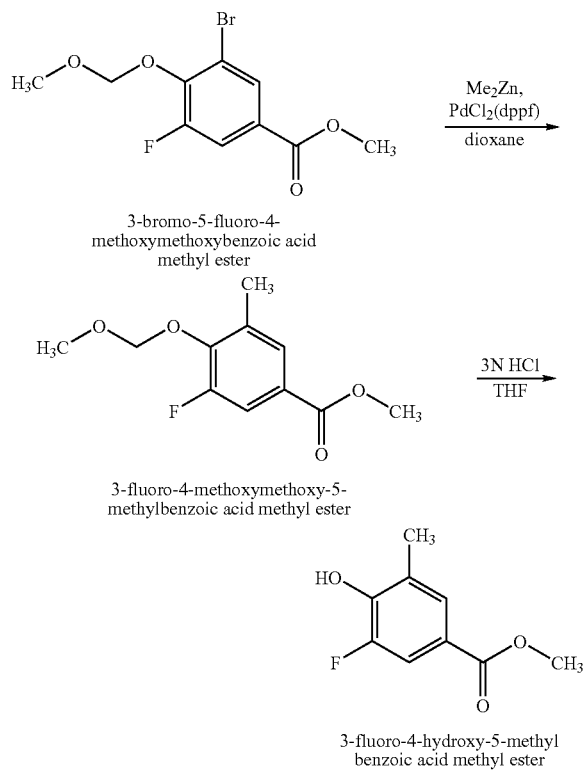

In the above reaction scheme, THF is tetrahydrofuran and PdCl$_2$(dppf) is (1,1'-bis(diphenylphosphino)ferrocene)dichloropalladium(II).

Hereinafter, each symbol has the same meaning as defined above.

a) 3-Fluoro-4-methoxymethoxy-5-methylbenzoic acid methyl ester

To a solution of 3-bromo-5-fluoro-4-methoxymethoxybenzoic acid methyl ester (301 mg) and (1,1'-bis(diphenylphosphino)ferrocene)dichloropalladium(II)(42 mg) in dioxane (5 mL) was added dimethylzinc (2M toluene solution) (2.1 mL). The mixture was stirred at 120° C. for 3 hours under heating and then cooled down to 0° C., and methanol (0.3 mL) was added thereto. The mixture was diluted with ether, washed with 1M hydrochloric acid and saturated brine, dried over anhydrous sodium sulfate and concentrated in vacuo. The residue was purified by column chromatography on silica gel (hexane:ethyl acetate=50:1, v/v) to give the title compound (197 mg).

b) 3-Fluoro-4-hydroxy-5-methylbenzoic acid methyl ester

3-Fluoro-4-methoxymethoxy-5-methylbenzoic acid methyl ester (194 mg) was treated in a similar manner to Reference Example 2e) to give the title compound (140 mg).

$^1$H-NMR (δ, 300 MHz, CDCl$_3$): 2.30 (3H, s), 3.88 (3H, s), 5.55 (1H, d, J=4.9 Hz), 7.62 (1H, dd, J=1.9, 12.5 Hz), 7.66 (1H, s).

Reference Example 4

Production of 4-hydroxy-5-methylisophthalic acid 1-ethyl ester 3-methyl ester

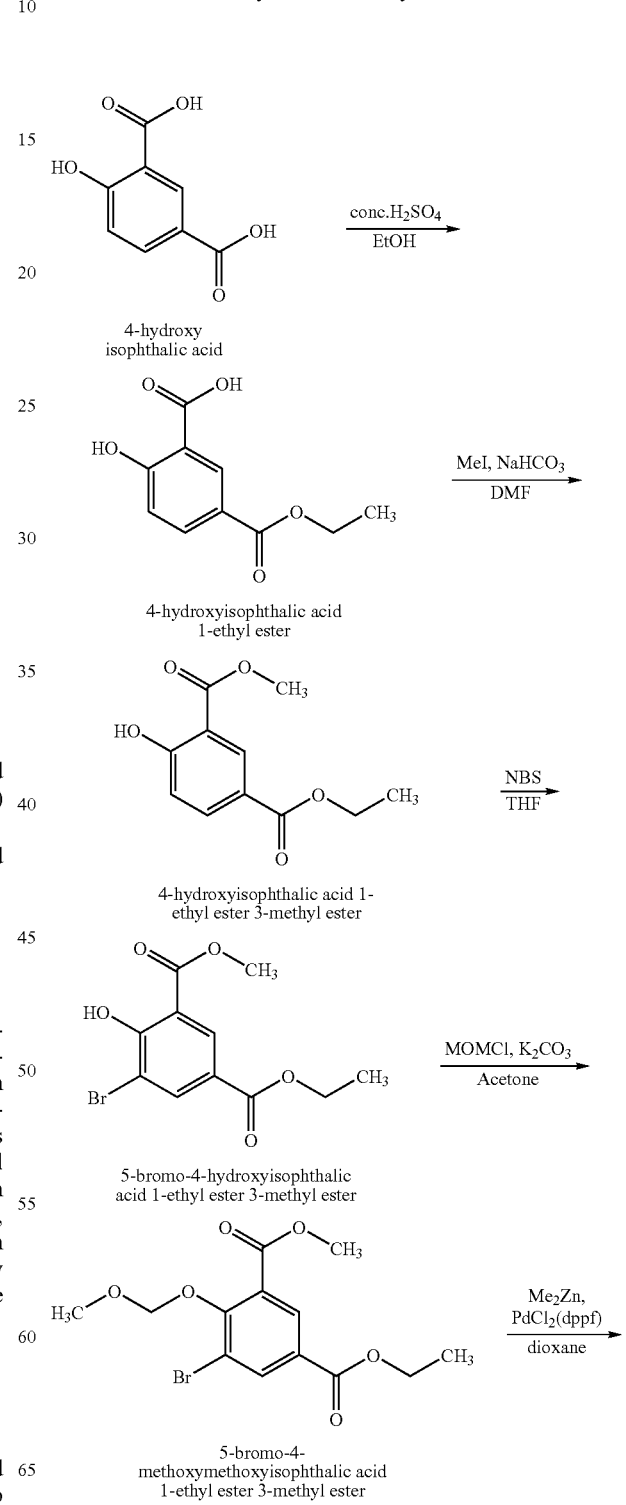

-continued

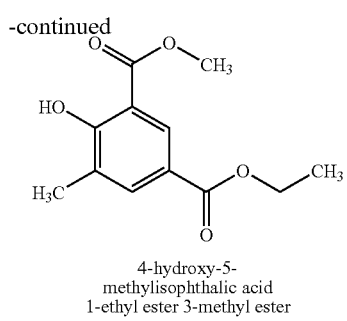

4-hydroxy-5-
methylisophthalic acid
1-ethyl ester 3-methyl ester

In the above reaction scheme, Et is ethyl; conc. $H_2SO_4$ is concentrated sulfuric acid; DMF is dimethylformamide; MOMCl is chloromethyl methyl ether; Me is methyl; and $PdCl_2$(dppf) is (1,1'-bis(diphenylphosphino)ferrocene)dichloropalladium(II). Hereinafter, each symbol has the same meaning as defined above.

a) 4-Hydroxyisophthalic acid 1-ethyl ester

To a solution of 4-hydroxyisophthalic acid (10.0 g) in ethanol (100 mL) was added conc. sulfuric acid (3.0 mL), and the mixture was heated for 4 hours under reflux. The reaction solution was allowed to stand for cooling to room temperature, and poured into ice-water. Sodium bicarbonate was added thereto while stirring until the pH reached 10 to 11. The resulting precipitated solid was filtered off. To the filtrate was added conc. hydrochloric acid until the pH reached 2 to 3, and the precipitated solid was filtered off. The filtered solid was recrystallized from methanol and water (2:1, v/v) to give the title compound (4.53 g).

b) 4-Hydroxyisophthalic acid 1-ethyl ester 3-methyl ester

To a solution of 4-hydroxyisophthalic acid 1-ethyl ester (4.51 g) in DMF (36 mL) were added methyl iodide (3.66 g) and sodium hydrogen carbonate (2.16 g). The mixture was stirred at 60° C. for 2 hours and then allowed to stand for cooling down to room temperature. The resulting precipitated solid formed upon addition of water was filtered off to give the title compound (4.20 g).

c) 5-Bromo-4-hydroxyisophthalic acid 1-ethyl ester 3-methyl ester

4-Hydroxyisophthalic acid 1-ethyl ester 3-methyl ester (4.51 g) was treated in a similar manner to Step b) of Reference Example 2 to give the title compound (4.21 g).

d) 5-bromo-4-methoxymethoxyisophthalic acid 1-ethyl ester 3-methyl ester

5-Bromo-4-hydroxyisophthalic acid 1-ethyl ester 3-methyl ester (4.20 g) was treated in a similar manner to Step c) of Reference Example 2 to give the title compound (4.36 g).

e) 4-Hydroxy-5-methylisophthalic acid 1-ethyl ester 3-methyl ester

5-Bromo-4-methoxymethoxyisophthalic acid 1-ethyl ester 3-methyl ester (3.0 g) was treated in a similar manner to Step a) of Reference Example 3 to give the title compound (1.69 g).
$^1$H-NMR (δ, 300 MHz, $CDCl_3$): 1.39 (3H, t, J=7.2 Hz), 2.30 (3H, s), 3.98 (3H, s), 4.36 (2H, q, J=7.2 Hz), 8.00 (1H, s), 8.42 (1H, d, J=2.2 Hz), 11.45 (1H, s).

Reference Example 5

Production of 4-hydroxy-3-methyl-5-trifluoromethylbenzoi acid methyl ester

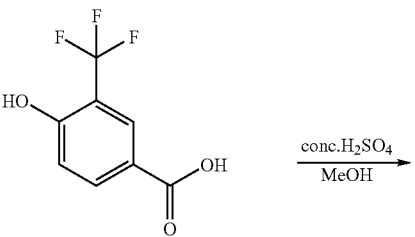

4-hydroxy-3-
trifluoromethyl
benzoic acid

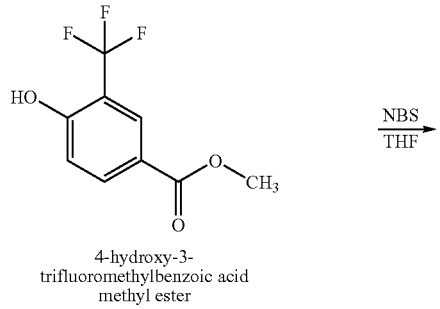

4-hydroxy-3-
trifluoromethylbenzoic acid
methyl ester

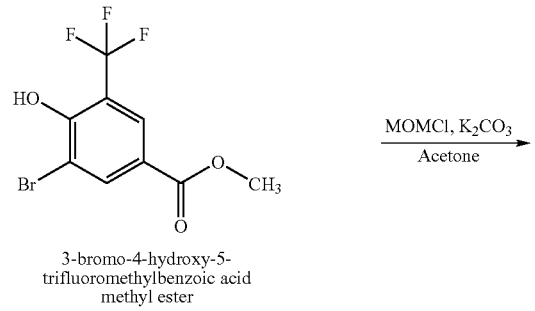

3-bromo-4-hydroxy-5-
trifluoromethylbenzoic acid
methyl ester

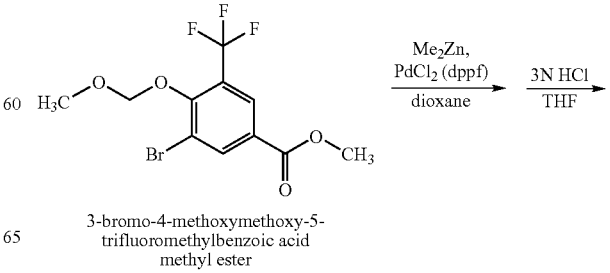

3-bromo-4-methoxymethoxy-5-
trifluoromethylbenzoic acid
methyl ester

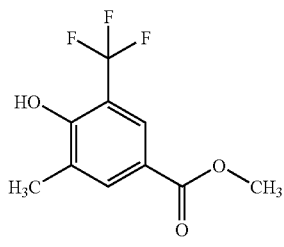

4-hydroxy-3-methyl-5-trifluoromethylbenzoic acid methyl ester

In the above reaction scheme, Me is methyl; conc. H$_2$SO$_4$ is concentrated sulfuric acid; NBS is N-bromosuccinimide; THF is tetrahydrofuran; MOMCl is chloromethyl methyl ether; and PdCl$_2$(dppf) is (1,1'-bis(diphenylphosphino)ferrocene)dichloropalladium(II). Hereinafter, each symbol has the same meaning as defined above.

a) 4-Hydroxy-3-trifluoromethylbenzoic acid methyl ester

To a solution of 4-hydroxy-3-trifluoromethylbenzoic acid (395 mg) in methanol (5 mL) was added conc. sulfuric acid (0.4 mL), and the mixture was heated for 6 hours under reflux. The reaction mixture was allowed to stand for cooling down to room temperature, and concentrated in vacuo. The residue was diluted with ethyl acetate, washed with water and saturated brine, and concentrated to give the title compound (403 mg).

b) 3-Bromo-4-hydroxy-5-trifluoromethylbenzoic acid methyl ester

4-Hydroxy-3-trifluoromethylbenzoic acid methyl ester (394 mg) was treated in a similar manner to Step b) of Reference Example 2 to give the title compound (412 mg).

c) 3-Bromo-4-methoxymethoxy-5-trifluoromethylbenzoic acid methyl ester

3-Bromo-4-hydroxy-5-trifluoromethylbenzoic acid methyl ester (831 mg) was treated in a similar manner to Step c) of Reference Example 2 to give the title compound (905 mg).

d) 4-Hydroxy-3-methyl-5-trifluoromethylbenzoic acid methyl ester

3-Bromo-4-methoxymethoxy-5-trifluoromethylbenzoic acid methyl ester (500 mg) was treated in a similar manner to Step a) and Step b) of Reference Example 3 to give the title compound (157 mg).

$^1$H-NMR (δ, 300 MHz, CDCl$_3$): 2.33 (3H, s), 3.91 (3H, s), 5.87-5.89 (1H, m), 8.02 (1H, s), 8.08 (1H, s).

Reference Example 6

Production of 3-ethoxy-4-hydroxy-5-methoxybenzoic acid methyl ester

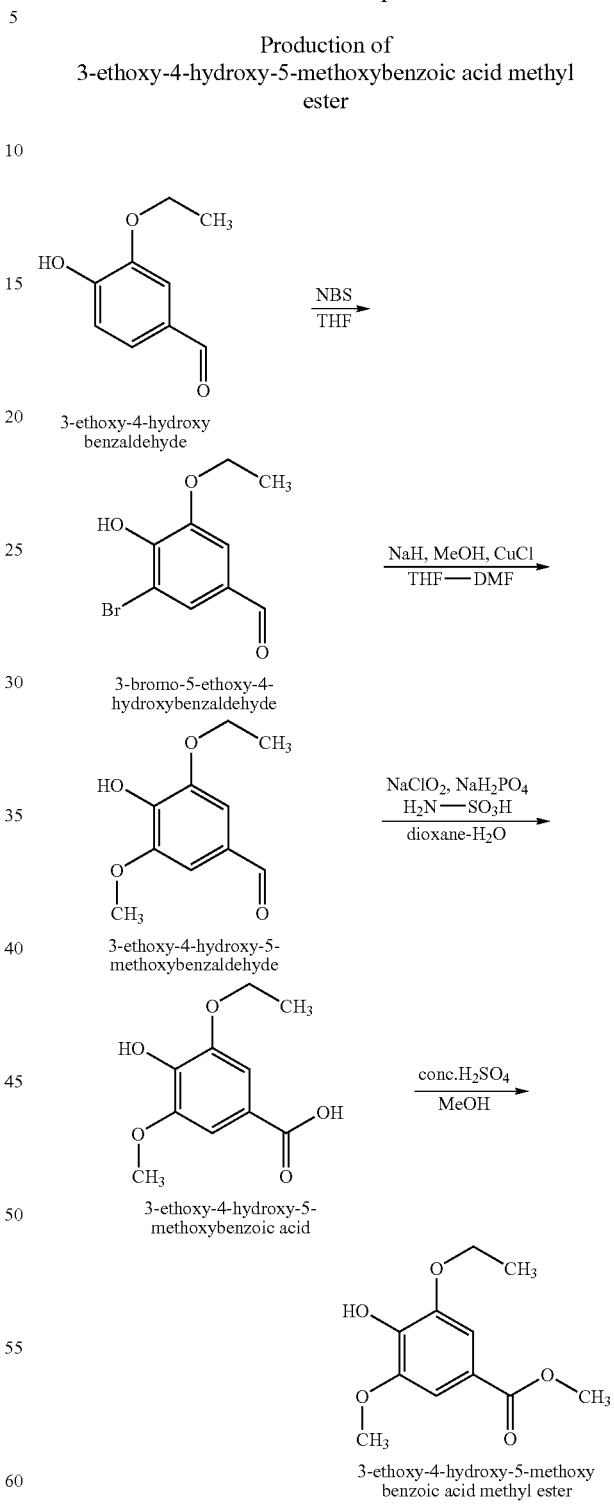

In the above reaction scheme, NBS is N-bromosuccinimide; THF is tetrahydrofuran; Me is methyl; DMF is dimethylformamide; and conc. H$_2$SO$_4$ is concentrated sulfuric acid. Hereinafter, each symbol has the same meaning as defined above.

a) 3-Bromo-5-ethoxy-4-hydroxybenzaldehyde

3-Ethoxy-4-hydroxybenzaldehyde (5.0 g) was treated in a similar manner to Step b) of Reference Example 2 to give the title compound (4.85 g).

b) 3-Ethoxy-4-hydroxy-5-methoxybenzaldehyde

To a suspension of sodium hydride (843 mg) in THF (5 mL) was added methanol (675 mg) under ice-cooling, and the mixture was stirred at room temperature for 0.5 hour. 3-Bromo-5-ethoxy-4-hydroxybenzaldehyde (1.29 g) in dimethylformamide (10 mL), and copper(I) chloride (31 mg) were added thereto, and the mixture was stirred at 120° C. for 4 hours under heating. The mixture was allowed to stand for cooling down to room temperature, diluted with ethyl acetate, washed with 1N hydrochloric acid, dried over anhydrous sodium sulfate, and then concentrated. The residue was purified by column chromatography on silica gel (hexane:ethyl acetate=2:1, v/v) to give the title compound (630 mg).

c) 3-Ethoxy-4-hydroxy-5-methoxybenzoic acid

To a solution of 3-ethoxy-4-hydroxy-5-methoxybenzaldehyde (578 mg), sodium dihydrogenphosphate (1.41 g), and amidosulfuric acid (429 mg) in dioxane (6 mL)-water (10 mL) was added an aqueous solution (3 mL) of sodium chlorite (400 mg) under ice-cooling. The mixture was stirred for 2 hours under ice-cooling. Hydrochloric acid was added thereto, and the reaction mixture was extracted with ethyl acetate. The extract was washed with 10% aqueous sodium thiosulfate and saturated brine, dried over anhydrous sodium sulfate, and concentrated to give the title compound (586 mg).

d) 3-Ethoxy-4-hydroxy-5-methoxybenzoic acid methyl ester

3-Ethoxy-4-hydroxy-5-methoxybenzoic acid (586 mg) was treated in a similar manner to Step a) of Reference Example 5 to give the title compound (558 mg).

Reference Example 7

Production of 4-(2-isopropyl-2H-tetrazol-5-yl)phenol

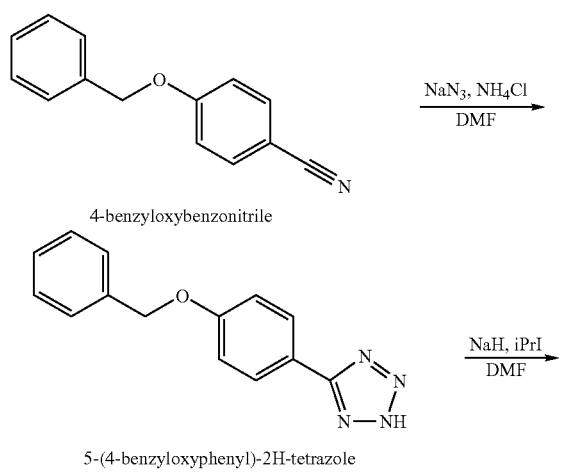

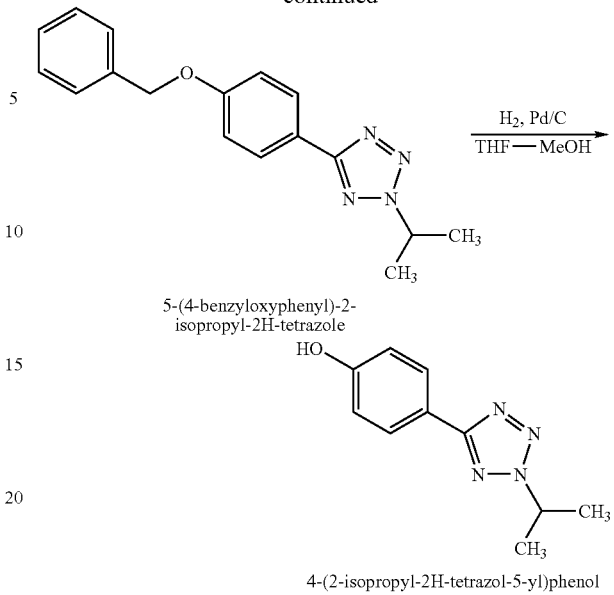

In the above reaction scheme, DMF is dimethylformamide; iPrI is isopropyl iodide; Pd/C is palladium carbon; THF is tetrahydrofuran; and Me is methyl. Hereinafter, each symbol has the same meaning as defined above.

a) 5-(4-Benzyloxyphenyl)-2H-tetrazole

To a solution of 4-benzyloxybenzonitrile (2.0 g) in dimethylformamide (15 mL) were added sodium azide (932 mg) and ammonium chloride (767 mg). The mixture was stirred at 110° C. overnight under heating and then allowed to stand for cooling to room temperature. 1N aqueous sodium hydroxide was added thereto to adjust the pH to about 10, followed by washing with diethyl ether. To the aqueous layer was added 1N hydrochloric acid, and the resulting precipitated solid was filtered to give the title compound (2.29 g).

b) 5-(4-Benzyloxyphenyl)-2-isopropyl-2H-tetrazole 5-(4-Benzyloxyphenyl)-2H-tetrazole (500 mg) was added to a suspension of sodium hydride (96 mg) in dimethylformamide (5 mL) under ice-cooling. The mixture was stirred at room temperature for 0.5 hour. After addition of isopropyl iodide (405 mg) thereto, the mixture was stirred at 60° C. for 2 hours under heating. The reaction mixture was allowed to stand for cooling down to room temperature, diluted with ethyl acetate, washed with water and saturated brine, dried anhydrous sodium sulfate, and concentrated. The residue was purified by column chromatography on silica gel (hexane: ethyl acetate=4:1, v/v) to give the title compound (571 mg).

c) 4-(2-Isopropyl-2H-tetrazol-5-yl)phenol

To a solution of 5-(4-benzyloxyphenyl)-2-isopropyl-2H-tetrazole (521 mg) in THF (5 mL)-methanol (5 mL) was added 7.5% palladium-carbon (60 mg). The mixture was stirred at room temperature for 3.5 hours under hydrogen atmosphere. The catalyst was filtered off through a Celite pad. The filtrate was concentrated to give the title compound (352 mg).

¹H-NMR (δ, 300 MHz, CDCl₃): 1.70 (6H, d, J=6.4 Hz), 5.09 (1H, sept, J=6.4 Hz), 5.59 (1H, s), 6.95 (2H, d, J=8.7 Hz), 8.04 (2H, d, J=8.7 Hz).

Reference Example 8

Production of 2-(4-methoxycarbonylphenyl)-6-methylnicotinic acid

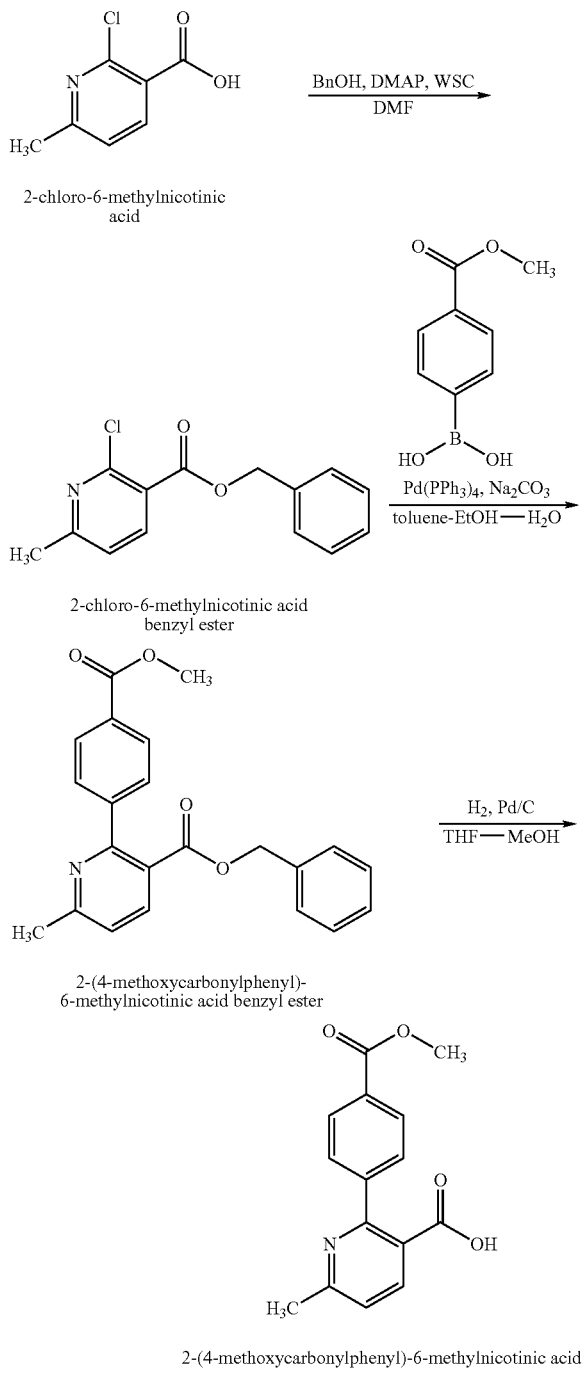

In the above reaction scheme, BnOH is benzyl alcohol; DMAP is 4-dimethylaminopyridine; WSC is 1-ethyl-3-(3'-dimethylaminopropyl)carbodiimide; DMF is dimethylformamide; Pd(PPh₃)₄ is tetrakis(triphenylphosphine) palladium (0); Pd/C is palladium-carbon; THF is tetrahydrofuran; Me is methyl; and Et is ethyl. Hereinafter, each symbol has the same meaning as defined above.

a) 2-Chloro-6-methylnicotinic acid benzyl ester

To a solution of 2-chloro-6-methylnicotinic acid (3.0 g), benzyl alcohol (2.27 g), 4-dimethylaminopyridine (2.56 g) in DMF (10 mL) was added 1-ethyl-3-(3'-dimethylaminopropyl) carbodiimide (WSC) hydrochloride (4.02 g). The mixture was stirred at room temperature overnight. The reaction mixture was diluted with ethyl acetate, washed successively with water, saturated aqueous sodium bicarbonate, water, and saturated brine, dried over anhydrous sodium sulfate, and concentrated. The residue was purified by column chromatography on silica gel (hexane:ethyl acetate=4:1, v/v) to give the title compound (3.6 g).

b) 2-(4-Methoxycarbonylphenyl)-6-methylnicotinic acid benzyl ester

2-Chloro-6-methylnicotinic acid benzyl ester (1.0 g) and 4-methoxycarbonylphenylboronic acid (722 mg) were treated in a similar manner to Step b) of Reference Example 1 to give the title compound (1.13 g).

c) 2-(4-Methoxycarbonylphenyl)-6-methylnicotinic acid 2-(4-Methoxycarbonylphenyl)-6-methylnicotinic acid benzyl ester (1.12 g) was treated in a similar manner to Step c) of Reference Example 7 to give the title compound (821 mg). ¹H-NMR (δ, 300 MHz, CDCl₃): 2.66 (3H, s), 3.93 (3H, s), 7.25 (1H, d, J=8.3 Hz), 7.57 (2H, d, J=8.3 Hz), 8.07 (2H, d, J=8.3 Hz), 8.14 (1H, d, J=8.3 Hz).

Reference Example 9

Production of 4-hydroxy-3-methoxy-5-ethylbenzoic acid methyl ester

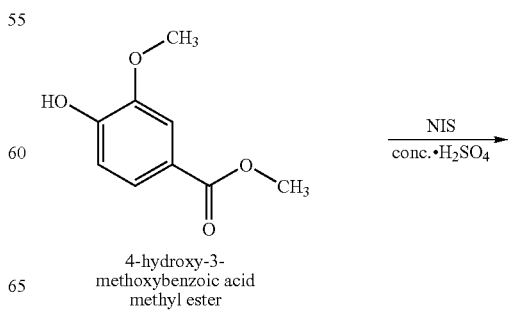

-continued

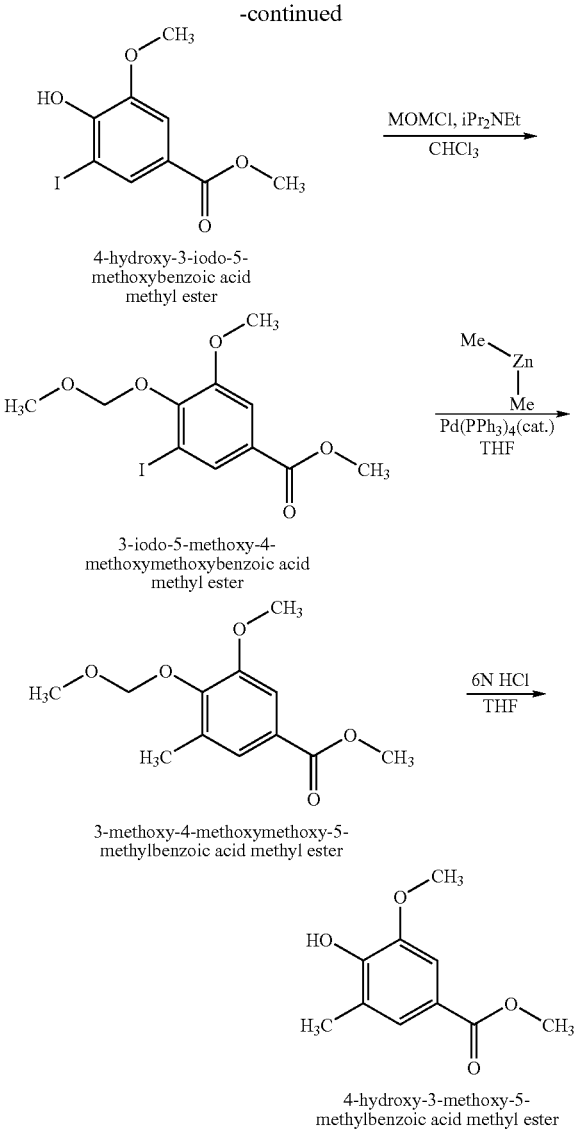

methyl ether (1.88 g) under ice-cooling, and the mixture was stirred at room temperature for 1 hour. The reaction solution was washed successively with ethyl acetate, 1N hydrochloric acid, water, and saturated brine, dried over anhydrous sodium sulfate, and concentrated. The residue was purified by column chromatography on silica gel with solvent (hexane:ethyl acetate=3:1, v/v) to give the title compound (2.70 g).

c) 3-Methoxy-4-methoxymethoxy-5-methylbenzoic acid methyl ester

To a solution of 3-iodo-5-methoxy-4-methoxymethoxy-benzoic acid methyl ester (700 mg) in THF (7 mL) were added tetrakis(triphenylphosphine)palladium(0) (115 mg) and 2M dimethylzinc/THF solution (1.20 mL), and the mixture was stirred at 80° C. for 30 minutes. The reaction solution was diluted with ethyl acetate, washed with 1N hydrochloric acid, water, and saturated brine, dried over anhydrous sodium sulfate, and concentrated in vacuo to give the title compound (767 mg) as a crude purified product of pale yellow oil.

d) 4-Hydroxy-3-methoxy-5-methylbenzoic acid methyl ester

To a solution of 3-methoxy-4-methoxymethoxy-5-methylbenzoic acid methyl ester (650 mg) in THF (5 mL) was added 6N-hydrochloric acid (5 mL), and the mixture was stirred at room temperature for 1 hour. The reaction solution was diluted with ethyl acetate, washed with water and saturated brine, dried over anhydrous sodium sulfate, and concentrated in vacuo. The residue was purified by column chromatography on silica gel (hexane:ethyl acetate=4:1, v/v) to give the title compound (365 mg).

$^1$H-NMR ($\delta$, 300 MHz CDCl$_3$): 2.27 (3H, s), 3.88 (3H, s), 3.93 (3H, s), 6.05 (1H, s), 7.41 (1H, d, J=1.8 Hz), 7.52 (1H, d, J=1.8 Hz).

Reference Example 10

Production of 4-hydroxy-3-methoxy-5-trifluoromethylbenzoic acid methyl ester

In the above reaction scheme; NIS is N-iodosuccinimide; conc. H$_2$SO$_4$ is concentrated sulfuric acid; MOMCl is chloromethyl methyl ether; iPr$_2$NET is diisopropylethylamine; Me is methyl; THF is tetrahydrofuran; and Pd(PPh$_3$)$_4$ is tetrakis(triphenylphosphine)palladium(0). Hereinafter, each symbol has the same meaning as defined above.

a) 4-Hydroxy-3-iodo-5-methoxybenzoic acid methyl ester

To a solution of 4-hydroxy-3-methoxybenzoic acid methyl ester (5.0 g) in tetrahydrofuran (20 mL) was added N-iodosuccinimide (6.17 g) at 0° C., and the mixture was stirred for 1 hour. The precipitated solid was filtered, washed with water, and dried to give the title compound (9.60 g).

b) 3-Iodo-5-methoxy-4-methoxymethoxybenzoic acid methyl ester

To a solution of 4-hydroxy-3-iodo-5-methoxybenzoic acid methyl ester (4.6 g) in chloroform (30 mL) were successively added diisopropylethylamine (3.88 g) and chloromethyl

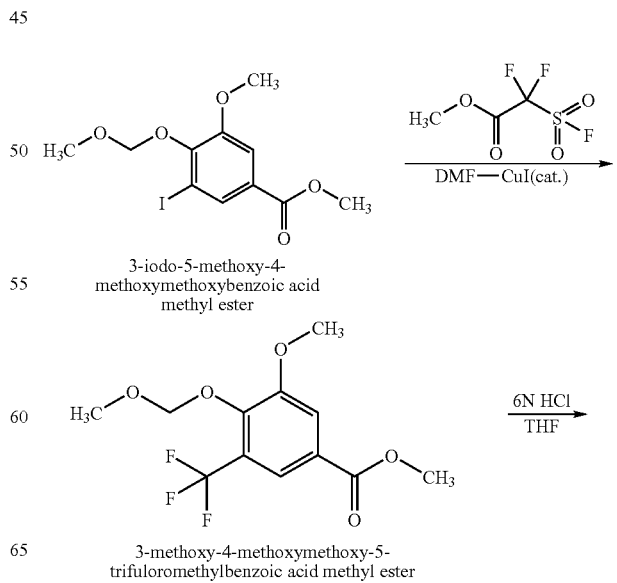

-continued

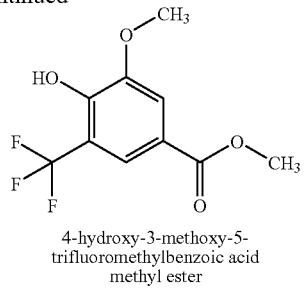

4-hydroxy-3-methoxy-5-
trifluoromethylbenzoic acid
methyl ester

In the above reaction scheme, DMF is dimethylformamide, and THF is tetrahydrofuran. Hereinafter, each symbol has the same meaning as defined above.

a) 3-Methoxy-4-methoxymethoxy-5-trifluoromethyl-benzoic acid methyl ester

To a solution of 3-iodo-5-methoxy-4-methoxymethoxy-benzoic acid methyl ester (500 mg) in DMF (5 mL) were added copper(I) iodide (135 mg) and fluorosulfonyl(difluoro)acetic acid methyl ester (409 mg). The mixture was stirred at 120° C. for 2 hours. The reaction temperature was further raised to 140° C., followed by stirring for 15 minutes. The reaction solution was diluted with ethyl acetate, washed with saturated sodium thiosulfate, water, and saturated brine, dried over anhydrous sodium sulfate, and concentrated in vacuo to give the title compound (453 mg) as a crude purified product of brown oil.

b) 4-Hydroxy-3-methoxy-5-trifluoromethylbenzoic acid methyl ester

To a solution of 3-methoxy-4-methoxymethoxy-5-trifluoromethylbenzoic acid methyl ester (453 mg) in THF (4 mL) was added 6N-hydrochloric acid (4 mL), and the mixture was stirred at room temperature for 30 minutes. The reaction solution was diluted with ethyl acetate, washed with water and saturated brine, dried over anhydrous sodium sulfate, and concentrated in vacuo. The residue was purified by column chromatography on silica gel (hexane:ethyl acetate=4:1 to 3:1, v/v) to give the title compound (186 mg).

$^1$H-NMR (δ, 300 MHz, CDCl$_3$): 3.92 (3H, s), 4.01 (3H, s), 6.50 (1H, s), 7.69 (1H, d, J=1.7 Hz), 7.91 (1H, d, J=1.7 Hz).

Reference Example 11

Production of 4-hydroxy-5-methylisophthalic acid dimethyl ester

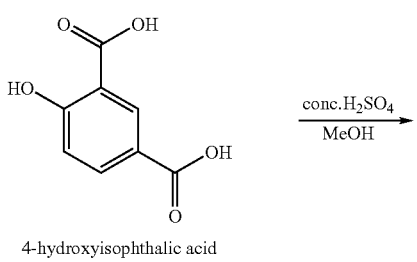

4-hydroxyisophthalic acid

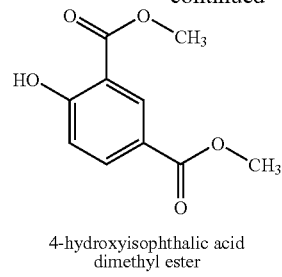

4-hydroxyisophthalic acid
dimethyl ester

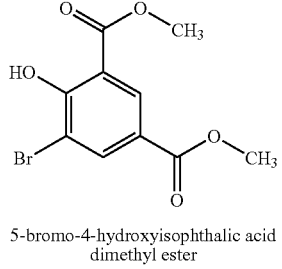

5-bromo-4-hydroxyisophthalic acid
dimethyl ester

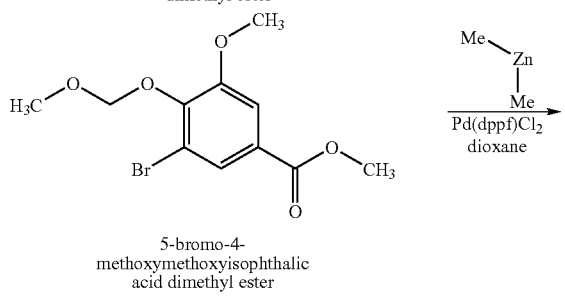

5-bromo-4-
methoxymethoxyisophthalic
acid dimethyl ester

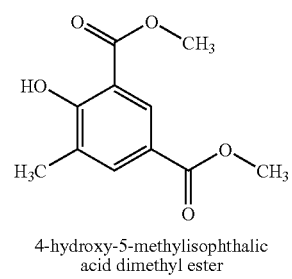

4-hydroxy-5-methylisophthalic
acid dimethyl ester

In the above reaction scheme, conc. H$_2$SO$_4$ is concentrated sulfuric acid; Me is methyl; NBS is N-bromosuccinimide; THF is tetrahydrofuran; and Pd(dppf)Cl$_2$ is (1,1'-bis(diphenylphosphino)ferrocene)dichloropalladium(II). Hereinafter, each symbol has the same meaning as defined above.

a) 4-Hydroxyisophthalic acid dimethyl ester

To a solution of 4-hydroxyisophthalic acid (16.0 g) in methanol (150 mL) was added conc. sulfuric acid (5 mL), and the mixture was heated for 22 hours under reflux. Then, the reaction solution was allowed to stand for cooling down to room temperature, diluted with water (150 mL), and added with sodium bicarbonate (15 g). The resulting precipitate was filtered, washed successively with water/methanol (1:1, v/v) (150 mL) and water, and dried to give the title compound (17.45 g).

b) 5-Bromo-4-hydroxyisophthalic acid dimethyl ester

To a solution of 4-hydroxyisophthalic acid dimethyl ester (10.51 g) in THF (100 mL) was added N-bromosuccinimide (9.34 g) under ice-cooling, and the mixture was stirred at room temperature for 2 hours. Water (200 mL) and saturated aqueous sodium bicarbonate (100 mL) were successively added to the reaction solution. The resulting precipitate was filtered, washed successively with saturated aqueous sodium bicarbonate and water, and dried to give the title compound (12.5 g).

c) 5-Bromo-4-methoxymethoxyisophthalic acid dimethyl ester

To a solution of 5-bromo-4-hydroxyisophthalic acid dimethyl ester (12.3 g) in chloroform (130 mL) were successively added diisopropylethylamine (8.24 g) and methoxymethyl chloride (4.11 g) under ice-cooling, and the mixture was stirred at room temperature overnight. The reaction solution was washed successively with 1N hydrochloric acid, water, and saturated brine, dried over anhydrous sodium sulfate, and concentrated. The residue was purified by column chromatography on silica gel (hexane:ethyl acetate=5:1, v/v) to give the title compound (8.52 g).

d) 4-Hydroxy-5-methylisophthalic acid dimethyl ester

To a solution of 5-bromo-4-methoxymethoxyisophthalic acid dimethyl ester (6.00 g) in dioxane (60 mL) were added [1,1' bis(diphenylphosphino)ferrocene]dichloropalladium (II) dichloromethane complex (1:1) (600 mg) and 1M dimethylzinc/hexane solution (20 mL), and the mixture was stirred at 120° C. for 5.5 hours under heating. The reaction solution was allowed to stand for cooling down to room temperature, and 1M hydrochloric acid (40 mL) was added dropwise thereto. After the reaction solution was diluted with ethyl acetate (100 mL), the insoluble material was filtered through a Celite pad. The organic layer was separated, washed successively with water and saturated brine, dried over anhydrous sodium sulfate, and concentrated in vacuo. The residue was purified by column chromatography on silica gel (hexane:ethyl acetate=9:1, v/v) to give the title compound (2.97 g).
$^1$H-NMR ($\delta$, 300 MHz, CDCl$_3$): 2.30 (3H, s), 3.90 (3H, s), 3.98 (3H, s), 8.00 (1H, d, J=2.3 Hz), 8.42 (1H, d, J=2.3 Hz), 11.46 (1H, s).

Working Example 1-1

3-{3-Dimethylcarbamoyl-4-[(4'-trifluoromethylbiphenyl-2-carbonyl)amino]phenyl}propionic acid phenyl ester (Compound 1-1)

a) 5-Iodo-2-nitrobenzoic acid

Sulfuric acid (40 mL) was poured into water (240 mL). After the solution was cooled down to 0° C., 5-amino-2-nitrobenzoic acid (23.6 g) was added, and then phosphoric acid (200 mL) was further added thereto. After cooling down to 10° C., an aqueous solution (20 mL) of sodium nitrite (9.2 g) was added dropwise thereto over 15 minutes. The mixture was stirred at room temperature for 1 hour and filtered through a Celite pad. The filtrate was added dropwise to an aqueous solution (400 mL) of potassium iodide (30 g). After the mixture was stirred at room temperature overnight, the resulting precipitated solid was filtered to give the title compound (30.0 g).

b) 5-Iodo-N,N-dimethyl-2-nitrobenzamide

5-Iodo-2-nitrobenzoic acid (15.5 g) was dissolved in chloroform (30 mL). Oxalyl chloride (13.4 g) was added thereto at 0° C., and then DMF (dimethylformamide) (0.1 mL) was further added. The mixture was stirred at room temperature for 2 hours, and then concentrated. After addition of toluene to the residue, the mixture was further concentrated. A solution of the concentrated residue in ethyl acetate (60 mL) was added dropwise to a mixed solution of 50% (w/w) aqueous dimethylamine (7.5 mL) saturated aqueous sodium bicarbonate (60 mL), and toluene (60 mL) under stirring and ice-cooling. The reaction solution was diluted with ethyl acetate, washed with saturated aqueous sodium bicarbonate and saturated brine, and concentrated to give the title compound (15.3 g).

c) 3-(3-Dimethylcarbamoyl-4-nitrophenyl)propionic acid ethyl ester

5-Iodo-N,N-dimethyl-2-nitrobenzamide (2.00 g) was dissolved in tetrahydrofuran (20 mL) and bis(triphenylphosphine)palladium(II) dichloride (0.128 g) was added thereto. After cooling down to 0° C., 0.5M 3-ethoxy-3-oxopropylzinc bromide solution (22.5 mL) was added dropwise thereto, the mixture was stirred at room temperature overnight. The reaction solution was concentrated, dissolved in ethyl acetate (100 mL), washed successively with 1N hydrochloric acid (30 mL) and saturated brine (30 mL), and dried over sodium sulfate. Further, the mixture was purified by column chromatography on silica gel (ethyl acetate:hexane=3:2, v/v) to give the title compound (1.52 g) as a brown oil.

d) 3-(4-Amino-3-dimethylcarbamoylphenyl)propionic acid ethyl ester 3-(3-Dimethylcarbamoyl-4-nitrophenyl)propionic acid ethyl ester (1.52 g) was dissolved in a mixed solution of THF (tetrahydrofuran) (15 mL) and ethanol (15 mL). 7.5% (w/w) palladium-carbon (300 mg) was added thereto, followed by stirring overnight at normal pressure in hydrogen atmosphere. The reaction solution was filtered through a Celite pad and concentrated to give the title compound (0.950 g) as a pale yellow oil.

e) 3-{3-Dimethylcarbamoyl-4-[(4'-trifluoromethylbiphenyl-2-carbonyl)amino]phenyl}propionic acid ethyl ester 3-(4-Amino-3-dimethylcarbamoylphenyl)propionic acid ethyl ester (1.52 g) was dissolved in ethyl acetate (10 mL), and trimethylamine (533 mg) was added thereto. After cooling down to 0° C., 4'-trifluoromethylbiphenyl-2-carbonyl chloride (synthesized from the corresponding carboxylic acid 0.529 g) was added thereto, and the mixture was stirred at room temperature overnight. After filtration of the insoluble material, the filtrate was concentrated and purified by column chromatography on silica gel (ethyl acetate:hexane=3:2, v/v) to give the title compound (0.843 g).

f) 3-{3-Dimethylcarbamoyl-4-[(4'-trifluoromethylbiphenyl-2-carbonyl)amino]phenyl}propionic acid 3-{3-Dimethylcarbamoyl-4-[(4'-trifluoromethylbiphenyl-2-carbonyl)amino]phenyl}propionic acid ethyl ester (0.843 g) was dissolved in ethanol (4 mL), and 4N aqueous sodium hydroxide (1 mL) was added thereto. The mixture was stirred at room temperature for 2 hours, concentrated, acidified with 1N hydrochloric acid, and extracted with ethyl acetate. The extract was washed with water and concentrated to give the title compound (0.740 g) as a colorless solid.

g) 3-{(3-Dimethylcarbamoyl-4-[(4'-trifluoromethyl-biphenyl-2-carbonyl)amino]phenyl}propionic acid phenyl ester 4-Dimethylaminopyridine (30 mg), phenol (23 mg), and 3-{3-dimethylcarbamoyl-4-[(4'-trifluoromethylbiphenyl-2-carbonyl)amino]phenyl}propionic acid (100 mg) were dissolved in acetone (1 mL). After addition of WSC hydrochloride (50 mg), the mixture was stirred at room temperature for 1 day. The reaction mixture was concentrated, and purified by column chromatography on silica gel (ethyl acetate:hexane=1:1, v/v) to give the title compound (Compound 1-1) (0.088 g) as a colorless solid.

Working Example 1-2

4-{3-Dimethylcarbamoyl-4-[(4'-trifluoromethylbiphenyl-2-carbonyl)amino]phenyl}butanoic acid 4-(3-methyl-[1,2,4]oxadiazol-5-yl)phenyl ester (Compound 1-2)

a) 4-(3-Methyl-[1,2,4]oxadiazol-5-yl)phenol

To a mixed solution of 4-hydroxybenzoic acid (1.0 g) in a mixed solution (15 mL) of toluene and THF (toluene:THF=2:1, v/v) was added carbonyldiimidazole (1.29 g), and the mixture was stirred at room temperature for 1 hour. Subsequently, N-hydroxyacetamide (644 mg) was added thereto, and the mixture was further heated at 150° C. for 2 hours under reflux. The reaction solution was allowed to stand for cooling down to room temperature, diluted with ethyl acetate, washed successively with water and saturated brine, dried over anhydrous sodium sulfate, and concentrated in vacuo. The residue was purified by column chromatography on silica gel (ethyl acetate:hexane=1:1, v/v) to give the title compound (132 mg).

b) 4-{(3-Dimethylcarbamoyl-4-[(4'-trifluoromethyl-biphenyl-2-carbonyl)amino]phenyl}butanoic acid 4-(3-methyl-[1,2,4]oxadiazol-5-yl)phenyl ester 4-(3-Methyl-[1,2,4]oxadiazol-5-yl)phenol (64 mg) and 4-{3-dimethylcarbamoyl-4-[(4'-trifluoromethylbiphenyl-2-carbonyl)amino]phenyl}butanoic acid (200 mg)(synthesized separately in a similar manner to Working Example 1-1) were treated (WSC condensation) in a similar manner to Step g) of Working Example 1-1 to give the title compound (Compound 1-2) (112 mg).

Working Examples 1-3 to 1-116

Compounds of Working Examples 1-3 to 1-116 shown in Tables 1 to 24 were obtained in a similar manner to Production Method 1 or Working Example 1-1. Structures and NMR data of these compounds and those of Working Examples 1-1 to 1-2 are shown in Tables 1 to 24. In the following tables, compounds of Working Examples 1-3 to 1-116 correspond to Compounds 1-3 to 1-116, respectively.

TABLE 1

| Example | Structure | NMR (δ, 300 or 400 MHz, CDCl$_3$) |
|---|---|---|
| 1-1 | [structure] | 2.73-3.07 (10H, m), 6.69-7.01 (2H, m), 7.07 (1H, d, J=1.9 Hz), 7.18-7.34 (5H, m), 7.44-7.58 (2H, m), 7.62 ((4H, brs), 7.69 (1H, dd, J=1.5 Hz, 7.2 Hz), 8.33 (1H, d=8.7 Hz), 9.05 (1H, brs). |
| 1-2 | [structure] | 2.04 (2H, quint, J=7.5 Hz), 2.47 (3H,s), 2.57 (2H, t, J= 7.5 Hz), 2.70 (2H, t, J=7.5 Hz), 2.87 (3H, brs), 2.94 (3H, brs), 7.00 (1H, d, J=1.5 Hz), 7.22-7.26 (3H, m), 7.38-7.62 (7H, m), 7.69 (1H, dd, J=7.5, 1.5 Hz), 8.12-8.15 (2H, m), 8.30 (1H, d, J=8.3 Hz), 8.97 (1H, s). |

TABLE 1-continued

| Example | Structure | NMR (δ, 300 or 400 MHz, CDCl₃) |
|---|---|---|
| 1-3 | 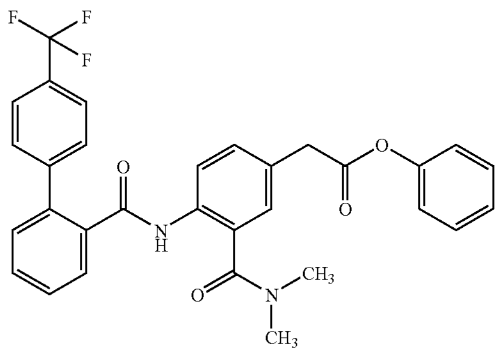 | 2.88 (3H, brs), 2.94 (3H, brs), 3.80 (2H, s), 7.02 (2H, d, J=7.5 Hz), 7.19-7.27 (2H, m), 7.31-7.43 (4H, m), 7.45-7.58 (2H, m), 7.62 (4H, brs), 7.70 (1H, dd, J=1.5 Hz, 7.5 Hz), 8.42 (1H, d, J=8.7 Hz), 9.16 (1H, brs). |
| 1-4 | 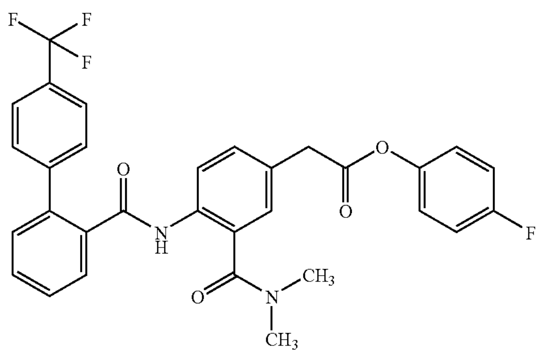 | 2.87 (3H, brs), 2.94 (3H, brs), 3.79 (2H, s), 6.95-7.09 (4H, m), 7.20 (1H, d, J=1.9 Hz), 7.34-7.44 (2H, m), 7.45-7.58 (2H, m), 7.62 (4H, brs), 7.70 (1H, dd, J=1.5 Hz, 7.5 Hz), 8.42 (1H, d, J=8.7 Hz), 9.14 (1H, brs). |
| 1-5 | 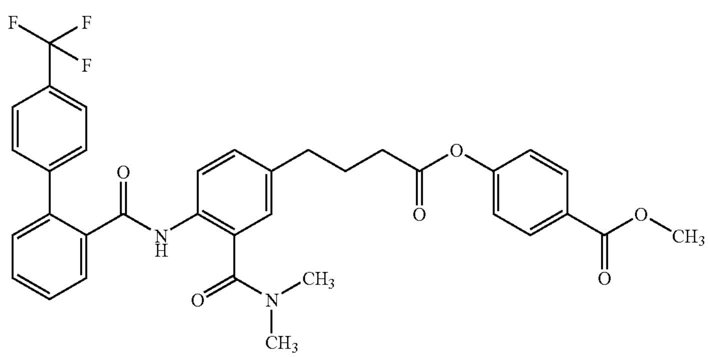 | 2.03 (2H, quint, J=7.4 Hz), 2.56 (2H, t, J=7.4 Hz), 1.69 (2H, t, J=7.4 Hz), 2.85 (3H, brs), 2.95 (3H, brs), 3.91 (3H, s), 7.00 (1H, d, J=1.9 Hz), 7.14 (2H, d, J=8.8 Hz), 7.22-7.28 (1H, m), 7.40 (1H, dd, J=1.4, 7.5 Hz), 7.46-7.56 (2H, m), 7.64 (4H, s), 7.69 (1H, dd, J=1.4, 7.5 Hz), 8.07 (2H, d, J=8.8 Hz), 8.30 (1H, d, J=8.4 Hz), 8.99 (1H, s) |
| 1-6 | 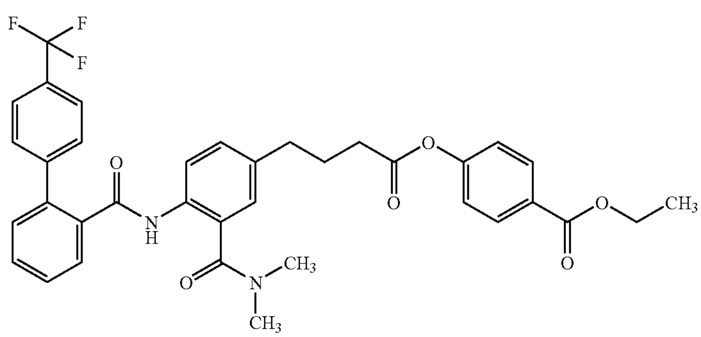 | 1.39 (3H, t, J=7.2 Hz), 1.95-2.10 (2H, m), 2.56 (2H, t, J=7.2 Hz), 2.69 (2H, t, J=7.5 Hz), 2.86 (3H, brs), 2.94 (3H, brs), 4.37 (4H, q, J=7.2 Hz), 7.00 (1H, 1.9 Hz), 7.13 (2H, d, J=8.7 Hz), 7.22-7.28 (1H, m), 7.40 (1H, dd, J=1.5 Hz, 7.2 Hz), 7.44-7.57 (2H, m), 7.62 (4H, brs), 7.69 ((1H, dd, J=1.9 Hz, 7.5 Hz), 8.07 (2H, d, J=8.7 Hz), 8.29 (1H, d, J=8.7 Hz), 8.98 (1H, brs). |

TABLE 2

| Example | Structure | NMR (δ, 300 or 400 MHz, CDCl₃) |
|---|---|---|
| 1-7 | 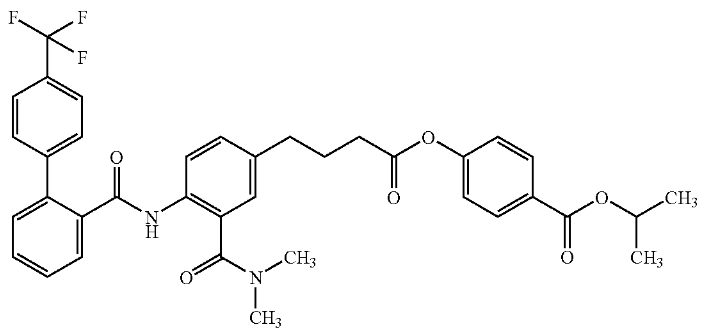 | 1.34 (6H, d, J=6.3 Hz), 2.01 (2H, quint, J=7.4 Hz), 2.54 (2H, t, J=7.4 Hz), 2.67 (2H, t, J=7.4 Hz), 2.83 (3H, brs), 2.93 (3H, brs), 5.22 (1H, sep, J=6.3 Hz), 6.98 (1H, d, J=1.8 Hz), 7.10 (2H, d, J=8.6 Hz), 7.20-7.26 (1H, m), 7.38 (1H, d, J=7.4 Hz), 7.43-7.56 (2H, m), 7.60 (4H, 2), 7.67 (1H, d, J=7.4 Hz), 8.04 (2H, d, J=8.8 Hz), 8.27 (1H, d, J=8.4 Hz), 8.97 (1H, s). |
| 1-8 | 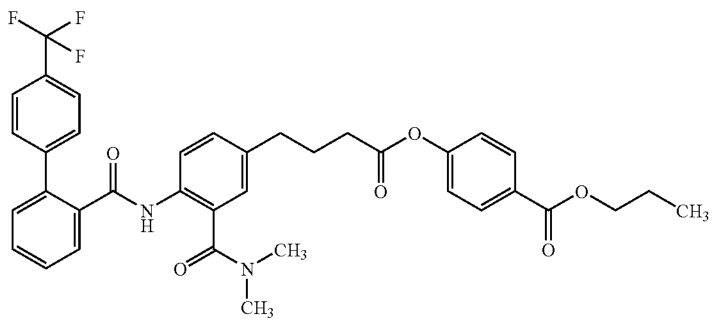 | 1.00 (3H, t, J=7.4 Hz), 1.71-1.82 (2H, m), 2.01 (2H, quint, J=7.4 Hz), 2.54 (2H, t, J=7.4 Hz), 2.67 (2H, t, J=7.4 Hz), 2.83 (3H, brs), 2.93 (3H, brs), 4.26 (2H, t, J=8.6 Hz), 6.98 (1H, d, J=1.8 Hz), 7.11 (2H, d, J=8.8 Hz), 7.20-7.26 (1H, m), 7.38 (1H, d, J=7.6 Hz), 7.43-7.56 (2H, m), 7.60 (4H, s), 7.67 (1H, d, J=7.4 Hz), 8.05 (2H, d, J=8.8 Hz), 8.28 (1H, d, J=8.4 Hz), 8.97 (1H, s) |
| 1-9 | 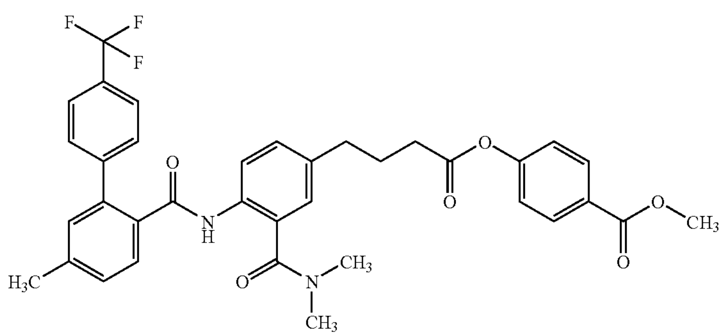 | 1.96-2.10 (2H, m), 2.44 (3H, s), 2.55 (2H, t, J=7.2 Hz), 2.61 (2H, t, J=7.4 Hz), 2.86 (3H, brs), 2.94 (3H, brs), 3.91 (3H, s), 6.99 (1H, d, J=1.9 Hz), 7.14 (2H J=8.7 Hz), 7.18-7.31 (3H, m), 7.55-7.64 (5H, m), 8.06 (2H, d, J=8.7 Hz), 8.29 (1H, d, J=8.7 Hz), 8.95 (1H, brs). |
| 1-10 | 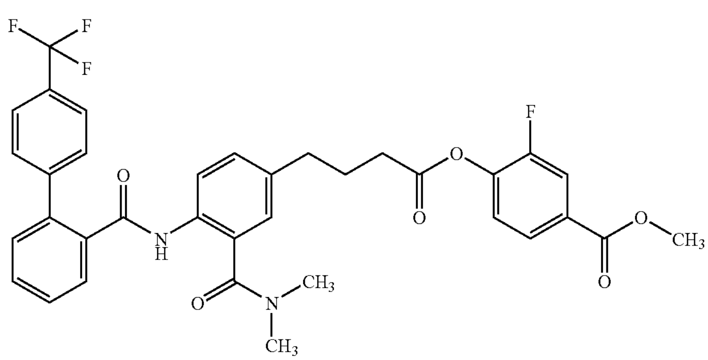 | 1.96-2.07 (2H, m), 2.57 (2H, dt, J=2.1, 7.2 Hz), 2.68 (2H, dt, J=2.1, 7.5 Hz), 2.83 (3H, brs), 2.93 (3H, brs), 3.90 (3H,d, J=2.3 Hz), 6.98 (1H, s), 7.13-7.19 (1H, m), 7.20-7.26 (1H, m), 7.35-7.40 (1H, m), 7.43-7.54 (2H, m), 7.59 (4H, d, J=2.1 Hz), 7.67 (1H, d, J=7.7 Hz), 7.78-7.86 (2H, m), 8.28 (1H, dd, J=2.1, 8.5 Hz), 8.98 (1H, s). |

TABLE 2-continued

| Example | Structure | NMR (δ, 300 or 400 MHz, CDCl₃) |
|---|---|---|
| 1-11 | 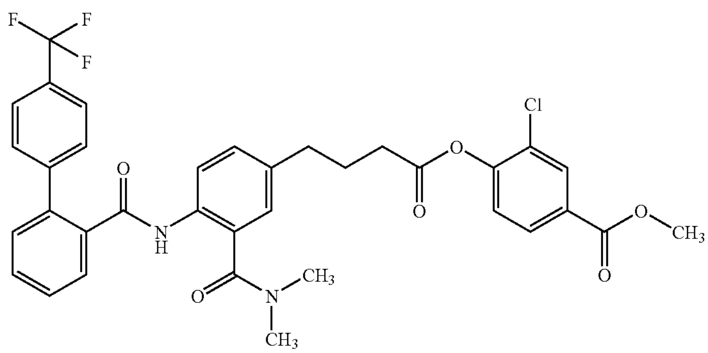 | 1.99-2.09 (2H, m), 2.60 (2H, t, J=7.2 Hz), 2.69 (2H, t, J=7.4 Hz), 2.84 (3H, brs), 2.93 (3H, brs), 3.90 (3H, s), 6.98 (1H, d, J=1.6 Hz), 7.17 (1H, d, J=8.4 Hz), 7.21-7.26 (1H, m), 7.37 (1H, d, J=7.6 Hz), 7.44-7.54 (2H, m) 7.60 (4H, s), 7.66 (1H, d, J=7.2 Hz), 7.94 (1H, dd, J=2.0, 8.4 Hz), 8.11 (1H, d, J=2.0 Hz), 8.28 (1H, d, J=8.5 Hz), 8.98 (1H, s) |

TABLE 3

| Example | Structure | NMR (δ, 300 or 400 MHz, CDCl₃) |
|---|---|---|
| 1-12 | 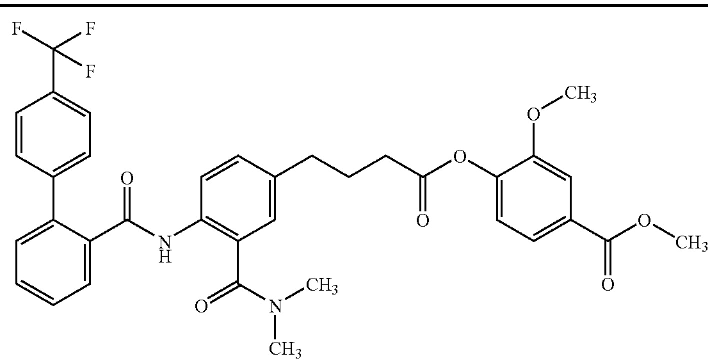 | 2.01 (2H, quint, J=7.4 Hz), 2.55 (2H, t, J=7.4 Hz), 2.69 (2H, t, J=7.4 Hz), 2.83 (3H, brs), 2.92 (3H, brs), 3.85 (3H, s), 3.90 (3H, s), 6.99 (1H, d, J=1.8 Hz), 7.05 (1H, d, J=8.1 Hz), 7.21-7.28 (1H, m), 7.37 (1H, dd, J=1.1, 7.7 Hz), 7.43-7.55 (2H, m), 7.60 (4H, s), 7.63-7.69 (3H, m), 8.27 (1H, d, J=8.3 Hz), 8.98 (1H, s) |
| 1-13 | 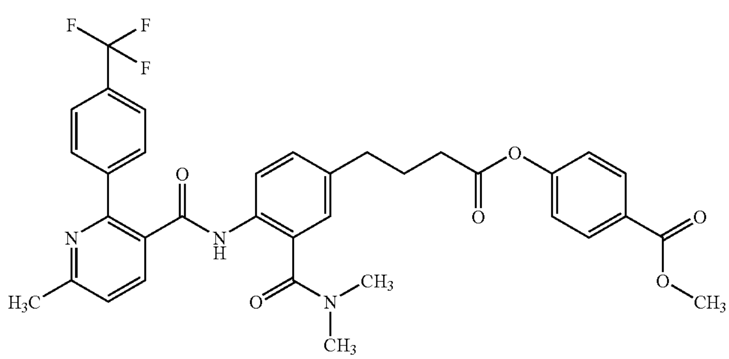 | 2.03 (2H, quint, J=7.5 Hz), 2.56 (2H, t, J=7.5 Hz), 2.66 (3H, s), 2.70 (2H, t, J=7.5 Hz), 2.86 (6H, brs), 3.91 (3H, s), 7.00 (1H, d, J=1.8 Hz), 7.11-7.16 (2H, m), 7.25-7.29 (2H, m), 7.63-7.65 (2H, m), 7.86-7.92 (3H, m), 8.04-8.09 (2H, m), 8.37 (1H, d, J=8.3 Hz), 9.12 (1H, s). |
| 1-14 | 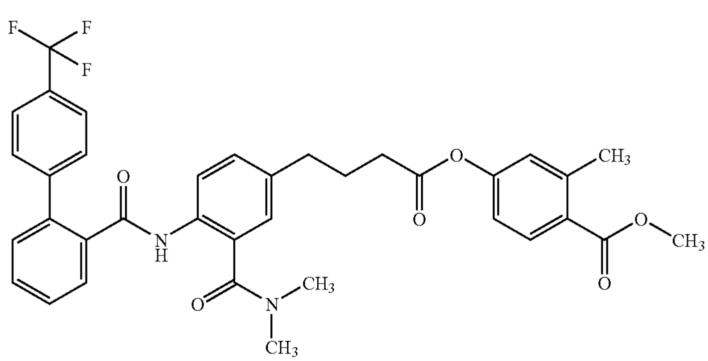 | 1.95-2.08 (2H, m), 2.54 (2H, t, J=7.2 Hz), 2.60 (3H, s), 2.69 (2H, t, J=7.5 Hz), 2.86 (3H, brs), 2.94 (3H, brs), 3.88 (3H, s), 6.92-7.02 (3H, m), 7.22-7.28 (1H, m), 7.40 (1H, dd, J=1.5 Hz, 7.2 Hz), 7.45-7.57 (2H, m), 7.62 (4H, brs), 7.69 (1H, dd, J=1.5 Hz, 7.6 Hz), 7.96 (1H, d, J=9.4 Hz), 8.29 (1H, J=8.7 Hz), 8.99 (1H, brs). |

TABLE 3-continued

| Example | Structure | NMR (δ, 300 or 400 MHz, CDCl₃) |
|---|---|---|
| 1-15 | 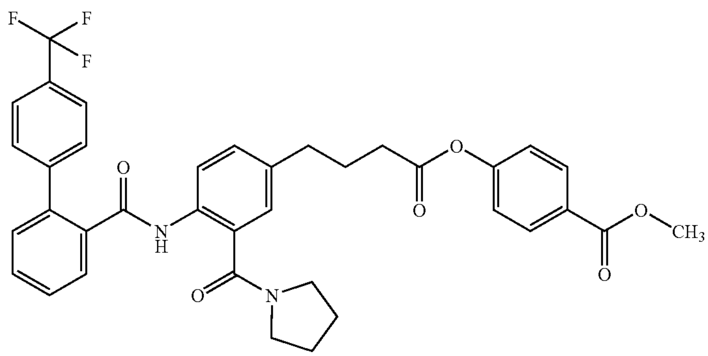 | 1.77-1.87 (2H, m), 1.88-1.98 (2H, m), 1.98-2.09 (2H, m), 2.56 (2H, dt, J=2.1, 7.4 Hz), 2.70 (2H, t, J=7.4 Hz), 3.35-3.42 (2H, m), 3.47-3.55 (2H, m), 3.92 (3H, d, J=2.1 Hz), 7.11-7.18 (3H, m), 7.21-7.27 (1H, m), 7.38 (1H, dt, J=1.6, 7.4 Hz), 7.44-7.55 (2H, m), 7.60 (4H, d, J=2.1 Hz), 7.68 (1H, dd, J=1.6, 7.2 Hz), 8.04-8.09 (2H, m), 8.27 (1H, dd, J=2.1, 8.6 Hz), 9.66 (1H, s). |
| 1-16 | 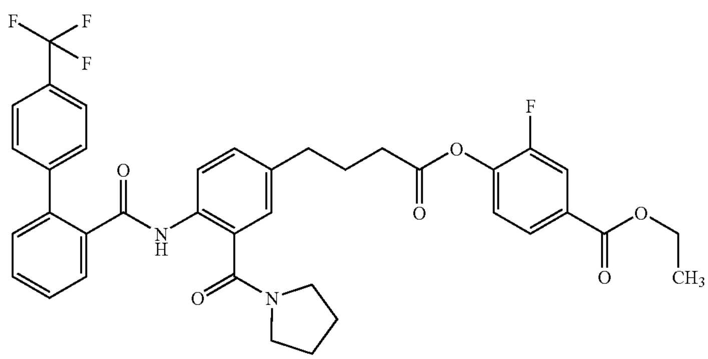 | 1.39 (3H, t, 7.2 Hz), 1.78-1.99 (4H, m), 2.04 (2H, quint, J=7.2 Hz), 2.60 (2H, t, J=7.2 Hz), 2.71 (2H, t, J=7.2 Hz), 3.40 (2H, t, J=6.4 Hz), 3.52 (2H, t, J=7.0 Hz), 4.38 (2H, q, J=7.2 Hz), 7.16-7.20 (2H, m), 7.22-7.27 (1H, m), 7.39 (1H, dd, J=1.4, 7.4 Hz), 7.44-7.56 (2H, m) 7.60 (4H, s), 7.68 (1H, dd, J=1.6, 7.4 Hz), 7.82-7.85 (2H, m), 8.28 (1H, d, J=8.4 Hz), 9.68 (1H, s). |

TABLE 4

| Example | Structure | NMR (δ, 300 or 400 MHz, CDCl₃) |
|---|---|---|
| 1-17 | 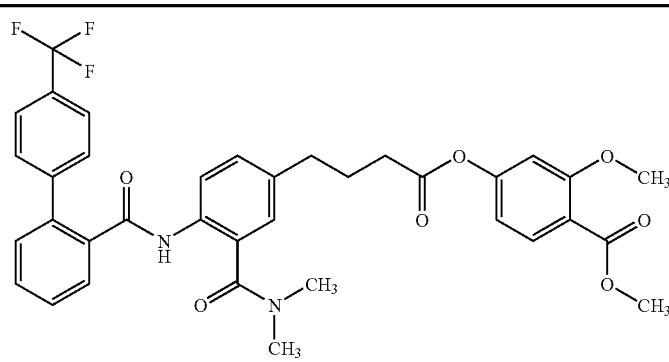 | 2.02 (2H, quint, J=7.4 Hz), 2.55 (2H, t, J=7.4 Hz), 2.69 (2H, t, J=7.4 Hz), 2.85 (3H, brs), 2.95 (3H, brs), 3.88 (3H, s), 3.89 (3H, s), 6.70-6.72 (2H, m), 7.00 (1H, d, J=2.1 Hz), 7.23-7.26 (1H, m), 7.40 (1H, dd, J=7.5, 1.4 Hz), 7.46-7.62 (6H, m), 7.69 (1H, dd, J=7.5, 1.4 Hz), 7.85 (1H, d, J=9.1 Hz), 8.30 (1H, d, J=8.6 Hz), 8.98 (1H, s). |
| 1-18 | 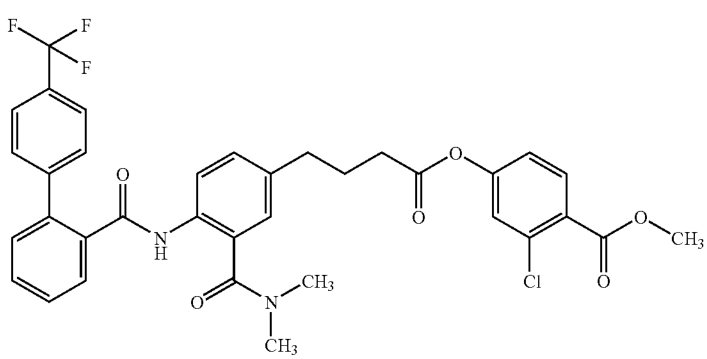 | 2.02 (2H, quint, J=7.4 Hz), 2.55 (2H, t, J=7.4 Hz), 2.68 (2H, t, J=7.4 Hz), 2.86 (3H, brs), 2.95 (3H, brs), 3.92 (3H, d, 0.7 Hz), 6.99 (1H, d, J=1.8 Hz), 7.03-7.08 (1H, m), 7.21-7.27 (2H, m), 7.40 (1H, dd, J=0.7, 7.4 Hz), 7.46-7.56 (2H, m), 7.64 (4H, s), 7.69 (1H, dd, J=1.4, 7.7 Hz), 7.89 (1H, dd, J=0.7, 8.6 Hz), 8.29 (1H, d, J=8.4 Hz), 8.98 (1H, s) |

TABLE 4-continued

| Example | Structure | NMR (δ, 300 or 400 MHz, CDCl₃) |
|---|---|---|
| 1-19 | 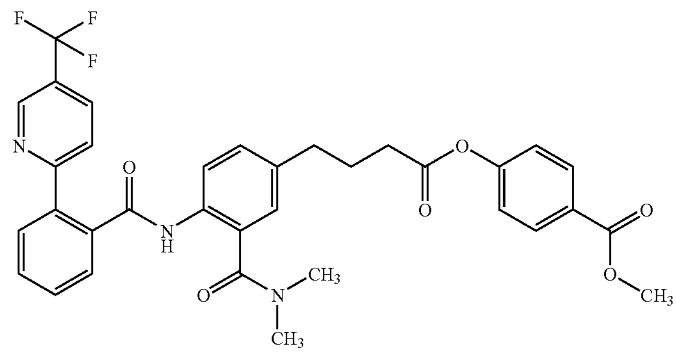 | 2.05 (2H, quint, J=7.6 Hz), 2.58 (2H, t, J=7.6 Hz), 2.72 (2H, t, J=7.6 Hz), 3.01 (6H, s), 3.91 (3H, s), 7.08-7.28 (4H, m), 7.52-7.73 (5H, m), 7.96 (1H, dd, J=8.3, 1.5 Hz), 8.05-8.08 (2H, m), 8.25 (1H, d, J=8.3 Hz), 8.86 (1H, s), 9.28 (1H, s). |
| 1-20 | 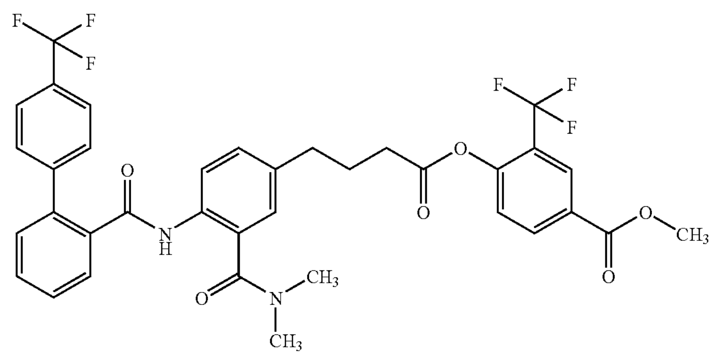 | 2.04 (2H, quint, J=7.4 Hz), 2.61 (2H, t, J=7.4 Hz), 2.69 (2H, t, J=7.4 Hz), 2.87 (3H, brs), 2.94 (3H, brs), 3.95 (3H, s), 7.00 (1H, d, J=1.9 Hz), 7.23-7.62 (9H, m), 7.69 (1H, dd, J=7.2, 1.5 Hz), 8.23-8.36 (3H, m), 9.00 (1H, s). |
| 1-21 | 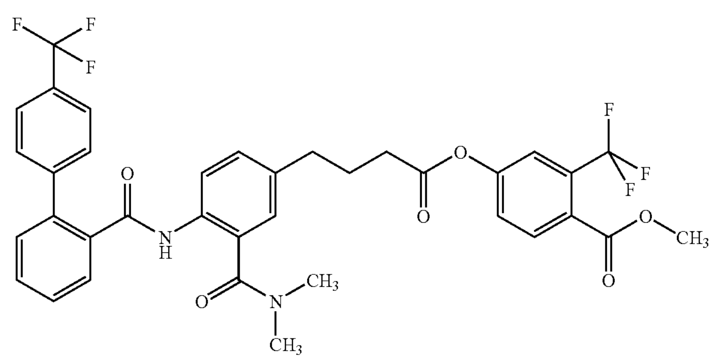 | 2.03 (2H, quint, J=7.5 Hz), 2.57 (2H, t, J=7.5 Hz), 2.69 (2H, t, J=7.5 Hz), 2.87 (3H, brs), 2.94 (3H, brs), 3.93 (3H, s), 7.00 (1H, d, J=2.3 Hz), 7.19-7.70 (10H, m), 7.69 (1H, d, J=7.6 Hz), 7.86 (1H, d, J=8.7 Hz), 8.30 (1H, d, J=8.3 Hz), 8.97 (1H, s). |
| 1-22 | 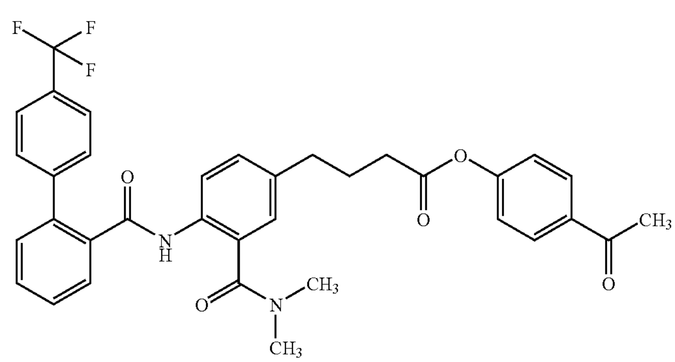 | 2.03 (2H, quint, J=7.6 Hz), 2.56 (2H, t, J=7.6 Hz), 2.59 (3H, s), 2.69 (2H, t, J=7.6 Hz), 2.87 (3H, brs), 2.94 (3H, brs), 7.00 (1H, d, J=1.9 Hz), 7.15-7.26 (3H, m), 7.38-7.62 (7H, m), 7.69 (1H, dd, J=7.5, 1.5 Hz), 7.98-8.00 (2H, m), 8.30 (1H, d, J=8.3 Hz), 8.98 (1H, s). |

TABLE 5

| Example | Structure | NMR (δ, 300 or 400 MHz, CDCl₃) |
|---|---|---|
| 1-23 | 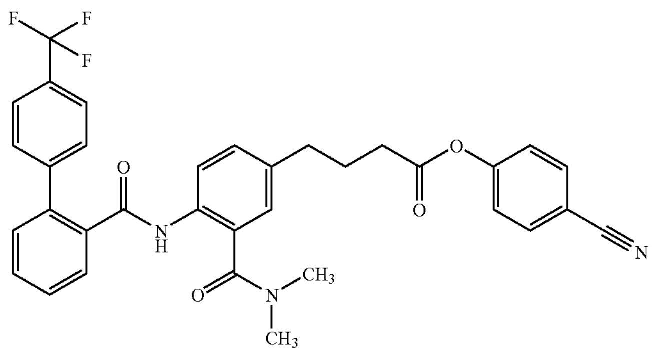 | 2.02 (2H, quint, J=7.4 Hz), 2.56 (2H, t, J=7.4 Hz), 2.69 (2H, t, J=7.4 Hz), 2.86 (3H, brs), 2.94 (3H, brs), 6.99 (1H, d, J=1.9 Hz), 7.18-7.26 (3H, m), 7.38-7.69 (10H, m), 8.29 (1H, d, J=8.6 Hz), 8.95 (1H, s). |
| 1-24 | 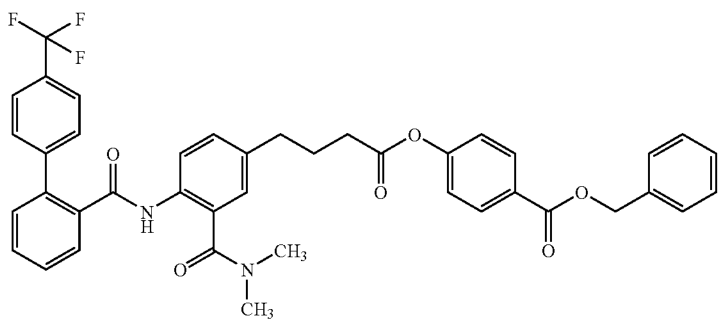 | 2.02 (2H, quint, J=7.5 Hz), 2.55 (2H, t, J=7.5 Hz), 2.69 (2H, t, J=7.5 Hz), 2.86 (3H, brs), 2.93 (3H, brs), 5.36 (2H, s), 6.99 (1H, d, J=1.1 Hz), 7.12-7.26 (3H, m), 7.34-7.61 (12H, m), 7.69 (1H, dd, J=7.2, 1.1 Hz), 8.09-8.11 (2H, m), 8.29 (1H, d, J=8.3 Hz), 8.98 (1H, s). |
| 1-25 | 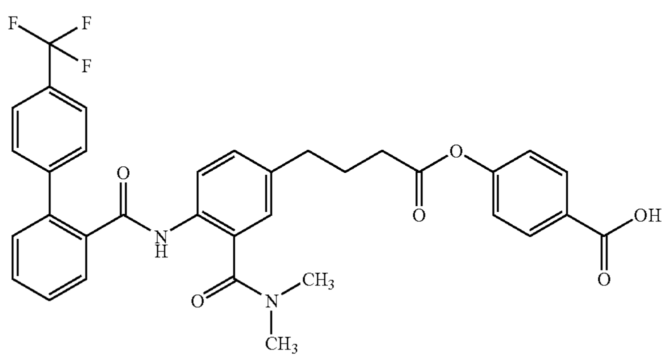 | 2.03 (2H, quint, J=7.2 Hz), 2.56 (2H, t, J=7.2 Hz), 2.69 (2H, t, J=7.2 Hz), 2.86 (3H, brs), 2.94 (3H, m), 7.38-7.62 (7H, m), 7.69 (1H, dd, J=7.2, 1.5 Hz), 8.09-8.12 (2H, m), 8.26 (1H, d, J=8.3 Hz), 8.98 (1H, s). |
| 1-26 | 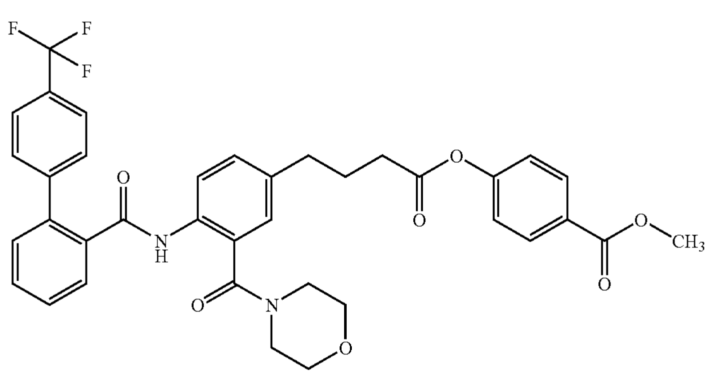 | 2.04 (2H, quint, J=7.4 Hz), 2.57 (2H, t, J=7.4 Hz), 2.71 (2H, t, J=7.4 Hz), 3.41-3.71 (8H, m), 3.92 (3H, s), 6.99 (1H, d, J=1.8 Hz), 7.10-7.16 (2H, m), 7.23-7.29 (1H, m), 7.41 (1H, dd, J=0.9, 7.4 Hz), 7.46-7.69 (7H, m), 8.05-8.13 (3H, m), 8.79 (1H, s). |

TABLE 5-continued

| Example | Structure | NMR (δ, 300 or 400 MHz, CDCl₃) |
|---|---|---|
| 1-27 | 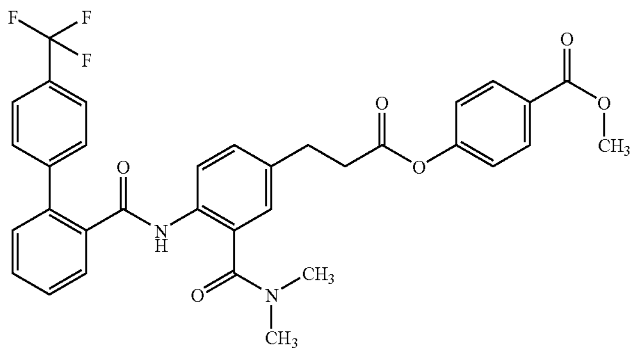 | 2.76-3.08 (1H, m), 3.91 (3H, 2), 6.99-7.06 (1H, m), 7.08 (2H, d, J=9.0 Hz), 7.19-7.58 (4H, m), 7.62 (4H, s), 7.66-7.72 (1H, m), 8.05 (2H, d, J=9.0 Hz), 8.33 (1H, d, J=8.7 Hz), 9.03 (1H, brs). |
| 1-28 | 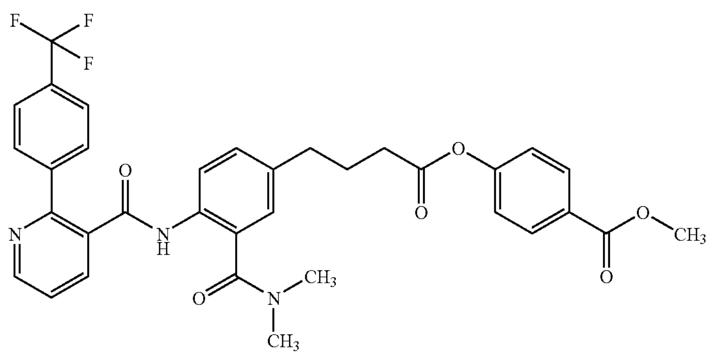 | 2.04 (2H, quint, J=7.5 Hz), 2.57 (2H, t, J=7.5 Hz), 2.71 (2H, t, J=7.5 Hz), 2.86 (6H, brs), 7.01 (1H, d, J=1.9 Hz), 7.14 (2H, d, J=8.7 Hz), 7.24-7.32 (1H, m), 7.42 (1H, dd, J=4.9 Hz, 7.9 Hz), 7.66 (2H, d, J=8.3 Hz), 7.89 (2H, d, J=8.3 Hz), 8.03 (1H, dd, J=7.9 Hz, 1.9 Hz), 8.07 (2H, d, J=8.7 Hz), 8.36 (1H, d, J=8.7 Hz), 8.79 (1H, dd, J=1.9 Hz, 4.9 Hz), 9.21 (1H, brs). |

TABLE 6

| Example | Structure | NMR (δ, 300 or 400 MHz, CDCl₃) |
|---|---|---|
| 1-29 | 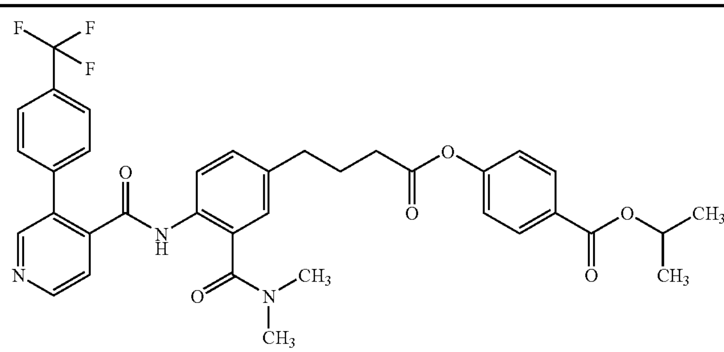 | 1.36 (6H, d, J=6.4 Hz), 2.04 (2H, quint, J=7.5 Hz), 2.57 (2H, t, J=7.5 Hz), 2.71 (2H, t, J=7.5 Hz), 2.86 (6H, brs), 5.24 (1H, sept, J=6.4 Hz), 7.01 (1H, d, J=1.8 Hz), 7.12 (1H, d, J=8.7 Hz), 7.24-7.32 (1H, m), 7.41 (1H, dd, J=4.8 Hz, 7.9 Hz), 7.66 (2H, d, J=7.9 Hz), 7.89 (2H, d, J=7.9 Hz), 7.99-8.04 (1H, m), 8.06 (2H, d, J=8.7 Hz), 8.36 (1H, d, J=8.7 Hz), 8.80 (1H, dd, J=1.9 Hz, 4.8 Hz), 9.12 (1H, brs). |
| 1-30 | 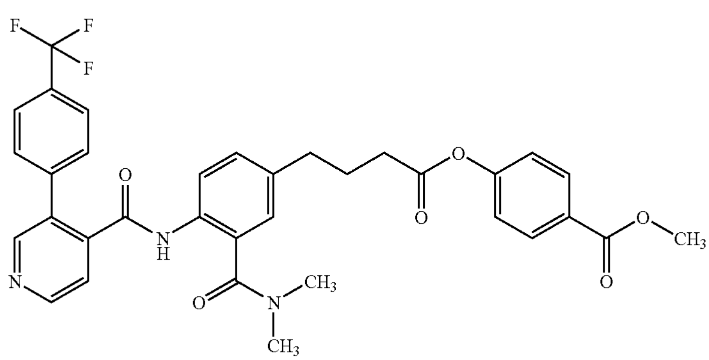 | 2.00-2.09 (2H, m), 2.57 (2H, t, J=7.4 Hz), 2.71 (2H, t, 7.7 Hz), 2.84-2.98 (6H, m), 3.91 (3H, s), 7.03 (1H, d, J=2.2 Hz), 7.13 (2H, d, J=8.6 Hz), 7.21-7.31 (1H, m), 7.57 (1H, d, J=4.6 Hz), 7.63 (2H, d, 8.5 Hz), 7.68 (2H, d, 8.5 Hz), 8.07 (2H, d, J=8.6 Hz), 8.28 (1H, d, J=8.3 Hz), 8.63-8.76 (2H, m), 9.29 (1H, m). |

TABLE 6-continued

| Example | Structure | NMR (δ, 300 or 400 MHz, CDCl₃) |
|---|---|---|
| 1-31 | 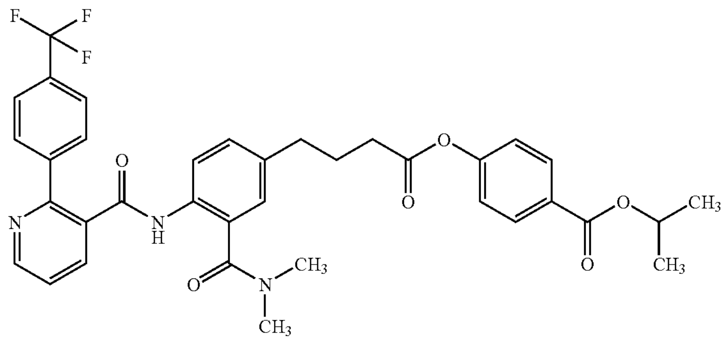 | 1.36 (6H, d, J=6.3 Hz), 2.03 (2H, quint, J=7.4 Hz), 2.56 (2H, t, J=7.4 Hz), 2.70 (2H, t, 7.7 Hz), 2.84-2.99 (6H, m), 5.24 (1H, sep, J=6.3 Hz), 7.03 (1H, d, J=2.2 Hz), 7.12 (2H, d, J=8.2 Hz), 7.23-7.29 (1H, m), 7.57 (1H, d, J=4.9 Hz), 7.64 (2H, d, 8.3 Hz), 7.68 (2H, d, 8.3 Hz), 8.06 (2H, d, J=8.2 Hz), 8.28 (1H, d, J=8.6 Hz), 8.67-8.81 (2H, m), 9.30 (1H, m). |
| 1-32 | 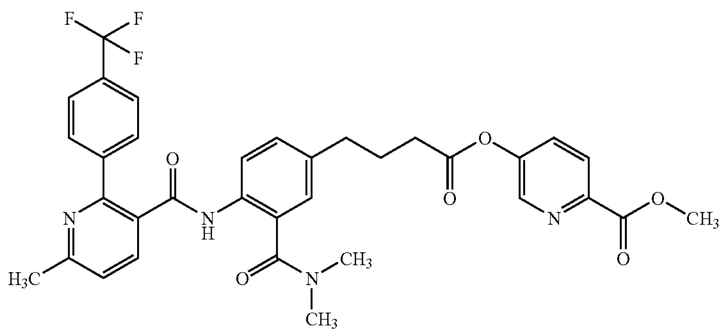 | 2.04 (2H, quint, J=7.5 Hz), 2.61 (2H, t, J=7.5 Hz), 2.67 (3H, s), 2.70 (2H, t, J=7.5 Hz), 2.87 (6H, brs), 4.01 (3H, s), 7.00 (1H, d, J=2.2 Hz), 7.25-7.28 (2H, m), 7.60-7.66 (3H, m), 7.86-7.92 (3H, m), 7.86-7.92 (3H, m), 8.19 (1H, d, J=9.0 Hz), 8.36 (1H, d, J=8.7 Hz), 8.52 (1H, d, J=2.7 Hz), 9.10 (1H, s). |
| 1-33 | 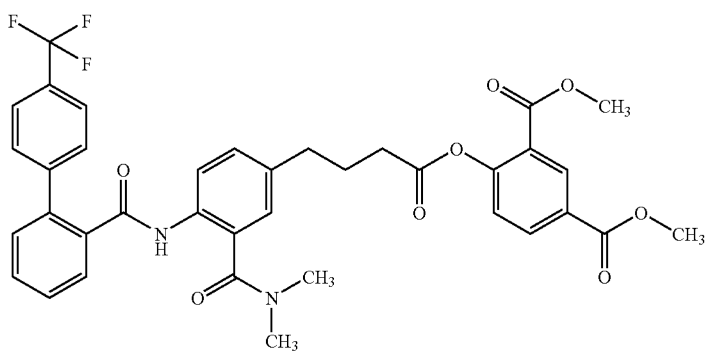 | 2.04 (2H, quint, J=7.2 Hz), 2.64 (2H, t, J=7.2 Hz), 2.71 (2H, t, J=7.2 Hz), 2.87 (3H, brs), 2.94 (3H, brs), 3.87 (3H, s), 3.94 (3H, s), 7.04 (1H, d, J=1.9 Hz), 7.15 (1H, d, J=8.7 Hz), 7.25-7.30 (1H, m), 7.39 (1H, dd, J=1.1 Hz, 7.5 Hz), 7.44-7.57 (2H, m), 7.69 (1H, dd, J=1.9 Hz, 7.2 Hz), 8.22 (1H, dd, J=2.3 Hz, 8.7 Hz), 8.30 (1H, d, J=8.7 Hz), 8.68 (1H, d, J=2.3 Hz), 9.00 (1H, brs). |

TABLE 7

| Example | Structure | NMR (δ, 300 or 400 MHz, CDCl₃) |
|---|---|---|
| 1-34 | 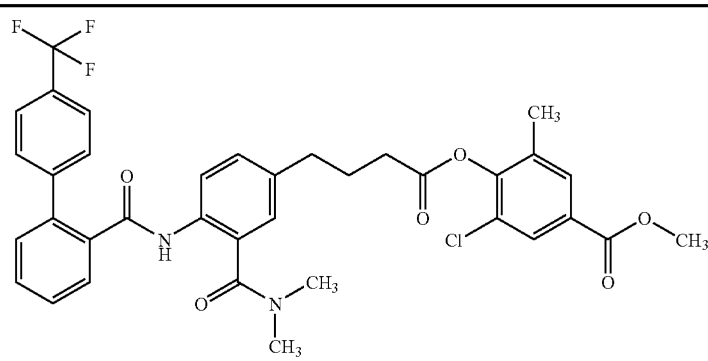 | 2.07 (2H, quint, J=7.2 Hz), 2.22 (3H, s), 2.64 (2H, t, J=7.2 Hz), 2.73 (2H, t, J=7.2 Hz), 2.86 (3H, brs), 2.94 (3H, brs), 3.91 (3H, s), 7.01 (1H, d, J=1.9 Hz), 7.25 (1H, dd, J=1.9 Hz, 8.7 Hz), 7.40 (1H, dd, J=1.1 Hz, 7.2 Hz), 7.44-7.57 (2H, m), 7.62 (4H, s), 7.69 (1H, dd, J=1.9 Hz, 7.2 Hz), 7.83 (1H, d, J=1.9 Hz), 7.96 (1H, d, J=1.9 Hz), 8.30 (1H, d, J=8.7 Hz), 9.00 (1H, brs). |

TABLE 7-continued

| Example | Structure | NMR (δ, 300 or 400 MHz, CDCl₃) |
|---------|-----------|-------------------------------|
| 1-35 | 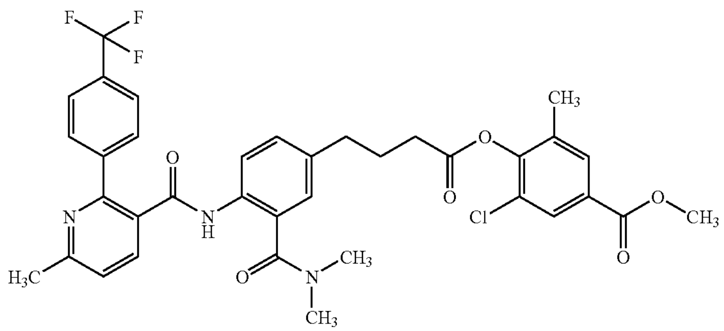 | 2.07 (2H, quint, J=7.1 Hz), 2.22 (3H, s), 2.64 (2H, t, J=7.1 Hz), 2.67 (3H, s), 2.73 (2H, t, J=7.1 Hz), 2.87 (6H, brs), 3.91 (3H, s), 7.02 (1H, d, J=1.9 Hz), 7.25-7.30 (2H, m), 7.63-7.66 (2H, m), 7.83-7.96 (5H, m), 8.37 (1H, d, J=8.7 Hz), 9.15 (1H, s). |
| 1-36 | 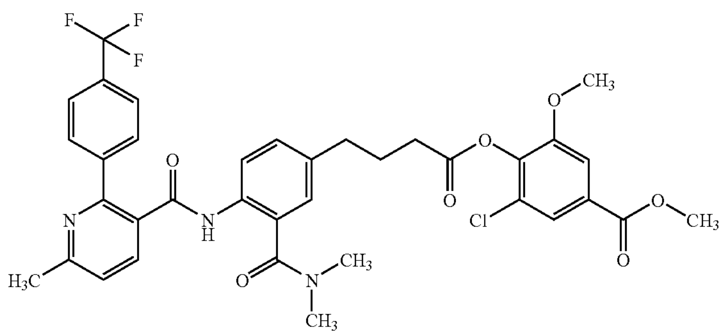 | 2.06 (2H, quint, J=7.2 Hz), 2.63 (2H, t, J=7.2 Hz), 2.66 (3H, s), 2.73 (2H, t, J=7.2 Hz), 2.86 (6H, brs), 3.88 (3H, s), 3.93 (3H, s), 7.02 (1H, d, J=2.3 Hz), 7.26 (1H, d, J=7.9 Hz), 7.27-7.32 (1H, m), 7.55 (1H, d, J=1.9 Hz), 7.65 (2H, d, J=8.3 Hz), 7.75 (1H, d, J=1.9 Hz), 7.87 (2H, d, J=8.3 Hz), 7.91 (1H, d, J=7.9 Hz), 8.36 (1H, d, J=8.7 Hz), 9.15 (1H, brs). |
| 1-37 | 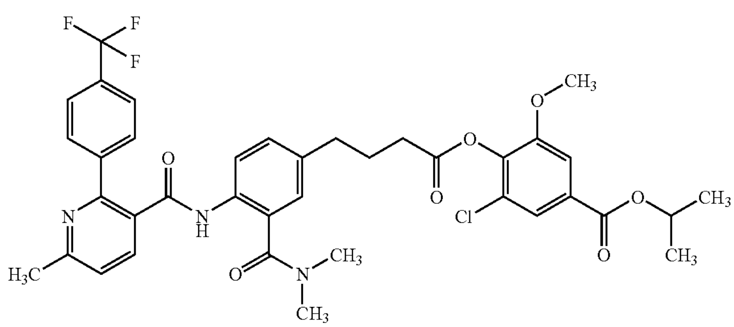 | 1.37 (6H, d, J=6.0 Hz), 2.06 (2H, quint, J=7.2 Hz), 2.63 (2H, t, J=7.2 Hz), 2.67 (3H, s), 2.73 (2H, t, J=7.2 Hz), 2.86 (6H, brs), 3.88 (3H, s), 5.25 (1H, sept, J=6.0 Hz), 7.02 (1H, d, J=2.3 Hz), 7.26 (1H, d, J=7.9 Hz), 7.27-7.31 (1H, m), 7.54 (1H, d, J=1.9 Hz), 7.65 (2H, d, J=8.3 Hz), 7.73 (1H, d, J=1.9 Hz), 7.87 (2H, d, J=8.3 Hz), 7.91 (1H, d, J=7.9 Hz), 8.87 (1H, d, J=8,7 Hz), 9.16 (1H, brs). |
| 1-38 | 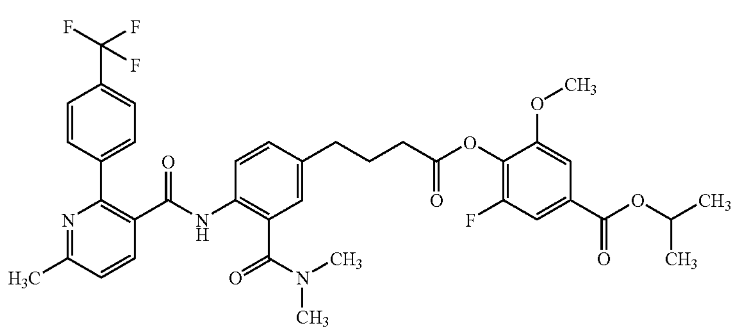 | 1.37 (6H, t, J=6.0 Hz), 2.05 (2H, quint, J=7.2 Hz), 2.62 (2H, t, J=7.2 Hz), 2.66 (3H, s), 2.72 (2H, t, J=7.2 Hz), 2.87 (6H, brs), 3.89 (3H, s), 5.24 (1H, sept, J=6.0 Hz), 7.02 (1H, d, J=1.9 Hz), 7.25-7.30 (2H, m), 7.46-7.49 (2H, m), 7.63-7.66 (2H, m), 7.86-7.93 (3H, m), 8.37 (1H, d, J=8.3 Hz), 9.16 (1H, s). |

TABLE 8

| Example | Structure | NMR (δ, 300 or 400 MHz, CDCl₃) |
|---|---|---|
| 1-39 | 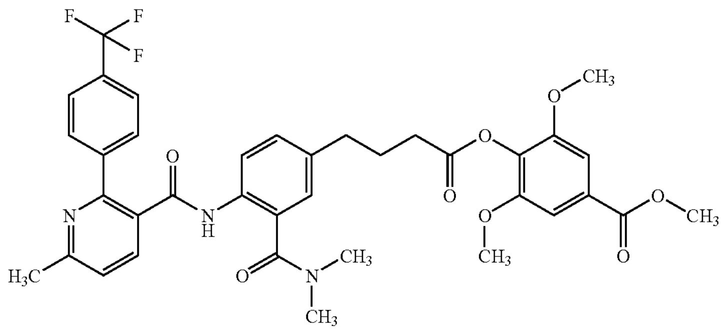 | 2.05 (2H, quint, J=7.2 Hz), 2.61 (2H, t, J=7.2 Hz), 2.66 (3H, s), 2.73 (2H, t, J=7.2 Hz), 2.86 (6H, brs) 3.86 (6H, s) 3.92 (3H, s), 7.03 (1H, d, J=1.9 Hz), 7.25-7.33 (4H, m), 7.63-7.66 (2H, m), 7.86-7.93 (3H, m), 8.36 (1H, d, J=8.7 Hz), 9.15 (1H, s). |
| 1-40 | 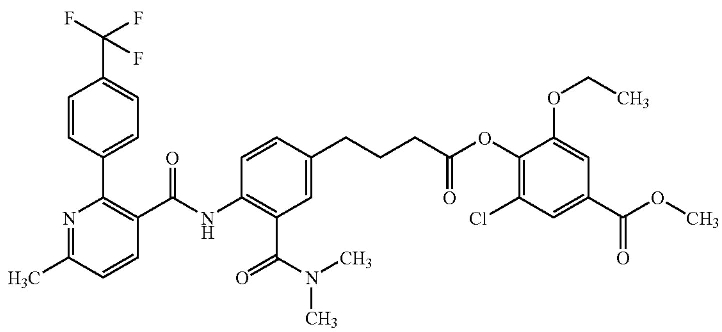 | 1.37 (3H, t, J=6.8 Hz), 2.06 (2H, quint, J=7.2 Hz), 2.63 (2H, t, J=7.2 Hz), 2.67 (3H, s), 2.74 (2H, t, J=7.2 Hz), 2.86 (6H, brs), 3.92 (3H, s), 4.12 (2H, q, J=6.8 Hz), 7.03 (1H, d, J=1.9 Hz), 7.25-7.31 (2H, m), 7.53 (1H, d, J=1.9 Hz), 7.63-7.66 (2H, m), 7.73 (1H, d, J=1.9 Hz), 7.86-7.93 (3H, m), 8.37 (1H, d, J=8.3 Hz), 9.16 (1H, s). |
| 1-41 | 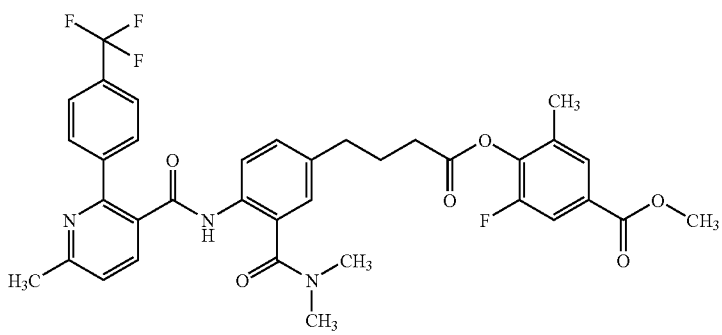 | 2.06 (2H, quint, J=7.2 Hz), 2.23 (3H, s), 2.63 (2H, t, J=7.2 Hz), 2.67 (3H, s), 2.72 (2H, t, J=7.2 Hz), 2.87 (6H, brs), 3.91 (3H, s), 7.01 (1H, d, J=1.9 Hz), 7.25-7.29 (2H, m), 7.63-7.68 (3H, m), 7.74 (1H, s), 7.86-7.93 (3H, m), 8.37 (1H, d, J=8.6 Hz), 9.16 (1H, s). |
| 1-42 | 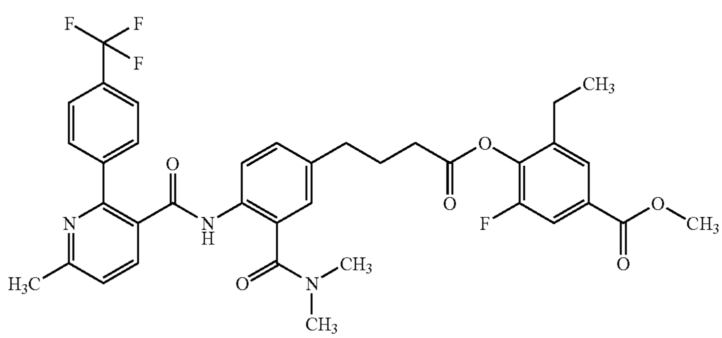 | 1.20 (3H, t, J=7.7 Hz), 2.06 (2H, quint, J=7.5 Hz), 2.55-2.65 (4H, m), 2.67 (3H, s), 2.72 (2H, t, J=7.5 Hz), 2.87 (6H, brs), 3.92 (3H, s), 7.01 (1H, d, J=2.3 Hz), 7.25-7.29 (2H, m), 7.63-7.69 (3H, m), 7.76 (1H, s), 7.86-7.93 (3H, m), 8.37 (1H, d, J=8.3 Hz), 9.16 (1H, s). |

TABLE 8-continued

| Example | Structure | NMR (δ, 300 or 400 MHz, CDCl₃) |
|---|---|---|
| 1-43 | 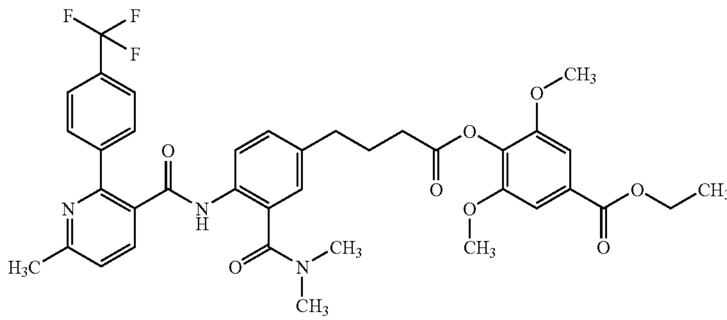 | 1.33 (3H, t, J=6.9 Hz), 1.93 (2H, quint, J=7.1 Hz), 2.57 (2H, t, J=7.1 Hz), 2.60 (3H, s), 2.70 (2H, t, J=7.1 Hz), 2.78 (3H, s), 2.87 (3H, s), 3.82 (6H, s), 4.34 (2H, q, J=6.9 Hz), 7.15 (1H, d, J=1.5 Hz), 7.27-7.30 (2H, m), 7.44 (2H, dd, J=2.2, 7.9 Hz), 7.80-7.91 (6H, m), 10.13 (1H, s). |
| 1-44 | 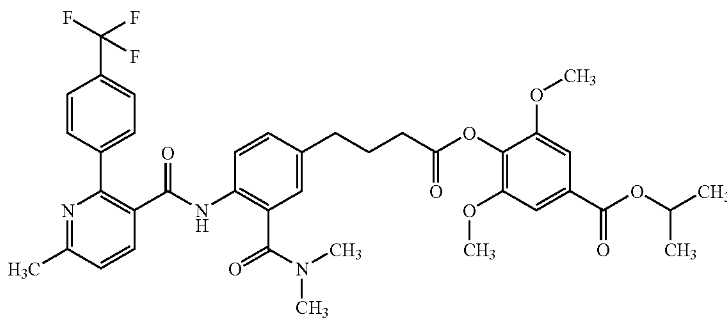 | 1.38 (6H, d, J=6.4 Hz), 2.05 (2H, quint, J=7.1 Hz), 2.60 (2H, t, J=7.1 Hz), 2.67 (3H, s), 2.73 (2H, t, J=7.1 Hz), 2.86 (6H, brs), 3.86 (6H, s), 5.25 (1H, sept, J=6.4 Hz), 7.04 (1H, d, J=2.3 Hz), 7.25-7.32 (4H, m), 7.65 (2H, d, J=8.7 Hz), 7.86-7.93 (3H, m), 8.36 (1H, d, J=8.2 Hz), 9.16 (1H, s). |

TABLE 9

| Example | Structure | NMR (δ, 300 or 400 MHz, CDCl₃) |
|---|---|---|
| 1-45 | 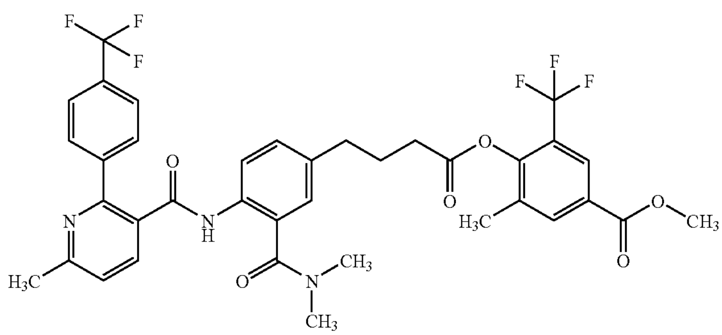 | 2.05 (2H, quint, J=7.2 Hz), 2.23 (3H, s), 2.62 (2H, t, J=7.2 Hz), 2.67 (3H, s), 2.70 (2H, t, J=7.2 Hz), 2.87 (6H, brs), 3.94 (3H, s), 7.01 (1H, d, J=1.8 Hz), 7.25-7.29 (2H, m), 7.65 (2H, d, J=8.1 Hz), 7.88 (2H, d, J=8.1 Hz), 7.91 (1H, d, J=8.1 Hz), 8.14-8.19 (2H, m), 8.38 (1H, d, J=8.1 Hz), 9.16 (1H, s). |
| 1-46 | 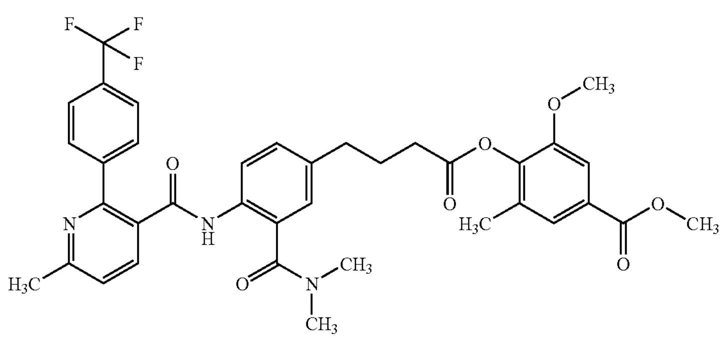 | 2.05 (2H, quint, J=7.2 Hz), 2.19 (3H, s), 2.60 (2H, t, J=7.2 Hz), 2.67 (3H, s), 2.73 (2H, t, J=7.2 Hz), 2.86 (3H, brs), 3.84 (3H, s), 3.91 (3H, s), 7.02 (1H, d, J=1.9 Hz), 7.24-7.31 (2H, m), 7.48 (1H, d, J=1.9 Hz), 7.56 (1H, d, J=1.9 Hz), 7.64 (2H, d, J=8.3 Hz), 7.88 (2H, d, J=8.3 Hz), 7.92 ((1H, d, J=7.9 Hz), 8.36 (1H, d, J=8.3 Hz), 9.15 (1H, brs). |

TABLE 9-continued

| Example | Structure | NMR (δ, 300 or 400 MHz, CDCl₃) |
|---|---|---|
| 1-47 | 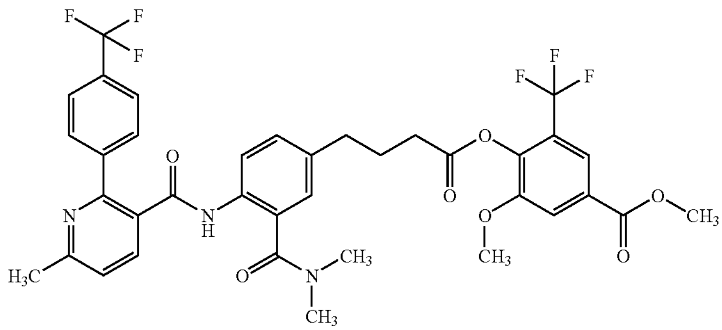 | 2.04 (2H, quint, J=7.2 Hz), 2.61 (2H, t, J=7.2 Hz), 2.66 (3H, s), 2.71 (2H, t, J=7.2 Hz), 2.86 (6H, brs), 3.91 (3H, s), 3.96 (3H, s), 7.02 (1H, d, J=1.9 Hz), 7.23-7.31 (2H, m), 7.65 (2H, d, J=8.3 Hz), 7.83 (1H, d, J=1.5 Hz), 7.88 (2H, d, J=8.3 Hz), 7.92 (1H, d, J=7.9 Hz), 7.94 (1H, d, J=1.5 Hz), 8.37 (1H, d, J=8.3 Hz), 9.16 (1H, brs). |
| 1-48 | 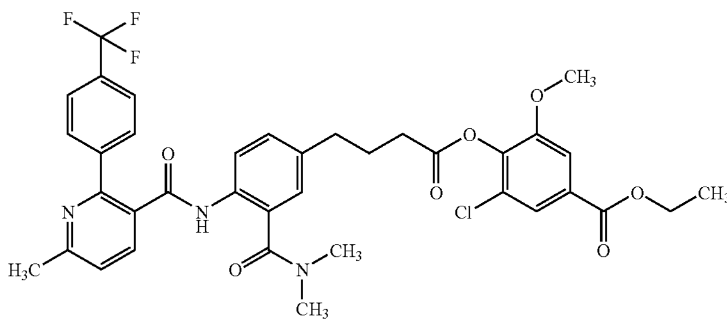 | 1.40 (3H, t, J=7.2 Hz), 2.06 (2H, quint, J=7.2 Hz), 2.63 (2H, t, J=7.2 Hz), 2.67 (3H, s), 2.73 (2H, t, J=7.2 Hz), 2.86 (6H, brs), 3.88 (3H, s), 4.39 (2H, q, J=7.2 Hz), 7.03 (1H, d, J=1.9 Hz), 7.24-7.31 (2H, m), 7.55 (1H, d, J=1.9 Hz), 7.65 (2H, d, J=8.3 Hz), 7.75 (1H, d, J=1.9 Hz), 7.88 (2H, d, J=8.3 Hz), 7.92 (1H, d, J=7.9 Hz), 8.37 (1H, d, J=8.3 Hz), 9.16 (1H, brs). |
| 1-49 | 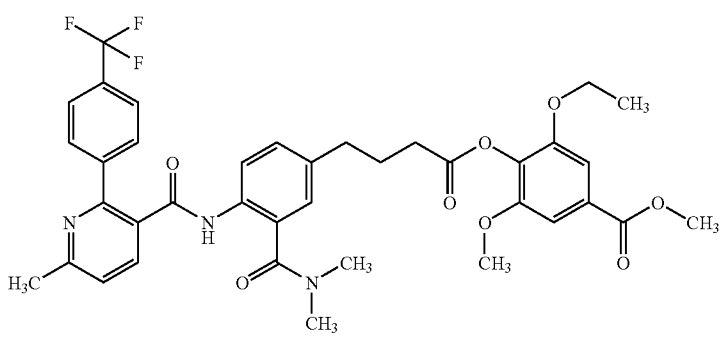 | 1.36 (3H, t, J=7.1 Hz), 2.05 (2H, quint, J=7.2 Hz)m 2.60 (2H, t, J=7.2 Hz), 2.67 (3H, s), 2.74 (2H, t, J=7.2 Hz), 2.86 (6H, brs), 3.86 (3H, s), 3.92 (3H, s), 4.10 (2H, q, J=7.1 Hz), 7.04 (1H, d, J=1.9 Hz), 7.25-7.31 (4H, m), 7.65 (2H, d, J=7.9 Hz), 7.88 (2H, d, J=7.9 Hz), 7.92 (1H, d, J=7.9 Hz), 8.36 (1H, d, J=8.3 Hz), 9.16 (1H, s). |

TABLE 10

| Example | Structure | NMR (δ, 300 or 400 MHz, CDCl₃) |
|---|---|---|
| 1-50 | 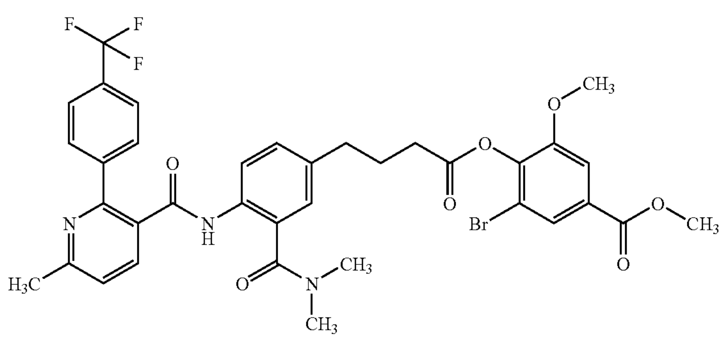 | 2.07 (2H, quint, J=7.2 Hz), 2.63 (2H, t, J=7.2 Hz), 2.67 (3H, s), 2.74 (2H, t, J=7.2 Hz), 2.86 (6H, brs), 3.87 (3H, s), 3.93 (3H, s), 7.03 (1H, d, J=1.9 Hz), 7.25-7.31 (2H, m), 7.59 (1H, d, J=1.9 Hz), 7.65 (2H, d, J=8.3 Hz), 7.86-7.93 (4H, m), 8.37 (1H, d, J=8.3 Hz), 9.15 (1H, s). |

TABLE 10-continued

| Example | Structure | NMR (δ, 300 or 400 MHz, CDCl₃) |
|---|---|---|
| 1-51 | 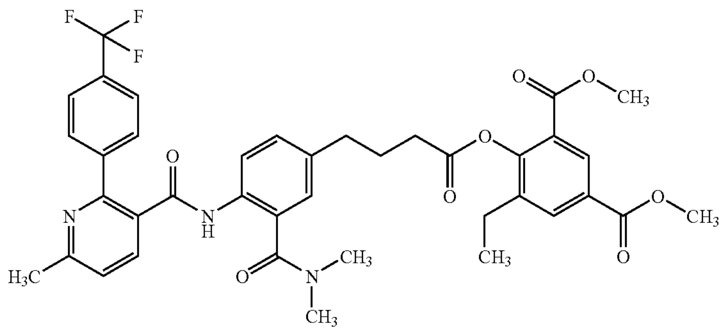 | 1.21 (3H, t, J=7.5 Hz), 2.06 (2H, quint, J=7.5 Hz), 2.60 (2H, q, J=7.5 Hz), 2.66 (3H, s), 2.67-2.78 (4H, m), 2.86 (6H, brs), 3.86 (3H, s), 3.94 (3H, s), 7.05 (1H, d, J=1.9 Hz), 7.23-7.33 (2H, m), 7.65 (2H, d, J=8.3 Hz), 7.88 (2H, d, J=8.3 Hz), 7.92 (1H, d, J=7.9 Hz), 8.13 (1H, d, J=1.9 Hz), 8.37 (1H, d, J=8.3 Hz), 8.52 (1H, d, J=1.9 Hz), 9.15 (1H, brs). |
| 1-52 | 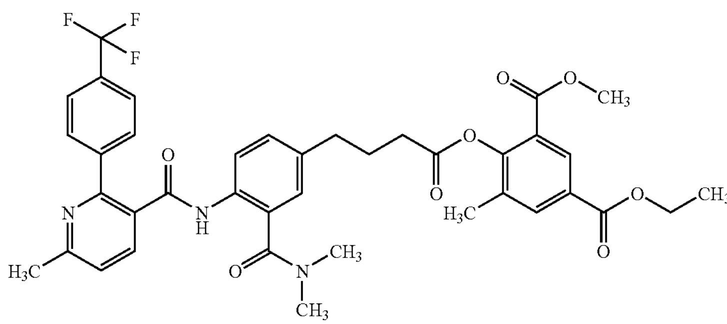 | 1.40 (3H, t, J=7.2 Hz), 2.06 (2H, quint, J=7.1 Hz), 2.25 (3H, s), 2.67 (2H, t, J=7.1 Hz), 2.67 (3H, s), 2.73 (2H, t, J=7.1 Hz), 2.87 (6H, brs), 3.86 (3H, s), 4.40 (2H, q, J=7.2 Hz), 7.05 (1H, d, J=1.9 Hz), 7.25-7.32 (2H, m), 7.65 (2H, d, J=8.3 Hz), 7.88 (2H, d, J=8.3 Hz), 7.92 (1H, d, J=7.9 Hz), 8.11 (1H, d, J=2.3 Hz), 8.36 (1H, d, J=8.3 Hz), 8.50 (1H, d, J=2.3 Hz), 9.15 (1H, s). |
| 1-53 | 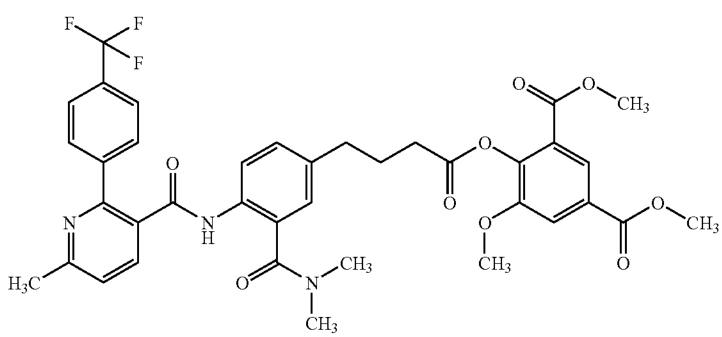 | 2.06 (2H, quint, J=7.2 Hz), 2.65 (2H, t, J=7.2 Hz), 2.67 (3H, s), 2.74 (2H, t, J=7.2 Hz), 2.87 (6H, brs), 3.87 (3H, s), 3.90 (3H, s), 3.95 (3H, s), 7.05 (1H, d, J=1.9 Hz), 7.25-7.32 (2H, m), 7.65 (2H, d, J=8.3 Hz), 7.80 (1H, d, J=1.9 Hz), 7.88 (2H, d, J=8.3 Hz), 7.92 (1H, d, J=7.9 Hz), 8.25 (1H, d, J=2.2 Hz), 8.36 (1H, d, J=8.3 Hz), 9.15 (1H, s). |
| 1-54 | 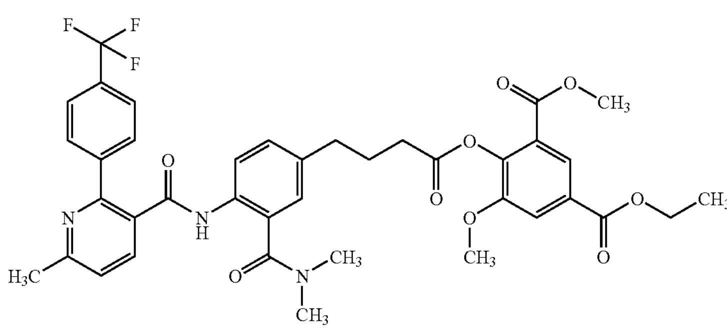 | 1.41 (3H, t, J=7.2 Hz), 2.06 (2H, quint, J=7.2 Hz), 2.65 (2H, t, J=7.2 Hz), 2.67 (3H, s), 2.74 (2H, t, J=7.2 Hz), 2.87 (6H, brs), 3.87 (3H, s), 3.90 (3H, s), 4.41 (2H, q, J=7.2 Hz), 7.05 (1H, d, J=2.2 Hz), 7.25-7.32 (2H, m), 7.65 (2H, d, J=8.3 Hz), 7.80 (1H, d, J=1.9 Hz), 7.88 (2H, d, J=7.9 Hz), 7.92 (1H, d, J=7.9 Hz), 8.24 (1H, d, J=1.9 Hz), 8.36 (1H, d, J=8.3 Hz), 9.15 (1H, s). |

TABLE 11

| Example | Structure | NMR (δ, 300 or 400 MHz, CDCl₃) |
|---|---|---|
| 1-55 | 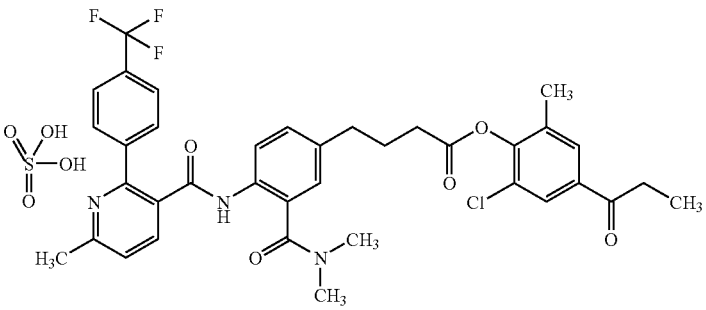 | 2.00 (2H, quint, J=7.1 Hz), 2.22 (3H, s), 2.61 (3H, s), 2.72 (4H, t, J=7.1 Hz), 2.78 (3H, s), 2.88 (3H, s), 3.87 (3H, s), 7.16 (1H, d, J=1.9 Hz), 7.30 (1H, dd, J=1.5, 8.3 Hz), 7.82 (2H, d, J=8.3 Hz), 7.88-7.91 (5H, m), 10.14 (1H, s). |
| 1-56 | 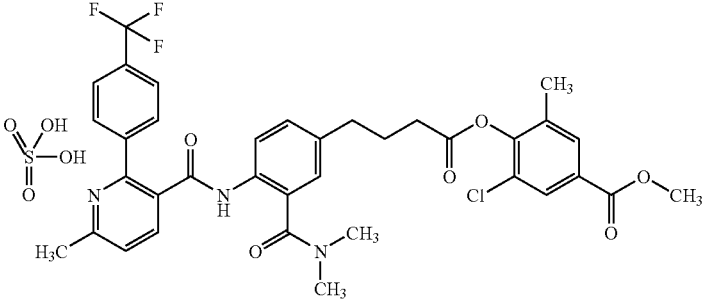 | 2.04 (2H, quint, J=7.2 Hz), 2.63 (2H, t, J=7.2 Hz), 2.73 (2H, t, J=7.2 Hz), 2.79-2.99 (9H, m), 3.86 (3H, s), 3.92 (3H, s), 5.09 (2H, brs), 7.01 (1H, d, J=1.5 Hz), 7.23-7.30 (1H, ms), 7.54 (1H, d, J=1.5 Hz), 7.61 (1H, d, J=2.3 Hz), 7.66 (2H, d, J=8.3 Hz), 7.73 (1H, d, J=1.5 Hz), 7.81 (1H, d, J=8.3 Hz), 7.92 (2H, d, J=8.3 Hz), 8.44 (1H, d, J=8.3 Hz), 9.90 (1H, brs). |
| 1-57 | 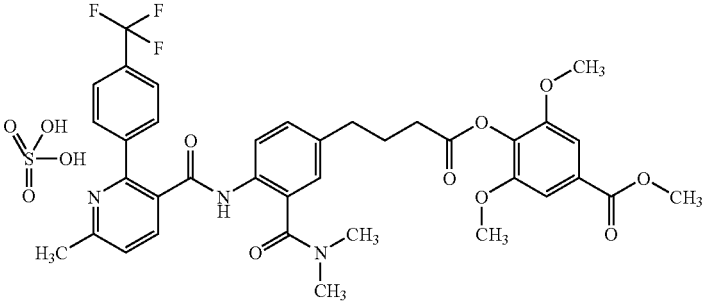 | 1.93 (2H, quint, J=7.2 Hz), 2.57 (2H, t, J=7.2 Hz), 2.61 (3H, s), 2.70 (2H, t, J=7.2 Hz), 2.78 (3H, s), 2.87 (3H, s), 3.82 (3H, s), 3.88 (3H, s), 7.14 (1H, s), 7.28-7.30 (3H, m), 7.45 (1H, d, J=8.3 Hz), 7.49 (1H, d, J=8.3 Hz), 7.81-7.92 (5H, m), 10.15 (1H, s). |
| 1-58 | 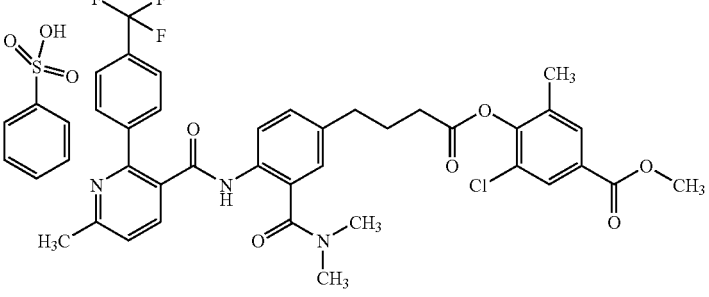 | 2.00 (2H, quint, J=7.1 Hz), 2.22 (3H, s), 2.61 (3H, s), 2.72 (4H, t, J=7.1 Hz), 2.78 (3H, s), 2.88 (3H, s), 3.87 (3H, s), 7.16 (1H, d, J=1.9 Hz), 7.27-7.35 (4H, m), 7.43-7.49 (2H, m), 7.58-7.61 (2H, m), 7.83 (2H, d, J=8.3 Hz), 7.89-7.92 (5H, m), 10.14 (1H, s). |
| 1-59 | 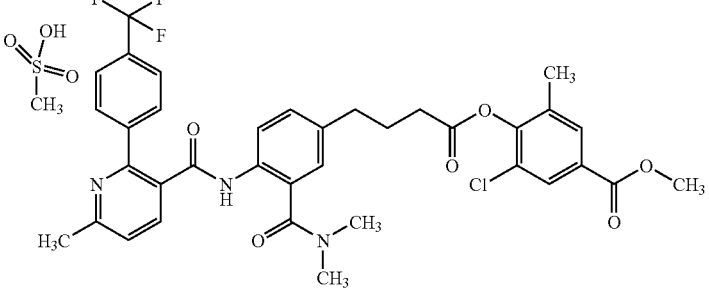 | 2.00 (2H, quint, J=7.1 Hz), 2.22 (3H, s), 2.34 (3H, s), 2.61 (3H, s), 2.72 (4H, t, J=7.1 Hz), 2.78 (3H, s), 2.88 (3H, s), 3.87 (3H, s), 7.16 (1H, d, J=1.9 Hz), 7.30 (1H, dd, J=1.9, 8.3 Hz), 7.43-7.49 (2H, m), 7.83 (2H, d, J=8.3 Hz), 7.89-7.92 (5H, m), 10.14 (1H, s). |

TABLE 11-continued

| Example | Structure | NMR (δ, 300 or 400 MHz, CDCl₃) |
|---|---|---|
| 1-60 | 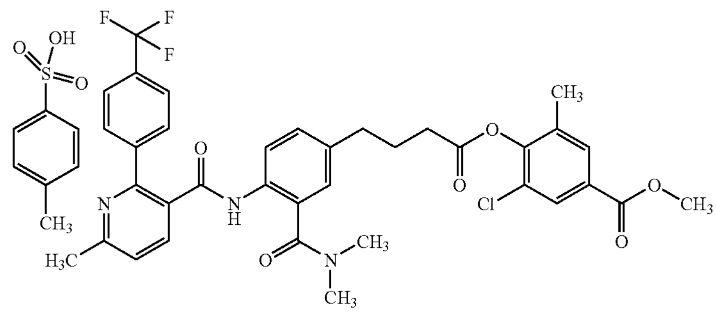 | 2.00 (2H, quint, J=7.1 Hz), 2.22 (3H, s), 2.29 (3H, s), 2.61 (3H, s), 2.72 (4H, t, J=7.1 Hz), 2.78 (3H, s), 2.88 (3H, s), 3.87 (3H, s), 7.10-7.16 (3H, m), 7.30 (1H, dd, J=1.9, 8.3 Hz), 7.43-7.49 (4H, m), 7.83 (2H, d, J=8.3 Hz), 7.89-7.91 (5H, m), 10.14 (1H, s). |

TABLE 12

| Example | Structure | NMR (δ, 300 or 400 MHz, CDCl₃) |
|---|---|---|
| 1-61 | 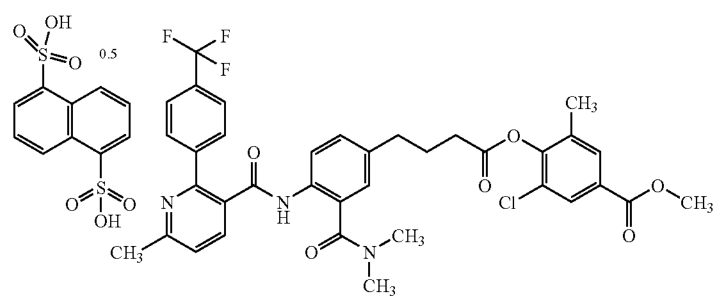 | 2.00 (2H, quint, J=7.1 Hz), 2.22 (3H, s), 2.61 (3H, s), 2.72 (4H, t, J=7.1 Hz), 2.78 (3H, s), 2.88 (3H, s), 3.87 (3H, s), 7.16 (1H, d, J=1.5 Hz), 7.30 (1H, dd, J=1.5, 8.3 Hz), 7.38-7.49 (3H, m), 7.83 (2H, d, J=8.3 Hz), 7.89—7.93 (6H, m), 8.86 (1H, d, J=8.7 Hz), 10.14 (1H, s). |
| 1-62 | 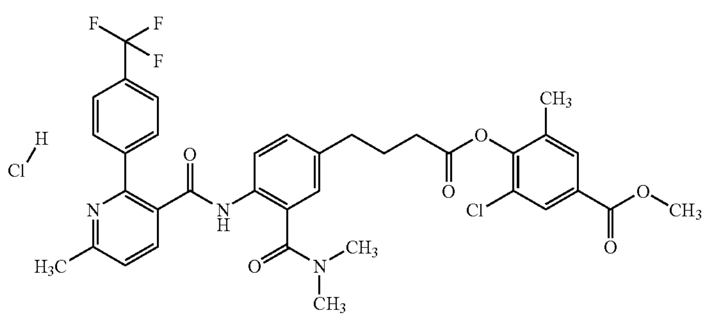 | 2.00 (2H, quint, J=7.1 Hz), 2.22 (3H, s), 2.61 (3H, s), 2.72 (4H, t, J=7.1 Hz), 2.78 (3H, s), 2.88 (3H, s), 3.87 (3H, s), 7.16 (1H, d, J=1.5 Hz), 7.30 (1H, dd, J=1.5, 8.3 Hz), 7.43-7.49 (2H, m), 7.83 (2H, d, J=8.3 Hz), 7.89-7.92 (5H, m), 10.15 (1H, s). |
| 1-63 | 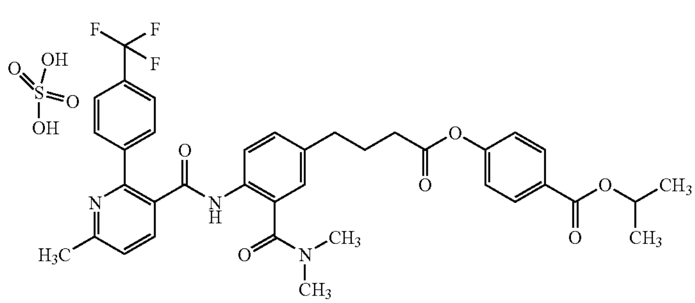 | 1.31 (6H, d, J=6.0 Hz), 1.96 (2H, quint, J=7.5 Hz), 2.59-2.64 (5H, m), 2.69 (2H, t, J=7.5 Hz), 2.77 (3H, s), 2.87 (3H, s), 5.13 (1H, sept, J=6.0 Hz), 7.16 (1H, d, J=1.9 Hz), 7.26 (2H, d, J=8.7 Hz), 7.28-7.31 (1H, m), 7.43-7.49 (2H, m), 7.81 (2H, d, J=8.3 Hz), 7.90 (3H, d, J=7.9 Hz), 7.98 (2H, d, J=8.7 Hz), 10.13 (1H, s). |

TABLE 12-continued

| Example | Structure | NMR (δ, 300 or 400 MHz, CDCl₃) |
|---|---|---|
| 1-64 | 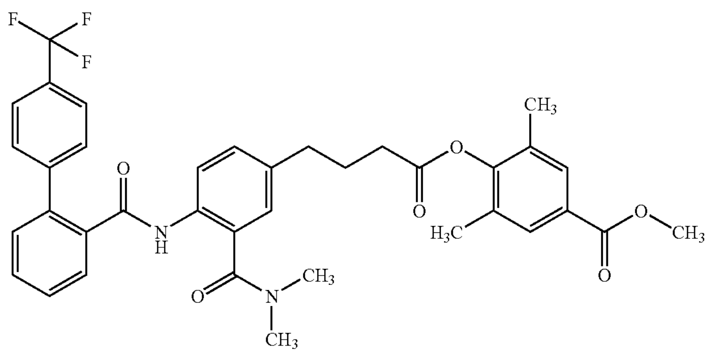 | 2.05 (2H, quint, J=7.5 Hz), 2.17 (6H, s), 2.61 (2H, t, J=7.5 Hz), 2.71 (2H, t, J=7.5 Hz), 2.87 (3H, brs), 2.95 (3H, brs), 3.89 (3H, s), 7.01 (1H, d, J=1.9 Hz), 7.23-7.26 (1H, m), 7.40 (1H, dd, J=1.5, 7.5 Hz), 7.46-7.57 (2H, m), 7.62 (4H, s), 7.69 (1H, dd, J=1.5, 7.5 Hz), 7.76 (2H, s), 8.31 (1H, d, J=8.3 Hz), 8.99 (1H, s). |
| 1-65 | 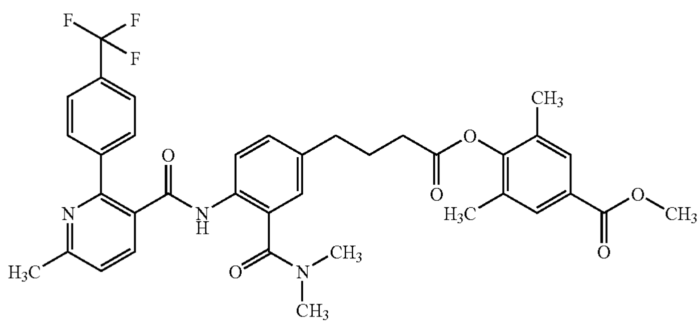 | 2.06 (2H, quint, J=7.5 Hz), 2.17 (6H, s), 2.61 (2H, t, J=7.5 Hz), 2.67 (3H, s), 2.72 (2H, t, J=7.5 Hz), 2.87 (6H, brs), 3.89 (3H, s), 7.01(1H, d, J=1.8 Hz), 7.25-7.29 (2H, m), 7.65 (1H, d, J=8.3 Hz), 7.76 (2H, s), 7.88 (2H, d, J=8.3 Hz), 7.91 (1H, d, J=7.9 Hz), 8.37 (1H, d, J=8.7 Hz), 9.14 (1H, s). |

TABLE 13

| Example | Structure | NMR (δ, 300 or 400 MHz, CDCl₃) |
|---|---|---|
| 1-66 | 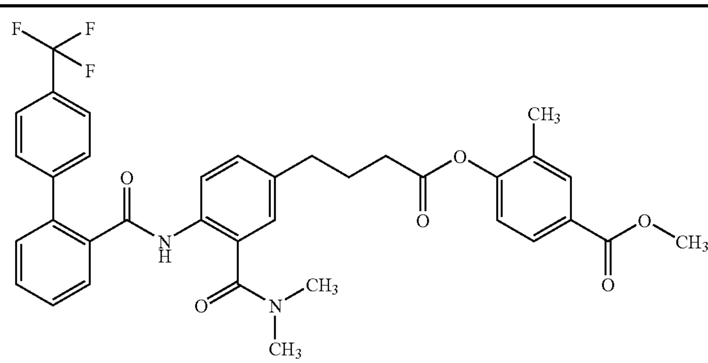 | 2.04 (2H, quint, J=7.5 Hz), 2.20 (3H, s), 2.58 (2H, t, J=7.5 Hz), 2.70 (2H, t, J=7.5 Hz), 2.86 (3H, brs), 2.94 (3H, brs), 3.90 (3H, s), 7.00 (1H, d, J=2.3 Hz), 7.06 (1H, d, J=8.3 Hz), 7.21-7.28 (1H, m), 7.40 (1H, dd, J=1.5 Hz, J=7.5 Hz), 7.44-7.57 (2H, m), 7.62 (4H, brs), 7.69 (1H, dd, J=1.5 Hz, J=7.5 Hz), 7.89 (1H, dd, J=1.9 Hz, J=8.3 Hz), 7.93 (1H, brs), 8.30 (1H, d, J=8.3 Hz), 8.99 (1H, brs). |
| 1-67 | 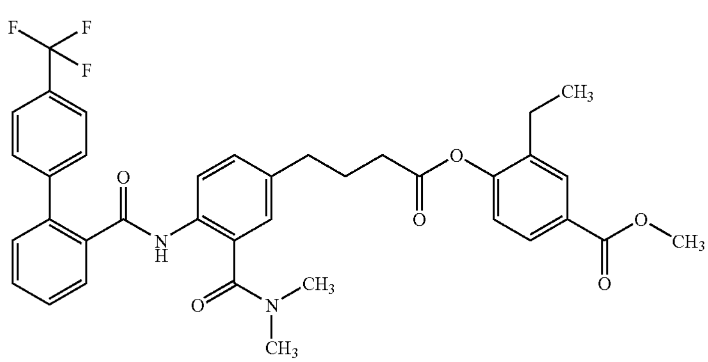 | 1.20 (2H, t, J=7.6 Hz), 2.04 (2H, quint, J=7.2 Hz), 2.52-2.61 (4H, m), 2.70 (2H, t, J=7.2 Hz), 2.86 (3H, brs), 2.94 (3H, brs), 3.91 (3H, s), 7.01 (1H, d, J=1.9 Hz), 7.06 (1H, d, J=8.6 Hz), 7.23-7.26 (1H, m), 7.40 (1H, dd, J=1.5, 7.5 Hz), 7.45-7.57 (2H, m), 7.62 (4H, s), 7.69 (1H, dd, J=1.9, 7.1 Hz), 7.90 (1H, dd, J=1.9, 8.7 Hz), 7.97 (1H, d, J=2.3 Hz), 8.31 (1H, d, J=8.3 Hz), 8.99 (1H, s). |

TABLE 13-continued

| Example | Structure | NMR (δ, 300 or 400 MHz, CDCl₃) |
|---|---|---|
| 1-68 | 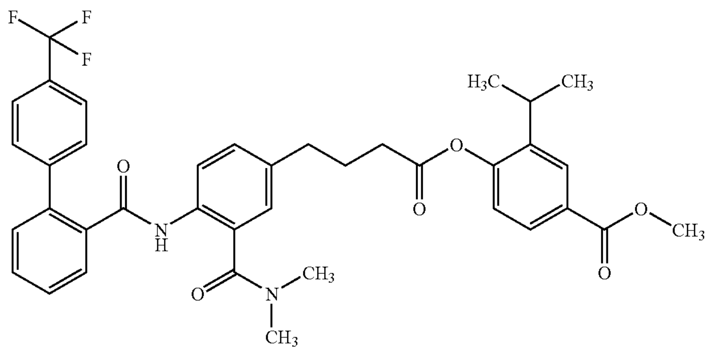 | 1.23 (6H, d, J=6.8 Hz), 2.05 (2H, quint, J=7.1 Hz), 2.59 (2H, t, J=7.1 Hz), 2.70 (2H, t, J=7.1 Hz), 2.86 (3H, brs), 2.95 (3H, brs), 3.02 (1H, sept, J=6.8 Hz), 3.91 (3H, s), 7.00-7.08 (2H, m), 7.23-7.26 (1H, m), 7.40 (1H, dd, J=1.1, 7.5 Hz), 7.46-7.57 (2H, m), 7.62 (4H, s), 7.69 (1H, dd, J=1.9, 7.1 Hz), 7.89 (1H, dd, J=1.9, 8.3 Hz), 8.02 (1H, d, J=2.2 Hz), 8.31 (1H, d, J=8.3 Hz), 8.99 (1H, s). |
| 1-69 | 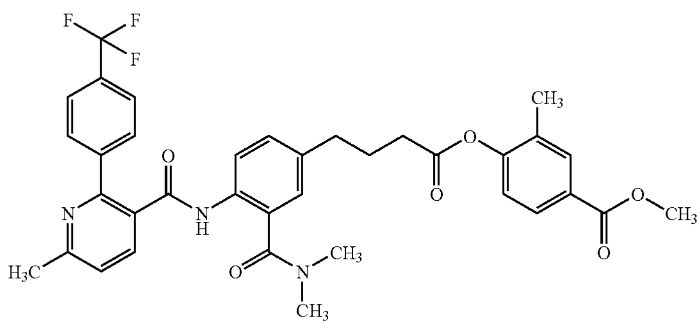 | 2.05 (2H, quint, J=7.2 Hz), 2.20 (3H, s), 2.59 (2H, t, J=7.2 Hz), 2.67 (3H, s), 2.71 (2H, t, J=7.2 Hz), 2.87 (6H, brs), 3.90 (3H, s), 7.01 (1H, d, J=1.9 Hz), 7.06 (1H, d, J=8.3 Hz), 7.25-7.29 (2H, m), 7.65 (2H, d, J=7.9 Hz), 7.86-7.94 (5H, m), 8.37 (1H, d, J=8.3 Hz), 9.14 (1H, s). |
| 1-70 | 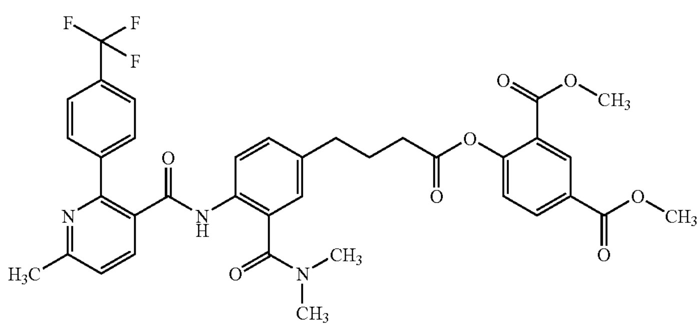 | 2.05 (2H, quint, J=7.2 Hz), 2.65 (2H, t, J=7.2 Hz), 2.67 (3H, s), 2.72 (2H, t, J=7.2 Hz), 2.86 (6H, brs), 3.87 (3H, s), 3.95 (3H, s), 7.04 (1H, d, J=2.3 Hz), 7.16 (1H, d, J=8.3 Hz), 7.25-7.32 (2H, m), 7.65 (2H, d, J=8.3 Hz), 7.88 (2H, d, J=8.1 Hz), 7.92 (1H, d, J=7.9 Hz), 8.22 (1H, dd, J=2.3, 8.3 Hz), 8.37 (1H, d, J=8.7 Hz), 8.68 (1H, d, J=2.3 Hz), 9.15 (1H, s). |

TABLE 14

| Example | Structure | NMR (δ, 300 or 400 MHz, CDCl₃) |
|---|---|---|
| 1-71 | 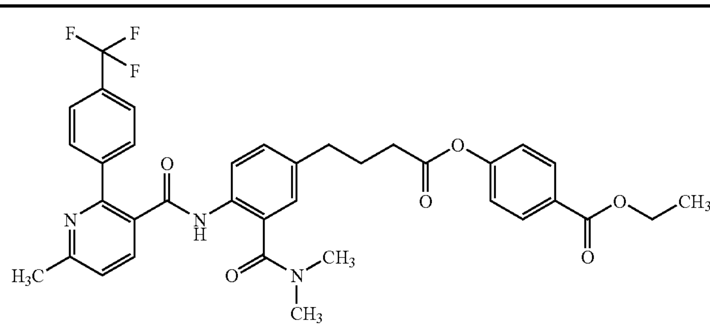 | 1.39 (3H, t, J=7.2 Hz), 2.03 (2H, quint, J=7.5 Hz), 2.56 (2H, t, J=7.5 Hz), 2.67 (3H, s), 2.70 (2H, t, J=7.5 Hz), 4.38 (2H, q, J=7.2 Hz), 7.01 (1H, d, J=2.3 Hz), 7.14 (2H, d, J=8.6 Hz), 7.25-7.29 (2H, m), 7.65 (2H, d, J=7.9 Hz), 7.88 (2H, d, J=7.9 Hz), 7.92 (1H, dd, J=7.9 Hz), 8.08 (2H, d, J=8.6 Hz), 8.37 (1H, d, J=8.6 Hz), 9.13 (1H, s). |

TABLE 14-continued

| Example | Structure | NMR (δ, 300 or 400 MHz, CDCl₃) |
|---|---|---|
| 1-72 | 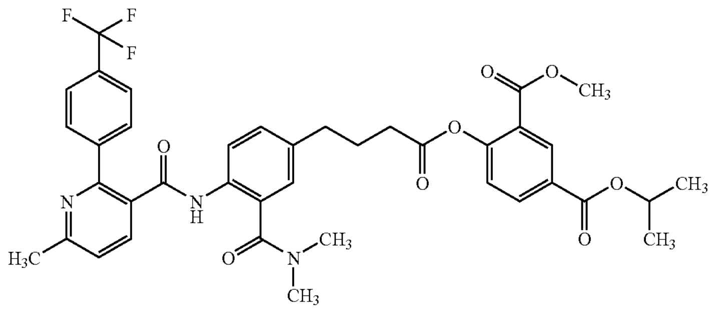 | 1.38 (6H, d, J=6.0 Hz), 2.05 (2H, quint, J=7.1 Hz), 2.64 (2H, t, J=7.1 Hz), 2.67 (3H, s), 2.72 (2H, t, J=7.1 Hz), 2.86 (6H, brs), 3.87 (3H, s), 5.27 (1H, sept, J=6.0 Hz), 7.04 (1H, d, J=1.9 Hz), 7.14 (1H, d, J=8.3 Hz), 7.25-7.31 (2H, m), 7.65 (2H, d, J=8.3 Hz), 7.88 (2H, d, J=7.9 Hz), 7.92 (1H, d, J=7.9 Hz), 8.22 (1H, dd, J=1.9, 8.6 Hz), 8.37 (1H, d, J=8.6 Hz), 8.65 (1H, d, J=2.2 Hz), 9.15 (1H, s). |
| 1-73 | 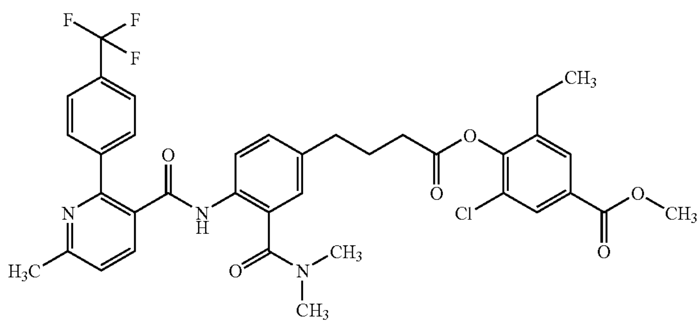 | 1.21 (3H, t, J=7.5 Hz), 2.07 (2H, quint, J=7.1 Hz), 2.57 (2H, q, J=7.5 Hz), 2.65 (2H, t, J=7.1 Hz), 2.67 (3H, s), 2.74 (2H, t, J=7.1 Hz), 2.87 (6H, brs), 3.92 (3H, s), 7.02 (1H, d, J=1.9 Hz), 7.25-7.30 (2H, m), 7.65 (2H, d, J=8.3 Hz), 7.86-7.93 (4H, m), 7.98 (1H, d, J=1.9 Hz), 8.37 (1H, d, J=8.3 Hz), 9.15 (1H, s). |
| 1-74 | 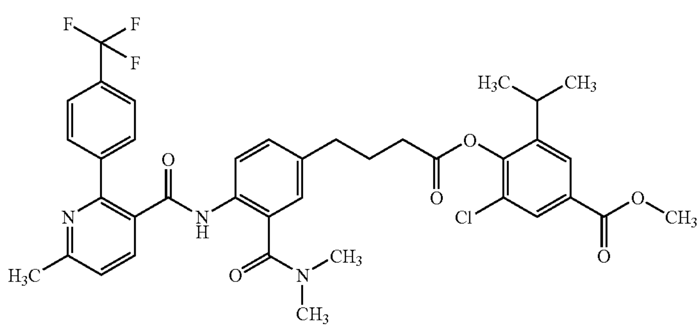 | 1.22 (6H, d, J=7.2 Hz), 2.07 (2H, quint, J=7.2 Hz), 2.65 (2H, t, J=7.2 Hz), 2.67 (3H, s), 2.74 (2H, t, J=7.2 Hz), 2.87 (6H, brs), 2.99 (1H, sept, J=7.2 Hz), 3.92 (3H, s), 7.02 (1H, d, J=2.2 Hz), 7.25-7.30 (2H, m), 7.65 (2H, d, J=8.3 Hz), 7.86-7.93 (4H, m), 7.97 (1H, d, J=1.8 Hz), 8.37 (1H, d, J=8.6 Hz), 9.15 (1H, s). |
| 1-75 | 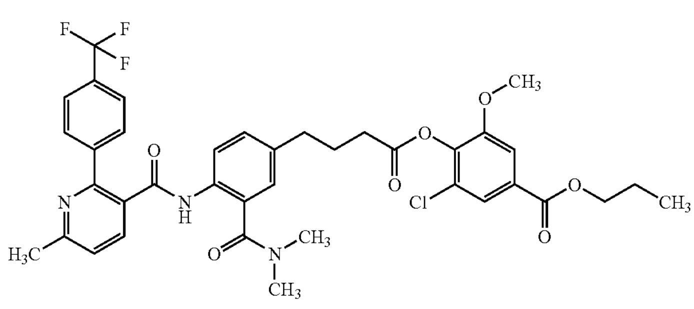 | 1.03 (3H, t, J=7.5 Hz), 1.80 (2H, sext, J=7.5 Hz), 2.06 (2H, quint, J=7.5 Hz), 2.63 (2H, t, J=7.5 Hz), 2.67 (3H, s), 2.73 (2H, t, J=7.5 Hz), 2.87 (6H, brs), 3.88 (3H, s), 4.29 (2H, t, J=7.5 Hz), 7.03 (1H, d, J=1.9 Hz), 7.23-7.32 (2H, m), 7.56 (1H, d, J=1.8 Hz), 7.65 (2H, d, J=7.9 Hz), 7.74 (1H, d, J=1.8 Hz), 7.88 (2H, d, J=7.9 Hz), 7.92 (1H, d, J=7.9 Hz), 8.37 (1H, d, J=8.3 Hz), 9.16 (1H, brs). |

TABLE 15

| Example | Structure | NMR (δ, 300 or 400 MHz, CDCl₃) |
|---|---|---|
| 1-76 | 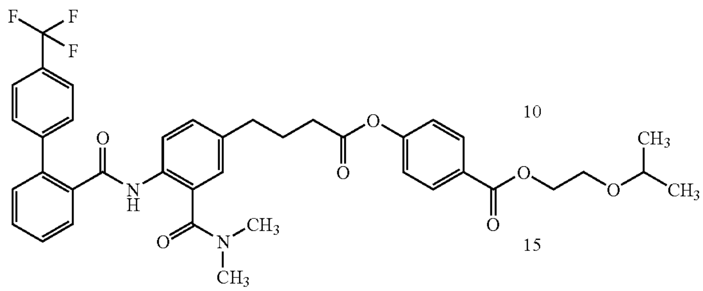 | 1.19 (6H, d, J=6.3 Hz), 2.03 (2H, quint, J=7.4 Hz), 2.56 (2H, t, J=7.4 Hz), 2.69 (2H, t, J=7.4 Hz), 2.85 (3H, brs), 2.94 (3H, brs), 3.62-3.68 (1H, m), 3.74 (2H, t, 5.0 Hz), 4.44 (2H, t, J=5.0 Hz), 6.99 (1H, d, 2.1 Hz), 7.14 (2H, d, J=8.5 Hz), 7.23-7.27 (1H, m), 7.40 (1H, dd, J=1.4 Hz, 7.4 Hz), 7.46-7.56 (2H, m), 7.62 (4H, s), 7.69 (1H, dd, J=1.7 Hz, 7.4 Hz), 8.09 (2H, d, J=8.5 Hz), 8.30 (1H, d, J=8.4Hz), 8.98 (1H, s) |
| 1-77 | 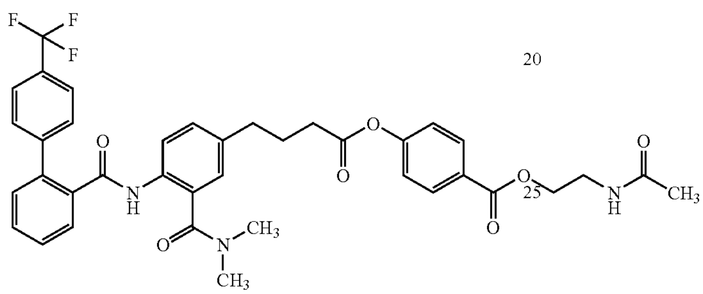 | 2.00-2.05 (5H, m), 2.56 (2H, t, J=7.5 Hz), 2.70 (2H, t, J=7.5 Hz), 2.86 (3H, brs), 2.95 (3H, brs), 3.65 (2H, dt, J=5.6 Hz, 10.5 Hz), 4.42 (2H, t, 5.6 Hz), 5.77-5.89 (1H, m), 7.00 (1H, d, 0.9 Hz), 7.50 (2H, d, J=8.6 Hz), 7.24-7.26 (1H, m), 7.40 (1H, dd, J=1.4 Hz, 7.4 Hz), 7.46-7.56 (2H, m), 7.62 (4H, s), 7.69 (1H, dd, J=1.4 Hz, 7.4 Hz), 8.07 (2H, d, J=8.6 Hz), 8.29 (1H, d, J=8.4 Hz), 8.98 (1H, s) |
| 1-78 | 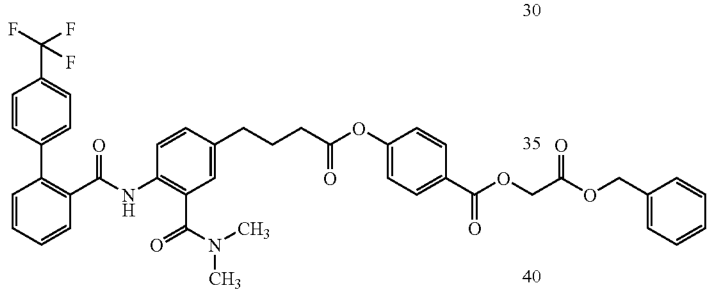 | 2.03 (2H, quint, J=7.5 Hz), 2.56 (2H, t, J=7.5 Hz), 2.69 (2H, t, J=7.5 Hz), 2.86 (3H, brs), 2.94 (3H, brs), 4.89 (2H, s), 5.23 (2H, s), 7.00 (1H, d, J=1.9 Hz), 7.16 (2H, d, J=8.7 Hz), 7.22-7.27 (1H, m), 7.36 (5H, brs), 7.40 (1H, dd, J=1.5 Hz, J=7.2 Hz), 7.45-7.57 (2H, m), 7.62 (4H, brs), 7.69 (1H, dd, J=1.5 Hz, J=7.5 Hz), 8.12 (2H, d, J=8.7 Hz), 8.29 (1H, d, J=8.3 Hz), 8.98 (1H, brs). |
| 1-79 | 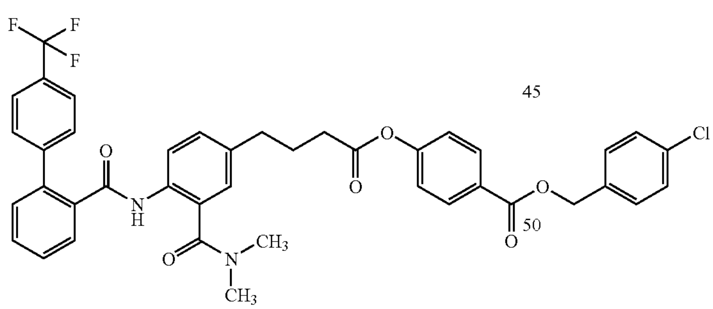 | 2.02 (2H, quint, J=7.2 Hz), 2.56 (2H, t, J=7.2 Hz), 2.69 (2H, t, J=7.1 Hz), 2.86 (3H, brs), 2.93 (3H, brs), 5.32 (2H, s), 6.99 (1H, d, J=1.9 Hz), 7.14 (2H, d, J=8.7 Hz), 7.21-7.27 (1H, m), 7.32-7.37 (5H, m), 7.44-7.57 (2H, m), 7.61 (4H, brs), 7.68 (1H, dd, J=1.9 Hz, J=7.2 Hz), 8.08 (2H, d, J=8.7 Hz), 8.29 (1H, d, J=8.7 Hz), 8.97 (1H, s). |
| 1-80 | 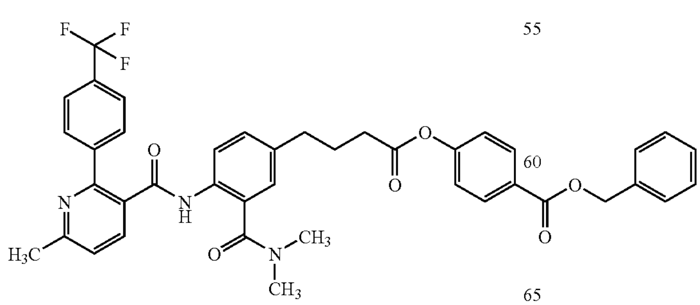 | 2.03 (2H, quint, J=7.1 Hz), 2.56 (2H, t, J=7.1 Hz), 2.66 (3H, s), 2.69 (2H, t, J=7.1 Hz), 2.86 (6H, brs), 5.36 (2H, s), 7.00 (1H, d, J=1.9 Hz), 7.14 (2H, d, J=8.7 Hz), 7.24-7.27 (2H, m), 7.34-7.44 (5H, m), 7.64 (2H, d, J=8.3 Hz), 7.87 (2H, d, J=8.3 Hz), 7.91 (1H, d, J=7.9 Hz), 8.11 (2H, d, J=8.7 Hz), 8.36 (1H, d, J=8.3 Hz), 9.12 (1H, s). |

TABLE 16

| Example | Structure | NMR (δ, 300 or 400 MHz, CDCl₃) |
|---|---|---|
| 1-81 | 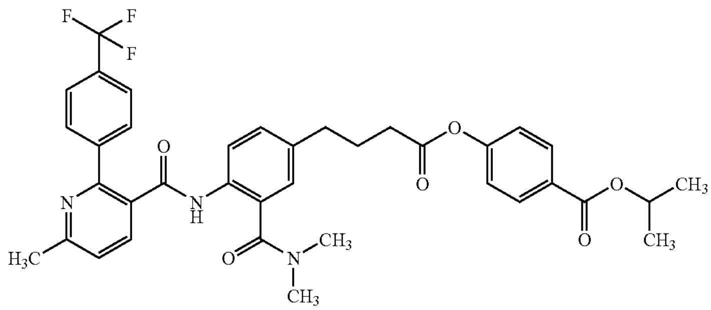 | 1.36 (6H, d, J=6.1 Hz), 2.03 (2H, quint, (J=7.1 Hz), 2.56 (2H, t, J=7.1 Hz), 2.67 (3H, s), 2.70 (2H, t, J=7.1 Hz), 2.86 (6H, brs), 5.24 (1H, sept, J=6.1 Hz), 7.00 (1H, d, J=1.9 Hz), 7.13 (2H, d, J=8.7 Hz), 7.25-7.27 (2H, m), 7.65 (2H, d, J=8.3 Hz), 7.88 (2H, d, J=8.3 Hz), 7.91 (1H, d, J=8.0 Hz), 8.07 (2H, d, J=8.7 Hz), 8.37 (1H, d, J=8.7 Hz), 9.13 (1H, s). |
| 1-82 | 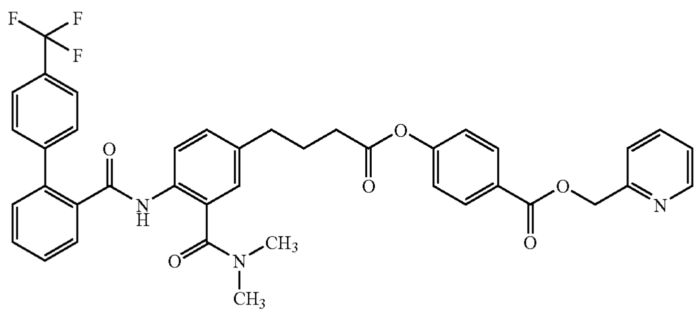 | 2.03 (2H, quint, J=7.1 Hz), 2.56 (2H, t, J=7.1 Hz), 2.69 (2H, t, J=7.1 Hz), 2.87 (3H, brs), 2.94 (3H, brs), 5.48 (2H, s), 7.00 (1H, d, J=1.8 Hz), 7.16 (2H, d, J=8.7 Hz), 7.23-7.26 (2H, m), 7.38-7.56 (4H, m), 7.62 (4H, s), 7.67-7.74 (2H, m), 8.15 (2H, d, J=8.3 Hz), 8.30 (1H, d, J=8.7 Hz), 8.61-8.62 (1H, m), 8.98 (1H, s). |
| 1-83 | 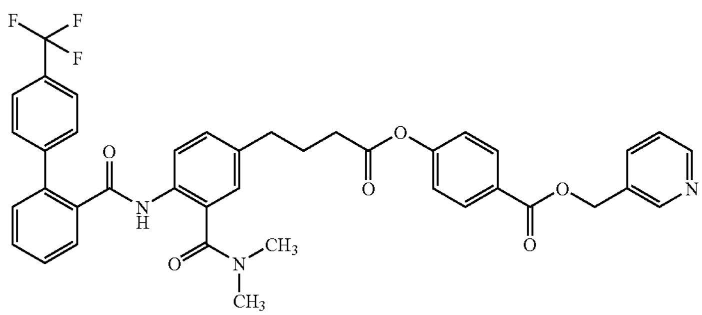 | 2.02 (2H, quint, J=7.2 Hz), 2.56 (2H, t, J=7.2 Hz), 2.69 (2H, t, J=7.2 Hz), 2.86 (3H, brs), 2.94 (3H, brs), 5.38 (2H, s), 7.00 (1H, d, J=1.9 Hz), 7.15 (2H, d, J=9.0 Hz), 7.23-7.26 (1H, m), 7.38-7.57 (4H, m), 7.61 (4H, s), 7.67-7.79 (2H, m), 8.09 (2H, d, J=8.7 Hz), 8.30 (1H, d, J=8.7 Hz), 8.30 (1H, d, J=8.7 Hz), 8.61 (1H, dd, J=1.9, 4.9 Hz), 8.72 (1H, d, J=1.9 Hz), 8.97 (1H, s). |
| 1-84 | 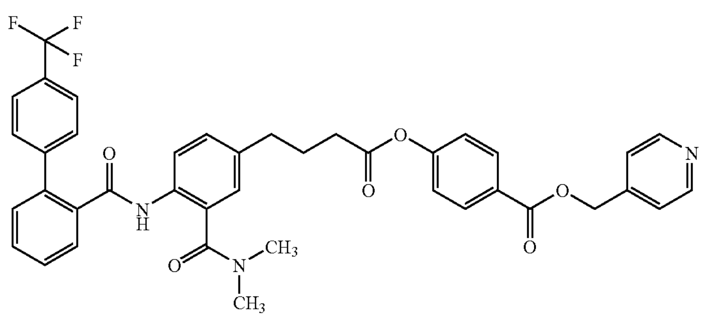 | 2.03 (2H, quint, j=7.2 Hz), 2.57 (2H, t, J=7.2 Hz), 2.70 (2H, t, J=7.2 Hz), 2.86 (3H, brs), 2.94 (3H, brs), 5.38 (2H, s), 7.00 (1H, d, J=1.9 Hz), 7.18 (2H, d, J=9.0 Hz), 7.23-7.26 (1H, m), 7.32 (2H, d, J=6.1 Hz), 7.40 (1H, dd, J=1.1, 7.9 Hz), 7.45-7.57 (2H, m), 7.62 (4H, s), 7.69 (1H, dd, J=1.5, 7.6 Hz), 8.13 (2H, d, J=9.0 Hz), 8.30 (1H, d, J=8.6 Hz), 8.63 (2H, d, J=6.0 Hz), 8.97 (1H, s). |
| 1-85 | 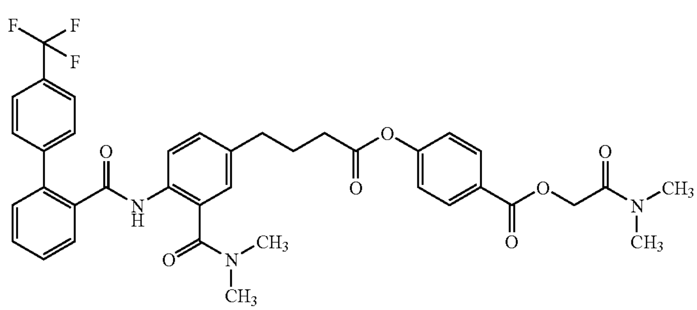 | 2.03 (2H, quint, J=7.5 Hz), 2.56 (2H, t, J=7.5 Hz), 2.69 (2H, t, J=7.5 Hz), 2.86 (3H, brs), 2.94 (3H, brs), 3.00 (3H, s), 3.04 (3H, s), 4.95 (2H, s), 7.00 (1H, d, J=1.5 Hz), 7.15 (2H, d, J=8.7 Hz), 7.22-7.27 (1H, m), 7.37-7.42 (1H, m), 7.44-7.57 (2H, m), 7.62 (4H, s), 7.66-7.71 (1H, m), 8.14 (2H, d, J=8.7 Hz), 8.29 (1H, d, J=8.3 Hz), 8.99 (1H, brs). |

TABLE 17

| Example | Structure | NMR (δ, 300 or 400 MHz, CDCl₃) |
|---|---|---|
| 1-86 | 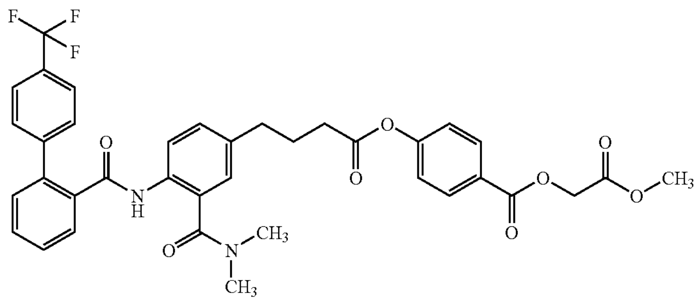 | 2.03 (2H, quint, J=7.2 Hz), 2.56 (2H, t, J=7.2 Hz), 2.69 (2H, t, J=7.2 Hz), 2.86 (3H, brs), 2.94 (3H, brs), 3.79 (3H, s), 4.86 (2H, s), 7.00 (1H, d, J=1.9 Hz), 7.16 (2H, d, J=9.0 Hz), 7.22-7.28 (1H, m), 7.40 (1H, dd, J=1.5 Hz, 7.5 Hz), 7.45-7.58 (2H, m), 7.62 (4H, brs), 7.69 (1H, dd, J=1.5 Hz, J=7.2 Hz), 8.12 (2H, d, J=9.0 Hz), 8.29 (1H, d, J=8.3 Hz), 8.98 (1H, brs). |
| 1-87 | 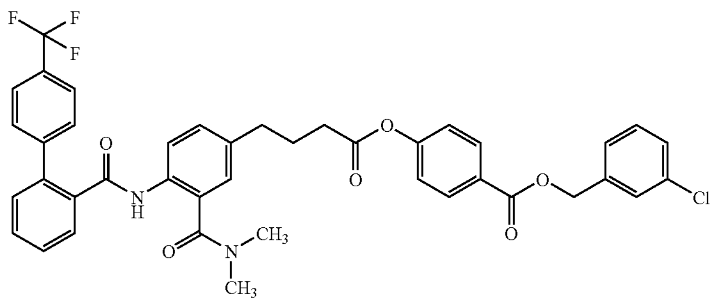 | 2.03 (2H, quint, J=7.2 Hz), 2.56 (2H, t, J=7.2 Hz), 2.60 (2H, t, J=7.2 Hz), 2.86 (3H, brs), 2.93 (3H, brs), 5.32 (2H, s), 6.99 (1H, d, J=1.5 Hz), 7.15 (2H, d, J=8.7 Hz), 7.21-7.34 (4H, m), 7.36-7.57 (4H, m), 7.61 (4H, brs), 7.68-7.69 (1H, m), 8.10 (2H, d, J=8.7 Hz), 8.29 (1H, d, J=8.3 Hz), 8.90 (1H, brs). |
| 1-88 | 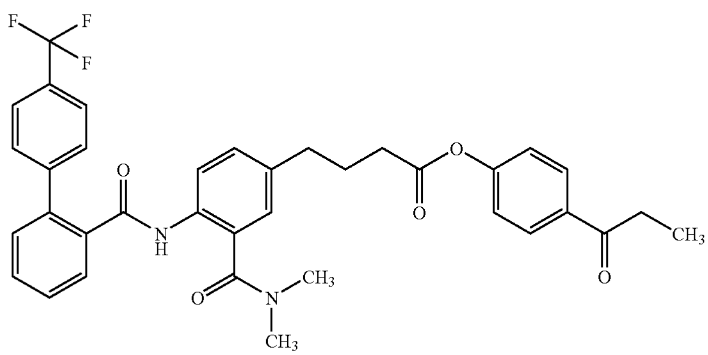 | 1.22 (3H, t, J=7.2 Hz), 2.03 (2H, quint, J=7.5 Hz), 2.56 (2H, t, J=7.5 Hz), 2.69 (2H, t, J=7.5 Hz), 2.87 (3H, brs), 2.93 (3H, brs), 2.99 (2H, q, J=7.2 Hz), 7.00 (1H, d, J=1.9 Hz), 7.16 (2H, d, J=8.7 Hz), 7.23-7.26 (1H, m), 7.40 (1H, dd, J=1.5, 7.5 Hz), 7.45-7.56 (2H, m), 7.62 (4H, s), 7.69 (1H, dd, J=1.9, 7.2 Hz), 8.00 (2H, d, J=8.7 Hz), 8.30 (1H, d, J=8.3 Hz), 8.98 (1H, s). |
| 1-89 | 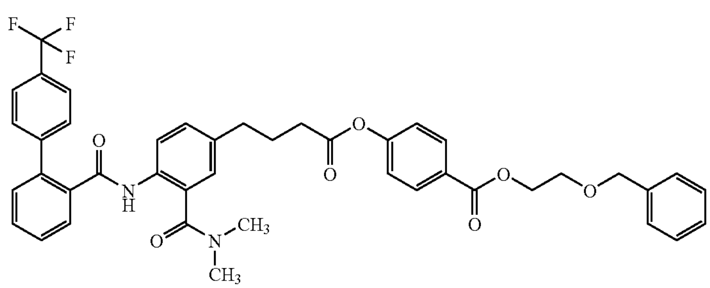 | 2.03 (2H, quint, J=7.5 Hz), 2.56 (2H, t, J=7.5 Hz), 2.70 (2H, t, J=7.5 Hz), 2.86 (3H, brs), 2.94 (3H, brs), 3.80 (2H, t, J=4.9 Hz), 4.50 (2H, t, J=4.9 Hz), 4.60 (2H, s), 7.00 (1H, d, J=1.9 Hz), 7.15 (2H, d, J=8.7 Hz), 7.23-7.41 (7H, m), 7.45-7.57 (2H, m), 7.62 (4H, s), 7.69 (1H, dd, J=1.9, 7.5 Hz), 8.09 (2H, d, J=9.0 Hz), 8.30 (1H, d, J=8.7 Hz), 8.98 (1H, s). |
| 1-90 | 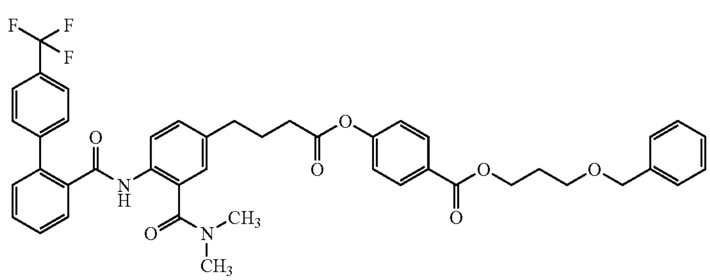 | 1.98-2.11 (4H, m), 2.56 (2H, t, J=7.5 Hz), 2.70 (2H, t, J=7.5 Hz), 2.87 (3H, brs), 2.94 (3H, brs), 3.62 (2H, t, J=6.0 Hz), 4.44 (2H, t, J=6.4 Hz), 4.52 (2H, s), 7.00 (1H, d, J=1.9 Hz), 7.12 (2H, d, J=8.7 Hz), 7.23-7.33 (6H, m), 7.40 (1H, dd, J=1.5, 7.5 Hz), 7.45-7.57 (2H, m), 7.62 (4H, s), 7.69 (1H, dd, J=1.5, 7.2 Hz), 8.03 (2H, d, J=9.0 Hz), 8.30 (1H, d, J=8.7 Hz), 8.98 (1H, s). |

TABLE 18

| Example | Structure | NMR (δ, 300 or 400 MHz, CDCl₃) |
|---|---|---|
| 1-91 | 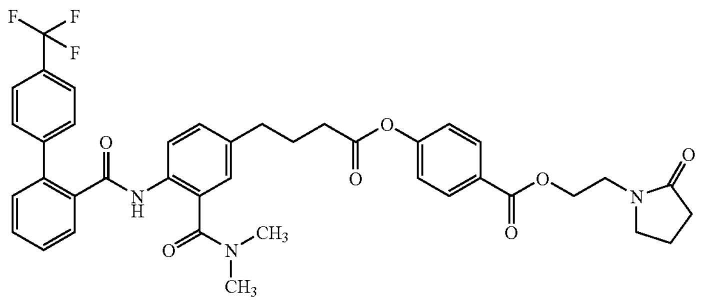 | 1.98-2.08 (4H, m), 2.38 (2H, t, J=7.5 Hz), 2.56 (2H, t, J=7.2 Hz), 2.69 (2H, t, J=7.2 Hz), 2.87 (3H, brs), 2.94 (3H, brs), 3.50 (2H, t, J=7.2 Hz), 3.68 (2H, t, J=5.2 Hz), 4.45 (2H, t, J=5.2 Hz), 4.45 (2H, t, J=5.2 Hz), 7.00 (1H, d, J=1.8 Hz), 7.15 (2H, d, J=8.7 Hz), 7.23-7.26 (1H, m), 7.40 (1H, dd, J=1.5, 7.5 Hz), 7.45-7.57 (2H, m), 7.62 (4H, s), 7.69 (1H, dd, J=1.5, 7.2 Hz), 8.06 (2H, d, J=8.7 Hz), 8.30 (1H, d, J=8.3 Hz), 8.98 (1H, s). |
| 1-92 | 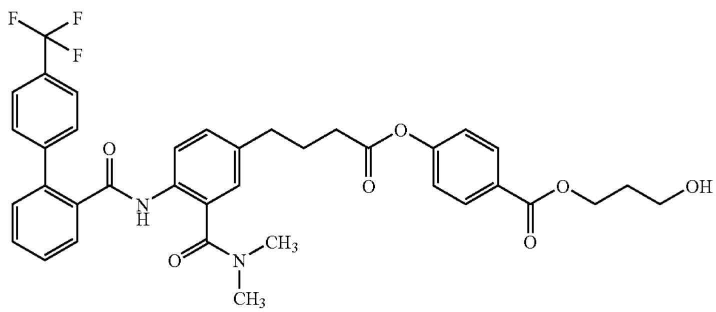 | 1.83 (1H, brs), 1.96-2.08 (4H, m), 2.56 (2H, t, J=7.2 Hz), 2.69 (2H, t, J=7.2 Hz), 2.86 (3H, brs), 2.94 (3H, brs), 3.72-3.80 (2H, m), 4.49 (2H, t, J=6.0 Hz), 7.00 (1H, d, J=1.8 Hz), 7.15 (2H, d, J=8.7 Hz), 7.23-7.26 (1H, m), 7.40 (1H, dd, J=1.5, 7.5 Hz), 7.45-7.57 (2H, m), 7.62 (4H, s), 7.69 (1H, dd, J=1.9, 7.2 Hz), 8.07 (2H, d, J=8.7 Hz), 8.30 (1H, d, J=8.3 Hz), 8.98 (1H, s). |
| 1-93 | 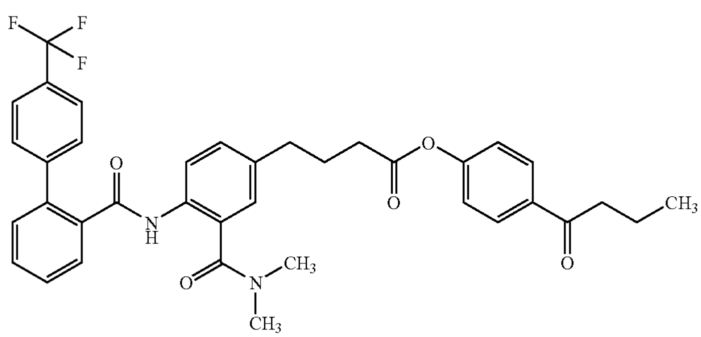 | 1.00 (3H, t, J=7.5 Hz), 1.77 (2H, sext, J=7.6 Hz), 2.03 (2H, quint, J=7.1 Hz), 2.56 (2H, t, J=7.1 Hz), 2.69 (2H, t, J=7.1 Hz), 2.87-2.95 (8H, m), 7.00 (1H, d, J=2.2 Hz), 7.16 (2H, d, J=8.7 Hz), 7.23-7.26 (1H, m), 7.40 (1H, dd, J=1.5, 7.5 Hz), 7.45-7.57 (2H, m), 7.62 (4H, s), 7.69 (1H, dd, J=1.5, 7.2 Hz), 8.00 (2H, d, J=8.7 Hz), 8.30 (1H, d, J=8.3 Hz), 8.98 (1H, s). |
| 1-94 | 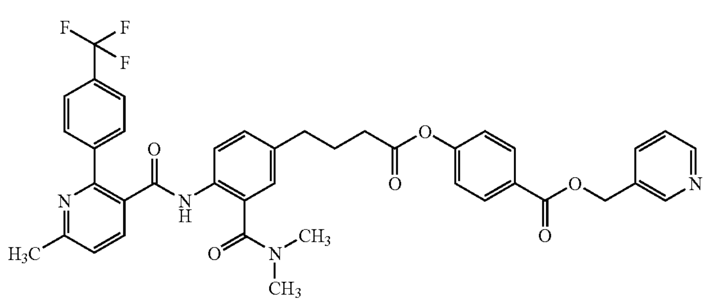 | 2.03 (2H, quint, J=7.2 Hz), 2.56 (2H, t, J=7.2 Hz), 2.66 (3H, s), 2.70 (2H, t, J=7.2 Hz), 2.86 (6H, brs), 5.38 (2H, s), 7.00 (1H, d, J=1.9 Hz), 7.15 (2H, d, J=8.7 Hz), 7.25-7.35 (3H, m), 7.64 (2H, d, J=7.9 Hz), 7.75-7.79 (1H, m), 7.87 (2H, d, J=8.3 Hz), 7.91 (1H, d, J=7.9 Hz), 8.09 (2H, d, J=8.7 Hz), 8.37 (1H, d, J=8.7 Hz), 8.61 (1H, dd, J=1.5, 4.6 Hz), 8.72 (1H, d, J=1.9 Hz), 9.12 (1H, s). |

TABLE 19

| Example | Structure | NMR (δ, 300 or 400 MHz, CDCl₃) |
|---|---|---|
| 1-95 | 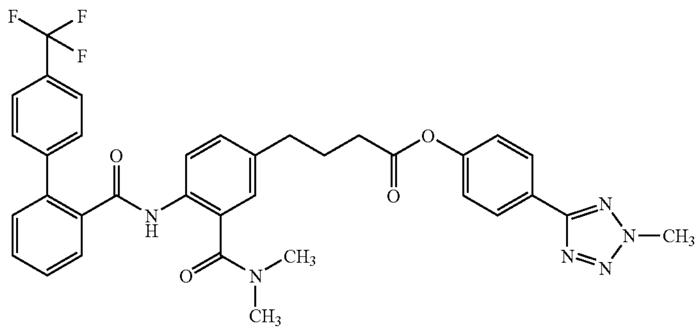 | 2.05 (2H, quint, J=7.5 Hz), 2.57 (2H, t, J=7.5 Hz), 2.71 (2H, t, J=7.5 Hz), 2.87 (3H, brs), 2.95 (3H, brs), 4.40 (3H, s), 7.01 (1H, d, J=1.9 Hz), 7.20 (2H, d, J=8.6 Hz), 7.24-7.28 (1H, m), 7.40 (1H, dd, J=1.9, 7.9 Hz), 7.45-7.57 (2H, m), 7.62 (4H, s), 7.69 (1H, dd, J=1.5, 7.6 Hz), 8.16 (2H, d, J=8.6 Hz), 8.31 (1H, d, J=8.6 Hz), 9.00 (1H, s). |
| 1-96 | 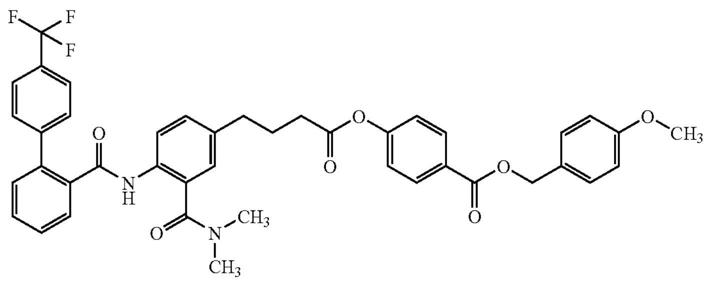 | 2.02 (2H, quint, J=7.5 Hz), 2.55 (2H, t, J=7.5 Hz), 2.69 (2H, t, J=7.5 Hz), 2.86 (3H, brs), 2.94 (3H, brs), 3.82 (3H, s), 5.29 (2H, s), 6.91 (2H, d, J=8.7 Hz), 6.99 (1H, d, J=1.9 Hz), 7.12 (2H, d, J=8.7 Hz), 7.21-7.27 (1H, m), 7.34-7.42 (3H, m), 7.44-7.57 (2H, m), 7.61 (4H, brs), 7.68 (1H, dd, J=1.9 Hz, J=7.5 Hz), 8.08 (2H, d, J=8.7 Hz), 8.29 (1H, d, J=8.7 Hz), 8.98 (1H, brs). |
| 1-97 | 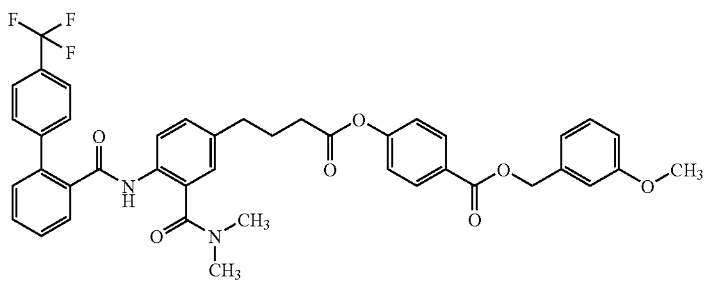 | 2.02 (2H, quint, J=7.2 Hz), 2.56 (2H, t, J=7.2 Hz), 2.69 (2H, t, J=7.2 Hz), 2.85 (3H, brs), 2.94 (3H, brs), 3.82 (3H, s), 5.33 (2H, s), 6.88 (2H, dd, J=2.3 Hz, J=7.9 Hz), 6.95-7.05 (3H, m), 7.14 (2H, d, J=8.7 Hz), 7.21-7.27 (1H, m), 7.30 (1H, t, J=7.9 Hz), 7.39 (1H, dd, J=1.5 Hz, J=7.5 Hz), 7.44-7.58 (2H, m), 7.61 (4H, brs), 7.69 (1H, dd, J=1.5 Hz, J=7.5 Hz), 8.10 (1H, d, J=8.7 Hz), 8.29 (1H, d, J=8.3 Hz), 8.98 (1H, brs). |
| 1-98 | 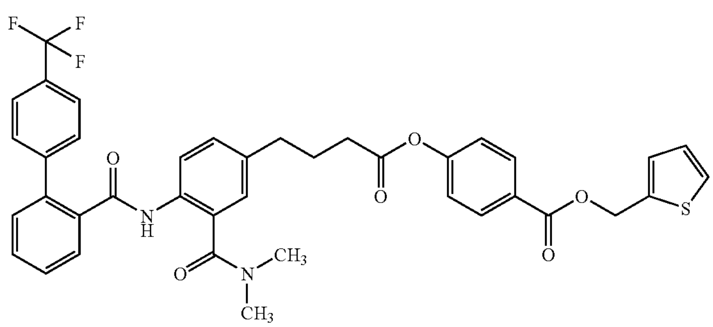 | 2.02 (2H, quint, J=7.2 Hz), 2.55 (2H, t, J=7.2 Hz), 2.69 (2H, t, J=7.2 Hz), 2.85 (3H, brs), 2.94 (3H, brs), 5.50 (2H, s), 6.99-7.02 (2H, m), 7.13 (2H, d, J=9.1 Hz), 7.16-7.17 (1H, m), 7.22-7.26 (1H, m), 7.34 (1H, dd, J=1.9, 5.3 Hz), 7.40 (1H, dd, J=1.9, 7.6 Hz), 7.47-7.57 (2H, m), 7.62 (4H, s), 7.69 (1H, dd, J=1.9, 7.2 Hz), 8.09 (2H, d, J=9.0 Hz), 8.30 (1H, d, J=8.7 Hz), 8.99 (1H, s). |
| 1-99 | 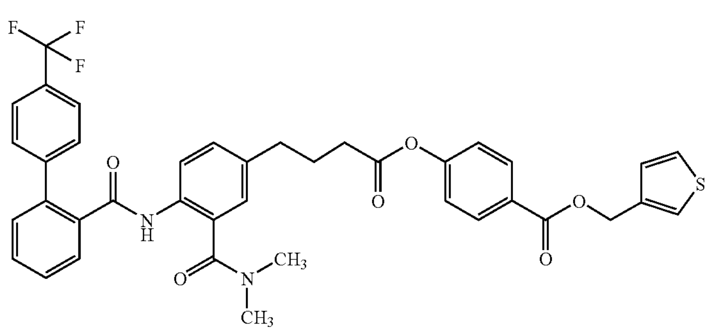 | 2.02 (2H, quint, J=7.5 Hz), 2.55 (2H, t, J=7.5 Hz), 2.69 (2H, t, J=7.5 Hz), 2.85 (3H, brs), 2.94 (3H, brs), 5.36 (2H, s), 7.00 (1H, d, J=1.9 Hz), 7.14 (2H, d, J=8.6 Hz), 7.16-7.18 (1H, m), 7.23-7.26 (1H, m), 7.33-7.54 (5H, m), 7.62 (4H, s), 7.69 (1H, dd, J=1.9, 7.2 Hz), 8.09 (2H, d, J=8.7 Hz), 8.30 (1H, d, J=8.7 Hz), 8.99 (1H, s). |

TABLE 20

| Example | Structure | NMR (δ, 300 or 400 MHz, CDCl₃) |
|---|---|---|
| 1-100 | 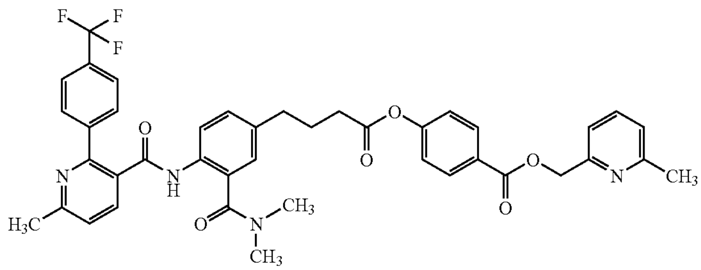 | 2.03 (2H, quint, J=7.5 Hz), 2.54-2.59 (5H, m), 2.67 (3H, s), 2.70 (2H, t, J=7.5 Hz), 2.86 (6H, brs), 5.44 (2H, s), 7.00 (1H, d, J=1.9 Hz), 7.11 (1H, d, J=8.0 Hz), 7.16 (2H, d, J=8.6 Hz), 7.23-7.29 (3H, m), 7.59 (1H, d, J=7.9 Hz), 7.65 (2H, d, J=8.3 Hz), 7.88 (2H, d, J=8.3 Hz), 7.91 (1H, d, J=8.0 Hz), 8.15 (2H, d, J=8.6 Hz), 8.37 (1H, d, J=8.6 Hz), 9.13 (1H, s). |
| 1-101 | 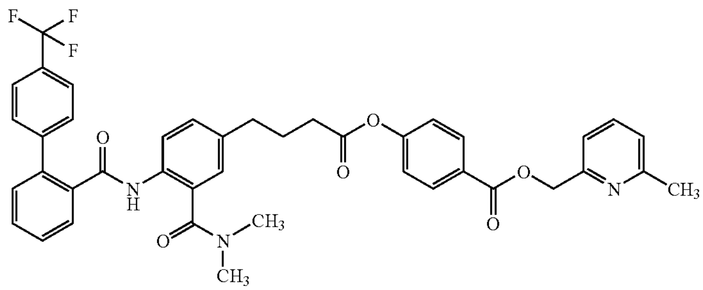 | 2.03 (2H, quint, J=7.1 Hz), 2.56 (2H, t, J=7.1 Hz), 2.57 (3H, s), 2.69 (2H, t, J=7.1 Hz), 2.86 (3H, brs), 2.94 (3H, brs), 5.44 (2H, s), 7.00 (1H, d, J=1.9 Hz), 7.11 (1H, d, J=7.9 Hz), 7.16 (2H, d, J=9.0 Hz), 7.22 (2H, d, J=7.9 Hz), 7.40 (1H, dd, J=1.9, 7.6 Hz), 7.43-7.62 (7H, m), 7.69 (1H, dd, J=1.9, 7.6 Hz), 8.15 (2H, d, J=8.6 Hz), 8.30 (1H, d, J=8.3 Hz), 8.99 (1H, s). |
| 1-102 | 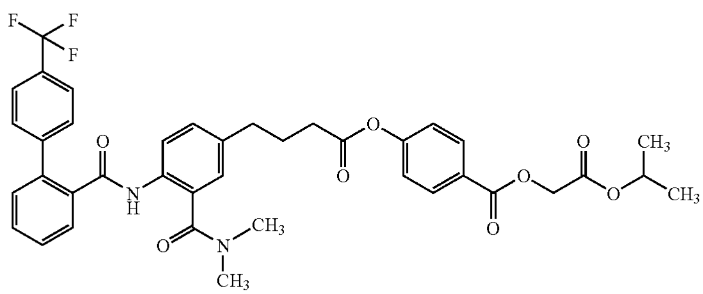 | 1.28 (6H, d, J=6.4 Hz), 2.03 (2H, quint, J=7.2 Hz), 2.56 (2H, t, J=7.2 Hz), 2.70 (2H, t, J=7.2 Hz), 2.87 (3H, brs), 2.94 (3H, brs), 4.80 (2H, s), 5.12 (1H, sept, J=6.4 Hz), 7.00 (1H, d, J=1.9 Hz), 7.17 (2H, d, J=8.7 Hz), 7.22-7.26 (1H, m), 7.40 (1H, dd, J=1.5 Hz, J=7.5 Hz), 7.44-7.57 (2H, m), 7.62 (4H, brs), 7.69 (1H, dd, J=1.9 Hz, J=7.5 Hz), 8.13 (2H, d, J=8.7 Hz), 8.30 (1H, d, J=8.3 Hz), 8.99 (1H, brs). |
| 1-103 | 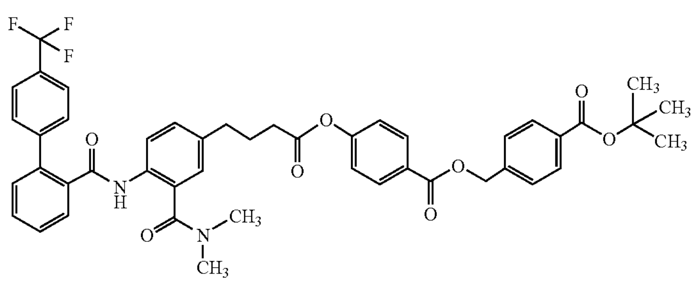 | 1.59 (9H, s), 2.02 (2H, quint, J=7.5 Hz), 2.56 (2H, t, J=7.5 Hz), 2.69 (2H, t, J=7.5 Hz), 2.86 (3H, brs), 2.94 (3H, brs), 5.40 (2H, s), 7.00 (1H, d, J=1.9 Hz), 7.15 (2H, d, J=8.7 Hz), 7.23-7.26 (1H, m), 7.40 (1H, dd, J=1.6, 7.6 Hz), 7.47 (2H, d, J=8.3 Hz), 7.51-7.54 (2H, m), 7.61 (4H, s), 7.69 (1H, dd, J=1.6, 7.6 Hz), 8.01 (2H, d, J=8.3 Hz), 8.11 (2H, d, J=9.0 Hz), 8.30 (1H, d, J=8.7 Hz), 8.98 (1H, 2). |
| 1-104 | 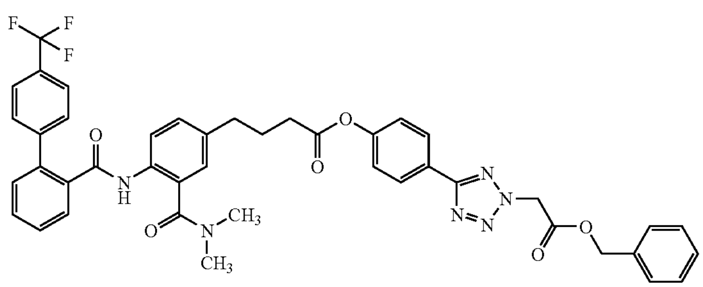 | 2.04 (2H, quint, J=7.2 Hz), 2.57 (2H, t, J=7.2 Hz), 2.71 (2H, t, J=7.2 Hz), 2.87 (3H, brs), 2.94 (3H, brs), 5.26 (2H, s), 5.49 (2H, s), 7.02 (1H, d, J=1.9 Hz), 7.21 (2H, d, J=8.7 Hz), 7.25-7.28 (1H, m), 7.33-7.57 (8H, m), 7.62 (4H, s), 7.69 (1H, dd, J=1.5, 7.6 Hz), 8.18 (2H, d, J=8.7 Hz), 8.31 (1H, d, J=8.2 Hz), 9.00 (1H, s). |

TABLE 21

| Example | Structure | NMR (δ, 300 or 400 MHz, CDCl₃) |
|---|---|---|
| 1-105 | 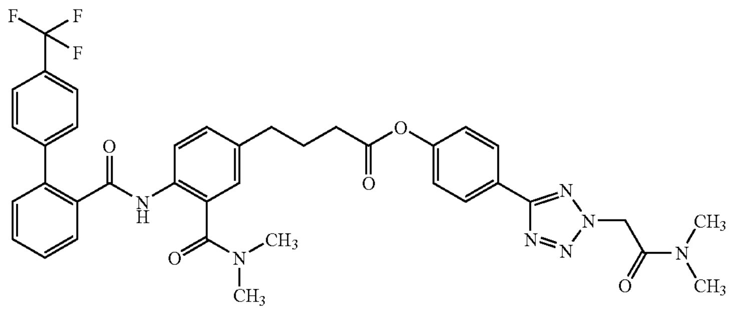 | 2.04 (2H, quint, J=7.5 Hz), 2.57 (2H, t, J=7.5 Hz), 2.70 (2H, t, J=7.5 Hz), 2.87 (3H, brs), 2.94 (3H, brs), 3.04 (3H, s), 3.14 (3H, s), 5.54 (2H, s), 7.02 (1H, d, J=1.9 Hz), 7.20 (2H, d, J=8.6 Hz), 7.24–7.28 (1H, m), 7.40 (1H, dd, j=1.5, 7.5 Hz), 7.45–7.57 (2H, m), 7.62 (4H, s), 7.69 (1H, dd, J=1.9, 7.2 Hz), 8.19 (2H, d, J=8.7 Hz), 8.31 (1H, d, J=8.3 Hz), 9.01 (1H, s). |
| 1-106 | 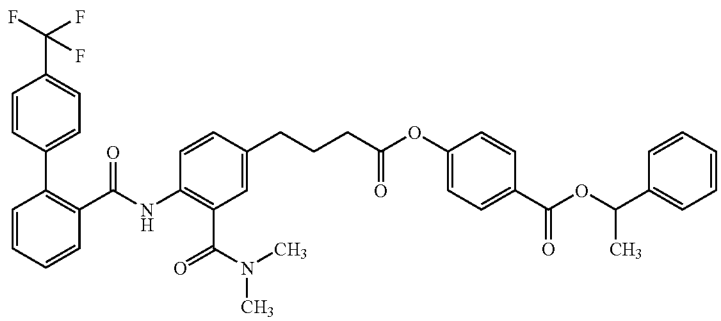 | 1.67 (3H, d, J=6.4 Hz), 2.02 (2H, quint, J=7.5 Hz), 2.56 (2H, t, J=7.5 Hz), 2.69 (2H, t, J=7.5 Hz), 2.86 (3H, brs), 2.94 (3H, brs), 6.12 (1H, q, J=6.4 Hz), 7.00 (1H, d, J=2.3 Hz), 7.14 (2H, d, J=8.7 Hz), 7.23–7.57 (9H, m), 7.62 (4H, s), 7.69 (1H, dd, J=1.5, 7.2 Hz), 8.10 (2H, d, J=8.7 Hz), 8.30 (1H, d, J=8.3 Hz), 8.99 (1H, s). |
| 1-107 | 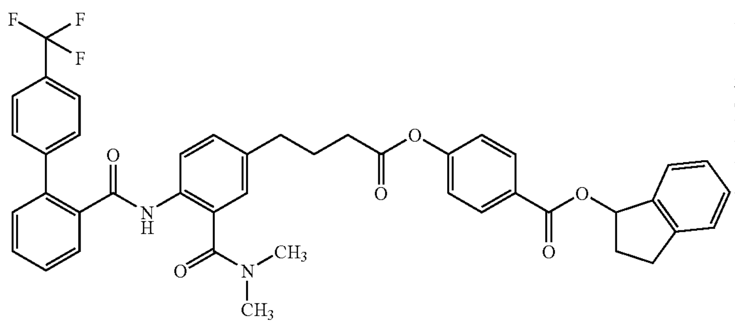 | 2.02 (2H, quint, J=7.5 Hz), 2.17–2.28 (1H, m), 2.55 (2H, t, J=7.5 Hz), 2.59–2.71 (3H, m), 2.80–2.99 (7H, m), 3.13–3.23 (1H, m), 6.45 (1H, dd, J=4.2, 7.2 Hz), 6.99 (1H, d, J=1.9 Hz), 7.11 (2H, d, J=8.7 Hz), 7.22–7.32 (4H, m), 7.39 (1H, dd, J=1.5, 7.6 Hz), 7.46–7.56 (3H, m), 7.61 (4H, s), 7.68 (1H, dd, J=1.5, 7.5 Hz), 8.07 (2H, d, J=8.7 Hz), 8.30 (1H, d, J=8.3 Hz), 8.99 (1H, s). |
| 1-108 | 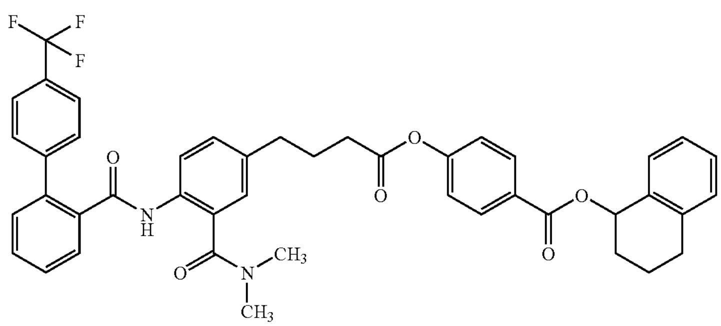 | 1.84–1.92 (1H, m), 1.97–2.14 (5H, m), 2.55 (2H, t, J=7.2 Hz), 2.68 (2H, t, J=7.2 Hz), 2.80–2.95 (8H, m), 6.24 (1H, t, J=4.6 Hz), 6.99 (1H, d, J=1.9 Hz), 7.11 (2H, d, J=8.7 Hz), 7.17–7.35 (5H, m), 7.39 (1H, dd, J=1.5, 7.9 Hz), 7.45–7.56 (2H, m), 7.61 (4H, s), 7.68 (1H, dd, J=1.5, 7.5 Hz), 8.08 (2H, d, J=9.0 Hz), 8.30 (1H, d, J=8.3 Hz), 8.99 (1H, s). |
| 1-109 | 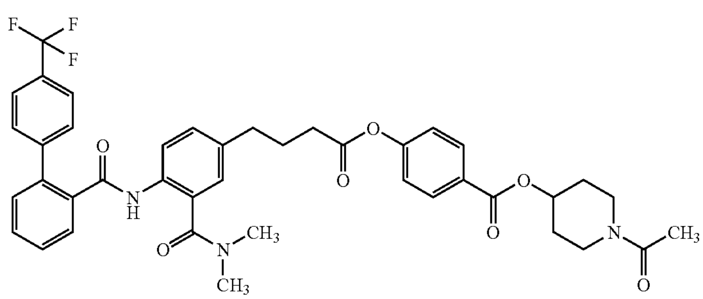 | 1.76–1.87 (2H, m), 1.93–2.08 (4H, m), 2.13 (3H, s), 2.56 (2H, t, J=7.2 Hz), 2.70 (2H, t, J=7.2 Hz), 2.86 (3H, brs), 2.95 (3H, brs), 3.37–3.60 (2H, m), 3.65–3.78 (1H, m), 3.88–3.98 (1H, m), 5.21–5.28 (1H, m), 7.00 (1H, d, J=2.2 Hz), 7.15 (2H, d, J=8.6 Hz), 7.23–7.26 (1H, m), 7.40 (1H, dd, J=1.5, 7.6 Hz), 7.46–7.57 (2H, m), 7.62 (4H, s), 7.69 (1H, dd, J=1.5, 7.5 Hz), 8.07 (2H, d, J=8.6 Hz), 8.30 (1H, d, J=8.3 Hz), 8.98 (1H, s). |

TABLE 22

| Example | Structure | NMR (δ, 300 or 400 MHz, CDCl₃) |
|---|---|---|
| 1-110 | 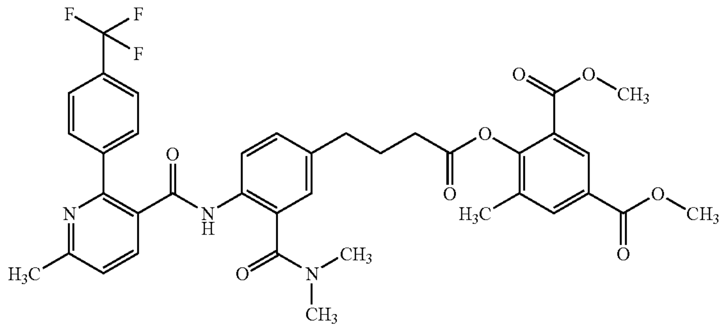 | 2.06 (2H, quint, J=7.5 Hz), 2.25 (3H, s), 2.65–2.70 (5H, m), 2.73 (2H, t, J=7.5 Hz), 2.87 (6H, brs), 3.86 (3H, s), 3.93 (3H, s), 7.05 (1H, d, J=1.9 Hz), 7.25–7.32 (2H, m), 7.65 (2H, d, J=8.3 Hz), 7.88 (2H, d, J=8.3 Hz), 7.92 (1H, d, J=7.9 Hz), 8.11 (1H, d, J=1.5 Hz), 8.37 (1H, d, J=8.7 Hz), 8.51 (1H, d, J=1.9 Hz), 9.16 (1H, s). |
| 1-111 | 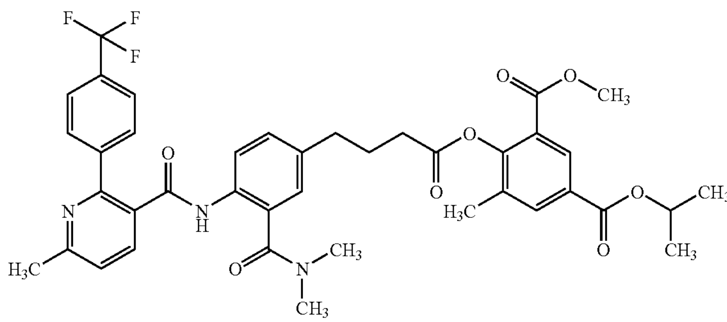 | 1.38 (6H, d, J=6.0 Hz), 2.06 (2H, quint, J=7.2 Hz), 2.25 (3H, s), 2.65–2.69 (5H, m), 2.73 (2H, t, J=7.2 Hz), 2.87 (6H, brs), 3.86 (3H, s), 5.26 (1H, sept, J=6.0 Hz), 7.05 (1H, d, J=1.9 Hz), 7.25–7.32 (2H, m), 7.65 (2H, d, J=8.3 Hz), 7.88 (2H, d, J=7.9 Hz), 7.92 (1H, d, J=7.9 Hz), 8.09 (1H, d, J=1.9 Hz), 8.37 (1H, d, J=8.7 Hz), 8.48 (1H, d, J=1.9 Hz), 9.16 (1H, s). |
| 1-112 | 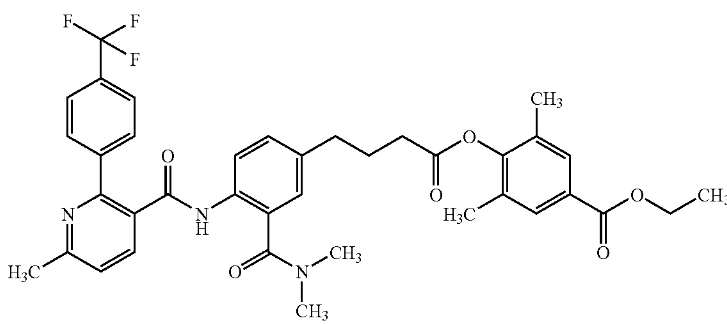 | 1.39 (3H, t, J=7.2 Hz), 2.08 (2H, quint, J=7.2 Hz), 2.23 (3H, s), 2.64 (2H, t, J=7.2 Hz), 2.67 (3H, s), 2.73 (2H, t, J=7.2 Hz), 2.87 (6H, brs), 4.37 (2H, q, J=7.2 Hz), 7.02 (1H, d, J=1.9 Hz), 7.25–7.30 (2H, m), 7.65 (2H, d, J=7.9 Hz), 7.83–7.89 (3H, m), 7.92 (1H, d, J=7.9 Hz), 7.97 (1H, d, J=1.9 Hz), 8.38 (1H, d, J=8.3 Hz), 9.16 (1H, s). |
| 1-113 | 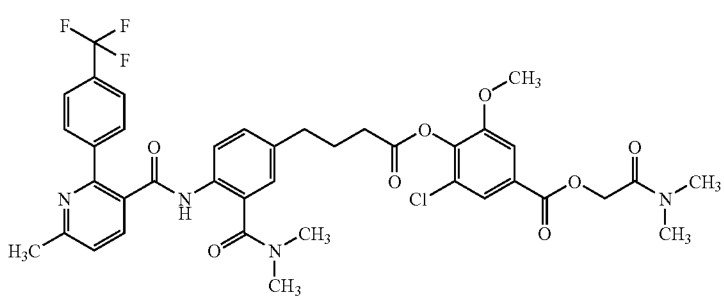 | 2.06 (2H, quint, J=7.1 Hz), 2.63 (2H, t, J=7.1 Hz), 2.67 (3H, s), 2.73 (2H, t, J=7.1 Hz), 2.87 (6H, brs), 3.01 (3H, s), 3.04 (3H, s), 3.87 (3H, s), 4.97 (2H, s), 7.03 (1H, d, J=1.9 Hz), 7.25–7.30 (2H, m), 7.62 (1H, d, J=1.9 Hz), 7.65 (2H, d, J=8.3 Hz), 7.84 (1H, d, J=1.9 Hz), 7.88 (2H, d, J=8.3 Hz), 7.92 (1H, d, J=7.9 Hz), 8.37 (1H, d, J=8.7 Hz), 9.17 (1H, s). |
| 1-114 | 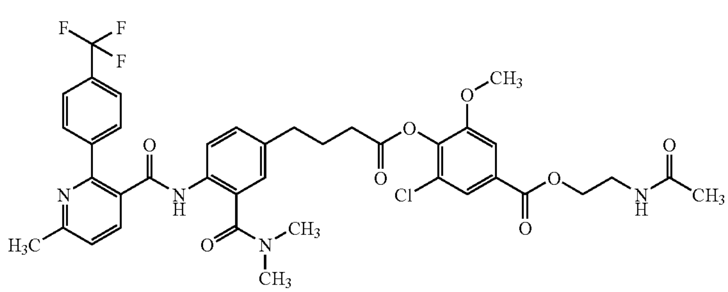 | 2.01 (3H, s), 2.06 (2H, quint, J=7.1 Hz), 2.64 (2H, t, J=7.1 Hz), 2.67 (3H, s), 2.73 (2H, t, J=7.1 Hz), 2.87 (6H, brs), 3.66 (2H, dd, J=5.3, 11.1 Hz), 3.89 (3H, s), 4.42 (2H, t, J=5.3 Hz), 5.80 (1H, brs), 7.02 (1H, d, J=1.9 Hz), 7.25–7.31 (2H, m), 7.56 (1H, d, J=1.9 Hz), 7.65 (2H, d, J=8.3 Hz), 7.73 (1H, d, J=1.9 Hz), 7.88 (2H, d, J=8.3 Hz), 7.92 (1H, d, J=7.9 Hz), 8.37 (1H, d, J=8.3 Hz), 9.15 (1H, s). |

TABLE 23

| Example | Structure | NMR (δ, 300 or 400 MHz, CDCl₃) |
|---|---|---|
| 1-115 | 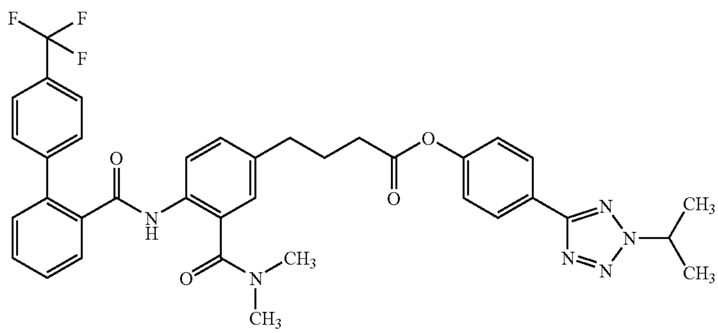 | 1.70 (6H, d, J=6.8 Hz), 2.04 (2H, quint, J=7.2 Hz), 2.57 (2H, t, J=7.2 Hz), 2.71 (2H, t, J=7.2 Hz), 2.87 (3H, brs), 2.95 (3H, brs), 5.10 (1H, sept, J=6.8 Hz), 7.01 (1H, d, J=2.3 Hz), 7.19 (2H, d, J=8.7 Hz), 7.25–7.28 (1H, m), 7.40 (1H, dd, J=1.5, 7.5 Hz), 7.45–7.54 (2H, m), 7.62 (4H, s), 7.69 (1H, dd, J=1.9, 7.2 Hz), 8.18 (2H, d, J=8.7 Hz), 8.31 (1H, d, J=8.2 Hz), 9.00 (1H, s). |
| 1-116 | 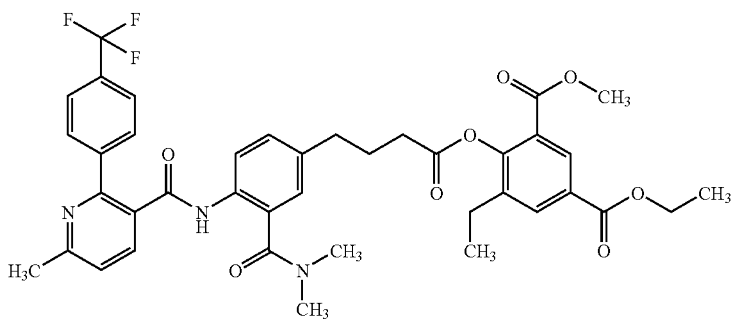 | 1.22 (3H, t, J=7.5 Hz), 1.41 (3H, t, J=7.2 Hz), 2.06 (2H, quint, J=7.5 Hz), 2.61 (2H, q, J=7.5 Hz), 2.65–2.70 (5H, m), 2.73 (2H, t, J=7.5 Hz), 2.87 (6H, brs), 3.86 (3H, s), 4.40 (2H, q, J=7.2 Hz), 7.05 (1H, d, J=1.9 Hz), 7.26 (1H, d, J=7.9 Hz), 7.30 (1H, dd, J=1.9, 8.3 Hz), 7.65 (2H, d, J=8.3 Hz), 7.88 (2H, d, J=7.9 Hz), 7.91 (1H, d, J=7.9 Hz), 8.13 (1H, d, J=1.9 Hz), 8.37 (1H, d, J=8.6 Hz), 8.51 (1H, d, J=1.9 Hz), 9.15 (1H, s). |
| 1-117 | 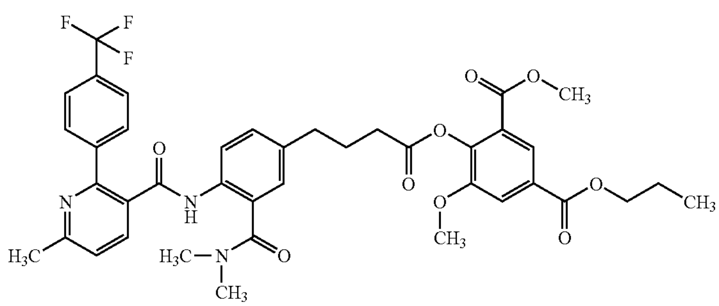 | 1.03 (3H, t, J=7.2 Hz), 1.75–1.87 (2H, m), 2.06 (2H, quint, J=7.1 Hz), 2.65 (2H, t, J=7.1 Hz), 2.66 (3H, s), 2.74 (2H, t, J=7.1 Hz), 2.86 (6H, brs), 3.87 (3H, s), 3.89 (3H, s), 4.31 (2H, q, J=6.8 Hz), 7.05 (1H, d, J=2.3 Hz), 7.26 (1H, d, J=7.9 Hz), 7.30 (1H, dd, J=2.3, 8.7 Hz), 7.65 (2H, d, J=8.3 Hz), 7.80 (1H, d, J=1.9 Hz), 7.88 (2H, d, J=7.9 Hz), 7.91 (1H, d, J=7.9 Hz), 8.23 (1H, d, J=1.9 Hz), 8.36 (1H, d, J=8.3 Hz), 9.15 (1H, s). |
| 1-118 | 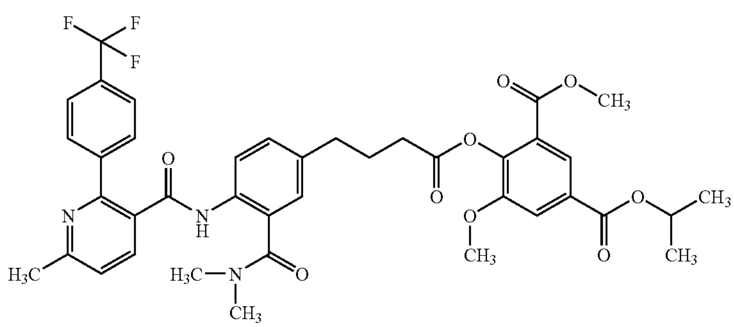 | 1.39 (6H, d, J=6.0 Hz), 2.06 (2H, quint, J=7.5 Hz), 2.64 (2H, t, J=7.5 Hz), 2.66 (3H, s), 2.74 (2H, t, J=7.5 Hz), 2.86 (6H, brs), 3.87 (3H, s), 3.90 (3H, s), 5.27 (1H, sept, J=6.0 Hz), 7.05 (1H, d, J=1.9 Hz), 7.26 (1H, d, J=7.9 Hz), 7.30 (1H, dd, J=1.9, 8.3 Hz), 7.65 (2H, d, J=8.3 Hz), 7.79 (1H, d, J=1.9 Hz), 7.88 (2H, d, J=8.3 Hz), 7.91 (1H, d, J=7.9 Hz), 8.21 (1H, d, J=1.9 Hz), 8.36 (1H, d, J=8.6 Hz), 9.15 (1H, s). |

TABLE 24

| Example | Structure | NMR (δ, 300 or 400 MHz, CDCl₃) |
|---|---|---|
| 1-119 | 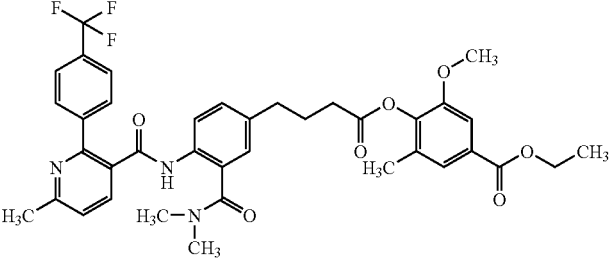 | 1.39(3H, t, J=7.2 Hz), 2.05(2H, quint, J = 7.5 Hz), 2.19(3H, s), 2.60 (2H, t, J=7.5 Hz), 2.66(3H, s), 2.73(2H, t, J=7.5 Hz), 2.86 (6H, brs), 3.84(3H, s), 4.37(2H, d, J = 7.2 Hz), 7.02 (1H, d, J=1.9 Hz), 7.23-7.32(2H, m), 7.48(1H, d, J=1.9 Hz), 7.56(1H, d, J = 1.9 Hz), 7.64 (2H, d, J=8.3 Hz), 7.87(2H, d, J=8.3 Hz), 7.91(1H, d, J=7.9 Hz), 8.36 (1H, d, J=8.7 Hz) 9.14 (1H, brs). |
| 1-120 | 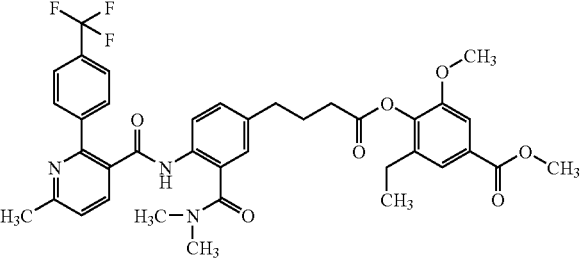 | 1.19(3H, t, J=7.5 Hz), 2.05(2H, quint, J = 7.5 Hz), 2.49-2.64 (4H, m), 2.66(3H, s), 2.73(2H, t, J=7.5 Hz), 2.86(6H, brs), 3.84 (3H, s), 3.91(3H, s), 7.02(1H, d, J=1.9 Hz), 7.23-7.31 (2H, m), 7.49(1H, d, J=1.9 Hz), 7.59(1H, d, J = 1.9 Hz), 7.64(2H, d, J=8.3 Hz), 7.87 (2H, d, J = 8.3 Hz), 7.91 (1H, d, J = 7.9 Hz), 8.36(1H, d, J = 8.3 Hz), 9.14(1H, brs). |
| 1-121 | 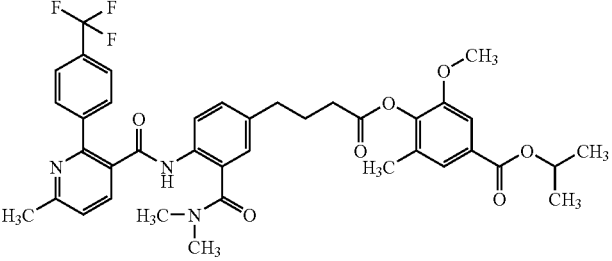 | 1.36(6H, d, J=6.2 Hz), 2.05(2H, quint, J = 7.5 Hz), 2.19(3H, s), 2.60(2H, t, J=7.5 Hz), 2.66(3H, s), 2.73(2H, t, J = 7.5 Hz), 2.86 (6H, brs), 3.84(3H, s), 5.24(1H, sept, J = 6.2 Hz), 7.02(1H, d, J = 1.9 Hz), 7.23-7.32 (2H, m), 7.47(1H, d, J = 1.9 Hz), 7.54 (1H, d, J = 1.9 Hz), 7.64(2H, d, J = 8.3 Hz), 7.88(2H, d, J = 8.3 Hz), 7.91(1H, d, J = 7.9 Hz), 8.36(1H, d, J = 8.4 Hz), 9.14(1H, brs). |
| 1-222 | 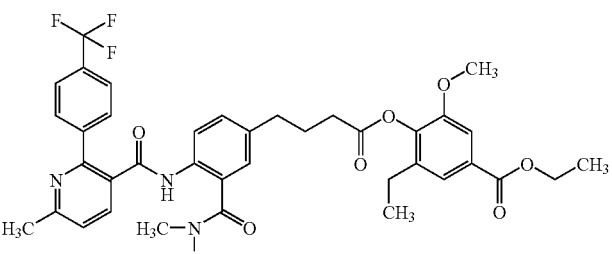 | 1.19(3H, t, J=7.6 Hz), 1.40(3H, t, J=7.1 Hz), 2.05(2H, quint, J = 7.5 Hz), 2.49-2.64 (4H, m), 2.67(3H, s), 2.73(2H, t, J=7.5 Hz), 2.86(6H, brs), 3.84(3H, s), 4.38 (2H, q, J=7.1 Hz), 7.02(1H, d, J = 2.3 Hz), 7.23-7.31 (2H, m), 7.49(1H, d, J=1.9 Hz), 7.58(1H, d, J=1.9 Hz), 7.65(2H, d, J=8.3 Hz), 7.87(2H, d, J = 8.3 Hz), 7.91(1H, d, J = 7.9 Hz),8.36 (1H, d, J=8.5 Hz), 9.14(1H, brs). |
| 1-123 | 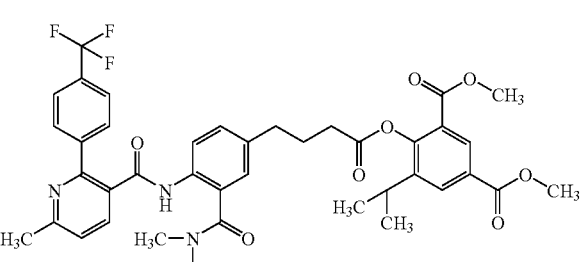 | 1.23(6H, d, J = 6.8 Hz), 2.06(2H, quint, J = 7.5 Hz), 2.65-2.76(7H, m), 2.87(6H, brs) 3.10(1H, sept, J = 6.8 Hz), 3.85(3H, s), 3.94(3H, s), 7.05(1H, d, J = 1.9 Hz), 7.26 (1H, d, J=7.9 Hz), 7.30(1H, dd, J=1.9, 8.7 Hz), 7.65(2H, d, J=7.9 Hz), 7.88(2H, d, J = 7.9 Hz), 7.91 (1H, d, J=7.9 Hz), 8.19 (1H, d, J=2.2 Hz), 8.37(1H, d, J=8.3 Hz), 8.51(1H, d, J=2.2 Hz), 9.15(1H, s). |

Working Example 2-1

4-[2-({3-Dimethylcarbamoyl-4-[(4'-trifluoromethyl-biphenyl-2-carbonyl)amino]benzyl}methylamino)acetoxy]benzoic acid methyl ester (Compound 2-1)

a) 4'-Trifluoromethylbiphenyl-2-carboxylic acid (2-dimethylcarbamoyl-4-vinylphenyl)amide To a solution of 4'-trifluoromethylbiphenyl-2-carboxylic acid (2-dimethylcarbamoyl-4-iodophenyl)amide (1.32 g) in toluene (15 mL) were added tributylvinyltin (935 mg) and tetrakistriphenylphosphine palladium(0) (142 mg), and the mixture was stirred at 140° C. for 1.5 hours under heating. The reaction solution was allowed to stand for cooling down to room temperature, and concentrated in vacuo. The residue was purified by column chromatography on silica gel (hexane:ethyl acetate=2:1, v/v) to give the title compound (783 mg).

b) 4'-Trifluoromethylbiphenyl-2-carboxylic acid (2-dimethylcarbamoyl-4-formylphenyl)amide To a mixed solution of 4'-trifluoromethylbiphenyl-2-carboxylic acid (2-dimethylcarbamoyl-4-vinylphenyl)amide (774 mg) in acetone (10 mL)-water (10 mL) were added osmium tetroxide (10% (w/w) microcapsule; 449 mg) and sodium metaperiodate (944 mg). The mixture was stirred at room temperature for 4 hours and filtered through a Celite pad. The filtrate was concentrated in vacuo. The residue was diluted with ethyl acetate, washed successively with water and saturated brine, dried over anhydrous sodium sulfate, and concentrated. The residue was purified by column chromatography on silica gel (hexane:ethyl acetate=3:2, v/v) to give the title compound (570 mg).

c) ({3-Dimethylcarbamoyl-4-[(4'-trifluoromethylbiphenyl-2-carbonyl)amino]benzyl}methylamino)acetic acid methyl ester To a solution of 4'-trifluoromethylbiphenyl-2-carboxylic acid (2-dimethylcarbamoyl-4-formylphenyl)amide (137 mg) and N-methylglycine methyl ester hydrochloride (45 mg) in dichloromethane (2 mL) was added sodium triacetoxyborohydride (97 mg). The mixture was stirred at room temperature for 4 hours, diluted with ethyl acetate, washed successively with saturated aqueous sodium bicarbonate and saturated brine, dried over anhydrous sodium sulfate, and concentrated in vacuo. The residue was purified by column chromatography on silica gel (chloroform:methanol=100:1, v/v) to give the title compound (120 mg).

d) ({3-Dimethylcarbamoyl-4-[(4'-trifluoromethylbiphenyl-2-carbonyl)amino]benzyl}methylamino)acetic acid To a mixed solution of ({3-dimethylcarbamoyl-4-[(4'-trifluoromethylbiphenyl-2-carbonyl)amino]benzyl}methylamino)acetic acid methyl ester (120 mg) in THF (1 mL)-methanol (3 mL) was added 4N aqueous sodium hydroxide (0.2 mL) The mixture was stirred at 50° C. for 2 hours under heating, allowed to stand for cooling down to room temperature, and concentrated in vacuo. After addition of water to the residue, 1N hydrochloric acid was added portionwise to the aqueous solution under ice-cooling to adjust the pH to 6 to 7, followed by extraction with ethyl acetate four times. The extract was dried over anhydrous sodium sulfate and concentrated to give the title compound (110 mg).

e) 4-[2-([3-Dimethylcarbamoyl-4-[(4'-trifluoromethylbiphenyl-2-carbonyl)amino]benzyl]methylamino)acetoxy]benzoic acid methyl ester {3-Dimethylcarbamoyl-4-[(4'-trifluoromethylbiphenyl-2-carbonyl)amino]benzyl}methylamino)acetic acid (107 mg) was treated in a similar manner to Step g) of Working Example 1-1 to give the title compound (Compound 2-1)(62 mg).

The structure and NMR data of the compound obtained are shown in Table 25.

TABLE 25

| Example | Structure | NMR (δ, 300 or 400 MHz, CDCl$_3$) |
|---|---|---|
| 2-1 | [structure] | 2.46 (3H, s), 2.85 (3H, brs), 2.94 (3H, brs), 3.50 (2H, s), 3.71 (2H, s), 3.92 (3H, s), 7.14–7.26 (3H, m), 7.35–7.62 (8H, m), 7.70 (1H, dd, J=7.1, 1.2 Hz), 8.06–8.09 (2H, m), 8.35 (1H, d, J=8.3 Hz), 9.12 (1H, s). |

Working Example 3-1

1-{3-Dimethylcarbamoyl-4-[(4'-trifluoromethylbiphenyl-2-carbonyl)amino]phenyl}piperidine-4-carboxylic acid 4-methoxycarbonylphenyl ester (Compound 3-1)

a) 5-Chloro-N,N-dimethyl-2-nitrobenzamide

To a solution of 5-nitro-2-chlorobenzoic acid (1 g), 1-hydroxybenzotriazolemonohydrate (1.14 g) and 1-ethyl-3-(3-dimethylaminopyridyl)carbodiimide hydrochloride (1.42 g) in N,N'-dimethylformamide (10 mL) were added dimethylamine hydrochloride (0.61 g) and triethylamine (1 mL). The mixture was stirred for all day and night, and then water was added. The reaction solution was extracted with ethyl acetate, and the extract was washed with saturated aqueous sodium bicarbonate and saturated brine, dried over magnesium sulfate, and concentrated to give the title compound (1.13 g).

b) 1-(3-Dimethylcarbamoyl-4-nitrophenyl)piperidine-4-carboxylic acid ethyl ester 5-Chloro-N,N-dimethyl-2-nitrobenzamide (1.131 g), 4-piperidinecarboxylic acid ethyl ester (0.77 mL), and potassium carbonate (1.4 g) were reacted in N,N'-dimethylformamide (20 mL) at 100° C. for 2 hours. Water was added to the reaction solution, and the mixture was extracted with ethyl acetate. The extract was washed with saturated aqueous sodium bicarbonate and saturated brine, dried over magnesium sulfate, and concentrated to give the title compound (1.578 g).

c) 1-(4-Amino-3-dimethylcarbamoylphenyl)piperidine-4-carboxylic acid ethyl ester 1-(3-Dimethylcarbamoyl-4-nitrophenyl)-piperidine-4-carboxylic acid ethyl ester (1.578 g) was dissolved in tetrahydrofuran (5 mL) and ethanol (5 mL). After addition of 7.5% (w/w) palladium-carbon (0.316 g) to the solution, the mixture was stirred for 5 hours at normal pressure in hydrogen atmosphere. The reaction solution was filtered through a Celite pad and concentrated to give the title compound, which was used without isolation in the subsequent reaction.

d) 1-{3-Dimethylcarbamoyl-4-[(4'-trifluoromethylbiphenyl-2-carbonyl)amino]phenyl}piperidine-4-carboxylic acid ethyl ester 1-(4-Amino-3-dimethylcarbamoylphenyl)-piperidine-4-carboxylic acid ethyl ester was dissolved in toluene (5 mL), and triethylamine (1.87 mL) was added thereto. The solution was cooled down to 0° C., and 4'-trifluoromethylbiphenyl-2-carbonyl chloride (synthesized from the corresponding carboxylic acid 1.44 g) was added thereto. The mixture was stirred at room temperature overnight. The insoluble matter was filtered off. After removal of the insoluble material by filtration, the filtrate was concentrated and purified by column chromatography on silica gel (acetone:hexane=5:1, v/v) to give the title compound (1.287 g).

e) 1-{3-Dimethylcarbamoyl-4-[(4'-trifluoromethylbiphenyl-2-carbonyl)amino]phenyl}piperidine-4-carboxylic acid 1-{3-Dimethylcarbamoyl-4-[(4'-trifluoromethylbiphenyl-2-carbonyl)amino]phenyl}piperidine-4-carboxylic acid ethyl ester was dissolved in methanol (5 mL), and 4N aqueous sodium hydroxide (1.5 mL) was added thereto. The solution was stirred at room temperature for 2 hours, concentrated, and acidified with 1N hydrochloric acid. The resulting precipitated solid was filtered and washed with water to give the title compound (1.064 g).

f) 1-{3-Dimethylcarbamoyl-4-[(4'-trifluoromethylbiphenyl-2-carbonyl)amino]phenyl}piperidine-4-carboxylic acid 4-methoxycarbonylphenyl ester 4-Dimethylaminopyridine (59 mg), 4-methoxycarbonylphenol ester (56 mg), and 1-{3-dimethylcarbamoyl-4-[(4'-trifluoromethylbiphenyl-2-carbonyl)amino]phenyl}piperidine-4-carboxylic acid (200 mg) were dissolved in acetone (3 mL). After addition of WSC hydrochloride (85 mg), the mixture was stirred at room temperature for 1 day. The reaction mixture was concentrated and purified by column chromatography on silica gel (acetone:hexane=5:1 to 3:1, v/v) to give the title compound (Compound 3-1) (0.124 g).

Working Example 3-2

1-{3-Dimethylcarbamoyl-4-[(4'-trifluoromethylbiphenyl-2-carbonyl)amino]phenyl}piperidine-4-carboxylic acid 2-fluoro-4-methoxycarbonylphenyl ester (Compound 3-2)

Instead of 4-methoxycarbonylphenol ester, 3-fluoro-4-methoxycarbonylphenol ester was subjected to a similar reaction to Working Example 3-1 to give 1-{3-dimethylcarbamoyl-4-[(4'-trifluoromethylbiphenyl-2-carbonyl)amino]phenyl}piperidine-4-carboxylic acid 2-fluoro-4-methoxycarbonylphenyl ester (Compound 3-2).

The structures and NMR data of the compounds obtained in Working Examples 3-1 to 3-2 are shown in Table 26.

TABLE 26

| Example | Structure | NMR (δ, 300 or 400 MHz, CDCl₃) |
|---|---|---|
| 3-1 | (structure) | 1.97–2.06 (2H, m), 2.12–2.21 (2H, m), 2.66–2.77 (1H, m), 2.78–3.01 (8H, m), 3.60 (2H, d, J=12.3 Hz), 3.92 (3H, s), 6.70 (1H, d, J=2.5 Hz), 6.98 (1H, dd, J=2.5, 9.3 Hz), 7.14–7.19 (2H, m), 7.39 (1H, dd, J=1.4, 7.4 Hz), 7.45–7.55 (2H, m), 7.62 (4H, d, 2.1 Hz), 7.67 (1H, dd, J=1.6, 7.6 Hz), 8.05–8.10 (2H, m), 8.13 (1H, dd, 2.1, 9.3 Hz), 8.59 (1H, s) |

TABLE 26-continued

| Example | Structure | NMR (δ, 300 or 400 MHz, CDCl₃) |
|---|---|---|
| 3-2 | (structure) | 2.00–2.09 (2H, m), 2.14–2.22 (2H, m), 2.72–3.02 (9H, m), 3.53–3.63 (2H, m), 3.93 (3H, s), 6.70 (1H, d, J=3.0 Hz), 6.98 (1H, dd, J=3.0, 9.3 Hz), 7.21 (1H, dd, 7.5, 8.5 Hz), 7.39 (1H, dd, J=1.2, 7.5 Hz), 7.45–7.55 (2H, m), 7.62 (4H, s), 7.67 (1H, dd, J=1.2, 7.4 Hz), 7.82–7.89 (2H, m), 8.14 (1H, d, J=8.8 Hz), 8.60 (1H, s) |

Working Example 4-1

3-Chloro-4-[4-(3-dimethylcarbamoyl-4-{[2-(4-methoxycarbonylphenyl)-6-methylpyridine-3-carbonyl]amino}phenyl)butyloxy]-5-methylbenzoic acid methyl ester (Compound 4-1)

a) 4-(3-Dimethylcarbamoyl-4-nitrophenyl)butanoic acid 4-(3-Dimethylcarbamoyl-4-nitrophenyl)butanoic acid ethyl ester (1.5 g) was treated in a similar manner (hydrolysis) to Step f) of Working Example 1-1 to give the title compound (1.37 g).

b) 4-(3-Dimethylcarbamoyl-4-nitrophenyl)butanoic acid benzyl ester

To a solution of 4-(3-dimethylcarbamoyl-4-nitrophenyl)butanoic acid (1.37 g) in DMF (10 mL) were added potassium carbonate (880 mg) and benzyl bromide (922 mg). The mixture was stirred at 60° C. for 3.5 hours under heating and then allowed to stand for cooling down to room temperature. After addition of water thereto, the mixture was extracted with ethyl acetate. The extract was washed successively with water and saturated brine, dried over anhydrous sodium sulfate, and concentrated. The residue was purified by column chromatography on silica gel (hexane:ethyl acetate=1:1, v/v) to give the title compound (1.39 g).

c) 4-(4-Amino-3-dimethylcarbamoylphenyl)butanoic acid benzyl ester

To a mixed solution of 4-(3-dimethylcarbamoyl-4-nitrophenyl)butanoic acid benzyl ester (1.39 g) in THF (5 mL), ethanol (15 mL), and water (5 mL) was added ammonium chloride (1.0 g). After heating to 100° C., iron (838 mg) was added thereto in twice. The mixture was further heated for 1.5 hours under reflux, allowed to stand for cooling down to room temperature, and filtered through a Celite pad. The filtrate was concentrated in vacuo. The residue was diluted with ethyl acetate, washed successively with saturated sodium bicarbonate, water, and saturated brine, dried over anhydrous sodium sulfate, and concentrated to give the title compound (1.14 g).

d) 4-{3-[4-(3-Benzyloxycarbonylpropyl)-2-dimethylcarbamoylphenylcarbamoyl]-6-methylpyridin-2-yl}benzoic acid methyl ester To a solution of 2-(4-methoxycarbonylphenyl)-6-methylnicotinic acid (322 mg) and DMF (one drop) in chloroform (3 mL) was added oxalyl chloride (0.21 mL) under ice-cooling. The mixture was continued to stir for one hour, and then concentrated. The residue was diluted with chloroform and added slowly dropwise to a solution of 4-(4-amino-3-dimethylcarbamoylphenyl)butanoic acid benzyl ester (400 mg) and triethylamine (273 mg) in ethyl acetate (5 mL) under ice-cooling. The mixture was stirred at room temperature overnight, diluted with ethyl acetate, washed with water and saturated brine, dried over anhydrous sodium sulfate, and concentrated. The residue was purified by column chromatography on silica gel (hexane:acetone=2:1, v/v) to give the title compound (582 mg).

e) 4-{3-[4-(3-Carboxypropyl)-2-dimethylcarbamoylphenylcarbamoyl]-6-methylpyridin-2-yl}benzoic acid methyl ester 4-[(3-[4-(3-Benzyloxycarbonylpropyl)-2-dimethylcarbamoylphenylcarbamoyl]-6-methylpyridin-2-yl]benzoic acid methyl ester (579 mg) was treated in a similar manner to Step c) of Reference Example 7 to give the title compound (507 mg).

f) 3-Chloro-4-[4-(3-dimethylcarbamoyl-4-{[2-(4-methoxycarbonylphenyl)-6-methylpyridine-3-carbonyl]amino}phenyl)butyloxy]-5-methylbenzoic acid methyl ester 4-{3-[4-(3-Carboxypropyl)-2-dimethylcarbamoylphenylcarbamoyl]-6-methylpyridin-2-yl}benzoic acid methyl ester (1.0 g) and 3-chloro-4-hydroxy-5-methylbenzoic acid methyl ester (390 mg) were treated in a similar manner to Step g) of Working Example 1-1 to give the title compound (Compound 4-1)(1.24 g).

Working Examples 4-2 to 4-4

Compounds of Working Examples 4-2 to 4-4 shown in Tables 27 were obtained in a similar manner to Production Method 4 or Working Example 4-1. The structures and NMR data of Working Examples 4-1 to 4-4 are shown in Table 27. In the following tables, the compounds of Working Examples 4-2 to 4-4 correspond to Compounds 4-2 to 4-4, respectively.

TABLE 27

| Example | Structure | NMR (δ, 300 or 400 MHz, CDCl₃) |
|---|---|---|
| 4-1 | 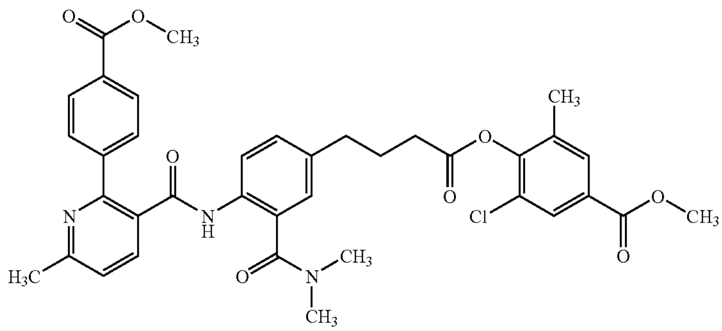 | 2.07 (2H, quint, J=7.1 Hz), 2.23 (3H, s), 2.64 (2H, t, J=7.1 Hz), 2.67 (3H, s), 2.72 (2H, t, J=7.1 Hz), 2.81 (3H, brs), 2.87 (3H, brs), 3.91 (6H, s), 6.99 (1H, d, J=1.9 Hz), 7.24–7.29 (2H, m), 7.80–7.84 (3H, m), 7.92 (1H, d, J=7.9 Hz), 7.97 (1H, d, J=2.3 Hz), 8.05 (2H, d, J=8.7 Hz), 8.37 (1H, d, J=8.3 Hz), 9.04 (1H, s). |
| 4-2 | 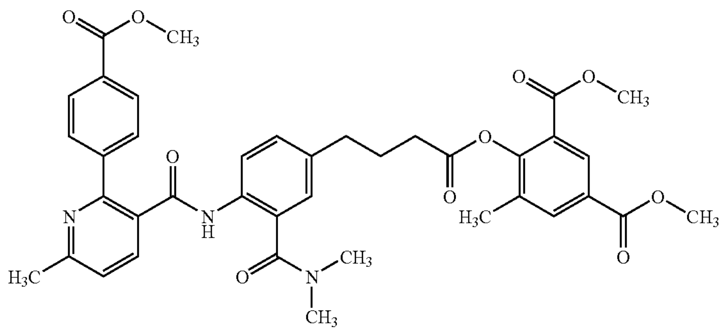 | 2.05 (2H, quint, J=7.2 Hz), 2.25 (3H, s), 2.67 (2H, t, J=7.2 Hz), 2.67 (3H, s), 2.72 (2H, t, J=7.2 Hz), 2.82 (3H, brs), 2.86 (3H, brs), 3.86 (3H, s), 3.91 (3H, s), 3.93 (3H, s), 7.02 (1H, d, J=1.9 Hz), 7.24–7.31 (2H, m), 7.82 (2H, d, J=8.3 Hz), 7.92 (1H, d, J=7.6 Hz), 8.05 (2H, d, J=8.3 Hz), 8.11 (1H, d, J=1.9 Hz), 8.36 (1H, d, J=8.3 Hz), 8.51 (1H, d, J=2.2 Hz), 9.04 (1H, s). |
| 4-3 | 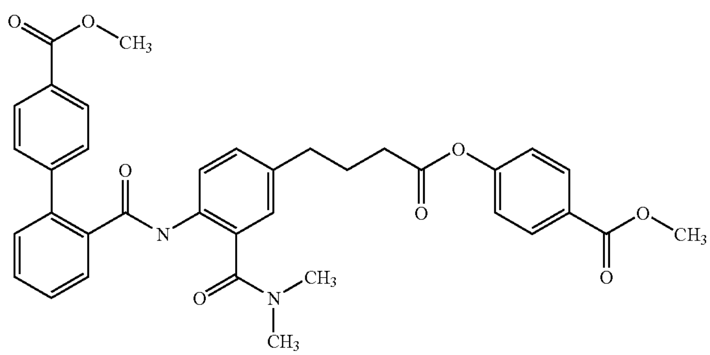 | 2.02 (2H, quint, J=7.2 Hz), 2.56 (2H, t, J=7.2 Hz), 2.68 (2H, t, J=7.2 Hz), 2.81 (3H, brs), 2.94 (3H, brs), 3.91 (6H, s), 6.97 (1H, d, J=2.2 Hz), 7.15 (2H, d, J=8.7 Hz), 7.22–7.29 (1H, m), 7.41–7.58 (5H, m), 7.70 (1H, dd, J=1.9, 7.5 Hz), 8.03 (2H, d, J=8.3 Hz), 8.07 (2H, d, J=8.7 Hz), 8.32 (1H, d, J=8.7 Hz), 8.89 (1H, s). |
| 4-4 | 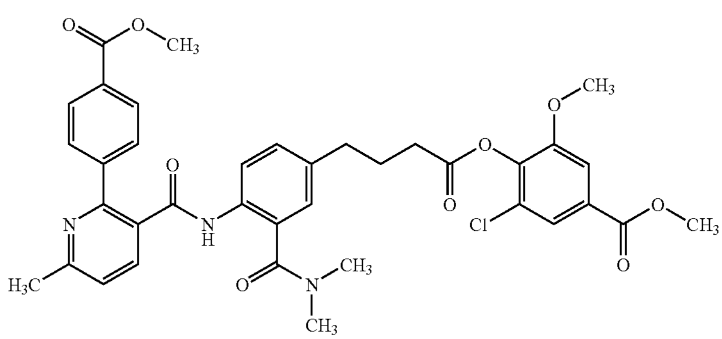 | 2.06 (2H, quint, J=7.2 Hz), 2.63 (2H, t, J=7.2 Hz), 2.67 (3H, s), 2.72 (2H, t, J=7.2 Hz), 2.81 (3H, brs), 2.86 (3H, brs), 3.88 (3H, s), 3.91 (3H, s), 3.93 (3H, s), 6.99 (1H, d, J=1.9 Hz), 7.26–7.29 (2H, m), 7.55 (1H, d, J=1.6 Hz), 7.75 (1H, d, J=1.9 Hz), 7.82 (2H, d, J=8.3 Hz), 7.93 (1H, d, J=7.9 Hz), 8.06 (2H, d, J=8.3 Hz), 8.37 (1H, d, J=8.7 Hz), 9.04 (1H, s). |

Test Example 1

Inhibition Test of Interliposomal Triglyceride (TG) Transfer Activity by MTP Microsomal triglyceride transfer protein (MTP) from human small intestine microsome (manufactured by Tissue Transforming Technologies, Inc.) was purified in such a way described below. Human small intestine microsome was dialyzed against 10 mM phosphate buffer (300 mL, pH 6.8) twice for about 2 hours and once for further not less than 12 hours, at about 4° C. After dialysis, the mixture was centrifuged at 4° C. and 15,000×g for 5 minutes and then the supernatant was recovered. The previously recovered supernatant was purified by column chromatography on diethylaminoethyl (DEAE) Sepharose using FPLC (Fast Performance Liquid Chromatography) system, and the purified MTP was used for the test as described below.

Small unilamellar-vesicle (SUV) liposome (hereinafter described as donor, containing 0.25% (mol/mol) triolein and 5% (mol/mol) cardiolipin) constituted by triolein labeled with $^{14}C$ and non-labeled SUV liposome (hereinafter described as acceptor, containing 0.250 (mol/mol) triolein) were prepared in such a way described below.

Firstly, in order to prepare the donor, there were volatilized under a stream of nitrogen gas a phosphatidylcholine solution containing phosphatidylcholine labeled with $^3H$, a cardiolipin solution, and a triolein solution containing triolein labeled with $^{14}C$ (each solution had been already dissolved in an appropriate organic solvent), or in order to prepare the acceptor, there were volatilized under nitrogen flow a phosphatidylcholine solution containing phosphatidylcholine labeled with $^3H$ and a cardiolipin solution (each solution had been already dissolved in an appropriate organic solvent). An appropriate amount of a reaction buffer (15 mM Tris-HCl buffer containing 1 mM EDTA.$Na_2$, 40 mM NaCl, and 0.5% (w/v) bovine serum albumin, pH 7.4) was added thereto to be emulsified. The emulsions were treated with ultrasonication under ice-cooling and centrifuged at 4° C. and 159,000×g for 2 hours. Each of the resulting supernatant was used for donor or acceptor.

Each radioactivity in the acceptor and the donor was measured by liquid scintillation counter, and a mixed solution of the acceptor and the donor was prepared with a reaction buffer so as to be a donor-derived radioactivity of 16,000 dpm/400 μL and a acceptor-derived radioactivity of 4,000 dpm/400 L. 400 μL of the mixed solution of the donor and the acceptor, 45 μL of the reaction buffer, 50 μL of MTP (20 μg/mL), and 5 μL of a sample dissolved in DMSO (dimethyl sulfoxide) or 5 μL of DMSO was mixed (total amount: 500 μL). The mixture was incubated at 37° C. for 1.5 hours. After completion of the incubation, 1.25 mL of a suspension of DEAE cellulose (66.7% (v/v)) in 15 mM Tris-HCl buffer (pH 7.4) containing 1 mM EDTA.$Na_2$ was added to the above solution. The mixture was centrifuged to separate the donor (adsorbed on the DEAE cellulose to precipitate) and the acceptor (the supernatant). The radioactivity in the acceptor was measured by liquid scintillation counter. The value obtained by subtracting the radioactivity in a blank group from the radioactivity in the acceptor of a DMSO group was determined as MTP-mediated TG transfer activity, and it was compared with the value obtained by subtracting the radioactivity in the blank group from the radioactivity in a sample group. Here, the blank was prepared by adding 10 mM phosphate buffer (pH 6.8) containing 250 mM NaCl in place of MTP. Inhibition rate (%) was calculated from values obtained according to the following equation.

Inhibition rate(%)=(1 minus((radioactivity of sample group minus radioactivity of blank group)/(radioactivity of DMSO group minus radioactivity of blank group)))×100.

50% Inhibition rate ($IC_{50}$) was determined on the basis of the above equation.

The results are shown in Tables 28 to 32. In the Tables 28 to 32, "+++" shows $IC_{50}$ value is less than 10 nM, "++" shows $IC_{50}$ value is 10 nM to less than 100 nM, and "+" shows $IC_{50}$ value is 100 nM to 1000 nM.

Test Example 2

Metabolic Stability Test in Liver S9

Human liver S9 (final concentration: 2 mg protein/mL), was suspended in 100 mM potassium phosphate buffer (pH 7.4, containing β-nicotinamide adenine dinucleotide phosphate: 1.3 mM, D-glucose-6-phosphate: 3.3 mM, magnesium chloride: 3.3 mM, glucose-6-phosphate dehydrogenase: 0.4 U/mL). The suspension was mixed with a solution of a sample dissolved in DMSO. The solution was incubated at 37° C. for 0, 10 and 60 minutes, and an acetonitrile containing formic acid (final concentration: 0.1%) was added thereto. The solutions were centrifuged, and the concentration of the sample (unchanged form) in the supernatant was determined by high performance liquid chromatography/mass spectrometry (LC/MS). Based on the data obtained, remaining rate (%) was calculated according to the following equation.

Remaining rate(%)=amount of sample 0, 10, or 60 minutes after incubation/amount of sample at zero time after incubation×100

Test Example 3

Metabolic Stability Test in Plasma

A sample dissolved in DMSO was added to plasma of human or animal species (mouse and hamster). The solutions were incubated at 37° C. for 0, 10 and 60 minutes, and acetonitrile containing formic acid (final concentration: 0.1%) was added thereto. The solutions were centrifuged, and the concentration of the sample (unchanged form) in the supernatant was determined by high performance liquid chromatography/mass spectrometry (LC/MS). Based on the data obtained, the remaining rate (%) was calculated according to the following equation.

Remaining rate(%)=amount of sample 0, 10, or 60 minutes after incubation/amount of sample at zero time after incubation×100

With respect to the compounds obtained in Working Examples according to the present invention (Compounds 1-1 to 1-115, 2-1, 3-1, 3-2, and 4-1 to 4-4), the results of the remaining rate in human liver S9 and plasma are shown in Tables 28 to 32.

In the tables, Buf. remaining rate was determined by stability test in buffer (pH 7.4) as described below.

Stability Test in Buffer (pH 7.4)

A sample dissolved in DMSO was mixed with a mixed solution of 100 mM potassium phosphate buffer and acetonitrile in the ratio of 7:3 (v/v). The mixture was incubated at 37° C. for 0, 10, and 60 minutes, and acetonitrile containing formic acid (final concentration: 0.1%) was added thereto. The solution was centrifuged, and the concentration of the sample (unchanged form) in the supernatant was determined by high performance liquid chromatography/mass spectrometry (LC/MS). Based on the data obtained, Buf. remaining rate (%) was calculated according to the following equation.

Buf. remaining rate(%)=amount of sample 0, 10, or 60 minutes after incubation/amount of sample at zero time after incubation×100

TABLE 28

| Compound No. | Human intestine MTP (IC$_{50}$(nM)) | Remaining rate in human liver S9 (%/10 min) | Remaining rate in human liver S9 (%/60 min) | Remaining rate in human plasma (%/10 min) | Remaining rate in human plasma (%/60 min) | Buf. remaining rate (%/10 min) | Buf. remaining rate (%/60 min) |
|---|---|---|---|---|---|---|---|
| 1-1 | ++ | 0 | 0 | 80 | 40 | 101 | 104 |
| 1-2 | +++ | 0 | 0 | 20 | 0 | 98 | 97 |
| 1-3 | + | 0 | 0 | 58 | 5 | 101 | 98 |
| 1-4 | + | 0 | 0 | 57 | 5 | 99 | 95 |
| 1-5 | +++ | 0 | 0 | 11 | 0 | 100 | 101 |
| 1-6 | +++ | 0 | 0 | 53 | 0 | 102 | 102 |
| 1-7 | +++ | 0 | 0 | 60 | 0 | 98 | 98 |
| 1-8 | +++ | 0 | 0 | 71 | 12 | 99 | 98 |
| 1-9 | +++ | 0 | 0 | 34 | 0 | 94 | 97 |
| 1-10 | +++ | 0 | 0 | 0 | 0 | 101 | 98 |
| 1-11 | +++ | 0 | 0 | 0 | 0 | 99 | 99 |
| 1-12 | +++ | 0 | 0 | 10 | 0 | 100 | 103 |
| 1-13 | +++ | 0 | 0 | 24 | 0 | 95 | 97 |
| 1-14 | +++ | 2 | 0 | 43 | 0 | 101 | 104 |
| 1-15 | +++ | 4 | 0 | 42 | 0 | 98 | 100 |
| 1-16 | +++ | 2 | 0 | 3 | 0 | 98 | 103 |
| 1-17 | ++ | 0 | 0 | 0 | 0 | 100 | 105 |
| 1-18 | +++ | 0 | 0 | 0 | 0 | 101 | 98 |
| 1-19 | ++ | 0 | 0 | 0 | 0 | 107 | 100 |
| 1-20 | ++ | 0 | 0 | 0 | 0 | 102 | 99 |
| 1-21 | ++ | 0 | 0 | 0 | 0 | 104 | 103 |
| 1-22 | ++ | 0 | 0 | 8 | 0 | 96 | 98 |
| 1-23 | ++ | 0 | 0 | 21 | 0 | 99 | 99 |
| 1-24 | +++ | 10 | 6 | 9 | 4 | 95 | 95 |
| 1-25 | + | 4 | 0 | 89 | 59 | 99 | 101 |

TABLE 29

| Compound No. | Human intestine MTP (IC$_{50}$(nM)) | Remaining rate in human liver S9 (%/10 min) | Remaining rate in human liver S9 (%/60 min) | Remaining rate in human plasma (%/10 min) | Remaining rate in human plasma (%/60 min) | Buf. remaining rate (%/10 min) | Buf. remaining rate (%/60 min) |
|---|---|---|---|---|---|---|---|
| 1-26 | ++ | 0 | 0 | 23 | 0 | 99 | 102 |
| 1-27 | ++ | 0 | 0 | 10 | 0 | 97 | 102 |
| 1-28 | +++ | 0 | 0 | 0 | 0 | 101 | 102 |
| 1-29 | +++ | 1 | 0 | 41 | 0 | 98 | 98 |
| 1-30 | ++ | 0 | 0 | 0 | 0 | 99 | 99 |
| 1-31 | ++ | 0 | 0 | 26 | 0 | 101 | 102 |
| 1-32 | + | 0 | 0 | 0 | 0 | 100 | 97 |
| 1-33 | +++ | 0 | 0 | 0 | 0 | 98 | 102 |
| 1-34 | +++ | 16 | 4 | 52 | 0 | 98 | 103 |
| 1-35 | +++ | 5 | 0 | 43 | 0 | 100 | 105 |
| 1-36 | +++ | 3 | 0 | 0 | 0 | 100 | 103 |
| 1-37 | +++ | 37 | 11 | 0 | 0 | 99 | 99 |
| 1-38 | ++ | 11 | 2 | 0 | 0 | 101 | 102 |
| 1-39 | +++ | 5 | 2 | 0 | 0 | 98 | 104 |
| 1-40 | +++ | 5 | 0 | 0 | 0 | 100 | 102 |
| 1-41 | +++ | 4 | 0 | 37 | 0 | 103 | 106 |
| 1-42 | +++ | 5 | 0 | 52 | 0 | 103 | 103 |
| 1-43 | +++ | 4 | 2 | 13 | 0 | 101 | 103 |
| 1-44 | +++ | 12 | 4 | 13 | 0 | 99 | 100 |
| 1-45 | +++ | 12 | 2 | 89 | 48 | 101 | 102 |
| 1-46 | +++ | 5 | 2 | 39 | 0 | 99 | 102 |
| 1-47 | +++ | 14 | 0 | 0 | 0 | 96 | 97 |
| 1-48 | +++ | 16 | 6 | 0 | 0 | 99 | 97 |
| 1-49 | +++ | 6 | 1 | 0 | 0 | 100 | 100 |
| 1-50 | +++ | 7 | 2 | 0 | 0 | 97 | 103 |

TABLE 30

| Compound No. | Human intestine MTP (IC$_{50}$(nM)) | Remaining rate in human liver S9 (%/10 min) | Remaining rate in human liver S9 (%/60 min) | Remaining rate in human plasma (%/10 min) | Remaining rate in human plasma (%/60 min) | Buf. remaining rate (%/10 min) | Buf. remaining rate (%/60 min) |
|---|---|---|---|---|---|---|---|
| 1-51 | +++ | 8 | 3 | 23 | 0 | 98 | 101 |
| 1-52 | +++ | 13 | 4 | 12 | 0 | 100 | 101 |
| 1-53 | +++ | 5 | 2 | 3 | 3 | 100 | 106 |
| 1-54 | +++ | 10 | 2 | 0 | 0 | 97 | 105 |
| 1-55 | +++ | | | | | | |
| 1-56 | +++ | | | | | | |
| 1-57 | +++ | | | | | | |
| 1-58 | +++ | | | | | | |
| 1-59 | +++ | | | | | | |
| 1-60 | +++ | | | | | | |
| 1-61 | +++ | | | | | | |
| 1-62 | +++ | | | | | | |
| 1-63 | +++ | | | | | | |
| 1-64 | +++ | 21 | 4 | 98 | 93 | 100 | 101 |
| 1-65 | +++ | 8 | 0 | 98 | 94 | 104 | 104 |
| 1-66 | +++ | 3 | 0 | 67 | 8 | 101 | 103 |
| 1-67 | +++ | 3 | 0 | 77 | 17 | 103 | 105 |
| 1-68 | +++ | 11 | 3 | 77 | 18 | 101 | 103 |
| 1-69 | ++ | 0 | 0 | 70 | 11 | 101 | 106 |
| 1-70 | +++ | 0 | 0 | 0 | 0 | 101 | 104 |
| 1-71 | +++ | 0 | 0 | 53 | 0 | 102 | 105 |
| 1-72 | +++ | 4 | 0 | 0 | 0 | 113 | 112 |
| 1-73 | +++ | 10 | 0 | 78 | 19 | 101 | 101 |
| 1-74 | +++ | 24 | 9 | 77 | 19 | 102 | 101 |
| 1-75 | +++ | 23 | 3 | 0 | 0 | 113 | 124 |

TABLE 31

| Compound No. | Human intestine MTP (IC$_{50}$(nM)) | Remaining rate in human liver S9 (%/10 min) | Remaining rate in human liver S9 (%/60 min) | Remaining rate in human plasma (%/10 min) | Remaining rate in human plasma (%/60 min) | Buf. remaining rate (%/10 min) | Buf. remaining rate (%/60 min) |
|---|---|---|---|---|---|---|---|
| 1-76 | +++ | 5 | 2 | 50 | 1 | 99 | 100 |
| 1-77 | +++ | 0 | 0 | 59 | 2 | 99 | 100 |
| 1-78 | +++ | 10 | 2 | 51 | 2 | 97 | 97 |
| 1-79 | +++ | 20 | 4 | 0 | 0 | 96 | 95 |
| 1-80 | +++ | 5 | 0 | 4 | 0 | 100 | 101 |
| 1-81 | +++ | 4 | 1 | 51 | 2 | 99 | 97 |
| 1-82 | +++ | 0 | 0 | 17 | 0 | 100 | 103 |
| 1-83 | +++ | 0 | 0 | 39 | 0 | 99 | 99 |
| 1-84 | +++ | 1 | 0 | 21 | 0 | 99 | 101 |
| 1-85 | +++ | 0 | 0 | 61 | 4 | 103 | 102 |
| 1-86 | +++ | 0 | 0 | 40 | 0 | 99 | 103 |
| 1-87 | +++ | 11 | 2 | 60 | 2 | 100 | 104 |
| 1-88 | +++ | 0 | 0 | 39 | 0 | 102 | 101 |
| 1-89 | +++ | 6 | 3 | 49 | 0 | 102 | 104 |
| 1-90 | +++ | 7 | 0 | 50 | 0 | 102 | 103 |
| 1-91 | +++ | 0 | 0 | 31 | 0 | 100 | 105 |
| 1-92 | +++ | 0 | 0 | 71 | 6 | 102 | 107 |
| 1-93 | +++ | 4 | 0 | 52 | 0 | 107 | 109 |
| 1-94 | +++ | 0 | 0 | 41 | 9 | 99 | 102 |
| 1-95 | +++ | 0 | 0 | 82 | 29 | 103 | 102 |
| 1-96 | +++ | 15 | 7 | 0 | 0 | 100 | 109 |
| 1-97 | +++ | 13 | 7 | 49 | 0 | 100 | 104 |
| 1-98 | +++ | 6 | 0 | 5 | 0 | 101 | 99 |
| 1-99 | +++ | 6 | 0 | 5 | 0 | 98 | 99 |
| 1-100 | +++ | 0 | 0 | 12 | 0 | 102 | 102 |

TABLE 32

| Compound No. | Human intestine MTP (IC$_{50}$(nM)) | Remaining rate in human liver S9 (%/10 min) | Remaining rate in human liver S9 (%/60 min) | Remaining rate in human plasma (%/10 min) | Remaining rate in human plasma (%/60 min) | Buf. remaining rate (%/10 min) | Buf. remaining rate (%/60 min) |
|---|---|---|---|---|---|---|---|
| 1-101 | +++ | 3 | 0 | 42 | 0 | 100 | 103 |
| 1-102 | +++ | 0 | 0 | 46 | 0 | 98 | 101 |
| 1-103 | +++ | 48 | 12 | 99 | 55 | 105 | 111 |
| 1-104 | +++ | 14 | 5 | 78 | 17 | 101 | 96 |
| 1-105 | +++ | 3 | 0 | 84 | 43 | 101 | 101 |
| 1-106 | +++ | 13 | 0 | 49 | 0 | 98 | 99 |
| 1-107 | +++ | 11 | 3 | 63 | 2 | 98 | 99 |
| 1-108 | +++ | 25 | 5 | 89 | 17 | 98 | 98 |
| 1-109 | +++ | 0 | 0 | 50 | 3 | 99 | 99 |
| 1-110 | +++ | 5 | 0 | 26 | 0 | 99 | 102 |
| 1-111 | +++ | 41 | 3 | 30 | 0 | 99 | 99 |
| 1-112 | +++ | 27 | 8 | 48 | 0 | 99 | 100 |
| 1-113 | +++ | 8 | 2 | 1 | 0 | 103 | 104 |
| 1-114 | +++ | 14 | 3 | 2 | 0 | 104 | 108 |
| 1-115 | +++ | 0 | 0 | 85 | 40 | 98 | 98 |
| 2-1 | ++ | 0 | 0 | 47 | 0 | 95 | 95 |
| 3-1 | ++ | 2 | 0 | 63 | 6 | 98 | 102 |
| 3-2 | ++ | 2 | 0 | 24 | 0 | 94 | 97 |
| 4-1 | +++ | 0 | 0 | 25 | 0 | 99 | 101 |
| 4-2 | +++ | 2 | 0 | 34 | 0 | 98 | 97 |
| 4-3 | +++ | 1 | 0 | 0 | 0 | 101 | 102 |
| 4-4 | +++ | 4 | 0 | 0 | 0 | 99 | 97 |

It is apparent from the above Test Example 1 (Inhibition test of interliposomal triglyceride (TG) transfer activity by MTP) that novel compounds of the present invention and their pharmaceutically acceptable salts possess excellent MTP inhibitory activity. In addition, it is apparent from Test Example 2 (Metabolic stability test in liver S9) that the novel compounds of the present invention and their pharmaceutically acceptable salts are metabolized rapidly even if a small amount of active compound has reached the liver. Furthermore, it is apparent from Test Example 3 (Metabolic stability test in plasma) that the novel compounds of the present invention and their pharmaceutically acceptable salts are metabolized rapidly in plasma.

From the results as mentioned above, it is understood that the novel compounds of the present invention and their pharmaceutically acceptable salts can inhibit lipid absorption in the small intestine. Further, those results reveal that the compounds are metabolized rapidly in plasma or liver, and thereby the compounds of this invention do not inhibit MTP in the liver, but selectively inhibit MTP in the small intestine.

Therefore, selective inhibition of MTP activity in the small intestine by the novel compounds of the present invention and their pharmaceutically acceptable salts can lower lipid absorption, which makes it possible to control triglyceride, cholesterol and lipoproteins such as LDL, etc. in blood or to control lipid in cells. Further, since the novel compounds of the present invention and their pharmaceutically acceptable salts do not affect liver MTP, accumulation of triglyceride does not occur in the liver. Consequently, inhibition of fatty liver generation as an adverse effect might be expected. Therefore, the novel compounds of the present invention and their pharmaceutically acceptable salts can be said that they can be novel MTP inhibitors having no adverse effects, that is to say, novel agents for the treatment or prophylaxis of hyperlipidemia, arteriosclerosis, coronary artery diseases, obesity, diabetes or hypertension, and further for the treatment or prophylaxis of pancreatitis, hypercholesterolemia, hypertriglyceridemia, etc., which substantially inhibit only MTP in the small intestine since they disappear more rapidly in comparison with conventional MTP inhibitors.

| Formulation 1 (production of capsules) | |
|---|---|
| 1) Compound 1-1 | 30 mg |
| 2) finely pulverized cellulose | 10 mg |
| 3) lactose | 19 mg |
| 4) magnesium stearate | 1 mg |

1), 2), (3), and (4) are mixed and filled into a gelatin capsule is filled with the mixture.

Formulation 2 (Capsule Preparation)

A capsule preparation is produced in a similar manner to Formulation 1 by use of Compounds 1-2 to 1-123, Compound 2-1, Compounds 3-1 to 3-2, or Compounds 4-1 to 4-4, instead of Compound 1-1.

| Formulation 3 (production of tablets) | |
|---|---|
| 1) Compound 1-1 | 30 g |
| 2) lactose | 50 g |
| 3) corn starch | 15 g |
| 4) carboxymethylcellulose calcium | 44 g |
| 5) magnesium stearate | 1 g |

The whole amount of 1), 2) and 3), and 30 g of 4) are kneaded with water, dried in vacuo, and sieved to give a granular powder. 14 g of 4) and 1 g of 5) are mixed with the granular powder and the mixture is compressed by tableting machine. In this way, there are obtained 1,000 tablets containing 30 mg of compound of Working Example 1 per one tablet.

Formulation 4 (Tablet Preparation)

A tablet preparation is produced in a similar manner to Formulation 1 by use of Compounds 1-2 to 1-123, Compound 2-1, Compounds 3-1 to 3-2, or Compounds 4-1 to 4-4, instead of Compound 1-1.

INDUSTRIAL APPLICABILITY

The present invention is useful for the treatment or prophylaxis of hyperlipidemia, arteriosclerosis, coronary artery diseases, obesity, diabetes, or hypertension, and further for the treatment or prophylaxis of pancreatitis, hypercholesterolemia, hypertriglyceridemia, and the like.

The invention claimed is:

1. A compound having the structural formula:

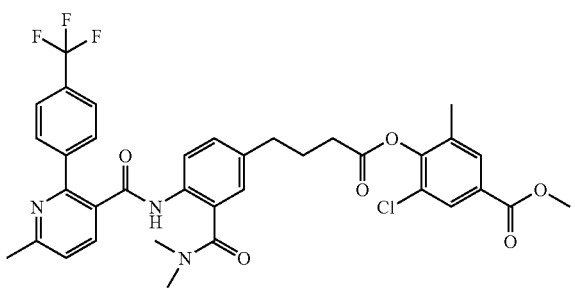

or a pharmaceutically acceptable salt thereof.

2. A compound having the structural formula:

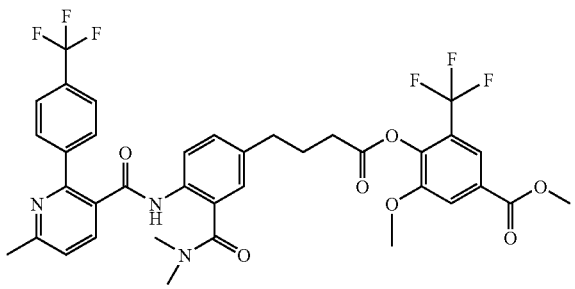

or a pharmaceutically acceptable salt thereof.

3. A compound having the structural formula:

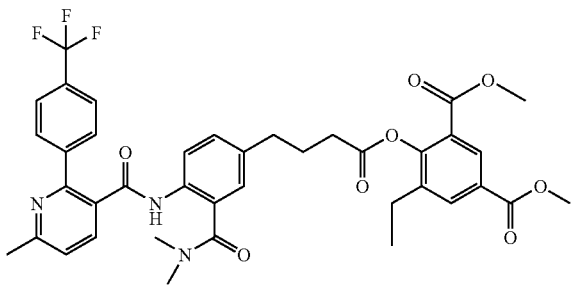

or a pharmaceutically acceptable salt thereof.

4. A compound having the structural formula:

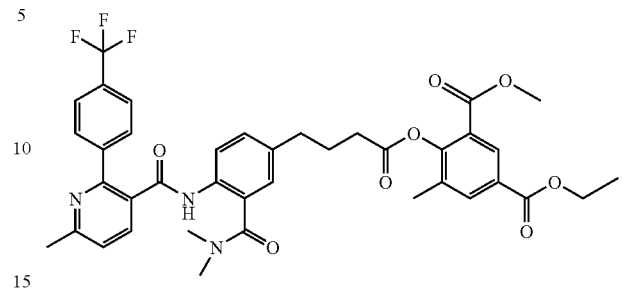

or a pharmaceutically acceptable salt thereof.

5. A compound having the structural formula:

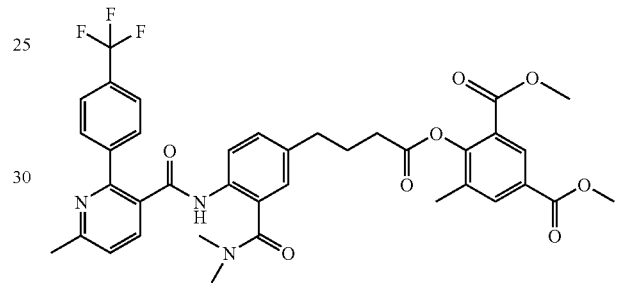

or a pharmaceutically acceptable salt thereof.

6. A pharmaceutical composition comprising the compound of any one of claims 1, 2, 3, 4, or 5, or a pharmaceutically acceptable salt thereof.

7. A method for the treatment or prophylaxis of a disease selected from hyperlipidemia, arteriosclerosis, coronary artery diseases, obesity, diabetes and hypertension, which comprises administering a pharmaceutically effective amount of the compound of any one of claims 1, 2, 3, 4, or 5, or a pharmaceutically acceptable salt thereof, to a mammal.

* * * * *